US009149518B2

(12) United States Patent
Zuckermann et al.

(10) Patent No.: US 9,149,518 B2
(45) Date of Patent: Oct. 6, 2015

(54) PORCINE REPRODUCTIVE AND RESPIRATORY SYNDROME VIRUS COMPOSITIONS AND USES THEREOF

(71) Applicant: THE BOARD OF TRUSTEES OF THE UNIVERSITY OF ILLINOIS, Urbana, IL (US)

(72) Inventors: Federico Zuckermann, Champaign, IL (US); Gabriela Calzada-Nova, Urbana, IL (US); William Schnitzlein, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 24 days.

(21) Appl. No.: 14/095,957

(22) Filed: Dec. 3, 2013

(65) Prior Publication Data

US 2014/0161768 A1 Jun. 12, 2014

Related U.S. Application Data

(60) Provisional application No. 61/734,919, filed on Dec. 7, 2012.

(51) Int. Cl.
*A61K 39/12* (2006.01)
*A61K 39/00* (2006.01)

(52) U.S. Cl.
CPC ......... *A61K 39/12* (2013.01); *A61K 2039/5254* (2013.01); *A61K 2039/552* (2013.01); *C12N 2770/10034* (2013.01)

(58) Field of Classification Search
None
See application file for complete search history.

(56) References Cited

U.S. PATENT DOCUMENTS

| | | | | |
|---|---|---|---|---|
| 5,476,778 | A | 12/1995 | Chladek | |
| 5,510,258 | A | 4/1996 | Sanderson | |
| 5,597,721 | A | 1/1997 | Brun | |
| 5,620,691 | A | 4/1997 | Wensvoort | |
| 5,690,940 | A | 11/1997 | Joo | |
| 5,866,401 | A | 2/1999 | Hesse | |
| 5,976,537 | A | 11/1999 | Mengeling | |
| 5,989,563 | A | 11/1999 | Chladek | |
| 6,001,370 | A | 12/1999 | Burch | |
| 6,042,830 | A | 3/2000 | Chladek | |
| 6,110,468 | A | 8/2000 | Collins | |
| 6,251,397 | B1 | 6/2001 | Paul | |
| 6,495,138 | B1 | 12/2002 | Van Nieuwstadt | |
| 6,660,513 | B2 | 12/2003 | Mengeling et al. | |
| 7,368,117 | B2 | 5/2008 | Fetzer | |
| 7,388,087 | B2 | 6/2008 | Zuckermann | |
| 7,767,653 | B2 * | 8/2010 | Zuckermann | 514/44 R |
| 8,202,717 | B2 | 6/2012 | Zuckermann | |
| 8,663,984 | B2 | 3/2014 | Zuckermann | |
| 2004/0073021 | A1 | 4/2004 | Zuckermann | |
| 2004/0101513 | A1 | 5/2004 | Zuckermann | |
| 2009/0022761 | A1 | 1/2009 | Zuckermann | |
| 2010/0227339 | A1 | 9/2010 | Yoon | |
| 2011/0177118 | A1 | 7/2011 | Zuckermann | |
| 2012/0213810 | A1 | 8/2012 | Burgard et al. | |
| 2012/0231540 | A1 | 9/2012 | Zuckermann | |
| 2013/0142824 | A1 | 6/2013 | Ni | |
| 2014/0161768 | A1 * | 6/2014 | Zuckermann et al. | 424/85.2 |
| 2014/0162362 | A1 | 6/2014 | Zuckermann | |

FOREIGN PATENT DOCUMENTS

| | | | |
|---|---|---|---|
| CA | 2418780 | A1 | 8/2003 |
| EP | 1838343 | B1 | 3/2010 |
| EP | 2251419 | A1 | 11/2010 |
| WO | WO 2006/074986 | | 7/2006 |
| WO | WO 2014/089117 | | 6/2014 |

OTHER PUBLICATIONS

Sequence alignmanr of SEQ ID No. 1 with Geneseq database access No. ADR9856, submitted Jun. 2007 by Dea, S. in CA 2418780.*

Sequence alignment of SEQ ID No. 14 with Geneseq access No. AGD56062 submitted on Jun. 2007 by Yoon et al. in WO 2007065151.*

The sequence alignment of SEQ ID No. 16 with UniProt access No. A4L5U6_PRRSV submitted May 2007 by Kim et al. in Veterinary Microbiology. 2007; 123: 1-14.*

The sequence alignment of SEQ ID No. 17 with Geneseq database access No. AAW25975 submitted Jun. 2007 by Paul et al. in WO 9640932.*

Sequence alignment of SEQ ID No. 19 with Geneseq access No. AAW84334 submitted Mar. 1999 by van Nieuwstadt et al. in WO 9850426.*

Balasuriya et al. (Veterinary Immunology and Immunopathology. 2004; 102: 107-129).*

Charerntantanakul (Veterinary Immunology and Immunopathology. 2009; 129: 1-13).*

Guoshun et al. (Vaccine. 2007; 25: 4193-4202).*

Shi et al. ("Preliminary evaluation on immunization of porcine IL-15 and PRRSV GP5 genes in mice [J]." Journal of Northeast Agricultural University 1 (2010): 028, abstract only).*

International Search Report and Written Opinion mailed May 22, 2014, corresponding to International Application No. PCT/US2013/072922 (6 pages).

Albina et al. (1998a) "Interferon-alpha response to swine arterivirus (PoAV), the porcine reproductive and respiratory syndrome virus," J. Interferon Cytokine Res. 18:485-490.

Albina et al. (1998b) "Immune responses in pigs infected with porcine reproductive and respiratory syndrome virus (PRRSV)," Vet. Immunol. Immunopathol. 61:49-66.

Buddaert et al. (1998) "In vivo and in vitro interferon (IFN) studies with the porcine reproductive and respiratory syndrome virus (PRRSV)," Adv. Exp. Med. Biol. 440:461-467.

Calzada-Nova et al. (May 11, 2012) "Effect of the host cell line on the vaccine efficacy of an attenuated porcine reproductive and respiratory syndrome virus," Vet. Immunol. Immunopathol. 148(1-2):116-125.

(Continued)

*Primary Examiner* — Shanon A Foley
(74) *Attorney, Agent, or Firm* — Lathrop & Gage LLP

(57) ABSTRACT

Provided herein are embodiments relating to porcine reproductive and respiratory syndrome (PRRS) virus, compositions comprising the virus, and methods of using the virus. The virus may be used to immunize a mammal, including swine. Methods for generating an immune response against PRRS virus in swine by administering a composition comprising the virus are provided.

13 Claims, 19 Drawing Sheets

(56) References Cited

OTHER PUBLICATIONS

Calzada-Nova et al. (2009) "Characterization of the cytokine and maturation responses of pure populations of porcine plasmacytoid dendritic cells to porcine viruses and toll-like receptor agonists," Vet. Immunol. Immunopathol. 135(1-2):20-33.

Calzada-Nova et al. (2010) "North American porcine reproductive and respiratory syndrome viruses inhibit type I interferon production by plasmacytoid dendritic cells," J. Virol. 85(6):2703-2713.

Cano et al. (2007) "Impact of a modified-live porcine reproductive and respiratory syndrome virus vaccine intervention on a population of pigs infected with a heterologous isolate," Vaccine 25:4382-4391.

Cella et al. (2000) "Plasmacytoid dendritic cells activated by influenza virus and CD40L drive a potent TH1 polarization," Nat. Immunol. 1(4):305-310.

Charley et al. (1990) "Characterization of blood mononuclear cells producing IFN alpha following induction by coronavirus-infected cells (porcine transmissible gastroenteritis virus)," Res. Immunol. 141(2):141-151.

Christianson et al. (1994) "Porcine reproductive and respiratory syndrome: a review," Swine Health and Prod. 2(2):10-28.

Collins et al. (1992) "Isolation of swine infertility and respiratory syndrome virus (isolate ATCC VR-2332) in North America and experimental reproduction of the disease in gnotobiotic pigs," J. Vet. Diagn. Invest. 4:117-126.

Ellingson et al. (2010) "Vaccine efficacy of porcine reproductive and respiratory syndrome virus chimeras," Vaccine 28:2679-2686.

Fitzgerald-Bocarsly et al. (2002) "Natural interferon-alpha producing cells: the plasmacytoid dendritic cells," Biotechniques, Suppl:16-20, 22, 24-29.

Fitzgerald-Bocarsly (2008) "Plasmacytoid dendritic cells and type I IFN: 50 years of convergent history," Cytokine Growth Factor Rev. 19(1):3-19.

Gauger et al. (2012) "Genetic and phenotypic characterization of a 2006 United States porcine reproductive and respiratory virus isolate associated with high morbidity and mortality in the field," Virus Res. 163:98-107.

Geall et al. (2012) "Nonviral delivery of self-amplifying RNA vaccines," Proc Natl Acad Sci USA 109(36):14604-14609.

Goldberg et al. (2003) "Quasispecies variation of porcine reproductive and respiratory syndrome virus during natural infection," Virology 317:197-207.

Gonin et al. (1999) "Seroneutralization of porcine reproductive and respiratory syndrome virus correlates with antibody response to the GP5 major envelope glycoprotein," J. Vet. Diagn. Invest. 11(1):20-26.

Gorbalenya et al. (2006) "Nidovirales: evolving the largest RNA virus genome," Virus Res. 117:17-37.

Goyal et al. (1993) "Porcine reproductive and respiratory syndrome," J. Vet. Diagn. Invest. 5:656-664.

Greiner et al. (2000) "Quantitative relationship of systemic virus concentration on growth and immune response in pigs," J. Anim. Sci. 78:2690-2695.

Halbur et al. (1995) "Comparison of the pathogenicity of two US porcine reproductive and respiratory syndrome virus isolates with that of the Lelystad virus," Vet. Pathol. 32(6):648-660.

Halbur et al. (1996) "Comparative pathogenicity of nine US porcine reproductive and respiratory syndrome virus (PRRSV) isolates in a five-week-old cesarean-derived, colostrum-deprived pig model," J. Vet. Diagn. Invest. 8:11-20.

Halbur et al. (1997) "Update on abortion storms and sow mortality," Swine Health and Prod. 5:73.

Harms et al. (2001) "Experimental reproduction of severe disease in CD/CD pigs concurrently infected with type 2 porcine circovirus and porcine reproductive and respiratory syndrome virus," Vet. Pathol. 38:528-539.

Horner et al. (1998) "Immunostimulatory DNA is a potent mucosal adjuvant," Cell Immunol. 190:77-82.

Huang et al. (2010) "Novel strategies and approaches to develop the next generation of vaccines against porcine reproductive and respiratory syndrome virus (PRRSV)," Virus Res. 154:141-149.

Hurd et al. (2001) "Outbreaks of porcine reproductive failure: Report on a collaborative field investigation," J. Swine Health Prod. 9(3):103-108.

Johnson et al. (2004) "Pathogenic and humoral immune responses to porcine reproductive and respiratory syndrome virus (PRRSV) are related to viral load in acute infection," Vet. Immunol. Immunopathol. 102:233-247.

Key et al. (2001) "Genetic variation and phylogenetic analyses of the ORF5 gene of acute porcine reproductive and respiratory syndrome virus isolates," Vet. Micro. 83:249-263.

Kim et al. (1993) "Enhanced replication of porcine reproductive and respiratory syndrome (PRRS) virus in a homogeneous subpopulation of MA-104 cell line," Arch. Virol. 133:477-483.

Kim et al. (2008) "Different biological characteristics of wild-type porcine reproductive and respiratory syndrome viruses and vaccine viruses and identification of the corresponding genetic determinants," J Clin Microbiol. 46:1758-1768.

Kimman et al. (2009) Challenges for porcine reproductive and respiratory syndrome virus (PRRSV) vaccinology. Vaccine 27:3704-3718.

Labarque et al. (2000) "Effect of cellular changes and onset of humoral immunity on the replication of porcine reproductive and respiratory syndrome virus in the lungs of pigs," J. Gen. Virol. 81:1327-1334.

Labarque et al. (2003) "Respiratory tract protection upon challenge of pigs vaccinated with attenuated porcine reproductive and respiratory syndrome virus vaccines," Vet. Microbiol. 95:187-197.

Lachman et al. (1995) "Cytokine-Containing Liposomes as Adjuvants for Subunit Vaccines" In: Ch. 29. *Pharmaceutical Biotechnology. Vaccine Design: The Subunit and Adjuvant Approach.* vol. 6. Eds.: Powell, M. F.; Newman, M. J. *Plenum Press.* New York.

Lachman et al. (1996) "Cytokine-containing liposomes as vaccine adjuvants," Eur. Cytokine Netw. 7:693-698.

Lauring et al. (2010) "Rationalizing the development of live attenuated virus vaccines," Nature Biotech. 28:573-579.

Lee et al. (2004) "Porcine reproductive and respiratory syndrome virus filed isolates differ in in vitro interferon phenotypes," Vet. Immunol. Immunopathol. 102:217-231.

Lefevre et al. (1986) "Molecular cloning and sequencing of a gene encoding biologically active porcine α-interferon," J. Interferon Res. 6:349-360.

Levy et al. (1975) "A modified polyriboinosinic-polyribocytidylic acid complex that induces interferon in primates," J. Infect. Dis. 132(4):434-439.

Loemba et al. (1996) "Kinetics of humoral immune response to the major structural proteins of the porcine reproductive and respiratory syndrome virus," Arch. Virol. 141:751-761.

Loving et al. (2006) "Differential type I interferon activation and susceptibility of dendritic cell populations to porcine arterivirus," Immunology 120(2):217-229.

Loving et al. (2006) "Innate cytokine responses in porcine macrophage populations: evidence of differential recognition of double-stranded RNA," J Immunol. 177:8432-8439.

Lowe et al. (2005) "Correlation of cell-mediated immunity against porcine reproductive and respiratory syndrome virus with protection against reproductive failure in sows during outbreaks of porcine reproductive and respiratory syndrome in commercial herds," J Am Vet Med Assoc. 226:1707-1711.

Magar et al. (1995) "Antigen comparison of Canadian and US isolates of porcine reproductive and respiratory syndrome virus using monoclonal antibodies to the nucleocapsid protein," Can. J. Vet. Res. 59:232-234.

Mardassi et al. (1994) "Identification of major differences in the nucleocapsid protein genes of a Québec strain and European strains of porcine reproductive and respiratory syndrome virus," J. Gen. Virol. 75:681-685.

Meier et al. (2003) "Gradual development of the interferon-gamma response of swine to porcine reproductive and respiratory syndrome virus infection or vaccination," Virology 309:18-31.

Meier et al. (2004) "Cytokines and synthetic double-stranded RNA augment the T helper 1 immune response of swine to porcine reproductive respiratory syndrome virus," Vet. Immunol. Immunopath. 102:299-314.

(56) References Cited

OTHER PUBLICATIONS

Meng (2000) "Heterogeneity of porcine reproductive and respiratory syndrome virus: implications for current vaccine efficacy and future vaccine development," Vet. Microbiol. 74:309-329.

Mengeling et al. (1996) "Comparison among strains of porcine reproductive and respiratory syndrome virus for their ability to cause reproductive failure," Am. J. Vet. Res. 57:834-839.

Mengeling et al. (1998) "Clinical effects of porcine reproductive and respiratory syndrome virus on pigs during the early postnatal interval," Am. J. Vet. Res. 59:52-55.

Meulenberg (2000) "PRRSV, the virus," Vet. Res. 31(1):11-21.

Murtaugh et al. (2002) "Immunological responses of swine to porcine reproductive and respiratory syndrome virus infection," Viral Immunol. 15:533-547.

Nelsen et al. (1999) "Porcine reproductive and respiratory syndrome virus comparison: divergent evolution on two continents," J. Virol. 73:270-280.

Nelson et al. (1994) "Serum immune responses to the proteins of porcine reproductive and respiratory syndrome (PRRS) virus," J. Vet. Diagn. Invest. 6(4):410-415.

Ni et al. (2012) "Emergence and pathogenicity of highly pathogenic Porcine reproductive and respiratory syndrome virus in Vientiane, Lao People's Democratic Republic," J. Vet. Diag. Invest. 24(2):349-354.

Nielsen et al. (2001) "Reversion of a live porcine reproductive and respiratory syndrome virus vaccine investigated by parallel mutations," J. Gen. Virol. 82:1263-1272.

Nowacki et al. (1993) "Age-related increase of porcine natural interferon alpha producing cell frequency and of interferon yield per cell," Vet. Immunol. Immunopathol. 37:113-122.

Oie Terrestrial Manual (2008) Chapter 1.1.8. Principles of Veterinary Vaccine production. Internet address, oie.int/fileadmin/.../1.1.08_VACCINE_PRODUCTION.pdf.

Oie Terrestrial Manual (2010) Chapter 2.8.7. Porcine Reproductive and Respiratory Syndrome Virus—internet address, .oie.int/fileadmin/Home/eng/Health.../2.08.07_PRRS.pdf (13 pages).

Opriessnig et al. (2002) "Comparison of molecular and biological characteristics of a modified live porcine reproductive and respiratory syndrome virus (PRRSV) vaccine (ingelvac PRRS MLV), the parent strain of the vaccine (ATCC VR2332), ATCC VR2385, and two recent field isolates of PRRSV," J. Virol. 76:11837-11844.

Ostrowski et al. (2002) "Identification of neutralizing and nonneutralizing epitopes in the porcine reproductive and respiratory syndrome virus GP5 ectodomain," J. Virol. 76:4241-4250.

Pachuk et al. (2000) "DNA vaccines—challenges in delivery," Curr. Opin. Mol. Ther. 2(2):188-198.

Prieto et al. (2009) "Influence of time on the genetic heterogeneity of Spanish porcine reproductive and respiratory syndrome isolates," Vet. J. 180:363-370.

Reed et al. (1938) "A simple method of estimating fifty per cent end points," Amer. J. Hyg. 27:493-497.

Roman et al. (1997) "Immunostimulatory DNA sequences function as T helper-1-promoting adjuvants," Nat. Med. 3(8):849-854.

Royaee et al. (2004) "Deciphering the involvement of innate immune factors in the development of the host responses to PRRSV vaccination," Vet. Immunol. Immunopathol. 102:199-216.

Sela (1987) Synthetic Vaccines. Ed: Arnon, R. vol. 1. CRC Press, Inc. Boca Raton, Florida. pp. 83-92.

Shi et al. (2010) "Phylogeny-based evolutionary, demographical, and geographical dissection of North American type 2 porcine reproductive and respiratory syndrome viruses," J. Virol. 84:8700-8711.

Thacker (2003) "Clinical manifestations of PRRS virus," In: Zimmerman, J., Yoon, K.J. (Eds.), PRRS Compendium, 2nd ed., National Pork Board, Des Moines, IA, pp. 5-11.

Tian et al. (2007) "Emergence of fatal PRRSV variants: unparalleled outbreaks of atypical PRRS in China and molecular dissection of the unique hallmark," PLoS One, 2007:6:e526.

Tian et al. (2009) "An attenuated live vaccine based on highly pathogenic porcine reproductive and respiratory syndrome virus (HP PRRSV) protects piglets against HP-PRRS," Vet. Microb. 138:34-40.

Truong et al. (2004) "A highly pathogenic porcine reproductive and respiratory syndrome virus generated from an infectious cDNA clone retains the in vivo virulence and transmissibility properties of the parental virus," Virology 325:308-319.

Ulmer et al. (2012) "RNA-based vaccines," Vaccine 30(30):4414-4418.

Van Reeth et al. (1999) "Differential production of proinflammatory cytokines in the pig lung during different respiratory virus infections: correlations with pathogenicity," Res. Vet. Sci. 67:47-52.

Van Slooten et al. (2000) "Liposomes Containing Interferon-Gamma as Adjuvant in Tumor Cell Vaccines," Pharm. Res. 17:42-48.

Van Slooten et al. (2001) "Liposomes as Sustained Release System for Human Interferon-gamma: Biopharmaceutical Aspects," Biochim. Biophys. Acta. 1530:134-145.

Vezina et al. (1996) "Antibody production and blastogenic response in pigs experimentally infected with porcine reproductive and respiratory syndrome virus," Can. J. Vet. Res. 60:94-99.

Wang et al. (2008) "Attenuation of porcine reproductive and respiratory syndrome virus strain MN184 using chimeric construction with vaccine sequence," Virology 371:418-429.

Wensvoort et al. (1991) "Mystery swine disease in The Netherlands: the isolation of Lelystad virus," Vet. Q. 13:121-130.

Wensvoort et al. (1992) "Antigenic comparison of Lelystad virus and swine infertility and respiratory syndrome (SIRS) virus," J. Vet. Diagn. Invest. 4:134-138.

Wesley et al. (1998) "Differentiation of a Porcine Reproductive and Respiratory Syndrome Virus Vaccine Strain from North American Field Strains by Restriction Fragment Length Polymorphism Analysis of ORF 5," J. Vet. Diagn. Invest. 10:140-144.

Yaeger (2002) "The diagnostic sensitivity of immunohistochemistry for the detection of porcine reproductive and respiratory syndrome virus in the lung of vaccinated and unvaccinated swine," J. Vet. Diagn. Invest. 14(1):15-19.

Yoon et al. (1995) "Characterization of the humoral immune response to porcine reproductive and respiratory syndrome (PRRS) virus infection," J. Vet. Diagn. Invest. 7:305-312.

Zhou et al. (2008) "Highly virulent porcine reproductive and respiratory syndrome virus emerged in China," Transbound Emerg Dis. 55:152-164.

Zhou et al. (2010) "Porcine reproductive and respiratory syndrome in China," Virus Res.154:31-37.

* cited by examiner

```
Nsp2  (amino acids 14 <> 523)

63                             72
89-46448-40     A  N  R  M  V/M  N  S  K  F  E    (SEQ ID NO:4)
794A61          .  .  .  .   V   .  .  .  .  .    (SEQ ID NO:5)
111698          .  .  .  .   V   .  .  .  .  .    (SEQ ID NO:5)
G16X            .  .  .  .   V   .  .  .  .  .    (SEQ ID NO:5)

334                            343
89-46448-40     L  A  N  Y  Y  R  A  Q  G         (SEQ ID NO:6)
794A61          .  .  .  .  .  .  .  .  .         (SEQ ID NO:6)
111698          .  .  .  .  H  .  .  .  .         (SEQ ID NO:7)
G16X            .  .  .  .  .  .  .  .  .         (SEQ ID NO:6)

488                            497
89-46448-40     D  L  F/S T  P  P  E  F  A  T     (SEQ ID NO:8)
794A61          .  .  S   .  .  .  .  L  .  .     (SEQ ID NO:9)
111698          .  .  S   .  .  .  .  L  .  .     (SEQ ID NO:9)
G16X            .  .  P   .  .  .  .  .  .  .     (SEQ ID NO:10)
```

Figure 4A

```
Protein E  (amino acids 1 - 73)

27                             36
89-46448-40     V  D  I  I  I  F  L  A  I  L     (SEQ ID NO:11)
794A61          .  .  .  .  .  .  .  .  .  .     (SEQ ID NO:11)
111698          .  .  .  .  .  .  .  .  .  .     (SEQ ID NO:11)
G16X            .  .  .  .  V  .  .  .  .  .     (SEQ ID NO:12)

56                             65
89-46448-40     A  I  L  R  T  R  P  A  I  E     (SEQ ID NO:13)
794A61          .  .  .  .  .  .  .  .  .  .     (SEQ ID NO:13)
111698          .  .  .  .  .  .  .  .  .  .     (SEQ ID NO:13)
G16X            .  .  .  .  A  .  .  .  .  .     (SEQ ID NO:14)
```

Figure 4B

```
GP3       (amino acids 1 - 254)

90                          99
89-46448-40       L  G  F  M  I  P  P/S  G  L  S    (SEQ ID NO:15)
794A61            .  .  .  .  V  .  S    .  .  .    (SEQ ID NO:16)
111698            .  .  .  .  V  .  S    .  .  .    (SEQ ID NO:16)
G16X              .  .  .  .  V  .  S    .  .  .    (SEQ ID NO:16)

209                         218
89-46448-40       S  V  R  V  L  Q  T  L  R  P    (SEQ ID NO:17)
794A61            .  .  .  .  .  .  .  .  .  .    (SEQ ID NO:17)
111698            .  .  .  .  F  .  .  .  .  .    (SEQ ID NO:18)
G16X              .  .  .  .  .  .  .  .  .  .    (SEQ ID NO:17)
```

Figure 4C

```
GP4       (amino acids 1 > 126)

23                          37
89-46448-40       S  S  S  L  A  D  I  K  T  N    (SEQ ID NO:19)
794A61            .  .  .  .  .  .  .  .  .  .    (SEQ ID NO:19)
111698            .  .  .  .  S  .  .  .  .  .    (SEQ ID NO:20)
G16X              .  .  .  .  .  .  .  .  .  .    (SEQ ID NO:19)
```

Figure 4D

FIG. 10
A. Comparison of the Predicted Amino Acid Sequences of Protein E Associated with PRRSV Isolates G16X, 46448-40, 794A61, and 111698

```
                     10        20        30        40
G16X:      M G S M Q S L F D K I G Q L F V D A F T E F L V S I V D I I V F L A I L F G F T
46448-40:  . . . . . . . . . . . . . . . . . . . . . . . . . . . . . I . . . . . . . . . .
794A61:    . . . . . . . . . . . . . . . . . . . . . . . . . . . . . I . . . . . . . . . .
111698:    . . . . . . . . . . . . . . . . . . . . . . . . . . . . . I . . . . . . . . . .

50        60        70    73
G16X:      I A G W L V V F C I R L V C S A I L R A R P A I H S E Q L Q K I L
46448-40:  . . . . . . . . . . . . . . . . . . . T . . . . . . . . . . . . .
794A61:    . . . . . . . . . . . . . . . . . . . T . . . . . . . . . . . . .
111698:    . . . . . . . . . . . . . . . . . . . T . . . . . . . . . . . . .
```

B. Amino Acid Sequences of Protein E Associated with PRRSV Isolate G16X

```
                     10        20        30        40
G16X:      M G S M Q S L F D K I G Q L F V D A F T E F L V S I V D I I V F L A I L F G F T 50        60        70    73
G16X:      I A G W L V V F C I R L V C S A I L R A R P A I H S E Q L Q K I L
```

C. Predicted Amino Acid Sequences of Protein E Associated with PRRSV Isolate 46448-40

```
                        10        20        30        40
46448-40:  M G S M Q S L F D K I G Q L F V D A F T E F L V S I V D I I I F L A I L F G F T 50        60        70    73
46448-40:  I A G W L V V F C I R L V C S A I L R T R P A I H S E Q L Q K I L
```

Fig. 11A. Comparison of the Predicted Amino Acid Sequences of GP4 Associated with PRRSV Isolates G16X (SEQ ID: 23), 89-46448-40 (SEQ ID: 23), 794A61 (SEQ ID: 23), and 111698 (SEQ ID: 24)

```
                       10                  20                  30                 40
G16X:      M A A S L L E L M V G F K C L L V S Q A F A C K P C F S S S L A D I K T N T T A
46448-40:  . . . . . . . . . . . . . . . . . . . . . . . . . . . . . . . . . . . . . . . .
794A61:    . . . . . . . . . . . . . . . . . . . . . . . . . . . . . . . . . . . . . . . .
111698:    . . . . . . . . . . . . . . . . . . . . . . . . . . . . . . . . . . . . . . . .

50                  60                  70                 80
G16X:      A A S F A V L Q D I S C L R H R N S A S E A I R K I P Q C R T A I G T P V Y I T
46448-40:  . . . . . . . . . . . . . . . . . . . . . . . . . . . . . . . . . . . . . . . .
794A61:    . . . . . . . . . . . . . . . . . . . . . . . . . . . . . . S . . . . . . . . .
111698:    . . . . . . . . . . . . . . . . . . . . . . . . . . . . . . . . . . . . . . . .

90                 100                 110                120
G16X:      I T A N V T D E N Y L H S S D L L M L S S C L F Y A S E M S E K G F K V V F G N
46448-40:  . . . . . . . . . . . . . . . . . . . . . . . . . . . . . . . . . . . . . . . .
794A61:    . . . . . . . . . . . . . . . . . . . . . . . . . . . . . . . . . . . . . . . .
111698:    . . . . . . . . . . . . . . . . . . . . . . . . . . . . . . . . . . . . . . . .

130                 140                 150                160
G16X:      V S G I V A V C V N F T S Y V Q H V R E F T Q R S L M V D H V R L L H F M T P E
46448-40:  . . . . . . . . . . . . . . . . . . . . . . . . . . . . . . . . . . . . . . . .
794A61:    . . . . . . . . . . . . . . . . . . . . . . . . . . . . . . . . . . . . . . . .
111698:    . . . . . . . . . . . . . . . . . . . . . . . . . . . . . . . . . . . . . . . .

170        178
G16X:      T M R W A T V L A C L F A I L L A I
46448-40:  . . . . . . . . . . . . . . . . . .
794A61:    . . . . . . . . . . . . . . . . . .
111698:    . . . . . . . . . . . . . . . . . .
```

Fig. 11B. SEQ ID 23. Predicted Amino Acid Sequences of GP4 Associated with PRRSV Isolate 89-46448-40

```
           10              20              30             40
46448-40: M A A S L L F L M V G F K C L L V S Q A F A C K P C F S S L A D I K T N T T A
                 50              60              70             80
46448-40: A A S F A V L Q D I S C L R H R N S A S E A I R K I P Q C R T A I G T P V Y I T
                 90             100             110            120
46448-40: I T A N V T D E N Y L H S S D L L M L S S C L F Y A S E M S E K G F K V V F G N
                130             140             150            160
46448-40: V S G I V A V C V N F T S Y V Q H V R E F T Q R S L M V D H V R L L H F M T P E
                170             178
46448-40: T M R W A T V L A C L F A I L L A I
```

Fig. 11C. SEQ ID 24. Predicted Amino Acid Sequences of GP4 Associated with PRRSV Isolate 111698

```
           10              20              30             40
111698:   M A A S L L F L M V G F K C L L V S Q A F A C K P C F S S L S D I K T N T T A
                 50              60              70             80
111698:   A A S F A V L Q D I S C L R H R N S A S E A I R K I P Q C R T A I G T P V Y I T
                 90             100             110            120
111698:   I T A N V T D E N Y L H S S D L L M L S S C L F Y A S E M S E K G F K V V F G N
                130             140             150            160
111698:   V S G I V A V C V N F T S Y V Q H V R E F T Q R S L M V D H V R L L H F M T P E
                170             178
111698:   T M R W A T V L A C L F A I L L A I
```

Fig 12A. Comparison of the Predicted Amino Acid Sequence of GP3 Associated with PRRSV Isolates G16X, 89-46448-40, 794A61, and 111698

```
               10        20        30        40
G16X:    MVNSCTFLHIFLCCSFLYSLCCAVVAGSNTTYCFWFPLVR
46448-40: ........................................
794A61:  ........................................
111698:  ........................................

50        60        70        80
G16X:    GNFSFELTVNYTVCPPCLTRQAAAEAYEPGRSLWCRIGYD
46448-40: ........................................
794A61:  ........................................
111698:  ........................................

90       100       110       120
G16X:    RCGEDDHDELGFMVPSGLSSEGHLTSVYAWLAFLSFSYTA
46448-40: ............I.P/S.......................
794A61:  ........................................
111698:  ........................................

130       140       150       160
G16X:    QFHPEIFGIGNVSRVYVDIERQLICAEHDGQNTTLPRHDN
46448-40: ........................................
794A61:  ........................................
111698:  ........................................

170       180       190       200
G16X:    ISAVFQTYYQHQVDGGNWFHLEWLRPFFSSWLVLNVSWFL
46448-40: ........................................
794A61:  ........................................
111698:  ........................................

210       220       230       240
G16X:    RRSPANHVSVRVLQTLRPTPPQRQALLSSKTSVALGIATR
46448-40: ........................................
794A61:  ........................................
111698:  .............F..........................

254
G16X:    PLRRFAKSLSAVRR
46448-40: ..............
794A61:  ..............
111698:  ..............
```

Fig. 12B. Seq ID 21. Predicted Amino Acid Sequence of GP3 Associated with PRRSV Isolate 89-46448-40

```
                    10         20         30         40
46448-40:  M V N S C T F L H I F L C

PORCINE REPRODUCTIVE AND RESPIRATORY SYNDROME VIRUS COMPOSITIONS AND USES THEREOF

CROSS REFERENCE TO RELATED APPLICATION

This application claims the benefit of U.S. Application Ser. 61/734,919 filed Dec. 7, 2012, which is incorporated herein by reference in entirety.

SEQUENCE LISTING

This application includes a sequence listing submission as an electronic *.txt file in ASCII format which is incorporated herein by reference in entirety.

FIELD OF THE INVENTION

This application relates to compositions containing a porcine reproductive and respiratory syndrome virus (PRRSV), and the use of such compositions including as vaccines.

BACKGROUND OF THE INVENTION

Porcine reproductive and respiratory syndrome (PRRS) is characterized by severe reproductive failure and a high rate of late abortion and early farrowing in sows, and respiratory disease and mortality in young pigs. PRRS is caused by a small, enveloped virus with a single-stranded positive-sense RNA genome, which belongs to the family Arteriviridae, genus *Arterivirus*. PRRS virus naturally replicates in alveolar macrophages, and is able to maintain a prolonged viremia, causing persistent infections that last for months in some instances. The disease suddenly emerged in the late 1980s in the US and Europe, and has since spread worldwide, causing major economic losses to the swine industry. The virus is able to persist on infected farms, mainly due to its presence in persistently infected carrier sows.

PRRS virus is classified in two genotypes based on its continent of origin. PRRS virus strains originating from North America are classified as type 2 genotype, while those originating from Europe are designated as type 1 genotype. Currently, both genotypes circulate globally. The two genotypes differ approximately 40% from each other at the genomic level and are also serologically distinct. Isolates within each genotype also exhibit considerable nucleotide sequence heterogeneity of up to 20%. PRRS virus appears to evolve by random mutation and intragenic recombination events.

Based on sequence analysis of Spanish strains, it has been estimated that PRRS virus exhibits a mutation rate of 1 to $3 \times 10^{-2}$ substitutions per site and year, which is similar to that of other rapidly evolving RNA viruses. The immense genetic variation of PRRS virus that has been observed over that last 25 years and the appearance in the field of PRRS virus isolates producing much higher morbidity and mortality than earlier isolates is remarkable. In addition, the fact that each stock of PRRS virus typically exists as a mixture of genetically related species is becoming increasingly recognized.

A common type of biologic used in veterinary medicine to protect animals from viral diseases consists of modified live virus (MLV) vaccines. The most frequently used method for producing an attenuated live virus vaccine is to serially passage the pathogenic virus in a substrate (usually cell culture) other than the natural host cell and/or in adverse conditions until it becomes sufficiently attenuated from its original virulence (disease-producing ability), but retains its ability to induce protective immunity. In 1996 the first MLV vaccine was introduced into the North American market and was based on the PRRS virus strain VR-2332 isolated in 1991. The attenuated vaccine strain was derived by 25 serial passages of this virus at 35-37° C. in simian kidney cells (MA-104/MARC-145) followed by 12 additional passages at 31° C. in the same type of cells, for a total of 36 passages.

Subsequently, in response to a perceived decrease in the protective efficacy of the original PRRS MLV vaccine, presumably due to evolving genetic changes in the genome of prevalent PRRS virus isolates, which resulted in the emergence of more virulent and genetically dissimilar (heterologous) strains of PRRS virus, a second version of an MLV vaccine was introduced in 1999. The rationale for this initiative was to increase the genetic homology of the vaccine strain over that of the contemporary viruses circulating in the field in the late 1990s. This attenuated vaccine strain was derived from the JA-142 PRRS virus isolated from a severe case of PRRS in 1997 and represented the 200th serial passage of this isolate at 37° C. in the monkey kidney cell line MARC-145. The two progenitor isolates for these vaccines, VR-2332 and JA-142, have been described to exhibit moderate and high levels of virulence, respectively, thus explaining the need for either a moderate number of passages under adverse conditions (VR-2332) or a much greater number of serial passages in a milder environment (JA-142) in cell culture in order to generate an attenuated vaccine virus. Notably, inoculation of these attenuated PRRS virus strains into swine results in a viremia lasting more than 4 weeks. During this time the virus is shed in body secretions, resulting in the transmission of the vaccine virus to unvaccinated animals. As a result, the use of these vaccines has led to their reversion from an attenuated to a virulent phenotype.

Infection of pigs with wild type PRRS virus or their vaccination with a live attenuated form of this pathogen elicits production of virus-specific but non-neutralizing antibodies and a meager production of neutralizing antibodies. In addition, during this time, limited quantities of interferon (IFN) gamma secreting cells (SC) are generated. Production of virus-neutralizing antibodies as well as virus-specific IFN gamma SC are considered to be the main determinants for eliciting protective immunity against PRRS virus. It is well accepted that PRRS virus inherently stimulates imbalanced (i.e., a strong humoral response characterized by abundant production of non-neutralizing antibodies and a limited, but potentially protective, T cell-mediated, IFN gamma-based cellular immunity) and non-protective immune responses. It had been previously proposed that the most relevant parameter determining development of the often-observed non-protective adaptive immune response to vaccination or infection is the lack of an adequate innate immune response elicited by PRRS virus. Usually, virus-infected cells secrete type I IFN (IFN alpha and IFN beta), which elicits molecular changes in the neighboring cells to help them protect themselves from virus infection. Notably, the IFN alpha response of pigs to infection with PRRS virus is nearly non-existent.

It has been postulated that the absence of an adequate innate immune response to infection or vaccination with PRRS virus could be at least partly responsible for the belated production of specific virus-neutralizing antibodies and the protracted development of a cell-mediated immune response of pigs against this virus. Thus, PRRS virus may circumvent the genesis of a Th-1 type response by not eliciting adequate IFN alpha production upon infection of its host. In this regard, it is known that plasmacytoid dendritic cells (pDC) play a central role in the induction of an early antiviral state due to their prompt and copious secretion of IFN alpha in addition to other cytokines, e.g. tumor necrosis factor (TNF) alpha and interleukin 6 (IL-6), that have a significant impact on the development of adaptive immunity. Even though pDC represent only a small fraction (<1%) of the porcine peripheral blood mononuclear cell (PBMC) population, they account for the majority of secreted IFN alpha in freshly isolated porcine PBMC samples. Notably, unlike other porcine viruses that stimulate pDC to secrete abundant amounts of IFN alpha, PRRS virus elicits a meager IFN alpha response by this cell subset, and even negatively affects their function by actively suppressing the ability of stimulated pDCs to secrete IFN alpha and TNF alpha. Such obstruction could be reasonably expected to have a significant impact on the nature of the host's subsequent adaptive immune response. Support for this hypothesis was provided by the enhancing effect that providing an exogenous source of IFN alpha at the time of immunization with a PRRS MLV vaccine had on the intensity of the PRRS virus-specific, T cell mediated IFN gamma response.

There is a long felt need in the art for an effective and economical vaccine to protect swine from the effects of PRRS infection so that losses will be minimized.

SUMMARY OF THE INVENTION

In an embodiment of the invention, provided herein is an isolated Porcine Reproductive and Respiratory Syndrome (PRRS) virus. The genome of the virus may encode a protein selected from the group consisting of an E protein comprising a valine at position 31 relative to SEQ ID NO: 25, an E protein comprising an alanine at position 60 relative to SEQ ID NO: 25, or a GP3 protein comprising a valine at position 94 relative to SEQ ID NO: 21. The genome of the virus may also encode an E protein comprising a valine at position 31 relative to SEQ ID NO: 25, an E protein comprising an alanine at position 60 relative to SEQ ID NO: 25, and a GP3 protein comprising a valine at position 94 relative to SEQ ID NO: 21. The genome of the virus may comprise the sequence of SEQ ID NO: 1 or an RNA equivalent thereof.

Also provided herein as an embodiment is a vaccine comprising the virus and a pharmaceutically acceptable carrier. The vaccine may also comprise an immunological adjuvant.

Further provided herein as an embodiment is a method of inducing an immune response specific for a PRRS virus in a mammal, which may comprise administering the vaccine to a mammal in need thereof. The vaccine may also comprise an immunological adjuvant.

In an embodiment, the immunological adjuvant may be interferon alpha (IFN-α); interferon beta (IFN-β); interleukin-12; interleukin-15 interleukin-18; a nucleic acid encoding interferon α; a nucleic acid encoding interleukin-12; a nucleic acid encoding interleukin-15; a nucleic acid encoding interleukin-18; a nucleic acid encoding interferon β; a material which induces or enhances the activity of interferon α; a material which induces or enhances the activity of interferon β; poly IC; or poly ICLC. The immunological adjuvant may be administered simultaneously with the vaccine, within 24 hours after the vaccine, or within 24 hours before the vaccine. The administration may be intramuscular, intradermal, mucosal, oral, sublingual, intraocular, intranasal, intravenous, intraperitoneal, topical, or transdermal. The administration may be intramuscular.

Further provided herein is an isolated Porcine Reproductive and Respiratory Syndrome (PRRS) virus deposited with the American Type Culture Collection designated as ATCC Patent Deposit No. PTA-120658.

In an embodiment, the invention provides an isolated strain of Porcine Reproductive and Respiratory Syndrome Virus (PRRSV), wherein said strain is G16X, 111698, or 794A61. In an embodiment, the strain is G16X. In an embodiment, the strain has a genomic RNA sequence set forth in SEQ ID NO:1 (strain G16X). In an embodiment, the invention provides an isolated strain of Porcine Reproductive and Respiratory Syndrome Virus (PRRSV), wherein said strain has a genomic RNA sequence set forth in SEQ ID NO:1 (strain G16X) or SEQ ID NO:3 (strain 111698). In an embodiment, the invention provides an isolated strain of PRRSV having a Protein E sequence characterized by sequences set forth in SEQ ID NO:12 and SEQ ID NO:14; a GP3 sequence characterized by SEQ ID NO:16 or SEQ ID NO:16 and SEQ ID NO:17; a Nsp2 sequence characterized by SEQ ID NO:7; and/or a GP4 sequence characterized by SEQ ID NO:19.

In an embodiment 6, the invention provides an isolated strain of PRRSV, wherein the strain has a nucleic acid sequence of at least 95% identity to SEQ ID NO:1 (G16X) and has one or more encoded amino acid substitutions relative to a protein sequence of PRRS virus strain 89-46448-40, selected from the group consisting of: Protein Nsp2 V/M67V; Protein Nsp2 P/S490P, Nsp2 P495L; Nsp2 Y338H; Protein E I31V; Protein E T60A; Protein GP3 I94V; and Protein GP3 P/S96S. In an embodiment, the strain has one or more encoded amino acids as follows: Protein Nsp2 67V; Protein Nsp2 490P; Protein Nsp2 Y338H; Protein Nsp2 P495L; Protein E 31V; Protein E 60A; Protein GP3 94V; Protein GP3 L213F; Protein GP3 96S and Protein GP4 A32S. In other embodiments, the strain has a percent identity level as described elsewhere herein. In an embodiment, advantageously a vaccine strain of PRRSV has a phenotype of high interferon alpha response, e.g., by macrophages when administered to a pig. In an embodiment 7, the invention provides an immunogenic composition comprising at least one isolated PRRSV strain selected from the group consisting of G16X, 111698, and the strain of embodiment 6, and further comprising a pharmaceutical carrier acceptable for veterinary use.

In an embodiment, the invention provides a method of inducing an immune response specific for Porcine Reproductive and Respiratory Syndrome Virus (PRRSV) in an animal, said method comprising the step of administering an immunogenic composition described herein to an animal. In an embodiment, the immunogenic composition further comprises an immunological adjuvant.

In an embodiment, an immunogenic composition further comprises an immunological adjuvant. In an embodiment, the immunological adjuvant comprises at least one of interferon α, interferon β, interleukin-12, interleukin-15 interleukin-18, a nucleic acid encoding interferon α which is expressed in a pig cell, a nucleic acid encoding interleukin-12 which is expressed in a pig cell, a nucleic acid encoding interleukin-15 which is expressed in a pig cell, a nucleic acid encoding interleukin-18 which is expressed in a pig cell, a nucleic acid encoding interferon β which is expressed in a pig cell, a material which induces or enhances the activity of interferon β or interferon α or both, and poly IC or poly ICLC. In an embodiment, an immunological adjuvant is administered simultaneously with the immunogenic composition, within 24 hours after the immunogenic composition, or within 24 hours before the immunogenic composition.

In an embodiment, administering of immunogenic composition is intramuscular, intradermal, mucosal, oral, sublingual, intraocular, intranasal, intravenous, intraperitoneal, topical, or transdermal. In an embodiment, administering is intramuscular.

BRIEF DESCRIPTION OF THE DRAWINGS

FIGS. 4A-4D provide predicted amino acid differences in the primary structure of the non-structural protein 2 (Nsp2, FIG. 4A), protein E (FIG. 4B), and glycoproteins GP3 (FIG. 4C) and GP4 (FIG. 4D) between PRRS virus isolate 89-46448-40 and the derived strains 794A61, 111698 and G16X. Bold letters indicate distinguishing amino acid sites within the predicted amino acid sequences of the intact protein E and GP3 and a continuous portion (indicated by < and >) of the Nsp2 and GP4 of PRRSV 89-46448-40, 794A61, 111698, and G16X. The boxed pairs of letters indicate polymorphic sites within some proteins of PRRS virus 89-46448-40.

FIG. 10A shows an alignment of the protein E amino acid sequences of PRRS virus strains G16X (SEQ ID NO: 26), 89-46448-40, 794A61, and 111698 (SEQ ID NO:25 for the latter three items). FIG. 10B shows the amino acid sequence of protein E from G16X (SEQ ID NO: 26), and FIG. 10C shows the amino acid sequence of protein E from strain 89-46448-40 (SEQ ID NO: 25).

FIG. 11A shows an alignment of the GP4 amino acid sequences of PRRS virus strains G16X (SEQ ID NO: 23), 89-46448-40 (SEQ ID NO: 23), 794A61 (SEQ ID NO: 23), and 111698 (SEQ ID NO: 24). FIG. 11B shows the amino acid sequence of GP4 from strain 89-46448-40 (SEQ ID NO: 23). FIG. 11C shows amino acid sequences of GP4 associated with PRRSV Isolate 89-46448-40 (SEQ ID NO. 24).

FIG. 12A shows an alignment of the GP3 amino acid sequence of PRRS virus strains G16X (SEQ ID NO: 22), 89-46448-40 (SEQ ID NO: 21), 794A61 (SEQ ID NO: 22), and 111698 (SEQ ID NO: 48). FIG. 12B shows the amino acid sequence of GP3 from strain 89-46448-40 (SEQ ID NO: 21). FIG. 12C shows amino acid sequence of GP3 associated with PRRSV Isolate G16X (SEQ ID NO: 22).

DETAILED DESCRIPTION

Figure 1:
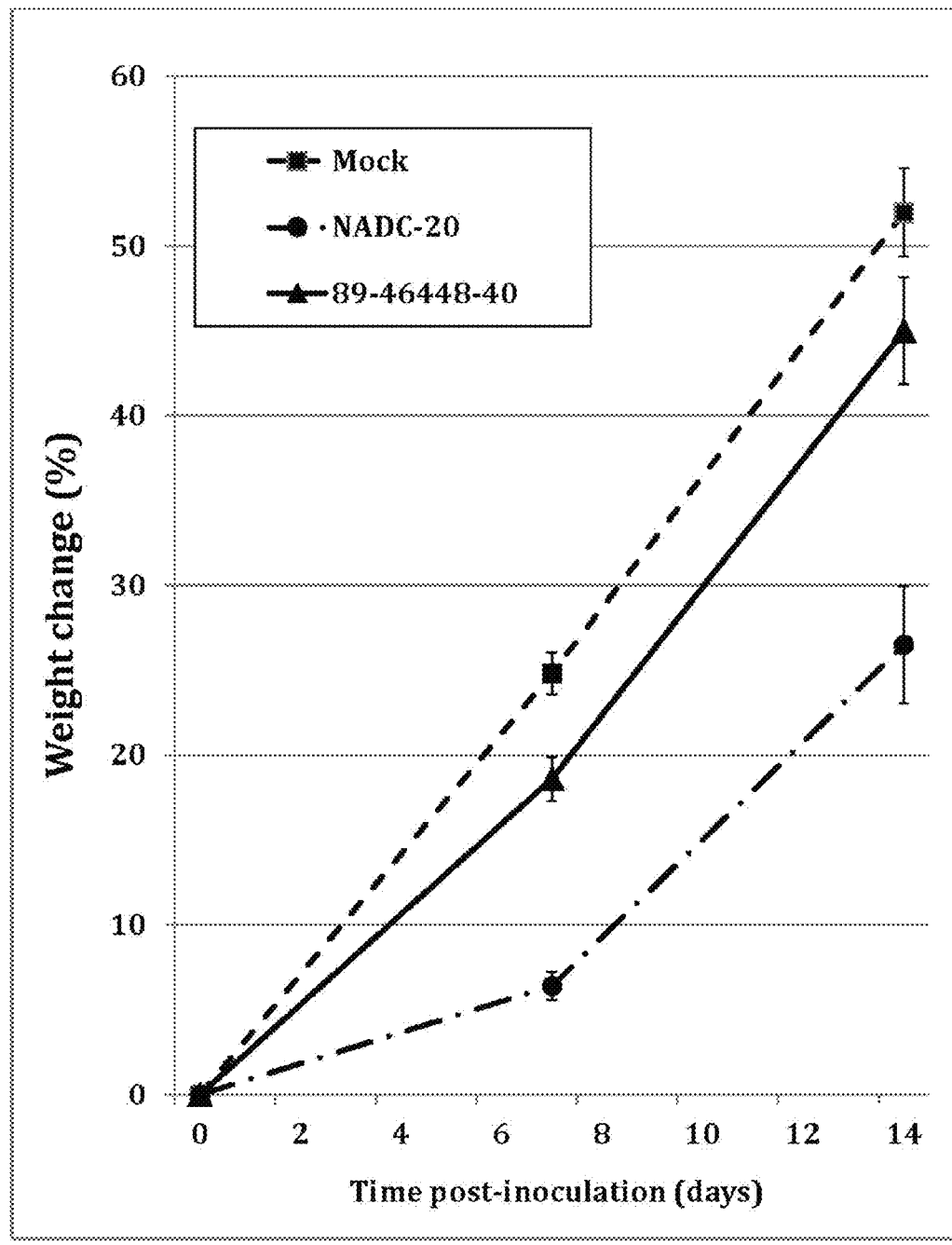
FIG. 1 illustrates body weight changes (%) in pigs at 7 and 14 days after infection with PRRS virus isolates 89-46448-40, NADC-20 or a mock inoculum. Percent body weight gain was determined based on the weight at the time of challenge. Mean values (±SEM) of each group were calculated.

Porcine reproductive and respiratory syndrome virus first appeared in the United States of America in the late 1980's. Convincing evidence of the need for new tools to control PRRS is best illustrated by the significant increase in the prevalence of PRRS in U.S. swine population over the last several years. Serological surveys conducted by the Animal and Plant Health Inspection Service (APHIS) indicate that the initial 35% prevalence of PRRS in grower/finisher American swine herds observed in 2000, increased to 53% by 2006. Since then, the prevalence continued to increase so that by 2009 the prevalence reached an alarmingly high 71%, representing a >200% increase over a nine year period. Now, more than 70% of the swine-herds in the U.S. are infected with North American type (genotype 2) PRRS virus, causing economic loses of over $664 million annually, making it the most costly disease to the pork industry.

Being a major economic problem for the pork industry, the National Pork Board (NPB) considers the control and elimination of PRRS virus from swine commercial herds a top priority. However, disease control has proven difficult to achieve largely because the RNA genome of this virus exhibits a high rate of mutation that results in a significant and constant genetic/antigenic virus diversification. This is clearly exemplified by the existence of 9 well-defined type 2 (or North American-like) PRRS virus lineages that exhibit major phylogenetic differences among them. The 9 distinct North American-like PRRS virus lineages have arisen since the first appearance of this major swine pathogen 25 years ago, and encompass the great genetic diversity of PRRSV virus currently existing in the world. These lineages are genetically distinct, as evidenced by an intra-lineage diversity of at least 11%. The great majority (>95%) of PRRS virus that has been isolated in the U.S. belong to four of these lineages, namely lineages 1, 5, 8 and 9.

It is generally thought that the level of protective efficacy of a PRRS MLV vaccine against disease resulting from infection with a virulent PRRS virus is largely dependent on the genetic similarity (homology) of the two viruses. Thus, based on the collective wisdom expressed in the art, the time-dependent increase in genetic diversity among contemporary PRRS virus strains should render an attenuated PRRS virus vaccine with an outdated genotype incapable of conferring sufficiently effective protective immunity against recently evolved PRRS viruses in pigs. Accordingly, it should be noted that the two currently available vaccines were generated from ancient wild-type viruses isolated in 1991 and 1997, and belong to either lineage 5 or 8, which are very distant phylogenetically from the great majority (60%) of PRRS virus strains currently circulating in the field, which belong to either lineage 1 or 9. While such divergence may impact the immunizing potential of the two commercial vaccines, other factors, such as the nature of the immunizing virus on its effectiveness as a vaccine, have not been considered.

The inventors have discovered three new variant strains called G16X, 794A61, and 111698, that were derived from the North American PRRS virus isolate 89-46448-40, and that surprisingly, stimulate IFN alpha considerably more strongly in virus-infected porcine alveolar macrophages as compared to the parental virus strain. The new variants were derived from the parental strain through plaque purification or end point dilution. The new several point mutations in the three variant strains distinguish them from the parental 89-46448-40 virus, which based on its ORF5 sequence belongs to the earliest PRRS virus lineage that appeared in North America, namely lineage 5. The 89-46448-40 virus naturally exhibits negligible virulence, and may be a mixed population of genetically related viruses that differ in their genomic nucleotide sequences by several single nucleotide mutations. The sequences of the virus strains G16X, 794A61, and 111698 differ by several synonymous and non-synonymous point mutations from the 89-46448-40 virus, which based on their ORF5 nucleotide sequence all belong to the type 2 PRRSV sublineage 5.1. The mutations in the genome of the three novel strains result in 2 to 5 amino acid changes compared to proteins encoded by the 89-46448-40 virus.

In addition, G16X unexpectedly does not inhibit the synthesis of interferon alpha by porcine macrophages exposed to the synthetic double stranded (ds) RNA molecule poly (I:C), unlike the 89-46448-40 virus. Instead, the G16X strain enhances the response to this molecule, which is already a strong inducer of the production of this cytokine by porcine alveolar macrophages. Notably, even though G16X, 794A61, and 111698 are nearly isogenic, they differ significantly from each other in their vaccine efficacies [poor (794A61), moderate (111698) and good (G16X)] in providing protection upon subsequent challenge with the highly virulent, and genetically dissimilar (heterologous) PRRS virus isolate belonging to lineage 8. Surprisingly, G16X has superior ability to generate a protective immune response in pigs to which this strain is administered, as compared to the other two strains (794A61 and 111698). This was evidenced by G16X causing a more rapid reduction and/or elimination of infectious lineage 8 (heterologous) challenge virus. In addition when evaluated for its vaccine efficacy against a different heterologous virulent type 2 PRRS virus belonging to lineage 1, the G16X virus is also capable of stimulating strong protective immunity.

In addition, because of the paltry virulence exhibited by the parental 89-46448-40 virus isolate, and the apparent vaccine efficacy of the three derived strains, the mutant PRRS viruses disclosed herein can be used as live PRRS virus vaccines without having to modify their biological character via serial passaging in cultured mammalian cells, or via attenuation. Furthermore, the risk of these vaccines developing a virulent phenotype is unlikely due to the natural negligible virulence of the progenitor virus isolate. Thus, the inventors made the contrarian discovery that virus strains derived from an ancient PRRS virus with negligible virulence can induce protective immunity in pigs against challenge with a heterologous (different lineage) virulent PRRS virus.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Cell" refers to a biological entity as would be understood in the art and which is intended to encompass a cell that may be a primary cell or a cell line. When several of these terms are used herein, it will be appreciated by one of ordinary skill that such usage is merely for purposes of emphasizing well understood distinctions. For example, the phrase "a cell or cell line" may emphasize the contrast between an original primary isolate versus an immortalized version which could be a direct derivative of the original primary isolate.

"Isolated" refers to a manipulated state that is different than that which is the natural state and/or is modified relative to a starting material, in which case the term is meant to be consistent with the concept of being purified. For example, an isolated primary cell is excised from a natural tissue or other source in a host organism and maintained apart from the original source. As another example, a cell component can be placed in culture or further separated from a lung lavage fluid-based sample, thus achieving a relatively isolated cell.

A "peptide" or "polypeptide" is a linked sequence of amino acids and may be natural, synthetic, or a modification or combination of natural and synthetic.

"Porcine reproductive and respiratory syndrome" or "PRRS" refers to the causative agent of a disease sometimes referred to as "mystery swine disease," "swine infertility and respiratory syndrome," and "blue ear disease." The terms "porcine reproductive and respiratory syndrome" or "PRRS" are intended to include antigenic, genetic and pathogenic variations among PRRS virus isolates as described in Wensvoort et al. 1992, J. Vet. Diagn. Invest., 4:134-138 and Mardassi et al., 1994, J. Gen. Virol., 75:681-685, the contents of which are incorporated herein by reference.

"Purified" refers to a condition wherein there has been a relative enrichment, separation, and/or removal of a substance relative to a starting material. The term can encompass conditions of an at least partial purification and does not necessarily imply an absolute state of purity. For example, the term can apply to a PRRS virus which is in a mixed stock but is predominantly isogenic, and which may be at least 75%, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% genetically homogeneous. "Purified" independently can be applicable to what may customarily be considered a pure virus preparation or stock.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

"Variant," when referring to a protein sequence disclosed herein, means a protein with a sequence that is at least 50, 55, 60, 65, 70, 75, 80, 81, 82, 83, 84, 85, 86, 87, 88, 89, 90, 91, 92, 93, 94, 95, 96, 97, 98, or 99% identical to a reference sequence. The variant may also retain at least one biological activity of a reference protein, and may also retain at least one immunological or immunogenic property of a reference sequence. The biological activity may be increasing IFN alpha activity.

2. PORCINE REPRODUCTIVE AND RESPIRATORY SYNDROME VIRUS a. Virus

Provided herein is a virus, which may be PRRS virus. The virus may be isolated, may be purified, may be attenuated, and may be a modified live virus. The virus may be able to stimulate a stronger IFN alpha response in porcine alveolar macrophage cells in comparison to a reference 89-46448-40 virus.

The virus may comprise a genome that encodes a protein, which may be NSP2, E, GP3, or GP4, which may comprise a sequence shown in FIG. 4, 10, 11, or 12, or a variant thereof. The virus may also comprise a genome that encodes a protein, which may be GP2 (SEQ ID NO: 31), GP5 (SEQ ID NO: 32), Matrix protein (SEQ ID NO: 33), Nucleocapsid protein (SEQ ID NO: 34), NSP1α (SEQ ID NO: 35), NSP1β (SEQ ID NO: 36), NSP2 (SEQ ID NO: 37), NSP3 (SEQ ID NO: 38), NSP4 (SEQ ID NO: 39), NSP5 (SEQ ID NO: 40), NSP6 (SEQ ID NO: 41), NSP7 (SEQ ID NO: 42), NSP8 (SEQ ID NO: 43), NSP9 (SEQ ID NO: 44), NSP10 (SEQ ID NO: 45), NSP11 (SEQ ID NO: 46), or NSP12 (SEQ ID NO: 47), or a variant thereof.

The NSP2 protein may comprise the sequence of SEQ ID NO: 4, which may represent amino acids 63-72 of the NSP2 protein, or a variant thereof. With reference to positions in SEQ ID NO: 4, the NSP2 protein may comprise a valine at position 5 (which may be 67V in the NSP2 protein). The NSP 2 protein may also comprise the sequence of SEQ ID NO: 6, which may represent amino acids 334-343 of full-length NSP2 protein, or a variant thereof. With reference to positions in SEQ ID NO: 6, the NSP2 protein may comprise a histidine at position 5 (which may be 338H in the NSP2 protein). The NSP2 protein may comprise the sequence of SEQ ID NO: 8, which may represent amino acids 488-497 of full-length NSP2 protein, or a variant thereof. With reference to positions in SEQ ID NO: 8, the NSP2 protein may comprise a proline at position 3 (which may be 490P in the NSP2 protein), and may comprise a leucine at position 8 (which may be 495L in the NSP2 protein). The sequence of the NSP2 protein may also comprise one or more of SEQ ID NOs: 5, 7, 9, and 10.

The E protein may comprise the sequence of SEQ ID NO: 25, or a variant thereof. With reference to positions in SEQ ID NO: 25, the E protein may comprise a valine at position 31 (31V), and may comprise an alanine at position 60 (60A). The sequence of the E protein may comprise SEQ ID NO: 26. The sequence of the E protein may also comprise SEQ ID NO: 11 or 12 at positions 27-36 with reference to positions in SEQ ID NO: 25, and may also comprise SEQ ID NO: 13 or 14 at positions 56-65, with reference to positions in SEQ ID NO: 25.

The GP3 protein may comprise the sequence of SEQ ID NO: 21, or a variant thereof. With reference to positions in SEQ ID NO: 21, the GP3 protein may comprise a valine at position 94 (94V), may comprise a serine at position 96 (96S), and may comprise a phenylalanine at position 213 (213F). The sequence of the GP3 protein may comprise SEQ ID NO: 22. The sequence of the GP3 protein may also comprise SEQ ID NO: 15 or 16 at positions 90-99, with reference to positions in SEQ ID NO: 21, and may also comprise SEQ ID NO: 17 or 18 at positions 209-218, with reference to positions in SEQ ID NO: 21.

The GP4 protein may comprise the sequence of SEQ ID NO: 23, or a variant thereof. With reference to positions in SEQ ID NO: 23, the GP4 protein may comprise a serine at position 32 (32S). The sequence of the GP4 protein may comprise SEQ ID NO: 24. The sequence of the GP4 protein may comprise SEQ ID NO: 19 or 20 at positions 28-37, with reference to positions in SEQ ID NO: 23.

The genome of the virus may encode an E protein comprising V31 and 60A, and a GP3 protein comprising 94V. The genome of the virus may also encode a NSP2 protein comprising 495L, and a GP3 protein comprising 94V. The genome of the virus may encode a NSP2 protein comprising 338H and 495L, a GP3 protein comprising 94V and 213F, and a GP4 protein comprising 32S.

The genome of the virus may comprise the sequence of a G16X, 794A61, or 111698 viral genome. The G16X virus may be a viral strain deposited under the Budapest Treaty on Oct. 22, 2013, with the American Type Culture Collection (ATCC), 10801 University Boulevard, Manassas, Va. 20110 USA, under the accession number PTA-120658 designated by the depository and with depositor Identification Reference PRRSV Virus G16X. The sequence of the G16X, 794A61, and 111698 virus genome may respectively be SEQ ID NO: 1, 2, and 3, or the RNA equivalent thereof. SEQ ID NOs: 1-3 lack the first 31 nucleotides at the 5' terminus of the G16X, 794A61, and 111698 viral genomes. The genome of the virus may also be a variant of a sequence disclosed herein. The genomic variant may be at least 40, 50, 55, 60, 65, 70, 75, 76, 77, 78, 79, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% identical to SEQ ID NO: 1, 2, or 3. The virus may also comprise a RNA equivalent of a PRRS virus genomic sequence described herein (i.e., an RNA that is 100% complementary to a DNA that is 100% complementary to a reference DNA sequence).

The % identity of a genomic sequence to another of interest may be determined by methods known in the art. For example, the % identity of the sequence may be determined by GAP (Needleman and Wunsch, 1970) analysis (GCG program) with a gap creation penalty=5, and a gap extension penalty=0.3. The query sequence may be at least 150 nucleotides in length, and the GAP analysis may align the two sequences over a region of at least 150 nucleotides. The query sequence may be at least 300 nucleotides in length and the GAP analysis may align the two sequences over a region of at least 300 nucleotides. The GAP analysis may align the two sequences over their entire length.

The variant may also comprise one or more mutations relative to a G16X, 794A61, or 111698 viral genome, which may be a deletion, insertion, or substitution thereof. The variant may allow the virus to provide an effective immune response in a mammal when administered thereto, and may allow the virus not to cause disease in the mammal. The mutation in the variant may be naturally occurring (i.e., may be isolated from a natural source), or may be synthetic (may be created by site-directed mutagenesis). The mutation in the variant may be introduced by any means known in the art.

The variant may hybridize to the G16X, 794A61, or 111698 genome under stringent conditions. The term "stringent hybridization conditions" and the like as used herein refers to parameters with which the art is familiar, including the variation of the hybridization temperature with length of an oligonucleotide. For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2.×SSC, 0.01% BSA at 50° C. Alternatively, the nucleic acid and/or oligonucleotides (which may also be referred to as "primers" or "probes" or "siRNA molecules" or "antisense molecules") hybridize to the region of a genome of interest, under conditions used in nucleic acid amplification techniques such as PCR.

b. Compositions

Also provided herein is a composition comprising the virus, or an immunogenic (antigenic) component thereof. The composition may be a vaccine. The vaccine may be capable of stimulating an immune response in a mammal. The virus may also reduce the severity of PRRS virus infection and its sequelae or symptoms in a mammal, and may prevent infection of a mammal by PRRS virus. The composition may comprise a carrier, which may be pharmaceutically acceptable, and may also comprise an immunologically acceptable adjuvant. The carrier and adjuvant may be acceptable for veterinary use, such as in swine. The composition may also comprise at least one immunostimulatory molecule.

(1) Adjuvants

The adjuvant may be a molecule capable of enhancing an immune system response to a vaccine, and may not substantially inhibit the immune response. Examples of adjuvants are found in "Vaccine design: the subunit and adjuvant approach," Michael F. Powell and Mark J. Newman, eds., Pharmaceutical Biotechnology v. 6, Plenum Press 1995, New York, see e.g., chapter 7 "A compendium of Vaccine Adjuvants and Excipients" by Frederick R. Vogel and Michael F. Powell and chapter 29, "Cytokine-containing liposomes as adjuvants for subunit vaccines" by Lachman et al., the contents of which are hereby incorporated by reference.

The adjuvant may be an interferon, which may be interferon α, interferon β, or a nucleic acid encoding interferon β, which may be expressed in a pig cell. The adjuvant may also be poly IC, poly ICLC, or a material that induces or enhances the activity of at least one of interferon α or β. The interferon may be an interferon protein, such as an interferon α protein, or may be a nucleic acid capable of expressing an interferon, such as an interferon α. Interferon generated by expression from the exogenously administered nucleic acid sequence may function alone or in combination with interferon generated by expression from endogenous nucleic acid sequences native to a mammal, to enhance immune response to a vaccine that is administered to the mammal. The interferon may directly or indirectly facilitate immune enhancement; for example, the interferon expressed from exogenously administered nucleic acid may induce or activate one or more intermediate species which in turn may facilitate immune enhancement.

The adjuvant may be present at a level sufficient to enhance an immune response to a vaccine administered to a mammal. Enhancement of immune response by the adjuvant may be measured as any significant increase, which may be statistically significant, in immune response compared to control response in the absence of the adjuvant as evaluated by any method accepted in the art. The adjuvant may comprise other ingredients as known in the art to facilitate delivery of an expressible nucleic acid to a cell or tissue for expression or facilitate delivery of the interferon inducer or enhancer to an appropriate cell or tissue. Dosage levels of the adjuvant may be determined by well-known methods.

The adjuvant may comprise both a nucleic acid capable of expressing an interferon and an immunostimulatory material that can induce or enhance the activity of an interferon. The combined amounts of the nucleic acid and the interferon inducer or enhancer may be sufficient to result in a measurable enhancement of immune response to a vaccine.

The adjuvant may comprise an expressible nucleic acid encoding an interferon α, a material which induces or enhances the activity of interferon β, or both. The material which induces or enhance activity of interferon α may be poly IC or poly ICLC. The quantity of polyIC or polyICLC may be in a range of 1 to 200 micrograms per kg of body weight. The adjuvant may also comprise an immunostimulatory sequence (ISS) or cytokine-encoding nucleic acid. The adjuvant may also be a cytokine, alum (aluminum hydroxide), aluminum phosphate, or calcium phosphate. The cytokine may be IL-2, IL-12, or a cytokine-containing liposome.

The adjuvant may comprise a mammalian expression vector containing porcine IFN alpha cDNA, which may be prepared by RT-PCR using RNA isolated from pig lymphocytes previously infected with pseudorabies virus (to stimulate IFN alpha production). Primers for performing the RT-PCR may be designed based on the nucleotide sequence of porcine IFN alpha cDNA (as described in Lefevre and La Bonnardiere 1986, the contents of which are incorporated herein by reference). Products of the anticipated size (590 bp) resulting from the RT-PCR may be cloned into the pCR®2.1 plasmid (Invitrogen Corp., Rockville, Md.), and an insert having the predicted restriction enzyme sites may be sequenced. The IFN alpha cDNA may be excised from the recombinant pCR®2.1 plasmid and placed under the transcriptional regulation of the cytomegalovirus promoter in pcDNA3 (Invitrogen) to generate pINA3. To verify that an active cytokine is encoded by the amplified cDNA, Chinese hamster ovary (CHO) cells may be transfected with pINA3 and single cell clones resistant to geneticin may be prepared. Supernatants from the clones may be tested for the ability to inhibit the replication of an interferon-inducer negative strain of vesicular stomatitis virus in Madin Derby bovine kidney (MDBK) cells. Clones producing from 0 to greater than 200,000 units (1 unit inhibits 50% of VSV replication) of IFN alpha may be detected.

The adjuvant may also comprise the chemical compound, polyICLC. The adjuvant may also comprise the following chemicals: Poly-L-Lysine, poly IC, and carboxymethylcellulose, low viscosity. Poly IC (500 mL; 4.0 mg/mL); poly-L-lysine (250 mL; 6.0 mg/mL); and 2% carboxymethylcellulose (250 mL) may be prepared in pyrogen-free 0.85% NaCl. Poly ICLC (stabilized polynucleotide) may be prepared following the method of Levy, Baer et al. (1975), the contents of which are incorporated herein by reference, with minor modifications. Poly I:C may be re-annealed by heating at 71° C. for 1 hour and cooling slowly. Annealed poly I:C may then be mixed with equal volumes of 6.0 mg/mL poly-L-lysine in normal saline and 2% carboxymethylcellulose. The final concentration of poly I:C may 1 mg/mL. This preparation may be stored at 4° C. until needed.

(2) Immunostimulatory Material

The composition may also comprise an immunostimulatory material that induces or enhances the activity of interferon, such as an interferon α. The immunostimulatory material may function to induce or enhance the activity of interferon generated from exogenously administered expressible nucleic acid or that generated from endogenous nucleic acids native to a mammal. The immunostimulatory material may function directly to induce or enhance interferon activity or indirectly by induction or enhancement of the activity or expression of an intermediate species. The immunostimulatory material may function to induce or enhance expression levels of an interferon or may otherwise enhance or activate interferon for enhancement of immune response. The immunostimulatory material may be interferon α, interleukin 12 (IL-12), IL-18, or IL-15.

(3) Carriers

The carrier may comprise saline or another suitable carrier known in the art. The carrier may be as described in Amon, R (Ed.), Synthetic Vaccines 1:83-92, CRC Press, Inc., Boca Raton Fla. (1987), the contents of which are incorporated herein by reference. The carrier may enable the compositions to be formulated as a tablet, pill, capsule, liquid, gel, syrup, slurry, suspension, or the like, which may be appropriate for oral ingestion. The carrier may also comprise an additional adjuvant, in which case it can be selected by standard criteria based on the antigen used, the mode of administration and the subject. The carrier may comprise an excipient or auxiliary that facilitates processing of the composition into a preparation that can be used pharmaceutically.

(4) Dose

The composition may comprise a dose of viral particles of the virus, which may be from $10^2$ to $10^{10}$, $10^2$ to $10^9$, $10^2$ to $10^8$, $10^2$ to $10^7$, $10^2$ to $10^6$, $10^2$ to $10^5$, $10^2$ to $10^4$, $10^3$ to $10^{10}$, $10^3$ to $10^9$, $10^3$ to $10^8$, $10^3$ to $10^7$, $10^3$ to $10^6$, $10^3$ to $10^5$, $10^4$ to $10^{10}$, $10^4$ to $10^9$, $10^4$ to $10^8$, $10^4$ to $10^7$, $10^4$ to $10^6$, or $10^5$ to $10^{10}$, $10^5$ to $10^9$, $10^5$ to $10^8$, or $10^5$ to $10^7$ virus particles.

(5) Formulation

The composition may comprise a cationic liposome, an anionic liposome, a cochleate, or a microcapsules. The liposome or cochleate may enhance in vivo transfection of the virus. The liposome may be a spherical lipid bilayer with an aqueous interior. All molecules present in an aqueous solution at the time of liposome formation may be incorporated into the aqueous interior. The liposomal contents may be both protected from the external microenvironment and, because liposomes fuse with cell membranes, efficiently delivered into the cell cytoplasm. Additionally, due to their hydrophobicity, certain small organic molecules may be directly administered intracellularly. The composition may also comprise another medicinal agent, a pharmaceutical agent, or a diluent.

The composition may be formulated as an aqueous solution, a liquid solution or suspension, a solid form suitable for solution or suspension into a liquid prior to injection, or as an emulsion. For injection, the composition may be formulated in an aqueous solution, which may be in a physiologically compatible buffer such as Hanks' solution, Ringer's solution, or physiological saline buffer. For transmucosal administration, penetrants appropriate to the barrier to be permeated are used in the formulation. Such penetrants are generally known in the art. The composition may be formulated with a cationic lipid or liposome. The composition formulated for oral administration may be in the form of a tablet, dragee, capsule, or solution, and may be formulated for delayed release or only to be released when the pharmaceutical reaches the small or large intestine.

The composition for parenteral administration may be formulated as an aqueous solution in water-soluble form. The suspension may be prepared as an oily injection suspension. The suspension may comprise a suitable lipophilic solvent or vehicle, which may be a fatty oil such as sesame oil, or a synthetic fatty acid ester, such as ethyl oleate or a triglyceride, or a liposome. The suspension for aqueous injection may contain a substance that increases the viscosity of the suspension, such as sodium carboxymethyl cellulose, sorbitol, or dextran. The suspension may also contain a suitable stabilizer or agent which increases the solubility of the composition to allow for the preparation of a highly concentrated solution.

The composition for oral use may be obtained by combining the active compounds with a solid excipient. Obtaining the composition may further comprise grinding a resulting mixture, and processing the mixture of granules, after adding suitable auxiliaries, to obtain tablets or dragee cores. The solid excipient may be a filler such as a sugar, including lactose, sucrose, mannitol, or sorbitol; a cellulose preparation such as maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP). The composition may also comprise a disintegrating agent, which may be a cross-linked polyvinyl pyrrolidone, agar, or alginic acid or a salt thereof such as sodium alginate.

The composition may be a dragee core, which may have a suitable coating. The coating may comprise a concentrated sugar solution, and may comprise gum arabic, talc, polyvinyl pyrrolidone, carbopol gel, polyethylene glycol, titanium dioxide, a lacquer solution, or a suitable organic solvent or solvent mixture. A tablet or dragee may comprise a coating comprising a dyestuff or pigment, which may be used for identification or to characterize different combinations of active compound doses.

The composition may be formulated for oral administration as a push-fit capsule comprising gelatin, or may be formulated as a sealed capsule comprising gelatin or a plasticizer, such as glycerol or sorbitol. The push-fit capsule may comprise the composition in admixture with a filler such as lactose, a binder such as starches, or a lubricant such as talc or magnesium stearate, or a stabilizer. The composition for oral administration may be formulated as a soft capsule, and the composition may be dissolved or suspended in a suitable liquid, such as a fatty oil, liquid paraffin, or liquid polyethylene glycol. The soft capsule may also comprise a stabilizer.

In the case of a composition comprising a DNA vaccine, the composition may comprise DNA incorporated in a liposome or cochleate to enhance in vivo transfection. The composition may comprise a genetic adjuvant, which may be an immunostimulatory sequence (ISS) or a cytokine-encoding nucleic acid. The genetic adjuvant may be as described in Homer A. A. et al., 1998, Immunostimulatory DNA is a potent mucosal adjuvant, Cell Immunology, 190:77-82, the contents of which are incorporated herein by reference.

(6) Method of Making

The composition may be manufactured in a manner that is itself known, such as by means of conventional mixing, dissolving, granulating, dragee-making, levitating, emulsifying, encapsulating, entrapping or lyophilizing processes.

3. METHOD OF GENERATING AN IMMUNE RESPONSE

Provided herein is a method of generating or inducing an immune response in a mammal, which may be a swine. The method may comprise administering the composition comprising the virus to a mammal in need thereof. The method may also comprise administering an immunogenic composition, which may be a booster, and may comprise administering an adjuvant as described herein. The composition may provide protective immunity to the mammal against a PRRS virus. The composition may also result in greater weight gain and less viremia in the mammal in comparison to a mammal in which the composition was not administered. The composition may induce immunity in the mammal, which may help achieve fewer abortions and/or normal farrowing, or reduce the severity of respiratory disease and mortality in the mammal, in comparison to a mammal to which the composition is not administered.

a. Mode of Administration

The composition comprising the virus may be administered by any effective route, which may be systemic or local. The administration may be parenteral, intramuscular, intradermal, subcutaneous, oral, mucosal, sublingual, intraocular, intranasal, intravenous, intraperitoneal, intramedullary, topical, or transdermal. The administration may also be rectal, vaginal, or intestinal. The administration may be by injection, which may be done using a needle and syringe. The administration may also be via electroporation, cationic microparticle, ultrasonic distribution, or via a biolistic particle.

The administration may also be based on a formulation of the composition with cationic a lipid or liposome, which may be applicable to either the DNA form or protein form of a cytokine adjuvant or to a chemical such as one capable of immune stimulation, for example by induction of an endogenous cytokine. Examples of such administration are described in Pachuk et al., 2000, Curr Opin Mol Ther April 2(2):188-98; Van Slooten et al. 2001, Biochim Biophys Acta 1530:134-45; Van Slooten et al., 2000, Pharm Res 17:42-48; Lachman et al., 1996, Eur Cytokine Netw 7:693-8, the contents of which are incorporated herein by reference.

The adjuvant may be included in the composition comprising the virus. The adjuvant also may be administered simultaneously with the composition comprising the virus or within 1, 2, 4, 8, 12, 18, or 24 hours thereof.

b. Timing of Administration

The composition may be administered to the mammal when the mammal is from about 2 weeks to about 30 weeks of age, or when the mammal is an adult. The composition may also be administered a second time about 2 to about 5 weeks after a first administration, and may also be administered an additional number of times. The composition may be administered to a breeding male or female, and may be administered prior to breeding or after farrowing.

The exact formulation, route of administration and dosage for generating the immune response may be chosen by the individual clinician or in view of the patient's condition, such as described in Fingl et. al., in The Pharmacological Basis of Therapeutics, 1975, Ch. 1 p. 1, the contents of which are incorporated herein by reference. The attending veterinarian or physician would know how to and when to terminate, interrupt, or adjust administration due to toxicity, or to organ dysfunctions, or other negative effects. Conversely, the attending practitioner would also know to adjust treatment to higher levels if the clinical response were not adequate (precluding toxicity). The magnitude of an administered dose in the management of the disorder of interest may vary with the severity of the condition to be treated and to the route of administration. The severity of the condition may, for example, be evaluated, in part, by standard prognostic evaluation methods. Further, the dose and perhaps dose frequency, may also vary according to the age, body weight, and response of the individual patient. A program comparable to that discussed above also may be used in veterinary medicine.

The present invention has multiple aspects, illustrated by the following non-limiting examples.

Example 1

PRRS Vaccine Components

Example 1. This Example shows specific examples of a vaccine described herein. In particular, the example describes three isolated and purified, nearly isogenic porcine reproductive and respiratory syndrome (PRRS) viruses, termed 794A61, 111698 and G16X, each of which was derived from stocks of the ancient North American PRRS virus isolate 89-46448-40, which naturally exhibits negligible virulence. The originating 89-46448-40 virus stocks comprised a mixed population of genetically related PRRS virus variants, from which the three strains were purified to homogeneity using either standard plaque assays or end-point dilution. Genomic sequence analysis of these three strains revealed that they differ from the viral genotypes present in the 89-46448-40 virus stocks by several synonymous and non-synonymous point mutations. The latter type of nucleotide mutations resulted in three of the structural and one of the non-structural viral proteins having novel amino acid changes that are not present in the parental virus population. The three isolated strains also differed biologically from the parental virus 89-46448-40 in their ability to stimulate a considerable interferon alpha response by virus-infected, porcine alveolar macrophages. In addition, unlike the parental 89-46448-40, the G16X strain did not inhibit synthesis of interferon alpha by porcine alveolar macrophages exposed to poly(I:C), but rather enhanced their response to this activating molecule. Remarkably, even though these three strains are nearly isogenic, they differed significantly from each other in regards to their vaccine potential, as demonstrated by the extent of their vaccine efficacies (poor, 794A61; moderate, 111698 and good, G16X) in providing protection upon subsequent challenge with a genetically dissimilar (heterologous) PRRS virus isolate. One vaccine isolate (G16X) distinguished itself from the other two strains (794A61 and 111698) by excelling in its ability to afford immunized pigs greater protection, as evidenced by a more rapid reduction and/or elimination of the virulent challenge virus from tissues.

The three PRRSV strains (G16X, 794A61 and 111698) were derived by either plaque purification (794A61 and G16X) or by end-point dilution (111698) from a low passage stock of the PRRS virus 89-46448-40. The 89-46448-40 virus was isolated at the National Veterinary Services Laboratory (NVSL) in Ames, Iowa, from specimens from animals submitted as a diagnostic case (designated 89-46448) from an Iowa farm which experienced a PRRS outbreak in 1989 (Wesley et al, 1998). Notably, the 89-46448 case represents one of the oldest publicly recorded outbreaks of PRRS from which PRRS virus was retrieved (Wesley et al., 1998). Accordingly, the 89-46448-40 virus likely represents one of the most temporally ancient PRRS virus isolated in the US. Virus isolation at NVSL was accomplished by overlaying monolayers of the MA-104 African green monkey cell line with clarified suspensions of macerated tissues prepared from infected animals. Virus isolation was indicated by the development of a cytopathic effect within 6-8 days after inoculation of the cell cultures as described by Kim et al. (1993, "Enhanced replication of porcine reproductive and respiratory syndrome (PRRS) virus in a homogeneous subpopulation of MA-104 cell line," Arch. Virol. 133, 477-83). Culture fluids were harvested at 10 days after inoculation and stored at −70° C. Subsequent passages of the 89-46448-40 virus isolate in MA-104 cells were performed at NVSL using methods described by Kim et al. (1993). Between late 1992 and early 1993, aliquots of several PRRS virus isolates, including the 89-46448-40 isolate, were distributed as reference PRRS viruses by NVSL to several veterinary diagnostic laboratories (VDL) in the US. The VDL at the University of Illinois (Urbana, Ill.) received a vial containing about 1 mL of culture medium collected from the second passage in MA-104 cells of the 89-46448-40 isolate (89-46448-40 MA104/2) from the specimen from which it was isolated. At the University of Illinois VDL, the MARC-145 cell line, a PRRS virus-permissive cell clone originating from MA-104 cells, was used as the host to prepare 89-46448-40 virus stocks from the 89-46448-40 MA104/2 aliquot. The virus was propagated using methods known in the art, and monolayers of MARC-145 cells grown in 75 cm$^2$ tissue culture flasks containing Eagle's Minimal Essential Medium (MEM) with pH adjusted to 7.2, to which 5% fetal calf serum, 0.15% sodium bicarbonate and antibiotics had been added (complete MEM) were used. The flasks containing the MARC-145 cells and 10 mL culture medium were incubated at 37° C. in an atmosphere of 5% $CO_2$ for several days until a confluent cell monolayer was established. At this point the cell monolayers were inoculated with 1 mL of diluted virus suspension and incubated for 1 h at 37° C. to allow virus absorption. The inoculum was then removed and 10 mL of fresh complete MEM added. The cell cultures were then incubated at 37° C. in an atmosphere of 5% $CO_2$ until a cytopathic effect, which occurred within 4 days, was observed. Once >75% of the cells in the monolayers exhibited a cytopathic effect, the contents of the flasks were harvested, combined into a single pool, divided into 1-2 mL aliquots in sterile glass vials and stored at −80° C. until needed. Titers of the virus stocks were determined by using standard techniques and MARC-145 cells (see Material and Methods, Example 1). For instance, the stock prepared in July, 1994 ("794 stock") had a titer of $10^{7.4}$ $TCID_{50}$ and corresponded to the second passage of the PRRS virus isolate 89-46448-40 in MARC-145 cells at the University of Illinois VDL, i.e., the fourth overall passage of this virus in cultured cells, including its isolation in MA-104 cells.

Both the 111698 and the 794A61 virus strains were isolated directly from the "794 stock" PRRS virus. To produce the 111698 virus, 1.0 mL of a 3000-fold dilution (MOI=0.001) of the "794" stock was used as inoculum to infect a monolayer of MARC-145 cells in a 75 cm2 tissue culture flask (in triplicate). After 4 days at 37° C. in a humidified 5% $CO_2$ atmosphere, at which time >75% of each of the three monolayers exhibited a cytopathic effect, the contents of the flasks were collected. The combined harvests were centrifuged at 2000 rpm for 10 min at 4° C. to remove cell debris and the supernatant, designated as 111698 virus, divided into aliquots and stored at −80° C. In contrast, the 794A61 virus was the product of a six-fold plaque-purification of the "794" stock. Initially, monolayers of MARC-145 cells in 35-mm diameter tissue culture dishes were overlaid with sequential 10-fold dilutions of the "794" stock in MEM, pH 7.2, supplemented with 10% fetal calf serum and 50 µg/mL gentamicin. After rocking at 1 h at ambient temperature, the inocula were removed, and the monolayers overlaid with 3 mL of a 1:1 mixture of 2×MEM supplemented with 6% fetal calf serum, 100 µg/mL gentamicin and 2% low-melting-point agarose. After 30 min at ambient temperature (to allow the agarose to harden), the plates were left at 37° C. and in a humidified 5% $CO_2$ atmosphere for 4 days. At this time to enhance visualization of the plaques, 100 µl of 100 mg/mL Thiazolyl Blue Tetrazolium bromide (Methylthiazolyldiphenyl-tetrazolium bromide, MTT) was placed on top of each agarose overlay and the cells were returned to a 37° C. and humidified 5% $CO_2$ atmosphere environment for 2-3 h before the plaques appeared as clear areas with darkened perimeters. Several well-isolated plaques in those monolayers successfully infected with the greatest dilution of inoculum were picked by using a Pasteur pipet and transferred into vials containing 0.5 mL of MEM supplemented with 10% fetal calf serum and 50 µg/mL gentamicin. One of the selected plaques was subjected to two cycles of freezing at −80° C. before use as inoculum. This process of plaque-purification was repeated an additional five times with a plaque picked after the sixth round being designated 794A61. After being subjected to two cycles of freezing at −80° C., 0.1 mL of the 794A61 preparation was used to infect a 35-mm diameter tissue culture plate as described above. However, in this case, the monolayer was overlaid with 3 mL MEM supplemented with 3% fetal calf serum and 50 µg/mL gentamicin. After 3 days in a 37° C. and humidified 5% $CO_2$ atmosphere environment, approximately 20% of the infected monolayer exhibited a cytopathic effect. At this time, the medium was collected, centrifuged at 2000 rpm for 10 min at 4° C. to remove cell debris and the supernatant, designated as 794A61 P1 virus, was stored at −80° C. An additional passaging of this virus in monolayers of MARC-145 cells in 75 cm$^2$ tissue culture flasks as described above at an MOI=0.01 was performed to produce the 794A61 P2 virus.

Isolation of the G16X virus proceeded indirectly from the "794 stock" virus, in that the inoculum source was the sequential passage of the "794 stock" virus in monolayers of MARC-145 cells in 75 cm² flasks. In this case, each monolayer had been infected with 1 mL of undiluted "794 stock" (MOI=1). After 3 days at 37° C. in a humidified 5% $CO_2$ atmosphere, at which time, >90% of each of the three monolayers exhibited a cytopathic effect, the contents of the flasks were collected. The combined harvests were centrifuged at 2000 rpm for 10 min at 4° C. to remove cell debris and the supernatant, designated as VR virus, divided into aliquots and stored at −80° C. This VR virus preparation was subjected to a five-fold plaque-purification as described above, except that at 4-5 days post-infection, the individual plaques were identified as opaque areas against a relatively clear, uninfected cell monolayer background. An isolated plaque from the fifth plaque-purification was passaged in a 35-mm diameter tissue culture dish under the conditions described above, as were the progeny from this infection and four subsequent infections of MARC-145 cells at various MOI in either 25- or 75 cm² tissue culture flasks. Supernatant medium from this 5th unselected passage of virus served as the initial inoculum for an additional six rounds of plaque-purification that utilized MTT for plaque visualization as described above. A well-isolated plaque picked after the sixth round was designated G16X and was propagated initially in a monolayer of MARC-145 cells in a 35-mm diameter tissue culture plate (G16X P1) and then twice sequentially in cm² flasks (G16X P2 and G16X P3) as described above for the production of the 794A61 virus.

It has been documented that the level of pathogenicity among PRRS virus isolates can vary considerably. Moreover, it has become evident that in the 25 years after the initial North American outbreaks of PRRS in 1987-1988, the virulence level of PRRS virus in the U.S. and other parts of the world has increased to an alarming intensity. The first noticeable upsurge in PRRS virus virulence occurred in 1996 when swine veterinarians and diagnosticians began to report disease outbreaks described as "swine abortion and mortality syndrome," "atypical PPRS," or "acute PRRS." This was confirmed in experimental studies, which showed not only that strains circulating in US swine-herds at the beginning of the PRRS epidemic in the late 1980's were less virulent than those that appeared in the summer of 1996 but that the latter were causing PRRS outbreaks of a higher severity. But, even in the early 1990s, varying disease severity in PRRS outbreaks was apparent. While mainly <10 week-old pigs were afflicted with a respiratory illness that ranged in intensity from mild to severe in the absence of reproductive failure, outbreaks of severe respiratory disease in older pigs and reproductive failure manifested, mostly by late term abortions in pregnant females, were also observed. In an attempt to discern distinguish levels of PRRS virus virulence, a concrete measurement of respiratory pathogenicity was developed. It involved scoring the percentage of the lungs affected with grossly visible pneumonia resulting from experimental infection of young swine with one of 9 different isolates of PRRS viruses reported exhibit different levels of virulence. This method enabled the categorization of PRRS viruses acquired in 1993 or earlier into high and low virulence isolates. Incongruent results, however, were obtained with this method of scoring and a different disease characteristic was used to assess virulence. In that case, the virulence levels of two isolates, previously categorized as either being high (VR-2385) or low (VR-2431), based on the gross pathology of the lungs of infected pigs, were shown be similar when evaluated in terms of the viruses' ability to induce late term reproductive failure.

A more reliable and more commonly used parameter to determine PRRS virus virulence is monitoring the amount of infectious virus in the blood stream (viremia) of infected pigs. For instance, inoculation of young swine with PRRS virus isolates classified as exhibiting either moderate or high levels of virulence reproducibly generate high levels of viremia that occur within 3 days after virus inoculation and can extend for more than 28 days. In contrast, administration of equivalent doses of attenuated (vaccine) PRRS virus strains that were derived from virulent strains by serial passage in simian cells produce significantly lower levels of viremia, although of similar (>28 days) duration. Notably, viremia resulting from infection with PRRS virus is negatively related to pig growth and positively associated with the severity of clinical disease. Lack of appetite is also a hallmark of PRRS virus infection and in young and fast growing pigs negatively impacts their rate of weight gain and feed efficiency. Likewise, infections with either moderately or highly virulent PRRS virus isolates strongly decrease the rate of weight-gain of grower pigs. On the other hand inoculation of swine with attenuated PRRS virus strains reduce pig growth minimally or not at all. Thus, while virulent PRRS viruses significantly inhibit the rate of growth of young pigs and generate a strong viremia, PRRS virus strains that have been made non-virulent (attenuated) by serial passage in cell culture do not affect the growth of young pigs and produce a comparatively weaker viremia.

Example 2

Isolation of PRRS Viruses

Example 2. This Example demonstrates isolation of mutant PRRS viruses. The PRRS virus isolate 89-46448-40 naturally exhibits a negligible level of virulence, which is akin to, if not lower than, the level of virulence that has been described for attenuated strains of PRRS virus that were generated by serial passage in vitro. The level of virulence possessed by the PRRS virus isolate 89-46448-40 was determined by assessing parameters which have been used previously to determine PRRS virus virulence, including the weight gain of virus-infected pigs, the magnitude and length of viremia in virus-infected pigs, and the gross pathology of the lungs of virus-infected pigs. The results obtained for measurements of all of these parameters support the conclusion that the virulence of the 89-46448-40 isolate in pigs is negligible.

To ascertain the level of virulence exhibited by the 89-46448-40 virus isolate, groups of 9-10-week-old pigs from a herd naïve for PRRS virus were inoculated with either the 89-46448-40 isolate or, as a comparison, with the high virulence "atypical PRRS" virus isolate NADC-20. Controls consisted of pigs given a mock inoculum. Before virus inoculation and at 4, 7, 10 and 14 days after inoculation, venous blood was collected from the jugular vein of each pig and the extent of viremia was determined quantitatively by measuring the amount of infectious virus present in each animal's serum. Body weights were recorded for all pigs on study days 0, 7 and 14 and the weight change from the day of challenge calculated. The extent of gross pathology of the pigs' lungs was scored at 14 days after inoculation using known methods.

The porcine alveolar macrophage cell line ZMAC (Calzada-Nova et al., 2012), was cultured using 75 cm² tissue culture flasks (Corning, Corning, N.Y.) in RPMI-1640 medium with L-glutamine (Mediatec, Herndon, Va.), supplemented with 10% fetal bovine serum (GIBCO®, Invitrogen, Grand Island, N.Y.), 1 mM sodium pyruvate (Mediatec) and 1× non-essential amino acids (Mediatec), and maintained at 37° C. in a 5% $CO_2$ atmosphere. Since porcine alveolar macrophages are the natural host cell for this virus, ZMAC cells are fully permissive to wild-type PRRS virus. Thus, this cell line was used to perform titration of PRRS virus from clinical (serum) samples and to prepare virus stocks for animal inoculation. The ZMAC cell line is free of adventitious agents including bovine viral diarrhea, porcine circovirus, mycoplasma, PRRS virus, porcine parvovirus and porcine adenovirus.

The "acute PRRS" virus isolate NADC-20 was passaged once in ZMAC cells directly from the serum of a diseased animal in order to create a stock of virus for animal inoculation. NADC-20 has been shown to produce significant respiratory disease in young pigs with total gross lung lesion scores ranging from 30-45% as well causing a substantial viremia of similar magnitude to that observed for other virulent PRRS virus isolates. The inoculum for the 89-46448-40 virus was prepared from the 7th passage in ZMAC cells starting from an original vial of 89-46448-40 virus prepared by NVSL (89-46448-40 MA104/2). The virus in the vial received from NVSL represented the second passage of the 89-46448-40 virus in MA-104 cells from a specimen of case 89-46448. For animal inoculation the viruses were diluted in a phosphate buffered solution (Mediatech) supplemented with 0.05% neonatal porcine serum (diluent) to obtain a virus titer of $10^4$ TCID$_{50}$/mL. The mock inoculum consisted of the diluent alone. The expected titer of infectious virus in those inocula prepared from either the 89-46448-40 or NADC-20 virus stock was verified afterwards by titration (TCID$_{50}$) in ZMAC cells.

Determination of infectious virus titer as determined as follows. Each virus inoculum was serially diluted ten-fold to a final dilution of $10^{-5}$ to $10^{-8}$, depending on the type of sample, in tubes containing 0.9 mL of RPMI-1640 medium (Mediatech) supplemented with 5% fetal bovine serum (Gibco). A 0.1 mL aliquot of each diluted sample being tested was transferred separately to quadruplicate wells that were present in a 96-well tissue culture plate and contained 0.1 mL medium having 3-4×$10^4$ ZMAC cells/well. After 96 h of culture at 37° C. in a humid environment with a 5% $CO_2$ atmosphere, the cells in each well were examined for the presence of a cytopathic effect by using an inverted microscope. Wells were scored as positive for virus infection when >90% of the cells within exhibited apoptosis and/or had lysed. The number of TCID$_{50}$ per sample was determined by using the method of Reed and Muench. Similar titrations of virus infectivity were performed on each serum and bronchoalveolar lavage (BAL) fluid sample collected from the individual, virus-infected or naïve pigs.

The body weight of each pig was measured by using a scale with a digital readout. The scale was calibrated using calibration weights before and after each use. All pigs were weighed on the first day of the study (immediately before virus infection) and at 7 and 14 days thereafter. The body weight gain attained by the individual pigs at 7 and 14 days after inoculation was calculated relative to their respective body weight on the day of virus exposure. Results are presented as the mean adjusted weight change±standard error of the mean (SEM) for each treatment group.

Bronchoalveolar lavage (BAL) samples were obtained. Fourteen days after virus challenge the animals were euthanized and their lungs removed intact from the thoracic cavity. BAL fluid samples were obtained from each lung by infusing into its right middle lobe sterile Dulbecco's phosphate buffered saline (Mediatech) with a 20 cc plastic syringe connected to a tubing infusion set (Butterfly 19×⅞ 12" tubing, Abbott Laboratories, Chicago, Ill.) from which the needle was cut. The tubing was inserted into the bronchi leading to the right middle lobe and the two clamped together with a string to avoid leakage. Afterwards, 10 mL of Dulbecco's phosphate buffered solution were slowly propelled into the lobe. After gently massaging the perfused lobe, the fluid was removed by slowly retracting the plunger. Typically half (5 mL) of the infused fluid was easily recovered. The BAL fluid was then transferred to a sterile 15 cc Falcon polypropylene conical tube (Becton Dickinson, Franklin Lakes, N.J.) and kept at 4° C. for no more than 4 h after collection. The BAL fluid was then clarified by centrifugation at 2000 rpm for 10 min, and the resultant fluid split into 1 mL aliquots in sterile RNAase and DNAase & pyrogen free, 1.7 mL Posi-Click Tubes (Denville Scientific) and stored at −80° C. until being tested for virus load.

Scoring of gross lung lesions was carried out as follows. Fourteen days after inoculation all of the animals were euthanized. Their lungs were removed from the thoracic cavity and the extent of gross lesions in this organ evaluated based on the scoring system described by Halbur et al. (1995). Briefly, each lung lobe was assigned a certain amount of points to reflect the approximate volume percentage of the entire lung represented by that lobe. For instance, ten points (five for dorsal and five for ventral aspects) were consigned to the right anterior lobe, right middle lobe, anterior part of the left anterior lobe and caudal part of the left anterior lobe. The accessory lobe was allotted 5 points and 27.5 points (15 for dorsal and 12.5 for ventral aspects) were given to each of the right and left caudal lobes to reach a total of 100 points. Based on examination of each lobe for the presence of macroscopic lung lesions, the extent of pneumonia in each lobe was estimated and that percentage times the respective, assigned lobe points, generated a value that when summed with the values determined for all of the other lobes produced a score indicative of the overall percentage of the entire lung afflicted with grossly visible pneumonia.

Mixed breed pigs (Yorkshire×Landrace×Duroc) from a PRRS-free farm were randomly assigned to isolation cubicles (3-4 pigs/cubicle) at two separate suites (8 cubicles/suite) with separate air handling at the animal bio-containment facility at the University of Illinois (Urbana, Ill.). Animals were fed a corn-based, non-medicated pig phase II diet (University of Illinois Feed Mill, Champaign, Ill.). The pigs were housed in accordance with biomedical level procedures, maintained on 12 h light/dark cycles, and had ad libitum access to water and feed. At 9-10 weeks of age the animals were infected intranasally and intramuscularly with 2 mL (1 mL per route with $10^4$ TCID$_{50}$/mL) with one of the two viruses (89-46448-40 or NADC-20) or with a mock inoculum (diluent alone). Cross-infection of pigs during the study was avoided by infecting all of the animals in a cubicle with the same type of virus isolate by only having pigs inoculated with one type of virus isolate in each suite. Mock-inoculated animals were kept in cubicles that were in the same suite as those housing the virus-infected animals but were geographically distinct. Strict bio-containment procedures were followed to keep the mock-inoculated pigs free of PRRS virus and avoid cross-contamination between suites. The animals were monitored daily for changes of vitality and signs of respiratory distress for an interval starting on the day of virus introduction and continuing through the next 14 days. Blood samples were collected form the jugular vein using MONOJECT™ blood collection tubes without additive (Tyco Healthcare Group, Mansfield, Mass.) before and at 4, 7, 10 and 14 days after inoculation. Serum was separated from the clotted blood by centrifugation, harvested and stored frozen at −80° C. in small aliquots in sterile 1.5 mL microcentrifuge tubes until tested. The level of viremia in the pigs was determined by measuring the amount of infectious virus in the prepared serum samples in ZMAC cells as described above. Clinical observations and analyses of serum samples confirmed that cross-contamination of PRRS virus isolates between containment suites and infection of mock-inoculated control pigs with PRRS virus did not occur. Each pig's body weight was determined immediately prior to virus infection and at 7 and 14 days thereafter. Fourteen days after virus exposure, all animals were euthanized and their lungs removed from the thoracic cavity and scored for gross pathology as described above.

Statistical analyses were performed as described. The General Linear Model Univariate procedure and the Fisher's LSD test were applied to assess differences between groups in regards to the extent of viremia ($\log_{10}$ TCID$_{50}$/mL) and gross lung pathology score, which for analysis was also $\log_{10}$ transformed. Dunnett's t-test (2-sided) was used to compare the pigs' proportion of weight change from the time of virus exposure to 7 and 14 days later to the same parameter measured in the reference (mock-inoculated) group. Statistical analyses were performed using the SAS® Software (Cary, N.C.). P-values of <0.01 were considered statistically significant.

Results. Effect of PRRS virus 89-46448-40 or NADC-20 on the weight gain of infected pigs. Grower pigs were infected with either the PRRS virus 89-46448-40 (n=6) or NADC-20 (n=10) isolate or were mock-infected (n=10) and the percent body weight gain of the individual animals at 7 and 14 days thereafter was determined and averaged for members of each group. (FIG. 1). At seven days after virus infection, the mock-treated control group exhibited a mean weight gain of 24.8±1% while this change was 18.6±2.2% for the 89-46448-40 virus-inoculated group. The average growth achieved by the 89-46448-40 virus-infected pigs represented ¾ of that realized by the control animals and the means of the increased weights of these two groups were not statistically different (p>0.09). In contrast, during the same period the NADC-20 virus-infected group attained on average only a 6.4±2.4% gain in weight, which was statistically different (p<0.001) from the corresponding, nearly 4-fold greater increase achieved by the mock-treated animals. Likewise, after the 14-day interval following virus inoculation, there was no significant difference (p>0.2) between the average weight gains of 45±2.5% and 52±1.6% by the 89-46448-40 virus-infected and mock-infected pigs, which in this case achieved a weight gain of 45±2.5% and 52±1.6%, respectively. Once again, growth of the NADC-20 virus-inoculated group was significantly impaired as compared to that of the control animals (p<0.001) as the former only realized on average a gain of 26.5±3.6%.

Figure 2:
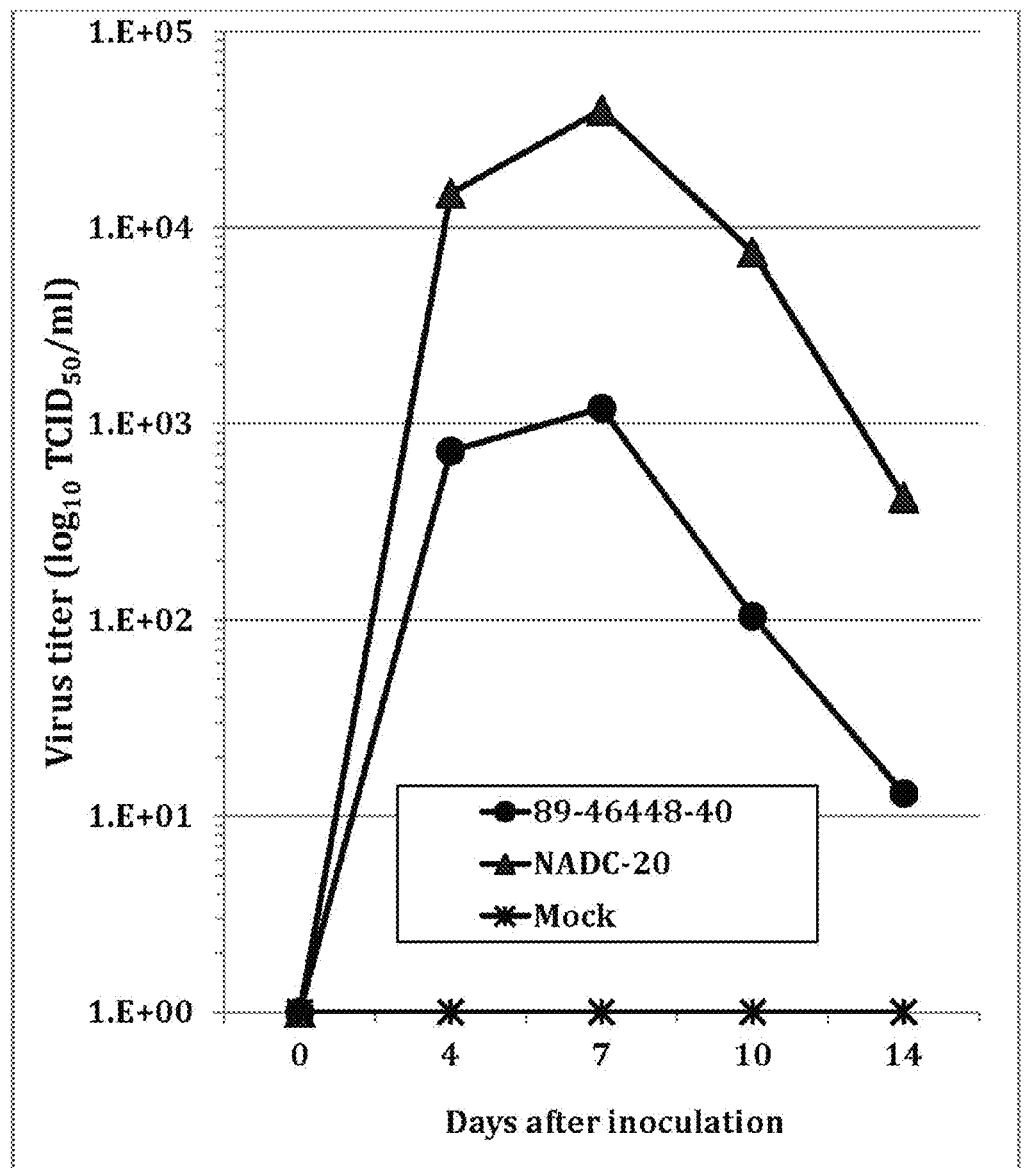
FIG. 2 shows serum viremia following infection of pigs with PRRS virus isolates 89-46448-40 or NADC-20 or a mock inoculum. The quantity of infectious virus ($TCID_{50}$/mL) in the pigs' serum samples was determined in ZMAC cells (ATCC No. PTA-8764, *Sus scrofa* (pig/swine) lung tissue cells).

Viremia and virus load in the lungs in pigs infected with PRRS virus isolates 89-46448-40 or NADC-20 was determined. When sampled just prior to inoculation, infectious virus was not detected in the sera of any of the animals, confirming their PRRS virus-free status (FIG. 2). Likewise, for the mock-inoculated group, viable virus was not found in any of the samplings taken after virus inoculation of the other animals, confirming that no unintentional infection of the control group had occurred. Four days after inoculation all of the animals infected with either NADC-20 or 89-46448-40 viruses were viremic. However, the group of pigs infected with the 89-46448-40 exhibited a significantly lower (p<0.001) level of viremia, with a group mean of $10^{2.9\pm0.19}$ TCID$_{50}$/mL, as compared to the NADC-20 group which exhibited a group mean of $10^{4.1\pm0.12}$ TCID$_{50}$/mL. The level of viremia peaked in both groups at 7 days post infection with the sera of NADC-20 virus-infected pigs showing an average viremia level of $10^{4.6\pm0.27}$ TCID$_{50}$/mL, which was >30-fold higher than the $10^{3.0\pm0.14}$ TCID$_{50}$/mL detected in sera from the 89-46448-40 virus-infected animals (p<0.001). By 10 days post infection the magnitude of the viremia began to decrease in both groups, but did so at a faster rate in the pigs infected with the 89-46448-40 isolate as indicated by the >70-fold lower average concentration of virus in the sera of the 89-46448-40 virus-inoculated group ($10^{2.0\pm0.4}$ TCID$_{50}$/mL) as compared to the that detected in the NADC-20 isolate-inoculated group ($10^{3.9\pm0.14}$ TCID$_{50}$/mL; p<0.001). Four days later, the average levels of viremia detected for the two groups still remained significantly different (p<0.005). However at this time only 50% of the 89-46448-40 virus-infected animals were viremic, while 90% of the animals inoculated with the NADC-20 virus were still viremic. At the time of euthanasia (14 days post virus exposure) infectious virus was found in the lungs of 90% of the pigs exposed to the NADC-20 virus with a resultant group geometric mean of $10^{3.3}$ TCID$_{50}$/mL. In contrast, this value was only $10^{1.1}$ TCID$_{50}$/mL for the group inoculated with the 89-46448-40 virus with only half of its members having a detectable infectious virus in their lungs.

Figure 3:
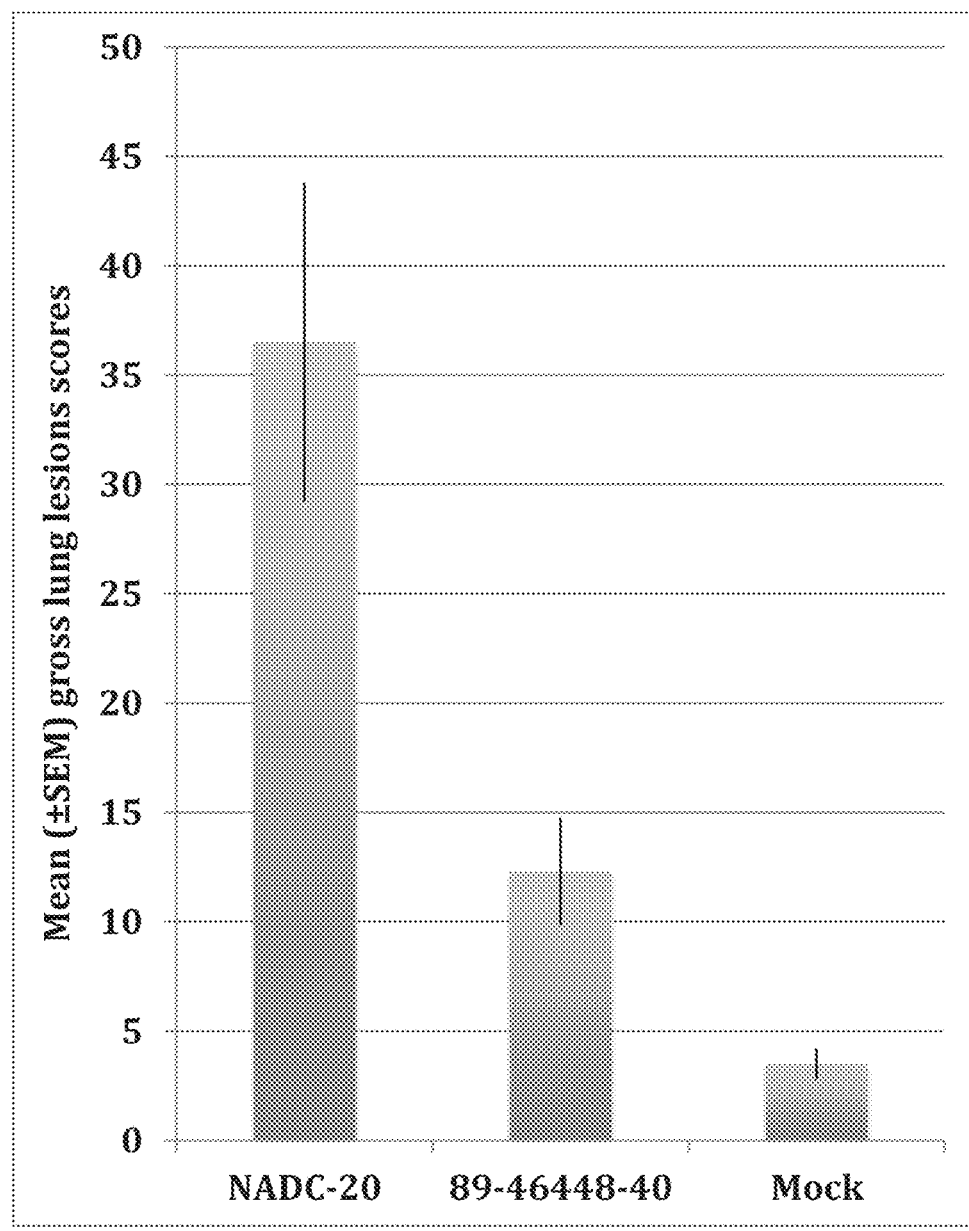
FIG. 3 demonstrates gross pathology scores of lungs from pigs infected 14 days earlier with PRRS virus isolates 89-46448-40 or NADC-20, or a mock inoculum. Gross lung pathology scores were determined based on a scoring system known in the art.

At 14 days post virus inoculation with PRRS virus 89-46448-40 or NADC-20, the lungs of all animals in the study were scored for gross lesions in order to quantify the extent of pneumonia. Individually, all pigs in the mock- or 89-46448-40 virus-inoculated groups were assessed with gross lung lesion scores of <25%. In contrast, 6 of the 10 members of the NADC-20-virus infected group were appraised to have gross lung lesion scores of >25%, including two pigs with scores of >75%. As expected, animals in the mock-inoculated control group had mostly normal lungs with individual scores ranging from 0 to 15% that averaged to a mean group score of 3.5±2% (FIG. 3). The mean increased to 12.3±3.3% when the pigs 89-46448-40 virus-inoculated group was calculated. Individually, their lungs were scored from a low of 0.7 to a high of 24%. These individual scores were much higher when evaluating the lungs of the NADC-20 virus-inoculated pigs. Here, individual gross lung lesion scores ranged from 7 to 78%, resulting in a group mean score of 36.5±7.7%. Because the scores given to individual pigs within each of the treatment groups varied >10-fold, the data was transformed to log 10 values for statistical analysis. After doing so, it was determined that there was no statistical difference between the average gross lung lesion scores of the mock-treated and 89-48448-40 virus-inoculated groups. However, a significant difference (p<0.001) was observed when this comparison was applied to the mock-treated and NADC-20 virus-inoculated groups.

The data in this example demonstrate that the 89-46448-40 PRRS virus isolate naturally exhibits a negligible level of virulence. For instance, pigs inoculated with the 89-46448-40 isolate maintained a growth rate equivalent to that achieved by its mock-treated cohorts. Moreover, the viremia resulting from inoculation of the pigs with the 89-46448-40 virus isolate was of significantly lower magnitude than the viremia observed in cohorts receiving the virulent PRRS virus isolate NADC-20. In addition, the length of viremia and the presence of virus in the lungs following the infection of young pigs with the 89-46448-40 virus isolate was of shorter duration than what has been reported for animals of similar age after infection with either other wild-type or attenuated strains of PRRS virus. Finally, the extent of pneumonia as indicated by the mean gross lung lesion scores was not statistically different when considering the mock-infected and 89-46448-40 virus-inoculated groups. In conclusion, the negligible level of virulence naturally exhibited by the PRRS virus isolate 89-46448-40 is akin to if not lower than what is observed with an attenuated strain of PRRS virus generated by serial passage in vitro.

Example 3

Genomic and Biologic Differences Between the Parental 89-46448-40 Virus and the G16X, 794A61 and 111698 PRRS Virus Strains Example 3. This Example demonstrates that the initial stock of the PRRS virus isolate 89-46448-40 was comprised of a discrete mixture of genetically related viruses. Three PRRS virus strains were derived and purified to homogeneity from the 89-46448-40 virus stock using either standard plaque assays (794A61 and G16X) or end-point dilution (111698). The genomes of the purified 794A61, 111698 and G16X virus strains differ from the virus population present in the initial 89-46448-40 virus stock by several non-synonymous and synonymous nucleotide point mutations. The latter resulted in 2, 3 or 5 amino acid changes, respectively, distributed among structural and non-structural viral proteins of 794A61, G16X and 111698 virus strains, which are not believed to be represented in the translated genomes of the 89-46448-40 parental virus stock. The viral proteins with predicted amino acid sequence changes that differentiate the three derived strains from the viruses in the parental 89-46448-40 stock include the non-structural protein (Nsp2), the structural protein E and glycoproteins (GP)$_3$ and GP4. See FIGS. 4A-4D. The 794A61, G16X and 111698 virus strains also differed biologically from the parental 89-46448-40 virus isolate, as shown by their ability to stimulate a considerable interferon alpha response by porcine alveolar macrophages. In addition, unlike the 89-46448-40 virus isolate, the G16X strain did not inhibit the production of interferon alpha by pig alveolar macrophages, but rather enhanced the synthesis of interferon alpha in response to their stimulation with poly(I:C).

TABLE 1

Amino acids among the PRRS virus strains 794A61, 111698 and G16X relating to progenitor virus 89-46448-40.

| PRRS virus strain | Position and predicted novel amino acid change in the corresponding PRRS virus protein | | | | Total no. of amino acid differences from 89-46448-40 |
| --- | --- | --- | --- | --- | --- |
| | NSP2 | E | GP3 | GP4 | |
| 794A61 | 495 (Leu) | — | 94 (Val) | — | 2 |
| 111698 | 338 (His) 495 (Leu) | — | 94 (Val) 213 (Phe) | 32 (Ser) | 5 |
| G16X | — | 31 (Val) 60 (Ala) | 94 (Val) | — | 3 |

As shown in Table 1, the viruses have one or more mutations in a protein including NSP2, E, GP3, and/or GP4, including one or more of the following: for NSP2, 495 Leu, 338 His; for E, 31 Val, 60 Ala; for GP3 94 Val, 213 Phe; for GP4, 32 Ser. Monolayers of the simian cell line, MARC-145, were prepared in 75 cm$^2$ tissue culture flasks containing complete MEM that consisted of Eagle's Minimal Essential Medium (MEM) with pH adjusted to 7.2 and supplemented with 5% fetal calf serum, 0.15% sodium bicarbonate and antibiotics. The flasks containing MARC-145 cells and 10 mL culture medium were incubated at 37° C. in an atmosphere of 5% $CO_2$. The porcine alveolar macrophage cell line ZMAC (ATCC Number PTA-8764), was cultured using Ultra-low adherence 75 cm$^2$ tissue culture flasks (Corning) in RPMI-1640 medium with L-glutamine (Mediatec, Herndon, Va., USA), supplemented with 10% fetal bovine serum (GIBCO®, Invitrogen, Grand Island, N.Y., USA), 1 mM sodium pyruvate (Mediatec) and 1× non-essential amino acids (Mediatec), and maintained at 37° C. in a 5% $CO_2$ atmosphere. The ZMAC cell line is free of adventitious agents, including bovine viral diarrhea, porcine circovirus, mycoplasma, PRRS virus, porcine parvovirus and porcine adenovirus.

All PRRS virus isolates used in this study were propagated in MARC-145 cell monolayers as described by Kim et al. (1993). For this purpose, confluent monolayers of MARC-145 cells were inoculated with 1 mL of virus suspension and incubated for 1 h at 37° C. to allow virus absorption. The virus inoculum was then removed, and 10 mL of fresh complete MEM added. The cell cultures were then incubated at 37° C. in an atmosphere of 5% $CO_2$ until cytopathic effects were observed (4 days). Once >75% of the cells in the monolayer exhibited cytopathic effects, the contents of the flask(s) were harvested and either purified or divided into several 1-2 mL aliquots in sterile glass or plastic vials and stored at −80° C. until needed. Purification of the viruses for use in biological assays began with the cell culture medium being first clarified by centrifugation at 2000 rpm and 4° C. for 10 min. The supernatant was then layered on top of a 3 mL solution of TE buffer (10 mM Tris, pH 8.0, 1 mM EDTA) containing 15% sucrose in SW28 rotor tubes (Beckman, Palo Alto, Calif.). The tubes were then centrifuged at 20,000 rpm and 4° C. for 3 h. The virus-containing pellets were then resuspended in 1 mL TE buffer, passed through a 0.2 µM syringe filter (Nalgene, Rochester, N.Y.) and stored in aliquots at −80° C. until needed.

The origins of the viruses used in this study have been described herein above. Viruses whose genomes were used for nucleotide sequencing analysis were: the original 89-46448-40 isolate provided by NVSL to the University of Illinois VDL (89-46448-40 MA104/2); the first passage of the six-fold plaque of the "794 stock" that was the second passage of 89-46448-40 MA104/2 in MARC-145 cells at the University of Illinois (794A61 P1); an end-point dilution (MOI=0.001) passage of the "794" stock in MARC-145 cells (111698); and the second passage of a plaque derived from two cycles of plaque-purification of the virus obtained during the first subsequent passage of the "794" stock at high MOI (MOI=1.0) in MARC-145 cells (G16X P2). Virus preparations used for evaluating the effect of PRRS virus on interferon alpha production by porcine alveolar macrophages were: i) the third passage of 89-46448-40 MA104/2 in MARC-145 cells (89-46448-40 P3); ii) the third passage of the 794A61 final plaque in MARC-145 cells (794A61 P3); iii) the third passage of 111698 virus in MARC-145 cells (111698 P3); iv) the fifth passage of the G16X final plaque in MARC-145 cells (G16X P5); v) the second passage of the wild-type NADC-20 virus preparation, that was originally passaged directly from the serum of an infected pig into ZMAC cells, and once in MARC-145 cells (NADC-20 P2), and, vi) the third passage of the FL-12 virus starting with a virus preparation derived by the transfection of ZMAC cells with the infectious clone of this virus and then passaged twice in MARC-145 cells (FL-12 P3).

Determination of infectious virus titer was carried out as follows. Virus preparations were serially diluted ten-fold in tubes containing 0.9 mL of complete MEM. A 0.1 mL aliquot of each diluted sample being tested was transferred separately to quadruplicate wells that were present in a 96-well tissue culture plate and contained 0.1 mL medium overlaying a nearly confluent monolayer of MARC-145 cells. After 5 days of culture at 37° C. in a humid environment with a 5% $CO_2$ atmosphere, the cells in each well were examined for the presence of a cytopathic effect by using an inverted microscope. Wells were scored as positive for virus infection when >90% of the cells within exhibited apoptosis and/or had lysed. The number of $TCID_{50}$ per sample was determined using the method of Reed and Muench.

To isolate the PRRS virus genomic RNA, RNA was extracted from samples of PRRS virus stocks 89-46448-40 MA104/2, G16X P2, 794A61 P1, and 111698 (described above) by using a QIAamp viral RNA minikit (Qiagen, Chatsworth, Calif.) according to manufacturer's instructions as described below. 140 µl of each sample was combined with 560 µl Buffer AVL containing 5.6 µl carrier RNA in a 1.5 mL Eppendorf tube, pulse-vortexed for 15 sec, and incubated at ambient temperature for 10 min. 560 µl of 100% ethanol was added to each tube and the contents were pulse-vortexed for 15 sec and centrifuged at 6000×g for 10 sec. 630 µl of each mixture was applied to the top surface of a QIAamp Mini spin column and centrifuged at 8000×g for 1 min. The eluant was discarded and the process repeated for the remainder of each mixture. Each column was then sequentially washed with 500 µl Buffer AW1 (8000×g for 1 min), and 500 µl Buffer AW2 (20,000×g for 3 min). Afterwards, the dried columns were centrifuged at 20,000×g for 1 min before 60 µl of Buffer AVE was applied to each column. Following 1 min incubation at ambient temperature, the RNA was eluted into 1.5 mL Eppendorf tubes during a 1 min centrifugation at 6000×g. Eluted RNAs were stored at −80° C. until needed.

Reverse transcription (RT) and polymerase chain reaction (PCR) amplifications of PRRS virus genomic RNA were performed as follows. PRRS virus 89-46448-40 MA104/2 and 794A61 P1 RNAs were reverse transcribed in the presence of 50 µM random hexamers (Invitrogen, Carlsbad, Calif.), 50 mM Tris (pH 8.3), 75 mM KCl, 3 mM $MgCl_2$, 10 mM DTT, 0.5 mM each of dATP, dCTP, dGTP, and dTTP and 25 units of mouse murine leukemia virus reverse transcriptase (Promega, Madison, Wis.)/µl reaction. The composition of the reaction mixture used for RT of the PRRS virus G16X P2 and 111698 genomes was the same except that the random hexamer primers were replaced with 0.5 µM RT REV primer (CAACTGCAGAGCTCATATGCAT) (SEQ ID NO: 30) or other primers whose sequences were complimentary to the virus genomic RNA. After denaturation of the RNAs and primers in either 0.5 mL Eppendorf tubes or 0.2 mL PCR tubes at 70° C. for 10 min and cooling at 4° C. for 2 min, the other components were added. The entire mixtures were either subjected to one cycle of 10 min at 25° C., one cycle of 50 min at 45° C., and one cycle of 15 min at 70° C. (random hexamer primers) or to one cycle of 60 min at 42° C. and one cycle of 15 min at 70° C. The resultant cDNAs were stored at −80° C. until needed.

PCR amplifications of PRRSV cDNAs to obtain amplicons for nucleotide sequencing were performed in 12.5 or 25 µl reaction mixtures. Their compositions were identical and consisted of 1 µl cDNA (prepared as described above) and 0.25 units IPROOF™ High-Fidelity DNA polymerase (Bio-Rad Laboratories, Hercules, Calif.) per 12.5 µl reaction mixture, 1× IPROOF™ HF buffer, and 0.2 mM each of dATP, dCTP, dGTP, and dTTP. PCR reaction mixes in 0.2 mL PCR tubes were either maintained at 70° C. in a thermocycler or at 4° C. on ice before the addition of PRRS virus-specific forward and reverse primers to a final concentration of 0.45 mM. In the latter case, samples were then immediately transferred to a thermocycler pre-heated to 70° C. For amplification, samples were subjected to one cycle of denaturation at 98° C. for 30 sec, thirty-seven cycles of denaturation at 98° C. for 10 sec, primer annealing at 56° C. to 58° C. for 30 sec, and product elongation at 72° C. for 1-3 min, and one cycle of 5 min at 72° C. The resultant amplicons were stored at −20° C. until electrophoresed in 0.7% agarose gels. Ethidium bromide-stained bands representing amplicons of the anticipated size were visualized using long wave ultraviolet light (366 nm), excised, purified by using a Zymoclean Gel DNA recovery kit (ZYMO Research, Orange, Calif.) and eluted from Zymo-Spin I columns in 10 µl RNAse-free $H_2O$ per sample.

In preparation for nucleotide sequence analysis, a 2.8 µl aliquot of each purified amplicon was combined with 5.2 µl 12.5% glycerol, 2.0 µl 5× sequencing buffer (400 mM Tris, pH 9.0, mM $MgCl_2$), and 1.0 µl BIGDYE® Terminator v3.0 or v3.1 Cycle Sequencing RR-24 (Applied Biosystems, Austin, Tex.) in a 0.2 mL PCR tube and maintained at 4° C. Upon addition of an individual sequencing primer to a final concentration of 1.5 mM, each tube was transferred to a thermocycler pre-heated to 70° C. Reactions are then subjected to one cycle of 1 min at 95° C. and 35 cycles of 15 sec at 95° C., 5 sec at 50° C., and 4 min at 60° C. The completed reactions were processed by the University of Illinois at Urbana-Champaign (UIUC) Core DNA Sequencing Facility, and the resulting chromatograms were visually inspected and edited with the SeqEd program (Applied Biosystems).

In order to assess the interferon alpha response of pig alveolar macrophages to PRRS virus, cultures of the porcine alveolar macrophage cell line ZMAC ($2.5×10^5$ cells per tube) were prepared in 12×75 mm polystyrene round bottom tubes (BD Falcon, Bedford, Mass.) containing 0.5 mL of RPMI-1640 with L-glutamine and HEPES (Mediatec, Herndon, Va.) and supplemented with 10% fetal bovine serum (GIBCO®, Invitrogen, Grand Island, N.Y.), 1 mM sodium pyruvate (Mediatec) and 1× non-essential amino acids (Mediatech). Each culture was mixed with 0.1 mL medium either lacking (mock-treated) or containing one of the following PRRS virus strains: 89-46448-40, G16X, 111698, 794A61, FL-12, or NADC-20, at a concentration determined to provide a multiplicity of infection (MOI) ranging from 0.04 to 5. The cultures were placed at 37° C. in a 5% $CO_2$ atmosphere, harvested 8 h later, and centrifuged for 10 min at 4° C. and 2000 rpm. The resultant cell-free, supernatant media were removed and tested for the presence of interferon alpha by using a specific ELISA.

To assess the effect of PRRS virus on the interferon alpha response of macrophages to polyinosinic:polycytidylic acid [poly(I:C)], individual cultures of $2.5×10^5$ ZMACcells in round bottom tubes containing 0.5 mL of supplemented RPMI-1640 medium were mixed with medium either lacking (mock-treated) or containing one of the following PRRS virus strains: 89-46448-40, G16X, 111698, 794A61, FL-12, or NADC-20, at a concentration determined to provide a MOI of 5. After a 2 h incubation at 37° C. in a 5% $CO_2$ atmosphere, the cell cultures were exposed to 10 µg/mL of poly(I:C) (Amersham Pharmacia Biotech, Inc. Piscataway, N.J.) and returned to the 37° C. and 5% $CO_2$ atmospheric environment. After an additional 8 h, the cultures were harvested were harvested and centrifuged for 10 min at 4° C. and 2000 rpm. The resultant cell-free, supernatant media were removed and tested for the presence of interferon alpha by using a specific ELISA.

Figure 6:
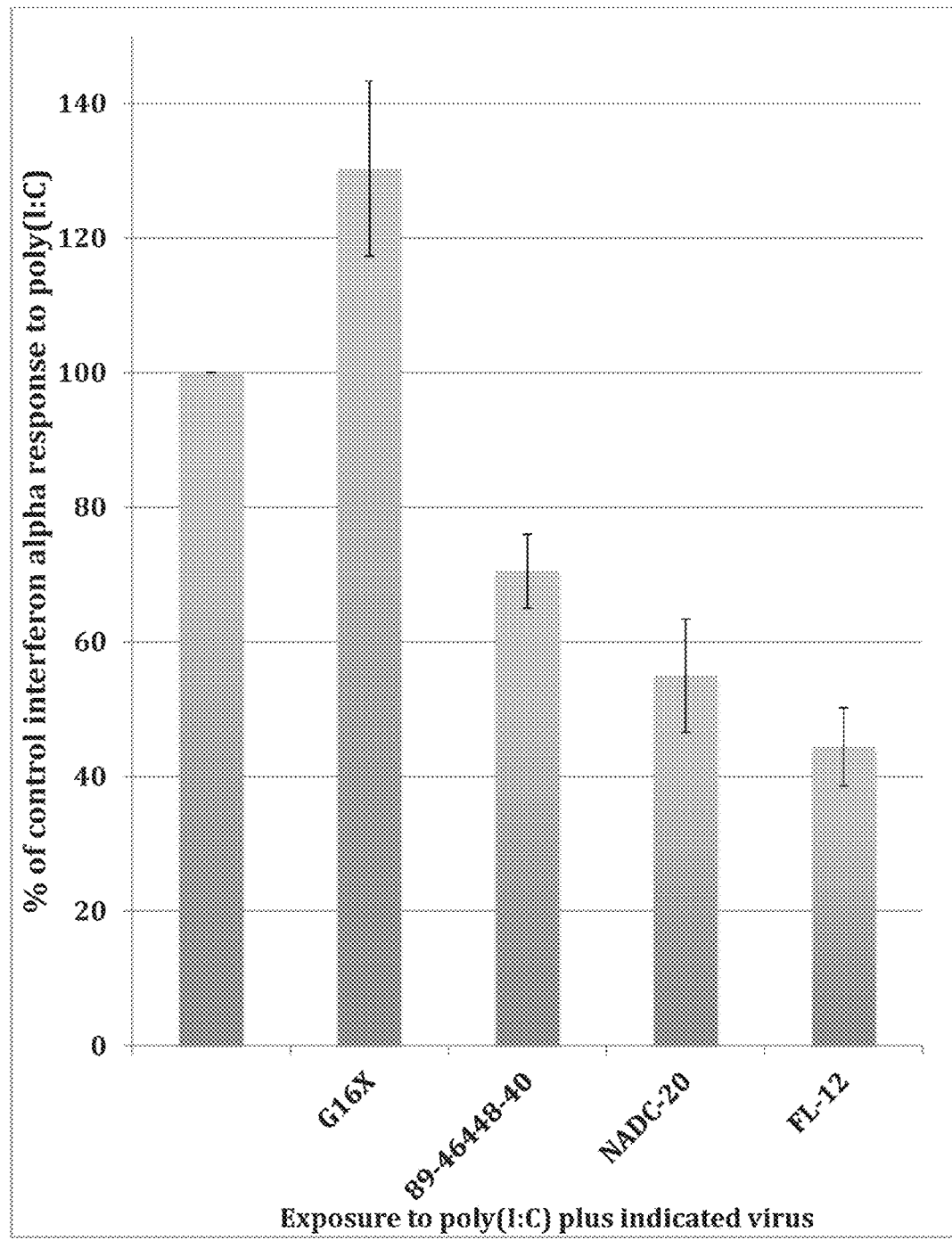
FIG. 6 shows the effects of different PRRS virus strains on the interferon alpha response of alveolar macrophages to poly(I:C). ZMAC cells were either mock-infected or infected with the indicated virus (MOI=5). After a 2 h incubation the cell cultures were exposed to 25 mg/mL of poly(I:C). Cell culture media were harvested 8 h later and tested for the presence of interferon alpha by ELISA specific for pig interferon alpha.

Results are presented as a percentage of the amount of IFN alpha detected in ZMAC cell cultures stimulated with poly(I:C) alone, which were given a value of 100%. The amount of IFN alpha detected in the supernatants of poly(I:C) treated ZMAC cell cultures at this cell concentration ranged from 11 to 35 ng/mL. The data presented in FIG. 6 represent the means (±SEM) of least three independent experiments.

Quantitation of porcine interferon alpha by using a specific ELISA was carried out as follows. Individual wells of a Nunc Immulon II 96-well plate (Thermo Fisher Scientific, Inc., Rockford, Ill., USA) were coated for 16 h at 4° C. with 50 μl of 5 μg/mL anti-pig interferon alpha mAb F17 (PBL InterferonSource, Piscataway, N.J., USA) in 0.1 M carbonate buffer (pH 9.6), washed 3 times with PBS containing 0.05% Tween 20 (PBS-T), and then incubated with 200 μl milk blocking solution (BioFix, Owings Mills, Md., USA) for 1 h at 25° C. After three washes with PBS-T, 50 μl cell culture supernatants or recombinant pig interferon alpha standards (PBL InterferonSource) diluted in RPMI complete medium were added to duplicate wells and left for 1.5 h at 25° C. After washing 5 times with PBS-T, each well was incubated with 50 μl of PBS-T containing 0.3 μg/mL biotin-labeled, anti-pig interferon alpha mAb K9 (PBL InterferonSource) and 0.5% milk blocking solution at 25° C. for 1.5 h. After 5 washes with PBS-T, each well was incubated with 50 μl PBS-T containing 20 ng/mL streptavidin conjugated to horse radish peroxidase (BIOSOURCE™, Invitrogen) for 20 min at 25° C. and then again washed 5 times with PBS-T. Color development was initiated at 25° C. with the addition of 100 μl TMB substrate (KPL, Gaithersburg, Md., USA) per well and terminated with 100 μl 1 M phosphoric acid. Optical densities were determined at 450 nm with a SPECTRAMAX Plus plate reader (Molecular Devices, Sunnyvale, Calif.). Results were averaged and the amounts of interferon alpha were determined by comparison to a standard curve generated from the values obtained with known quantities of this cytokine.

Results. Amino acid differences between the proteins of PRRS virus 89-46448-40 and the three derived strains 794A61, 111698 and G16X were determined. A comparison of the nucleotide sequences comprising more than 99% of the entire genomes of three PRRS virus strains (794A61, 111698, and G16X; Tables 3-5), corresponding to the translated portions of the virus genome that result in expressed proteins for each of these three PRRS virus strains (see also Tables 1-2 and FIGS. 4A-4D) that were derived from the 89-46448-40 virus isolate, revealed 24 single nucleotide differences among them. In addition, the 794A61 virus had a unique 111 nucleotide deletion in the Nsp2 gene (amino acid positions 674-710). Of the 13 single nucleotide substitutions that influenced amino acid sequence, seven resulted in amino acid changes not represented in the genomes of the 89-46448-40 virus stock. The seven amino acids distinguishing these three viruses from their progenitor 89-46448-40 isolate, are distributed within the portions of Nsp2, protein E, GP3 and GP4 (designated by bold letters in FIGS. 4A-4D). Furthermore, in the case of the parental 89-46448-40 virus stock, the analysis indicted that amino acid positions 67 and 490 of Nsp2 and position 96 of GP3 (indicated by boxed letters in FIGS. 4A and 4C), were predicted to be polymorphic based on the incidence of double peaks at the three relevant locations in the genome sequence chromatograms. Thus, the original 89-46448-40 stock prepared at NVSL (89-46448-40 MA104/2) appeared to be comprised of a heterogeneous, but closely related, population of viruses. In this regard, PRRS virus is known to exist as a quasispecies distribution of related virus genotypes. Accordingly, such limited diversity within the 89-46448-40 MA104/2 virus stock is consistent with what is commonly observed for non-purified PRRS virus stocks. In contrast, such ambiguity in regards to nucleotide identity was not observed during the sequencing of the genomes of the 794A61, 111698, and G16X viruses, thus indicating their genomic homogeneity. Further testament to the genomic homogeneity of the three purified virus strains, only one of the two alternative amino acids at each polymorphic site observed in the 89-46448-40 virus stock (boxed letters in FIG. 4) was predicted to be present in their respective proteins (indicated by italic letters in FIG. 4) based on the virus genome sequence which exhibited a single unambiguous peak at the relevant locations in the respective virus genome sequence chromatograms. It is important to note that some of the seven amino acid changes were exclusive to one of the derived viruses. For instance, the 111698 strain had unique amino acids at positions 338, 213, and 32 in Nsp2, GP3, and GP4, respectively. Moreover, the G16X strain was distinct in regards to amino acid positions 31 and 60 in protein E (FIG. 4B). Interestingly, the mutation at amino acid position 94 in the GP3 was common to all three of PRRSV strains, 794A61, 111698, and G16X.

Without wishing to be bound by any particular theory, it is believed that the mutation to encode alanine rather than threonine at amino acid 60 in Protein E is responsible for or contributes to the advantageous immunizing phenotype of the G16X isolate, alone or in combination with the isoleucine to valine change at amino acid 31 in Protein E may further contribute to this phenotype. It is acknowledged that other changed amino acids as shown in FIGS. 4A-4D may also contribute to the phenotype of the G16X isolate.

Figure 5:
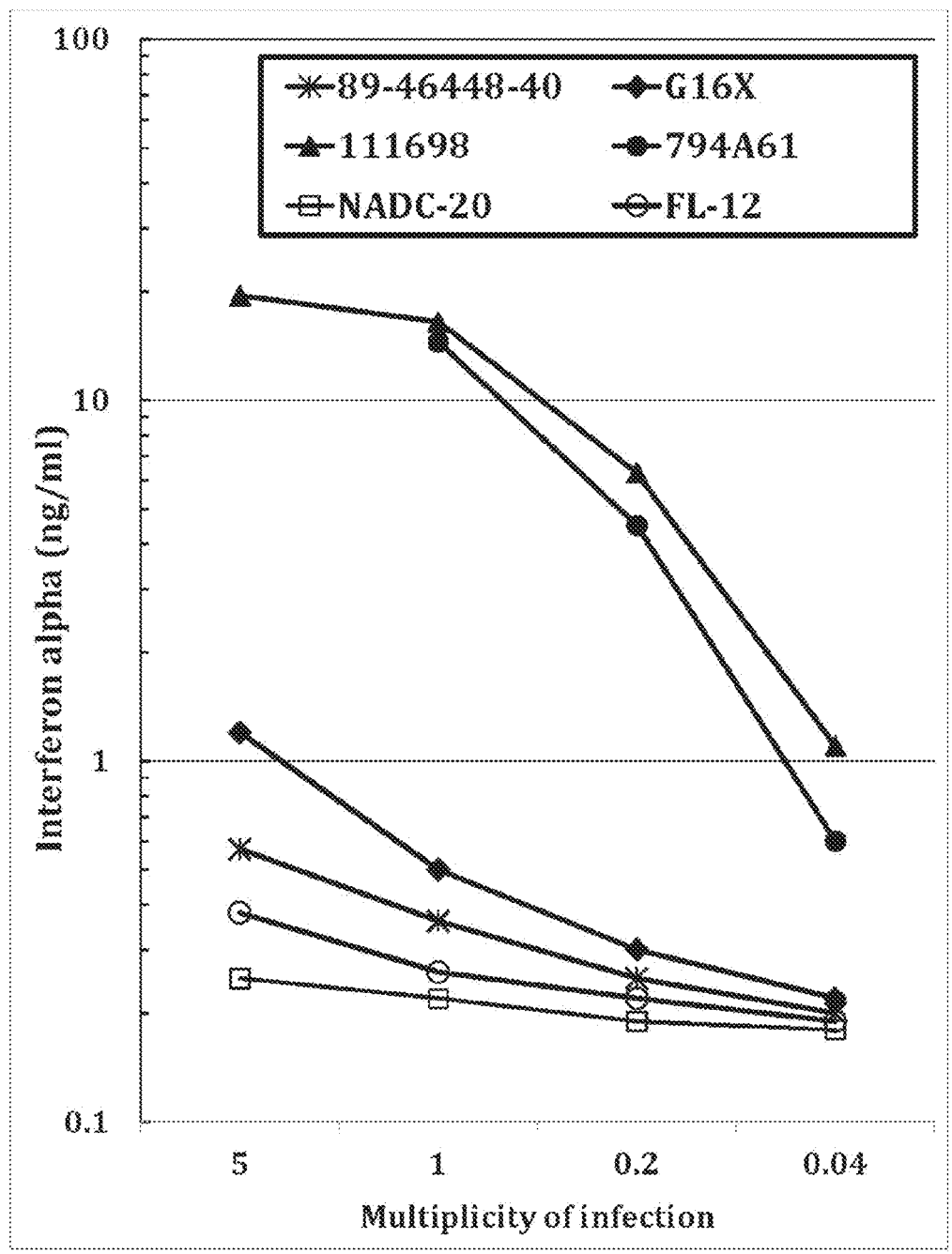
FIG. 5 shows interferon alpha response of pig alveolar macrophages to infection with different types of PRRS virus. ZMAC cells were infected with PRRS virus at the indicated multiplicities of infection (MOI). The amount of interferon alpha in the culture supernatant collected at 8 h after the cells were exposed to the indicated virus was determined by ELISA specific for pig interferon alpha.

The effects of PRRS virus 89-46448-40 and the three derived strains on interferon alpha production by porcine alveolar macrophages were determined. Previous studies have shown that very low to negligible amounts of interferon alpha are produced by porcine alveolar macrophages when exposed to PRRS virus, with some slight variation between the responses elicited by different PRRS virus field isolates. To ascertain differences between the parental 89-46448-40 isolate and the three strains derived from it, the interferon alpha response of the porcine alveolar macrophage cell line ZMAC to their exposure to any of these four related viruses was studied. For comparison, the interferon alpha response provoked by NADC-20 and FL-12, two wild-type PRRS virus isolates, was also investigated. Exposure of ZMAC cells to either 89-46448-40, FL-12 or NADC-20 virus isolates resulted in a meager interferon alpha response, analogous in magnitude to the response by elicited by other wild-type PRRS virus isolates from pig alveolar macrophages. In contrast, the exposure of alveolar macrophages to the G16X strain at the highest multiplicity of infection (MOI) tested (MOI=5) elicited a response that was two-fold larger in magnitude than the response elicited by its progenitor isolate (89-46448-40) at the same MOI (FIG. 5). Notably, infection of the ZMAC cells to either the 111698 or 794A61 viruses elicited the secretion of copious amounts of interferon alpha that were 34- or 40-fold greater, respectively, than that released in response to their progenitor 89-46448-40 isolate. Further evidence that the G16X strain differed biologically from the 89-46448-40 virus isolate was obtained when the cells were exposed to PRRS virus before being exposed to poly(I:C), which strongly stimulates interferon alpha production by pig alveolar macrophages (Loving et al., 2006). Typically, exposure of ZMAC cells to poly(I:C) alone results in the production of 10-30 ng/mL of interferon alpha. Exposure of the ZMAC cells to either 89-46448-40, NADC-20 of FL-12 virus for 2 h before their stimulation with poly(I:C) strongly inhibited (>25%) the interferon alpha response of the ZMAC cells to poly(I:C). In contrast, rather than being inhibited, the secretion of this cytokine by ZMAC cells in response to their stimulation with poly(I:C) was enhanced by approximately 30% in the presence of the G16X virus (FIG. 6).

In summary, the data demonstrate that the stock of 89-46448-40 virus isolate originated from NVSL (89-46448-40 MA104/2) was comprised of a mixture of viruses of related genotypes. The example also shows that the three purified PRRS virus strains 794A61, 111698 and G16X differed from the parental 89-46448-40 virus population by several synonymous and non-synonymous nucleotide point mutations. The latter mutations resulted in 2, 3 or 5 amino acid changes distributed among Nsp2 and structural proteins protein E, GP3 and GP4, respectively, that distinguish them from the parental virus. These three strains also differed biologically from the progenitor 89-46448-40 virus, as shown by their unique ability to stimulate interferon alpha production by porcine alveolar macrophages.

Example 4

PRRS Virus Vaccine

Example 4. This Example demonstrates differences in the vaccine efficacies of the PRRS virus strains 794A61, 111698 and G16X in an experimental respiratory challenge model of PRRS in grower pigs. Vaccine effectiveness took into account factors indicative of protection from clinical disease including the rate of pig growth, the magnitude and duration of viremia in the pig, and the presence of virus in the pigs' lungs. The results are summarized in Table 2. Based on these parameters the protective efficacy against the same heterologous challenge virus for these three nearly isogenic PRRS virus strains was rated as poor (794A61), moderate (111698) or good (G16X).

TABLE 2

Outcomes of the vaccination challenge study.

| | Vaccine efficacy parameter | | | |
|---|---|---|---|---|
| Vaccine strain | Reduction/ elimination of viremia | Minimize reduction in pig growth | Reduction/ elimination of lung-associated virus | Vaccine efficacy rating |
| 794A61 | ++ (1) | − (3) | − (3) | Poor |
| 111698 | +++ (1) | ++ (1) | − (3) | Moderate |
| G16X | +++ (1) | ++ (1) | ++ (2) | Good |

Key: +++ indicates strong effect; ++ indicates good effect; + indicates moderate effect; − indicates no effect. (1),(2),(3): Level of statistical significance when comparing the indicated vaccinated group to the unvaccinated challenge control group.
(1) $p \leq 0.001$;
(2) $p < 0.005$;
(3) $p > 0.4$ (not significant).

Materials and Methods. Monolayers of the simian cell line, MARC-145, were prepared in 75 cm² tissue culture flasks containing complete MEM that consisted of Eagle's Minimal Essential Medium (MEM) with pH adjusted to 7.2 and supplemented with 5% fetal calf serum, 0.15% sodium bicarbonate and antibiotics. The flasks containing MARC-145 cells and 10 mL culture medium were incubated at 37° C. in an atmosphere of 5% $CO_2$. The porcine alveolar macrophage cell line ZMAC, was cultured using Ultra-low adherence T75 tissue culture flasks (Corning, Corning, N.Y.) in RPMI-1640 medium with L-glutamine (Mediatec, Herndon, Va.), supplemented with 10% fetal bovine serum (GIBCO®, Invitrogen, Grand Island, N.Y.), 1 mM sodium pyruvate (Mediatec) and 1× non-essential amino acids (Mediatec), and maintained at 37° C. in a 5% $CO_2$ atmosphere.

The three PRRS virus isolates (794A61, 111698, and G16X) used as potential vaccines in this study were propagated in MARC-145 cell monolayers as described in the art. Confluent monolayers of MARC-145 cells were inoculated with 1 mL of virus suspension and incubated for 1 h at 37° C. to allow virus absorption. The virus inoculum was then removed and 10 mL of fresh complete MEM added. The cell cultures were then incubated at 37° C. in an atmosphere of 5% $CO_2$ until cytopathic effects were observed (within 4 days). Once >75% of the cells in the monolayer exhibited cytopathic effects, the contents of the flask(s) were harvested and either purified or divided into several 1-2 mL aliquots in sterile glass or plastic vials and stored at −80° C. until needed. The "acute PRRS" virus isolate NADC-20 used as the challenge virus was passaged once in ZMAC cells directly from the serum of a diseased animal in order to create a stock of virus for animal inoculation. The NADC-20 virus has been shown to produce significant respiratory disease in young pigs, with total gross lung lesion scores ranging from 30-45% and substantial viremia of similar magnitude to that observed for other virulent PRRS virus isolates. For animal inoculation the viruses were diluted in a phosphate buffered solution (Mediatech) supplemented with 0.05% neonatal porcine serum (diluent) to obtain a virus titer of $10^4$ $TCID_{50}$/mL. The mock inoculum consisted of the diluent alone.

The origins of the three vaccine viruses used in this study have been described in detail herein above. The stocks of these viruses used for vaccination are: the second passage of the six-fold plaque purified isolate of the "794 stock" that was the second passage of 89-46448-40 MA104/2 (original 89-46448-40 isolate provided by NVSL to the University of Illinois VDL) in MARC-145 cells (794A61 P2); an end-point dilution (MOI=0.001) passage of the "794" stock in MARC-145 cells (111698); and the third passage of a plaque derived from two cycles of plaque-purification of virus obtained during the first subsequent passage of the "794" stock at high MOI (MOI=1.0) in MARC-145 cells (G16X P3).

Prior to inoculation, the vaccine and challenge virus stocks were diluted in Dulbecco's phosphate buffered solution (Mediatech, Manassas, Va.) supplemented with 0.05% neonatal porcine serum to obtain an infectious dose of 104.1 or 104.7 $TCID_{50}$/mL, respectively. The expected titers of each inoculum were verified on the day of use by titration in MARC-145 cells (three vaccines) or ZMAC cells (NADC-20 challenge virus) as described below.

To quantitate the amount of infectious virus (infectious virus titer) in the preparations to be used for vaccination, the virus stocks were serially diluted ten-fold in tubes containing 0.9 mL of complete MEM. A 0.1 mL aliquot of each diluted sample being tested was transferred separately to quadruplicate wells that were present in a 96-well tissue culture plate and contained 0.1 mL medium overlaying a nearly confluent monolayer of MARC-145 cells. After 5 days of culture at 37° C. in a humid environment with a 5% $CO_2$ atmosphere, the cells in each well were examined for the presence of cytopathic effects using an inverted microscope. Wells were scored as positive for virus infection when >90% of the cells within exhibited apoptosis and/or had lysed. The number of $TCID_{50}$ per sample was determined by using the method of Reed and Muench (Reed and Muench, 1938).

To determine the quantity of infectious virus in the challenge virus preparation, the NADC-20 stock was serially diluted ten-fold in tubes containing 0.9 mL of RPMI-1640 medium (Mediatech) supplemented with 5% fetal bovine serum (Gibco). A 0.1 mL aliquot of each diluted sample being tested was transferred separately to quadruplicate wells in a 96-well tissue culture plate and contained 0.1 mL medium having 3-4×$10^4$ ZMAC cells/well. After 96 h of incubation at 37° C. in a humid environment with a 5% $CO_2$ atmosphere, the cells in each well were examined for the presence of cytopathic effects using an inverted microscope. Wells were scored as positive for virus infection when >90% of the cells within exhibited apoptosis and/or had lysed. The number of TCID$_{50}$ per sample was determined by using the method of Reed and Muench. Similar titrations of virus infectivity using ZMAC cells were performed on each serum and bronchoalveolar lavage (BAL) fluid sample collected from the individual, virus-infected or naïve pigs.

The body weight of each pig was measured by using a scale with a digital readout. The scale was calibrated using calibration weights before and after each use. All pigs were weighed on the day of virus challenge (immediately before inoculation) and at 7 days thereafter. The body weight gained by the individual pigs at 7 days after challenge was calculated relative to their respective body weight on the day of NADC-20 virus inoculation. Results are presented as the mean adjusted weight change±standard error of the mean (SEM) for each treatment group.

Seven days after NADC-20 virus challenge, the animals were euthanized and their lungs removed intact from the thoracic cavity. Bronchoalveolar (BAL) fluid samples were obtained from each lung by infusing into its right middle lobe sterile Dulbecco's phosphate buffered saline (Mediatech) with a 20 cc plastic syringe connected to a tubing infusion set (Butterfly 19×⅞ 12" tubing, Abbott Laboratories, Chicago, Ill.) from which the needle was cut. The tubing was inserted into the bronchi leading to the right middle lobe and the two clamped together with a string to avoid leakage. Afterwards, 10 mL of Dulbecco's phosphate buffered solution were gently propelled into the lobe. After gently massaging the perfused lobe, the fluid was removed by slowly retracting the plunger. Typically half (5 mL) of the infused fluid was easily recovered. The BAL fluid was then transferred to a sterile 15 cc Falcon polypropylene conical tube (Becton Dickinson, Franklin Lakes, N.J.) and kept at 4° C. for no more than 4 h after collection. The BAL fluid was then clarified by centrifugation at 2000 rpm for 10 min, and the resultant fluid split into 1 mL aliquots in sterile RNAase and DNAase & pyrogen free, 1.7 mL Posi-Click Tubes (Denville Scientific) and stored at −80° C. until being tested for virus load.

Viremia was detected and measured using quantitative RT-PCR, with primers as described herein below. RNA was extracted from serum samples obtained from PRRS virus-vaccinated and naïve pigs at seven days after challenge with the NADC-20 virus by using a QIAamp viral RNA minikit (Qiagen, Chatsworth, Calif.) according to manufacturer's instructions and as described below. 140 µl of each sample was combined with 560 µl Buffer AVL containing 5.6 µl carrier RNA in a 1.5 mL Eppendorf tube, pulse-vortexed for 15 sec, and incubated at ambient temperature for 10 min. 560 µl of 100% ethanol was added to each tube and the contents were pulse-vortexed for 15 sec and centrifuged at 6000×g for 10 sec. 630 µl of each mixture was applied to the top surface of a QIAamp Mini spin column and centrifuged at 8000×g for 1 min. The eluant was discarded and the process repeated for the remainder of each mixture. Each column was then sequentially washed with 500 µl Buffer AW1 (8000×g for 1 min) and 500 µl Buffer AW2 (20,000×g for 3 min). Afterwards, the dried columns were centrifuged at 20,000×g for 1 min before 60 µl of Buffer AVE was applied to each column. Following a 1 min incubation at ambient temperature, the RNA was eluted into 1.5 mL Eppendorf tubes during a 1 min centrifugation at 6000×g. Eluted RNAs were stored at −80° C. until needed.

Serum RNA samples were reverse transcribed in the presence of 0.5 µM reverse, complementary primer (CACACGGTCGCCCTAATTG) (SEQ ID NO: 27), 50 mM Tris (pH 8.3), 75 mM KCl, 3 mM MgCl$_2$, 10 mM DTT, 0.5 mM each of dATP, dCTP, dGTP, and dTTP and 25 units of mouse murine leukemia virus reverse transcriptase (Promega, Madison, Calif.)/µl reaction. After denaturation of the RNAs and primers in either 0.5 mL Eppendorf tubes or 0.2 mL PCR tubes at 70° C. for 10 min and cooling at 4° C. for 2 min, the other components were added. The entire mixtures were either subjected to one cycle of 10 min at 25° C., one cycle of 50 min at 45° C., and one cycle of 15 min at 70° C. (random hexamer primers) or to one cycle of 60 min at 42° C. and one cycle of 15 min at 70° C. The resultant cDNAs were stored at −80° C. until needed.

Real-time PCR for the amplification/detection of PRRSV genomes in the reaction mixtures was performed by using the TaqMan Universal PCR Master Mix, an ABI SDS 7000 machine (Applied Biosystems, Foster City, Calif.), forward primer TGGTGAATGGCACTGATTGAC (SEQ ID NO: 28), the above-mentioned reverse primer, and TaqMan probe, 6-FAM-TGTGCCTCTAAGTCACC (SEQ ID NO: 29) (where FAM is 6-carboxyfluorescein). Primers and probe were designed with Primer Express, version 2.0, software (Applied Bio systems) and were purchased from Integrated DNA Technologies, Inc. (IDT, Coralville, Iowa), and Applied Biosystems, respectively. PRRS virus RNA copy number was determined by comparison of the obtained threshold cycle (CT) values to a standard curve generated by using known amounts of RNA transcripts corresponding to approximately 9% of the 3'-terminal region of the genome of PRRS virus strain G16X.

Thirty cross-bred (Yorkshire×Landrace) pigs at 35±2 days of age were obtained from the PRRS virus-free swine herd at the University of Illinois, College of Veterinary Medicine, Swine Research Farm (Urbana, Ill.). The pigs were randomly distributed to isolation cubicles (n=3 pigs/cubicle) at the Biocontainment Facility at the University of Illinois. A thermal climate of 24° C. to 28° C. was maintained in the cubicles. Pigs were fed a corn-based phase II diet that provided nutrient concentrations that met or exceeded the estimated requirements of high-lean pigs. The animals were housed in groups of 3 in accordance with biomedical level procedures in ten 182-×243-cm cubicles, maintained on 12 h light/dark cycles, and had ad libitum access to water and feed. After a 5-day period of acclimation, animals in 6 of the cubicles were injected once intramuscularly in the rump area with a 2 mL suspension containing $10^{4.1}$ TCID$_{50}$/mL of either G16X-P3, 794A61-P2 or 111698 virus, for a total of 2 cubicles per type of vaccine virus (n=6 pigs). Six animals in two additional cubicles were mock-vaccinated with 2 mL of diluent (PBS supplemented with 0.5% pig serum). Six pigs in the remaining two cubicles were not immunized and were used as strict controls. At 39.5±0.5 days after vaccination, all of the immunized animals as well as the six mock-vaccinated pigs were challenged with $10^{5.3}$ TCID$_{50}$ of the virulent PRRS virus isolate NADC-20. The challenge inoculum consisted of 4 mL of NADC-20 virus at a concentration of $10^{4.7}$ TCID$_{50}$/mL administered in 2 mL doses intranasally and intramuscularly. The body weight of each animal was determined immediately prior to and at 7 days after virus challenge. The animals were monitored daily for changes of vitality and signs of respiratory distress for an interval starting on the day of challenge and continuing throughout the next 7 days. Serum samples were collected immediately before and at 7 days after challenge, and the levels of viremia ascertained by measuring the amount of PRRS virus genomes/mL of serum using quantitative real-time PCR. Seven days after the challenge, the animals were euthanized and their lungs removed intact from their thorax. BAL samples were collected from the right middle lobe and amount of infectious virus in them determined by titration in ZMAC cells.

Statistical analyses were carried out as follows. The General Linear Model Univariate procedure and the Fisher's LSD test were applied to assess differences between groups in regards to the extent of viremia (viral genome copy number/mL) and amount of infectious virus in the lungs ($TCID_{50}$/mL). For analysis both of these measurements were transformed to log 10 values and compared to the group mean of the mock-vaccinated-challenged group. Dunnett's t-test (2-sided) was used to compare the vaccinated pigs' differential weight change before and after virus challenge to the same parameter measured in the reference mock-vaccinated-challenged group. Analyses were performed using the statistical SAS software (Cary, N.C.). P-values of <0.01 were considered statistically significant.

Figure 7:
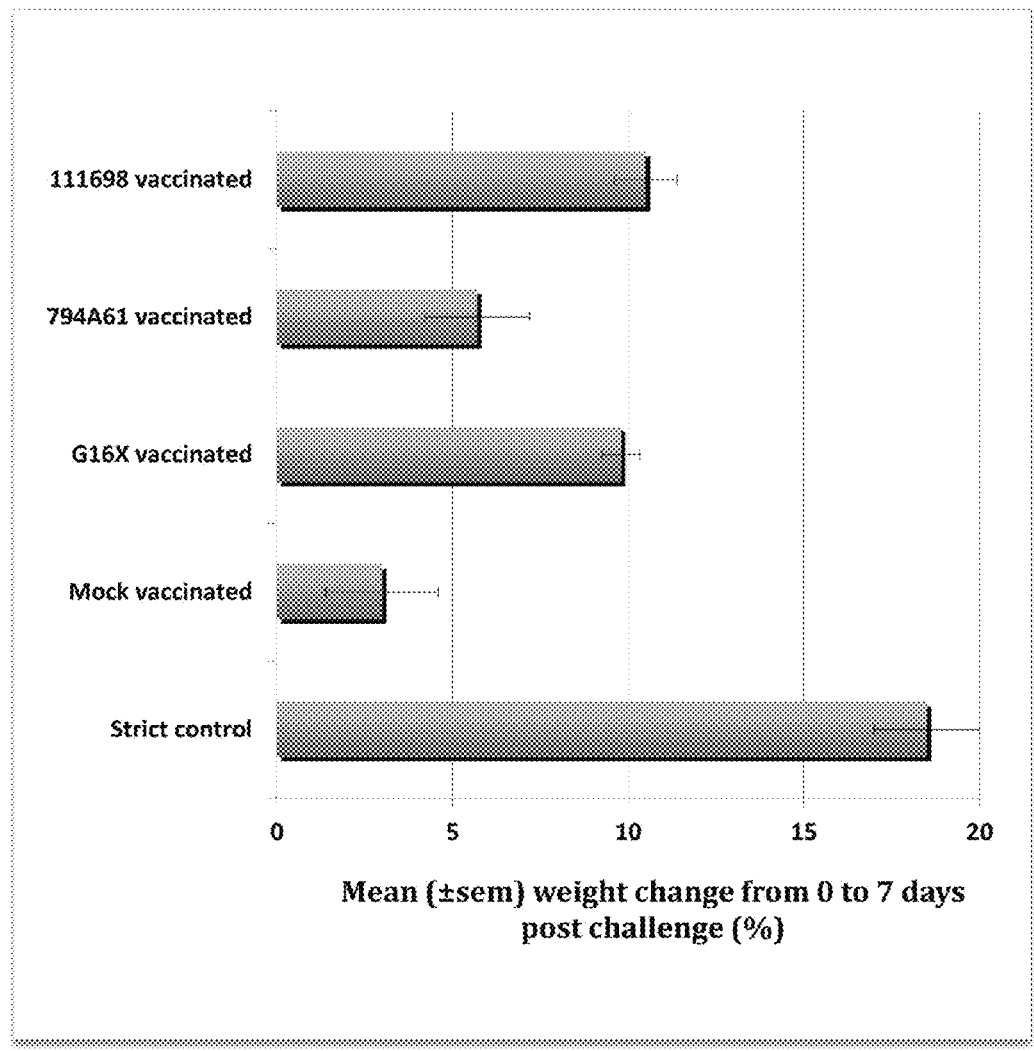
FIG. 7 provides body weight changes (%) in PRRS virus naïve and vaccinated pigs at 7 days after challenge with virulent PRRS virus. Percent body weight gain was determined based on the weight at the time of challenge. Mean values (±SEM) of each group were calculated.

In order to assess the vaccine efficacy of the PRRS virus strains 794A61, 111698 and G16X, groups of pigs were either immunized with one of these viruses or mock-vaccinated and challenged about 5.5 weeks later with the virulent "acute PRRS" strain NADC-20. An additional group of pigs remained PRRS virus naive and served as strict controls. On the day of challenge, the average body weight of all 30 pigs in the study was 49.9±3 kg. No significant differences were found between the mean body weight established for any of the three vaccinated groups and that of either the mock-vaccinated or strict control group. Thus, exposure to any of the three vaccine strains had no obvious impact on animal growth. In contrast, inoculation of the non-vaccinated animals with the NADC-20 virus was associated with a drastic reduction of their potential growth during the ensuing 7 days as evidenced by a meager 3±1.6% weight change, one sixth of the average 18.5±1.54% weight gained by the strict controls (FIG. 7). Likewise, immunization of pigs with the 794A61 vaccine was unsuccessful in this regard as these virus-challenged animals experienced an average weight gain of 5.7±1.5% that was not statistically different (p>0.4) from that recorded for the virus-challenged, mock-vaccinated group. However, as compared to this control group, prior vaccination of the animals with the G16X or 111698 viruses significantly (p≤0.001) counteracted the negative effect of challenge with NADC-20 virus in that these two groups posted average body weight gains of 9.8±0.54% and 10.5±1.1%, respectively (FIG. 7).

Figure 8:
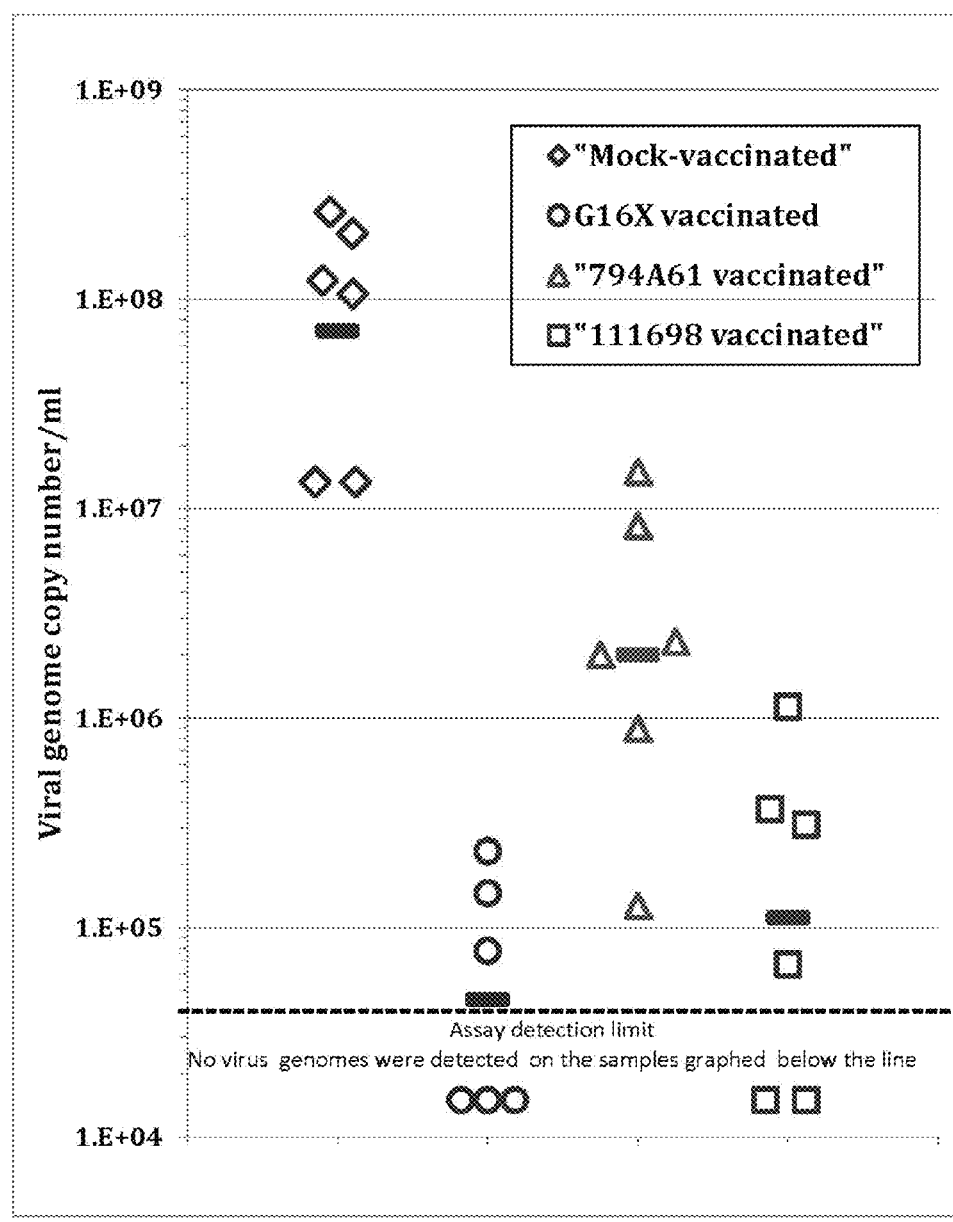
FIG. 8 illustrates the extents and frequencies of viremia in PRRS virus naïve and vaccinated pigs after challenge with virulent PRRS virus. The number of PRRS virus genome copies in serum samples collected from pigs at seven days after challenge with virulent PRRS virus was determined by quantitative real time PCR.

The effect of PRRS virus vaccination on the level of viremia in NADC-20 virus-challenged pig was determined. As expected, none of the strict control pigs, which had not been directly exposed to PRRS virus, had measurable quantities of infectious virus in their sera when sampled together with the other animals at 7 days post NADC-20 virus challenge. Thus, cross-contamination between cubicles did not occur. Likewise, at this time, infectious virus was not evident in the sera of any of the G16X virus-vaccinated pigs. On the other hand, infectious PRRS virus was readily detected in the sera from all six mock-vaccinated animals as well as in 3 and 4 of the six group members that had been vaccinated with either 794A61 or 111698, respectively. To more accurately measure the level of viremia in these animals, especially the apparently PRRS virus-negative members of the G16X vaccinated group, a quantitative real-time PCR assay was employed (FIG. 8). As expected, PRRS viral genomes were not detected in the sera from any of the strict control pigs. In contrast, the virus-challenged, mock-vaccinated animals had a very high virus load in their serum with a group average of $10^{7.85}$ virus genome copies/mL. The level of viremia was significantly lower (p<0.001) for the pigs immunized with the 794A61, 111698 or G16X virus as indicated by their group averages of $10^{6.3}$, $10^{5.0}$, and $10^{4.6}$ virus genome copies/mL, respectively. It should also be noted that PRRS virus genomes could not be demonstrated in the serum from 2 and 3 of the 6 animals vaccinated with the 111698 and G16X virus, respectively, by using this very sensitive assay.

Figure 9:
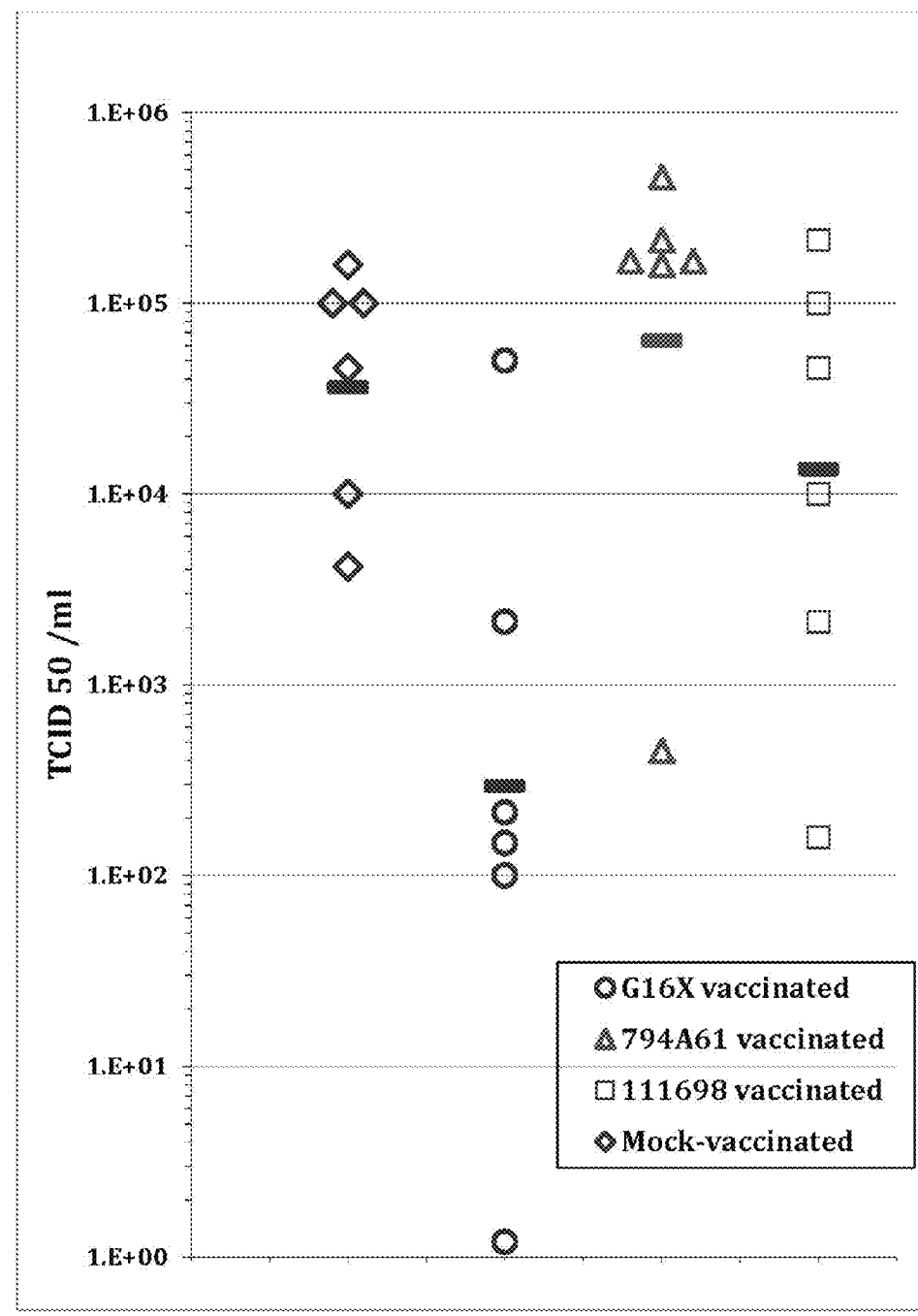
FIG. 9 shows the virus loads in the BAL fluid of PRRS virus naïve and vaccinated pigs after challenge with virulent PRRS virus. The quantity of infectious virus ($TCID_{50}$/mL) in the pigs' BAL fluid samples collected at 14 days post challenge with virulent PRRS virus was titrated in ZMAC cells.

The effect of PRRS virus vaccination on the virus load in the lungs of NADC-20 virus-challenged pigs was determined. At 7 days after challenge with NADC-20 virus, the BAL fluid collected from the lungs of pigs that had previously been mock-vaccinated or immunized with either 794A61 or 111698 virus, had similar amounts of infectious virus, with statistically similar group averages of $10^{4.5}$, $10^{4.8}$, and $10^{4.1}$ $TCID_{50}$/mL, respectively (FIG. 9). In contrast, the BAL fluid samples from the G16X virus-vaccinated group had an average titer of $10^{2.4}$ $TCID_{50}$/mL that was significantly less (p<0.005) than the value determined for the mock-vaccinated group. Moreover, one of the pigs inoculated with the G16X virus lacked detectable infectious virus in its BAL fluid, indicating that the challenge virus had been cleared from its body.

Based on the results presented it was determined that the nearly isogenic PRRS virus strains 794A61, 111698 and G16X can be reasonably rated with respect to vaccine efficacy as poor, moderate and good, respectively.

Example 5

G16X PRRS Virus Vaccine

Example 5. This Example demonstrates the ability of the G16X virus, to provide heterologous protective immunity to pigs vaccinated with this virus and challenge with a virulent type 2 PRRS virus of a different lineage, namely of lineage 1. In this study the efficacy of two PRRS vaccine viruses was tested. One group of animals was vaccinated with the vaccine candidate G16X. A second group of pigs was vaccinated with the commercially available Ingelvac PRRS MLV. The study was a blinded, placebo controlled study. To achieve masking, all personnel involved in daily observations, clinical scoring, assessment of gross and microscopic lung pathology and the processing of samples and interpretation of laboratory results remained masked throughout the experimental phase study.

Twenty-four 6-weeks old pigs were purchased from the University of Illinois Veterinary Research Farm. The herd of swine at this farm is known to be free of all major swine pathogens including PRRS virus, influenza, mycoplasma and circovirus. The negative status for PRRS antibodies of the study animals was confirmed by serology prior to the start of the study. All 24 animals were ear tagged and randomly assigned to a treatment group (four groups and 6 pigs per group) and then transferred to a BSL2 animal containment facility. All of the pigs allocated to the same treatment group (6 pigs) were penned together. After a 7-day period of acclimation each group of pigs was vaccinated according to their treatment allocation as follows:

Group 1: Each pig in the mock vaccine was injected intramuscularly with 2 ml of vaccine diluent.

Group 2: Each pig in this group received one dose of Ingelvac PRRS MLV (Serial No. 245-D45). The vaccine was reconstituted and administered intramuscularly according to the manufacturer instructions (titration of the inoculum indicated that the total dose administered was $4\times10^4$ $TCID^{50}$).

Group 3: Each pig in this group received an intramuscular injection of 2 ml containing a total of $4\times10^4$ $TCID_{50}$ of G16X live PRRS virus vaccine.

The fourth group served as a strict (environmental) control and was not vaccinated. Twenty-eight days after vaccination all of the animals in groups 1, 2 and 3 were challenged with $4\times10^4$ $TCID_{50}$ of the highly virulent PRRS virus isolate LTX1. Based on a phylogenetic analysis of nucleotide sequence of the GP5 gene, the LTX1 virus is thought to belong to lineage 1 of the type 2 (North American-like) PRRSV. The GP5 of the LTX1 virus has a <88% homology with either of the two vaccines used. The LTX1 virus was isolated in 2012 from a sow farm in Illinois, which was suffering from a severe outbreak of PRRS virus. The syndrome observed was characterized by a conception rate of 60%, late term abortions and stillbirths. In addition, there was a 6 week period with 100% pre-wean mortality, followed by 2 more weeks of 80% mortality of pre-wean pigs. The outbreak was so severe that the owner of the farm and the attending veterinarian decided to depopulate the farm. Half the dose of the challenge virus was given intranasally using a nasal sprayer and the other half by intramuscular injection. Subsequently the animals were monitored daily for the next 14 days for clinical signs. Blood samples were collected immediately before and at 7, 10 and 14 days after the virus challenge. Body weight was recorded on the day of challenge and at 7, 10 and 14 days after the challenge. At 14 days after the challenge the animals were euthanized and the lungs examined for gross pathology. Samples were taken for histopathology and a bronchoalveolar lavage performed. All method used were as previously described in the art, except that the BAL fluid collected was tested for infectious virus load using the porcine alveolar macrophage cell line ZMAC.

a. Vaccination with the G16X Virus Stimulates a Strong Interferon-Alpha Response at 4 Days Post-Vaccination.

Figure 13:
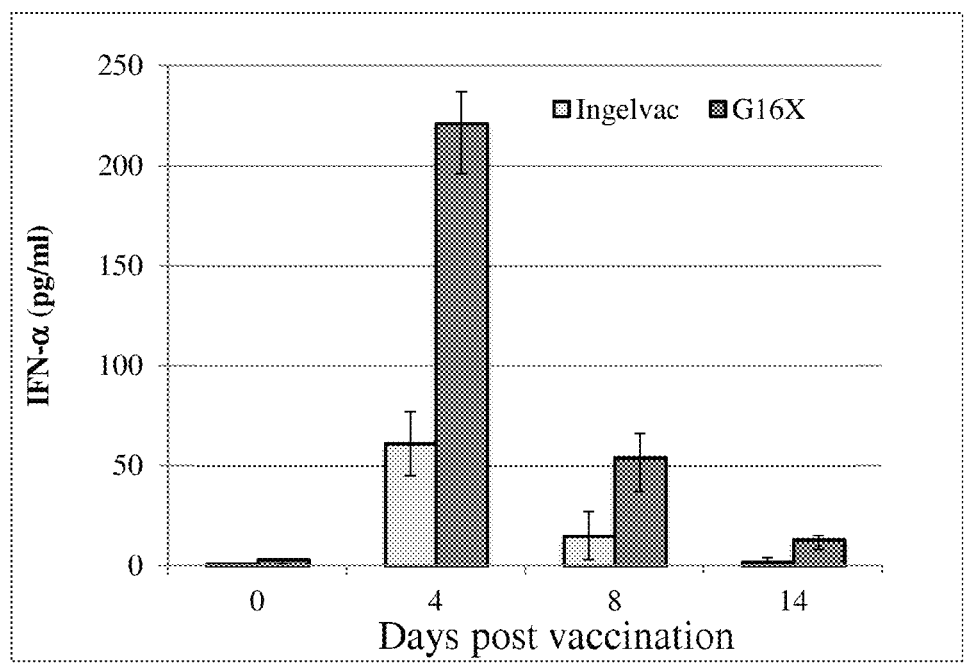
FIG. 13 shows serum Interferon alpha levels in pigs after their inoculation with either Ingelvac PRRS MLV or G16X. Two groups of pigs (n=6) were inoculated with either Ingelvac PRRS MLV or G16X as described in materials and methods. Serum samples were collected at the indicated time points after vaccination and the level of interferon alpha measured by ELISA. Data represent the mean±SE of the 6 samples tested per time point in each treatment group. Mock-vaccinated animals had <2 pg/ml of serum in each time point tested (data not shown).

In this study, it was discovered that the G16X virus has a unique biological property, namely that 4 days after the intramuscular administration of G16X vaccine virus into pigs, a vigorous systemic interferon alpha response was detectable in their serum. This response began to subside 4 days later (day 8 post vaccination) and was still present at 14 days post vaccination (FIG. 13). In contrast, pigs inoculated with the Ingelvac PRRS MLV vaccine exhibited a much lower (4-fold) response at the peak of the response (day 4 post vaccination) and was not detectable by day 14. These results confirm that the G16X virus has a unique biotype regarding the interferon alpha response of pigs to their exposure to this virus.

b. Efficacy of the G16X Vaccine in Regards to Pig Weight Gain in Pigs Challenged with a Highly Virulent PRRS Virus At the time of challenge, the average body weight of the 24 pigs in the study was 51±4 kg, and there no differences in the average body weight between groups. Likewise, no clinical signs were observed in the animals immunized with either the commercial PRRS MLV vaccine or the G16X virus. These results indicate that just like the commercially available MLV vaccine, the G16X virus, which was derived from a naturally non-virulent virus, is also not virulent. Thus, exposure of the pigs to either vaccine G16X or Ingelvac PRRS MLV had no obvious impact on their growth or health.

Figure 14:
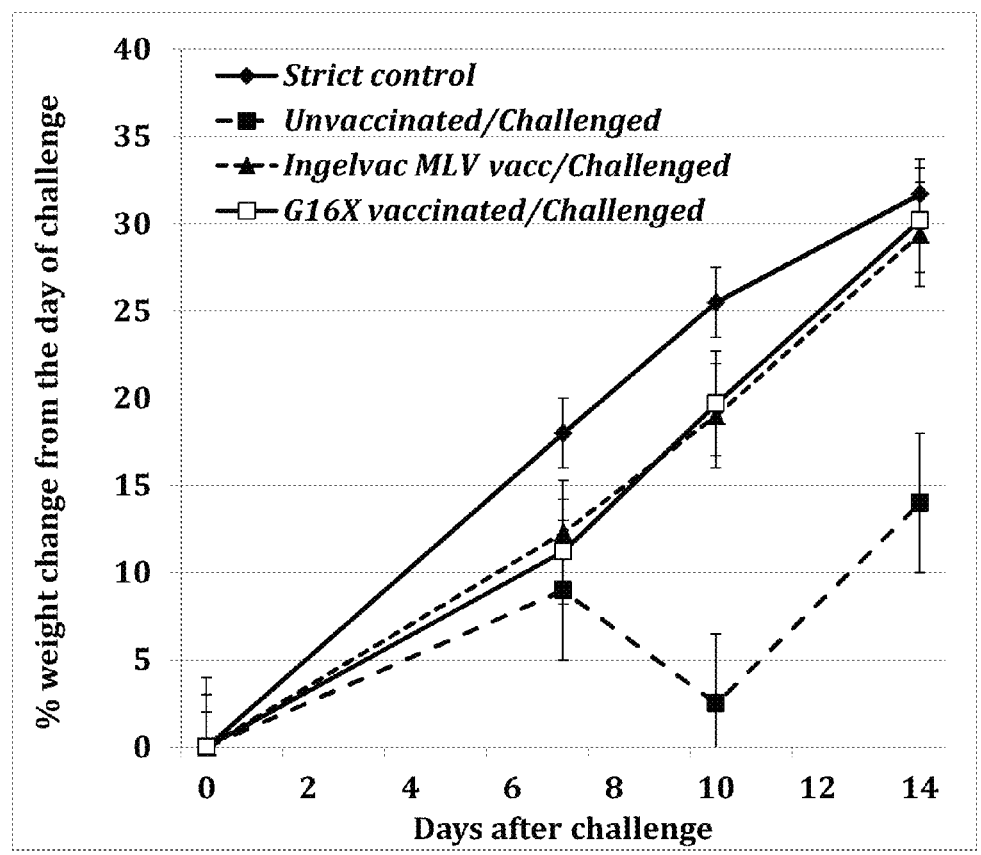
FIG. 14 shows body weight (BW) changes in pigs after exposure to virulent PRRS virus. Mock-vaccinated, Ingelvac PRRS MLV-vaccinated or G16X virus-vaccinated pigs (n=6 for each group) were weighed immediately prior to and at 7, 10 and 14 days after challenge with the wild-type PRRSV isolate LTX1. Unchallenged and unvaccinated animals (strict controls, n=6) were also weighed at these four time points. The changes in BW during the ensuing 7-, 10- and 14-days after challenge were determined on an individual basis and the % weight change relative to its BW at the time of challenge calculated. Results represent the mean % weight change of each group +/−SDEV. All groups consist of six animals per group except the G16X group. This group had six animals until day 10 when the group was reduced to 5 animals. One animal in this group was eliminated because it developed an intestinal torsion that required that the animal be euthanized at day 10 after virus challenge.
Figure 15:
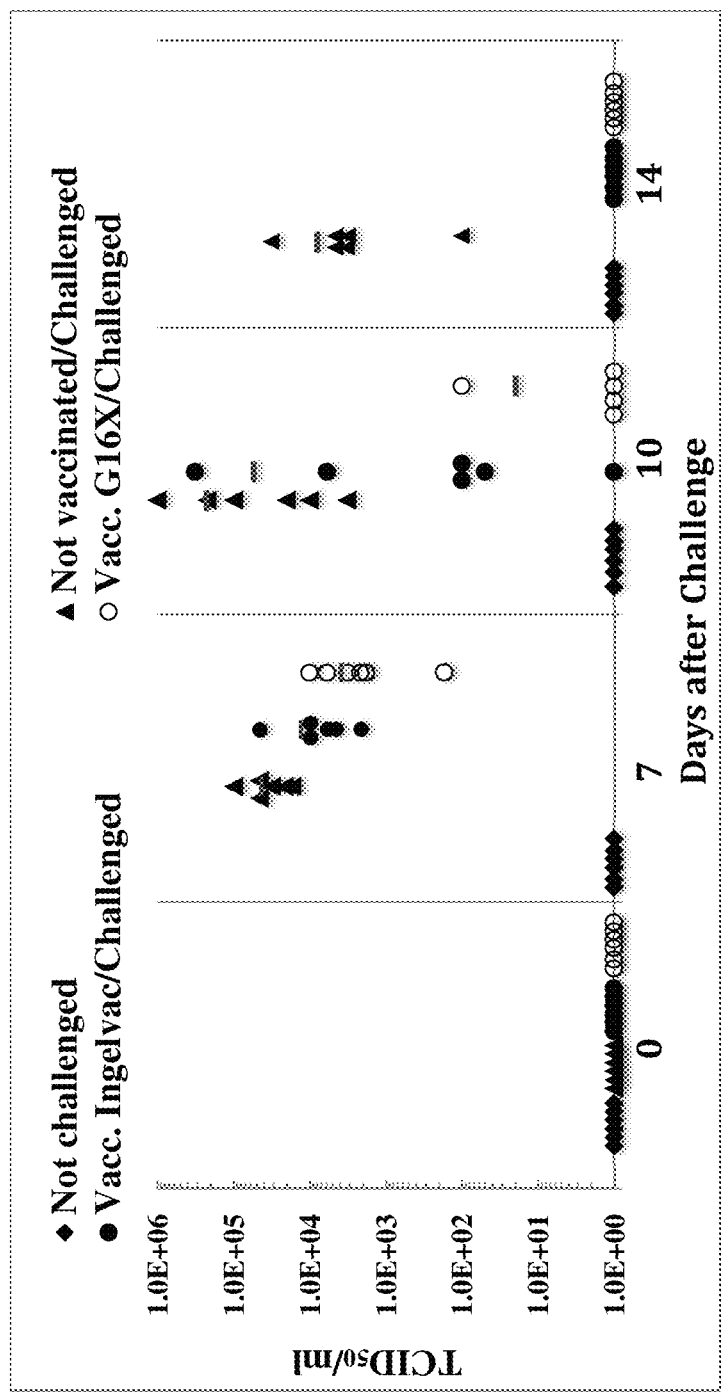
FIG. 15 shows the extent and frequency of viremia in pigs after exposure to virulent PRRS virus. Serum samples were collected from Mock-vaccinated, Ingelvac PRRS MLV-vaccinated or G16X virus-vaccinated animals immediately prior to and at the indicated days after challenge with the wild-type PRRS virus LTX1. Samples were also taken at these time points for the unchallenged and unvaccinated animals (strict controls) (n=6). The virus loads in the sera were determined by performing infectious virus titrations in ZMAC cells. Results are presented for individual pigs and then averaged for members of each group (horizontal red bars). One pig in the G16X group was eliminated from the trail at 10 days after challenge (see FIG. 14 legend).
Figure 16:
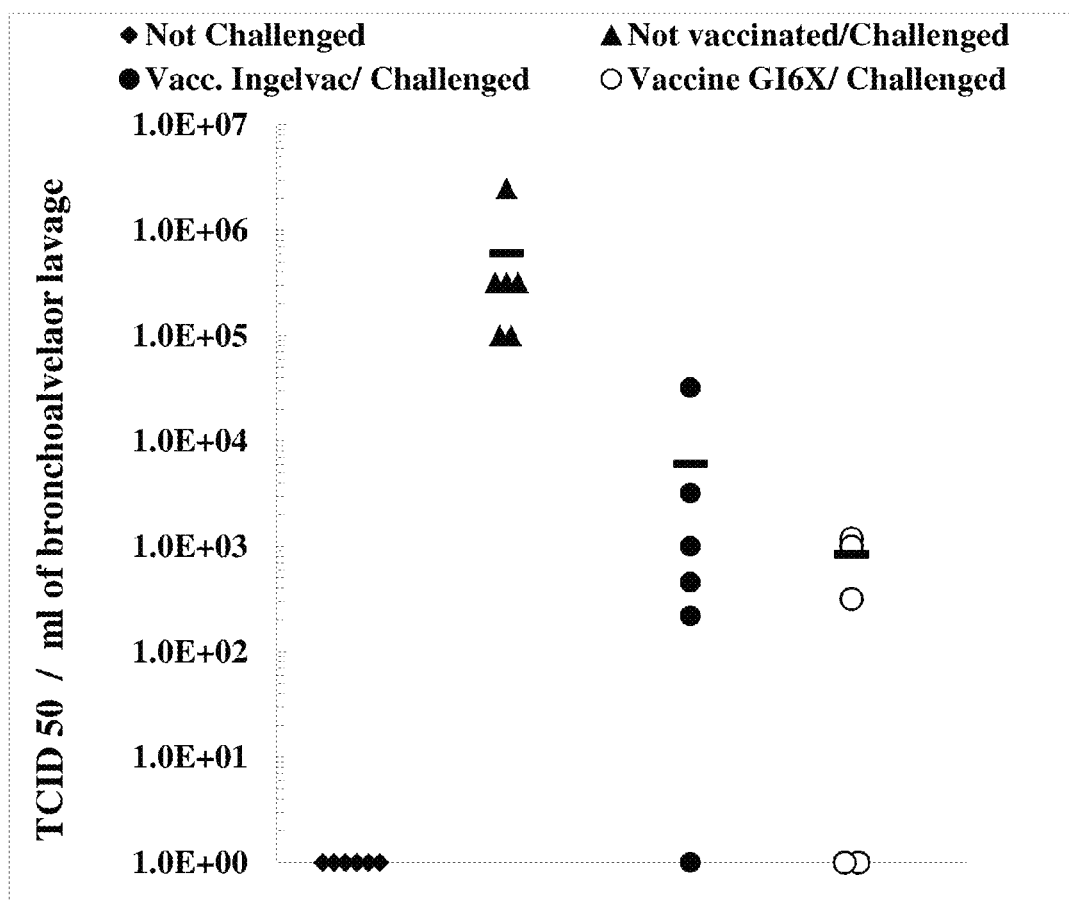
FIG. 16 shows virus load in the BAL fluid of pigs after exposure to virulent PRRS virus. BAL fluid was collected from the lungs of Mock-vaccinated, Ingelvac PRRS MLV-vaccinated or G16X virus-vaccinated animals at 14 days after challenge with the wild-type PRRS virus LTX1. Samples were also obtained at this time from unchallenged and unvaccinated animals (strict controls) (n=6). The virus load in the BAL fluid of each animal was determined by performing infectious virus titrations in ZMAC cells. Results are presented for individual pigs and then averaged for members of each group using only virus positive samples (horizontal bars).

To measure the protective immunity elicited by the two vaccines being examined with regards to pig growth, the % body weight gain was calculated for each animal from the day of virus challenge to 7, 10 and 14 days after virus challenge. The pigs in the unchallenged (strict control) group exhibited a steady rate of growth with an average increase of 32% in 14 days (FIG. 14). As compared with the strict control group, infection of the Mock-vaccinated pigs with PRRS virus LTX1 caused a noticeable decrease in their rate of growth, and resulted in a net body weight loss from 7 to 10 days after challenge. Afterwards the animals began to gain body weight back, ending with a 14% weight gain from the time of challenge (FIG. 14). Prior immunization of the animals with either vaccine counteracted the negative effect of challenge with LTX1 virus in that the groups receiving either vaccine posted similar average BW gains of about 12%, 19% and 29% at 7, 10 and 14 days post challenge, respectively.

c. Efficacy of the G16X Vaccine in Regards to the Control of Viremia in Pigs Infected with a Heterologous Highly Virulent PRRS Virus At the time of challenge (28 days post vaccination) none of the pigs in the trial had a detectable infectious virus in their serum. All of the animals that were mock vaccinated and then challenged with the LTX1 virus exhibited high levels of viremia at 7, 10 and 14 days after challenge (FIG. 15). All of the pigs in the two vaccinated groups were viremic at days 7 post challenge with no major differences between these two groups. However, by 10 days only 1 of the 5 animals vaccinated with the G16X virus was still viremic. In contrast, 5 of the 6 animals vaccinated with the Ingelvac PRRS MLV were viremic. By 14 days after vaccination, all of the animals in both vaccinated groups no longer had detectable infectious virus in their blood stream.

d. Efficacy of the G16X Vaccine in Regards to the Control of Virus Load in the Lungs of Pigs Infected with a Highly Virulent PRRS Virus At 14 days after challenge with the LTX1 virus, not surprisingly the greatest virus load in the pigs' BAL fluids was found for all members of the non-vaccinated group (FIG. 16, average of $10^{5.8}$ $TCID_{50}$/ml). At this time, only three of the five animals that had been immunized with G16X virus grown in ZMAC cells still had detectable amounts of PRRS virus in their BAL fluid. The average load in these three positive animals was $10^{2.9}$ $TCID_{50}$/ml. This represents a >700 fold reduction on the group average amount of virus that was present in the lung of the unvaccinated and challenged control pigs. In contrast, infectious virus was still detected in the BAL fluids of five of the six pigs vaccinated with the Ingelvac PRRS MLV. Moreover, their average virus load in these five positive animals was $10^{3.8}$ $TCID_{50}$/ml, which was approximately 10-fold greater than that measured for the immunized group immunized with the G16X virus.

In summary this example demonstrates that the G16X virus, akin to the commercial MLV vaccine is not virulent, but has superior efficacy to the commercially available MLV vaccine in a heterologous challenge with virulent type 2 PRRS virus of a different lineage.

Example 6

Sequence Information

Example 6. Embodiments of the invention can relate to one or more nucleic acid or protein sequences including the items described herein. Any sequence information, including such submitted separately in electronic format, is considered part of the description herewith and is incorporated herein by reference.

TABLE 3

```
SEQ ID NO: 1
catttgtgtt gtcaggagct gtgaccattg gcacagccca aaacttgctg cacggaagcg    60
cccttctgtg acagcctcct tcagggagc ttgggggtct ttccctagca ccttgcttcc    120
```

TABLE 3-continued

| | | | | | |
|---|---|---|---|---|---|
| ggagttgcac | tgctttacgg | tctctccacc | cctttaacca | tgtctgggat | acttgatcgg | 180 |
| tgcacgtgta | cccccaatgc | cagggtgttt | atggcggagg | gccaagtcta | ctgcacacga | 240 |
| tgcctcagtg | cacggtctct | ccttcctctg | aatctccaag | tttctgaact | cggggtgcta | 300 |
| ggcctattct | acaggcccga | agagccactc | cggtggacgt | tgccacgtgc | attccccact | 360 |
| gttgagtgct | cccccgccgg | ggcctgctgg | cttctgcaa | ttttccaat | tgcacgaatg | 420 |
| accagtggaa | acctgaactt | ccaacaaaga | atggtacggg | tcgcagctga | actttacaga | 480 |
| gccggccagc | tcacccctac | agtcttaaag | actttacaag | tttatgaacg | gggttgccgc | 540 |
| tggtacccca | tcgtaggacc | tgtccctgga | gtggccgttt | tcgccaactc | cctacatgtg | 600 |
| agtgataaac | ctttcccggg | agcaactcac | gtgttaacca | acctgccgct | cccgcagaga | 660 |
| cccaagcctg | aagactttg | cccctttgag | tgtgctatgg | ctaccgtcta | tgacattggt | 720 |
| catgacgccg | tcatgtatgt | ggccgaaggg | aaagtctcct | gggcccctcg | tggcggggat | 780 |
| gaagtgaaat | ttgaaactgt | ccccgggag | ttggagttga | ttgcgaatcg | actccgcacc | 840 |
| tccttcccgc | cccaccacac | agtggacatg | tctaagttcg | ccttcacagc | cctgggcgt | 900 |
| ggtgttcta | tgcgggtcga | acgccaacac | ggctgcctcc | ccgctgacac | tgtccctgaa | 960 |
| ggcaactgct | ggtggagctt | gtttaacttg | ctcccactgg | aagttcagaa | caaagaaatt | 1020 |
| cgccatgcta | accaatttgg | ctaccagacc | aagcatggtg | tctctggcaa | gtacctacag | 1080 |
| cggaggctgc | aagttaatgg | tctccgagca | gtaactgacc | tgaatggacc | tatcgtcgta | 1140 |
| cagtacttct | ccgttaagga | gagttggatc | cgccacttga | aactggcgga | agaacccagc | 1200 |
| taccctgggt | ttgaggacct | cctcagaata | agggttgagc | ccaacacgtc | gccattggct | 1260 |
| gacaaggatg | aaaaaatttt | ccggtttggc | agtcacaagt | ggtacggcgc | tggaaagaga | 1320 |
| gcaaggaaag | cacgctctag | tgcgactgct | acagtcgctg | gccgcgcttt | gtccgttcgt | 1280 |
| gaaacccggc | aggccaagga | gcacgaggtt | gccggcgcca | acaaggctgg | gcacctcaaa | 1440 |
| cattactccc | cgcctgccga | agggaattgt | ggttggcact | gcatttccgc | catcgccaac | 1500 |
| cggatggtga | attccaaatt | tgaaaccacc | cttcccgaaa | gagtgagacc | ttcagatgac | 1560 |
| tgggctactg | acgaggatct | tgtgaatgcc | atccaaatcc | tcaggctccc | tgcggccttg | 1620 |
| aacaggaacg | gcgcttgtgc | tagcgccaag | tacgtactta | agctggaagg | tgagcattgg | 1680 |
| actgtcactg | tgacccctgg | gatgtcccct | tctttgctcc | ctcttgaatg | tgttcagggc | 1740 |
| tgttgtgagc | ataagggcag | tcttggttcc | ccagatgcag | tcgaggtttt | cggatttgac | 1800 |
| cctgcttgcc | ttgaccggct | ggctgaggtg | atgcacctgc | ctagcagtgc | tatcccagcc | 1860 |
| gctctggccg | aaatgtccgg | cgattccgat | cgttcggctt | ccccggtcac | caccgtgtgg | 1920 |
| actgtttcgc | agttctttgc | ccgccacaat | ggagggaatc | accctgacca | agtgcgctta | 1980 |
| gggaaaatta | tcagcctttg | tcaggtgatt | gaggactgct | gctgttccca | gaacaaaacc | 2040 |
| aaccgggtca | ccccggagga | ggtcgcagca | aagattgacc | tgtaccttcg | tggcgcaaca | 2100 |
| aatcttgaag | aatgcttggc | caggcttgag | aaagcgcgcc | cgccacgcgt | aatggacacc | 2160 |
| tcctttgatt | gggatgttgt | gctccctggg | gttgaggcgg | caactcagac | gaccgaactg | 2220 |
| ccccaggtca | accagtgtcg | cgctctggtc | cctgttgtaa | ctcaaaagtc | cttggacaac | 2280 |
| aactcggtcc | cctgaccgc | cttttcactg | gctaactact | actaccgtgc | gcaaggtgac | 2340 |
| gaagttcgtc | accgtgaaag | actaaccgcc | gtgctctcca | agttggaagg | ggttgttcga | 2400 |
| gaagaatatg | ggctcatgcc | aaccgggcct | ggtccacggc | ccacactgcc | acgcgggctc | 2460 |
| gacgaactca | aagaccagat | ggaggaggac | ttgctgaaac | tggctaacgc | ccagacgact | 2520 |

TABLE 3-continued

```
tcggacatga tggcctgggc agtcgagcag gttgacctaa aaacttgggt caagaactac    2580
ccgcggtgga caccaccacc ccctccgcca aaagttcagc ctcgaaaaac gaagcctgtc    2640
aagagcttgc cagagagaaa gcctgtcccc gccccgcgca ggaaggttgg gtccgattgt    2700
ggcagcccga tttcattggg cgacgatgtc cctaacagtt gggaagattt ggctgttggt    2760
agccccttcg atctcccgac cccacctgag ccggcaacac cttcaagtga gctggtgatt    2820
gtgtccgcac cgcaatgcat cttcaggccg gcgacaccct tgagtgagcc ggctccaatt    2880
cccgcacccc gcggggttgt gtctcgaccg gtgacaccct tgaatgagcc gataccgtgt    2940
cccgcaccgc ggcgtaagtt tcagcagatg agaagattga gttcggcggc ggtaatcccg    3000
ccgtaccagg acgagcccct agatttgtct gcttcctcac agactgaata tgaggcctct    3060
cccctagcac cgccgcagag cgagggtgtt ctgggagtag aggggcagga agctgaggaa    3120
gccctaagtg aaatctcgga catgtcgggt aacattaaac ctgcgtccgt atcatcaagc    3180
agctccttgt ccagcgtgag aatcactcgc ccaaaatact cagctcaagc catcatcgac    3240
tcgggcgggc cctgcagtgg gcatctccaa gaggtaaagg aaacatgcct cagtatcatg    3300
cgcgaggcat gtgatgcgac taagcttgat gaccctgcta cgcaggagtg gctttctcgc    3360
acgtgggatc gggtggacat gctgacttgg cgcaacacgt ctgcctacca ggcgtttcgc    3420
accttagatg gcaggttaaa gttcctccca aaaatgatac tcgagacacc gccgccctat    3480
ccgtgtgagt ttgtgatgat gcctcacacg cctgcacctt ccgtaggtgc ggagagcgac    3540
cttaccattg gctcagtcgc tactgaagat gttccacgca tcctcgagaa aatagaaaat    3600
gtcggcgaga tgaccaacca gggacccttg gccttctccg aggataaaacc ggtagatgac    3660
caacttgcca aagaccccg gatatcgtcg cagaggtctg acgagagcac atcagctccg    3720
cccgcaggca caggtggcgc cggctcattt accgatttgc cgccttcgga cggcgtggat    3780
gcggacggag gggggccgtt ttggacggta aaaagaaaag ctgaaaggct ctttgaccaa    3840
ccgagccgtc aggtttttga cctcgtctcc catctccctg ttttcttctc acgccttttc    3900
aaccctggcg gtggttattc tccgggtgat tgggggttttg cagcttttac tctattgtgc    3960
ctctttttat gttacagtta cccagccttt ggtattgctc ccctcttggg tgtgtttttct   4020
gggtcctctc ggcgcgttcg aatgggggtt tttggctgct ggttggcttt tgctgttggt    4080
ccgttcaagc ctgtgtccga cccagtcggc gctgcttgtg agtttgactc gccagagtgt    4140
agaaatatcc ttcattcttt tgagcttctc aaaccttggg accctgttcg cagccttgtt    4200
gtgggccccg tcggtctcgg tcttgccatt cttggcaggt tactgggcgg ggcacgcagc    4260
atctggcact ttttgcttag gcttggcatt gttgcagact gtgtcttggc tggagcttat    4320
gtgctttctc aaggtaggtg taaaaagtgc tggggatctt gtataagaac tgctcctaat    4380
gaggtcgctt ttaacgtgtt tccttttaca cgtgcgacca ggtcgtcact aatcgacctg    4440
tgcgatcggt tttgtgcgcc aaaaggcatg gaccccattt ttctcgccac tgggtggcgc    4500
gggtgctggg ccggccgaag ccccattgag caaccctctg aaaaacccat cgcgtttgcc    4560
cagttggatg aaaagaagat tacgctagg actgtggtcg cccagcctta tgaccccaac    4620
caagccgtaa agtgcttgcg ggtattgcag gcgggtgggg tgatggtggc taaggcagtc    4680
ccaaaagtgg tcaaggtttc cgctgttcca ttccgagccc ccttctttcc caccggagtg    4740
aaagttgacc ctgaatgcag ggtcgtggtt gaccccgaca ctttcaccgc agctctccgg    4800
tctggctact ccaccacaaa cctcgtcctc ggtgtagggg attttgccca gctgaatgga    4860
ttaaaaatca ggcaaatttc caagccttca ggaggaggcc cacacctcat ggctgccctg    4920
```

TABLE 3-continued

```
catgttgcct gctcgatggc tttgcacatg cttgctggga tttatgtgac tgcggtgggt    4980
tcttgcggca ccggcaccaa cgacccgtgg tgcgctaacc cgtttgccgt ccctggctac    5040
ggacctggct ctctctgcac gtccagattg tgcatttccc aacatggcct taccctgccc    5100
ttgacagcac tcgtggcggg attcggtatt caagaaattg ccttggtcgt tttgattttt    5160
gtttccatcg gaggcatggc tcacaggttg agttgtaagg ctgatatgct gtgtgttttg    5220
cttgcaattg ccagctatgt ttgggtacct cttacctggt tgctttgtgt gtttccttgc    5280
tggttgcgct gttttttcttt gcatcccctc accatcctat ggttggtgtt tttcttgatt    5340
tctgtgaata tgccttcagg aatcttggcc atggtgttgt tggtttctct ttggcttctt    5400
ggtcgttata ctaatgttgc tggtcttgtc accccctacg acattcatca ttacactagt    5460
ggcccccgcg gtgttgccgc cttggctacc gcaccagatg ggacctactt ggccgctgtc    5520
cgccgcgctg cgttgactgg ccgcaccatg ctgtttaccc cgtcccagct gggtctctt     5580
cttgagggtg ctttcagaac tcgaaaaccc tcactgaaca ccgtcaatgt ggtcgggtcc    5640
tccatgggct ctggcggggt gttcaccatc gacggaaaaa ttaagtgcgt aactgccgca    5700
catgtcctta cggcaattc agctagggtt tccggggtcg gcttcaatca aatgcttgac     5760
tttgacgtaa agggagattt cgccatagct gattgcccga attggcaagg ggctgccccc    5820
aagacccaat tctgcaagga tgggtggact ggccgtgcct attggctaac atcctctggc    5880
gtcgaacccg gcgtcattgg aaaaggattc gccttctgct tcaccgcgtg cggcgattcc    5940
gggtccccag tgatcaccga ggccggtgag cttatcggcg ttcacacggg atcaaataaa    6000
caaggaggag gcatcgttac gcgcccctca ggccagtttt gtaatgtggc acccatcaag    6060
ctaagcgaat taagtgaatt ctttgctggg cctaaggtcc cgctcggtga tgtgaaggtt    6120
ggcagccaca taattaaaga cataggcgag gtgccttcag atctttgtgc cttgcttgct    6180
gccaaacctg aactgaagg aggcctctcc accgtccaac ttctttgtgt gttttctc      6240
ctgtggagaa tgatgggaca tgcctggacg cccttggttg ctgtgggttt cttatcttg    6300
aatgaggttc tcccagccgt cctggtccgg agtgtttctct cctttggaat gtttgtgcta   6360
tcctggctca cgccatggtc tgcgcaagtt ctgatgatca ggcttctaac agcagccctt   6420
aacaggaaca gatggtcact tgccttttc agcctcggtg cagtgaccgg ttttgtcgca    6480
gatcttgcgg ctactcaggg gcatccgttg caggcagtta tgaatttgag cacctatgca    6540
ttcctgcctc ggatgatggt tgtgacctca ccagtcccag tgattgcgtg tggtgttgtg    6600
cacctacttg ccatcatttt gtacttgttt aagtaccgtg gcctgcacca atccttgtt    6660
ggtgatggag tgttctctgc ggctttcttc ctgcgatact tgccgagggg aaagttgagg    6720
gaagggggtgt cgcaatcctg cggaatgaat catgagtctc tgactggtgc cctcgctatg   6780
agactcaatg acgaggactt ggatttcctt acgaaatgga ctgatttaa gtgctttgtt    6840
tctgcgtcca acatgaggaa tgcagcgggt caatttatcg aggctgccta tgctaaagca   6900
cttagagtag agcttgccca gttggtgcag gttgataaag ttcgaggaac tttggccaaa    6960
cttgaagcct ttgctgatac cgtggcaccc caactctcgc ccggtgacat tgttgtcgct    7020
ctcggccata cgcctgttgg cagtatcttc gacctaaagg ttggtagcac caagcatacc    7080
ctccaagcca ttgagaccag agtccttgct gggtccaaaa tgaccgtggc gcgcgtcgtc   7140
gacccgaccc ccacgccccc acccgcacct gtgcccatcc ccctcccacc gaaagttctg   7200
gagaatggcc ccaacgcttg gggggatgag gaccgtttga ataagaagaa gaggcgcagg   7260
atggaagccc tcggcatcta tgttatgggc gggaaaaagt accagaaatt tgggataag    7320
```

TABLE 3-continued

| | |
|---|---|
| aattccggtg atgtgtttta tgaggaggtc cataataaca cagatgagtg ggagtgtctc | 7380 |
| agagttggcg accctgccga cttttgaccct gagaagggaa ctctgtgtgg acatgtcacc | 7440 |
| attgaagata aggcttacca tgtttacacc tcatcatctg gtaagaagtt cttggtcccc | 7500 |
| gtcaatccag agaatggaag agtccaatgg gaagctgcaa agctttccgt agagcaggcc | 7560 |
| cttggtatga tgaacgtcga cggcgaactg actaccaaag aactggagaa actgaaaaga | 7620 |
| ataattgaca aactccaggg cctgactaag gagcagtgtt taaactgcta gccgccagcg | 7680 |
| gcttgacccg ctgtggtcgc ggcggcttgg ttgttactga acagcggta aaaatagtca | 7740 |
| aatttcacaa ccggaccttc accctgggac ctgtgaattt aaaagtggcc agtgaggttg | 7800 |
| agctaaaaga cgcggttgag cacaaccaac acccggttgc gagaccggtc gatggtggtg | 7860 |
| ttgtgctcct gcgttccgcg gttccttcgc ttatagacgt cttgatctcc ggtgctgatg | 7920 |
| catctcccaa gttgcttgcc catcacgggc cgggaaacac tgggatcgat ggcacgctct | 7980 |
| gggattttga gtccgaagcc actaaagagg aagtcgcact tagtgcgcaa ataatacagg | 8040 |
| cttgtgacat taggcgcggc gacgctcctg aaattggtct cccttacaag ctgtaccctg | 8100 |
| ttaggggtaa ccctgagcgg gtaaaaggag ttctacagaa tacaaggttt ggagacatac | 8160 |
| cttacaaaac ccccagtgat actggaaacc cagtgcacgc ggctgcctgc cttacgccca | 8220 |
| acgccactcc ggtgactgat gggcgctccg tcttggccac gaccatgccc tccgggtttg | 8280 |
| agttgtatgt accaaccata ccagcgtctg tccttgatta ccttgattct aggcctgact | 8340 |
| gccctaaaca gttgacagag cacggctgtg aagatgccgc actgagagac ctctccaaat | 8400 |
| atgacttgtc cacccaaggc tttgttttac ctggagtttt tcgccttgta cggaaatacc | 8460 |
| tgtttgccca tgtaggtaag tgcccacccg ttcatcggcc ttctacttac cctgctaaga | 8520 |
| attctatggc tggaataaat gggaataggt tcccaaccaa ggatattcag agcgtccctg | 8580 |
| aaatcgacgt tctgtgtgca caggctgtgc gggaaaactg gcaaactgtt accccttgta | 8640 |
| ctcttaagaa acagtattgc gggaagaaga agactaggac catactcggc accaataatt | 8700 |
| ttatcgcgct agcccaccga gcagcgttga gtggtgtcac ccagggcttc atgaaaaagg | 8760 |
| cgtttaactc gcccatcgcc ctcggaaaaa acaagtttaa ggagctacag accccggtcc | 8820 |
| taggcaggtg ccttgaagct gatcttgcat cctgcgaccg atccacacct gcaattgtcc | 8880 |
| gctggttttgc cgccaacctc ctttatgaac ttgcctgcgc tgaagagcat ttaccgtcgt | 8940 |
| acgtgctgaa ctgctgccac gacttactgg tcacgcaatc cggcgcagtg actaagagag | 9000 |
| gtggcctgtc gtctggcgac ccgatcacct ctgtgtctaa caccatttac agtttggtga | 9060 |
| tctatgcaca gcatatggtg ctcagttact tcaaaagtgg tcaccccat ggcctcttgt | 9120 |
| tcttacaaga ccagctaaag tttgaggaca tgctcaaggt tcaaccctg atcgtctatt | 9180 |
| cggacgacct cgtgctgtat gccgagtctc ccaccatgcc aaactatcac tggtgggttg | 9240 |
| aacacctgaa ttcgatgctg gggtttcaga cggatccaaa aagacagcc ataacagact | 9300 |
| cgccatcatt tctaggctgt agaataataa atggacgcca gctagtcccc aaccgtgaca | 9360 |
| ggattctcgc ggccctcgcc taccacatga aggcgagtaa tgtttctgaa tactacgcct | 9420 |
| cagcggctgc aatactcatg gacagctgtg cttgtttgga gtatgatcct gaatggtttg | 9480 |
| aagaacttgt agttggaata gcgcaatgcg cccgcaagga cggttacagc tttcccggca | 9540 |
| cgccgttctt tatgtccatg tgggaaaaac tcaggtccaa ttatgagggg aagaagtcga | 9600 |
| gagtgtgcgg gtactgcggg gccccggccc cgtacgctac tgcctgtggc ctcgacgtct | 9660 |
| gcatttacca cacccactc caccagcatt gtccagtcac aatctggtgt ggccatccag | 9720 |

TABLE 3-continued

```
cgggttctgg ttcttgtagt gagtgcaaat ccctgtagg gaaaggcaca agcccttag   9780
acgaggtgct ggaacaagtc ccgtacaagc ccccacggac cgttatcatg cgtgtggagc   9840
agggtcttac ccccttgac ccaggtagat accagactcg ccgcggatta gtctccgtca   9900
ggcgtggaat caggggaaat gaggttgaac taccagacgg tgattatgct agtaccgcct   9960
tgctccctac ctgtaaagag atcaacatgg tcgctgttgc ttccaatgta ttgcgcagca  10020
ggttcatcat tggtccaccc ggtgctggga aaacatactg gctccttcaa caggtccagg  10080
atggtgatgt tatttacaca ccaacccacc agaccatgct tgacatgatt agggctttgg  10140
ggacgtgccg gttcaacgtc ccggcaggca caacgctgca attccccgtc cctcccgta   10200
ccggtccgtg ggttcgcatc ctggccggcg gttggtgtcc tggcaagaat tccttcctgg  10260
atgaagcagc gtattgcaat caccttgatg tcttgaggct tcttagcaaa actaccctca  10320
cctgtctggg agacttcaaa caactccacc cagtgggttt tgattctcat tgctatgttt  10380
ttaacatcat gcctcaaact caactgaaga ccatctggag gtttggacag aatatctgtg  10440
atgccatcca gccagattac agggacaaac tcatgtccat ggtcaacaca acccgtgtga  10500
cctacgtgga aaagcctgtc aggtatgggc aagtcctcac cccctaccac agggaccgag  10560
aggacgacgc catcactatt gactccagtc aaggcgccac attcgatgtg gttacactgc  10620
atttgcccac aaaagattca ctcaacaggc agagagccct tgttgctatc caggggcaa   10680
gacatgctat ctttgtgtat gacccacaca ggcagctgca gagcctgttt gatcttcctg  10740
caaaaggtac acccgtcaac cttgcagtgc accgcgacgg gcagctgatc gtgctagata  10800
gaaataacaa agaatgcacg gttgctcagg ctctaggtaa cggagataaa tttagggcca  10860
cagacaaacg cgttgtagat tctctccgcg ccatttgtgc tgatctagaa gggtcgagct  10920
ctccgctccc caaggtcgca cacaacttgg gattttattt ttcacctgat ttaacacagt  10980
ttgctaaact cccagcagaa cttgcacctc actggcctgt ggtgacaacc cagaacaatg  11040
aaaagtggcc agatcggctg gttaccagcc ttcgccctat ccataaatat agccgcgcgt  11100
gcatcggtgc cggctatatg gtgggcccct cggtgtttct aggcactcct ggggttgtgt  11160
catactatct cacaaaattt gttaagggcg aggctcaagt gcttccggag acggttttca  11220
gcaccggccg aattgaggta gactgccggg aatatcttga tgatcgggag cgagaggttg  11280
ctgcgtccct cccacatgcc ttcattggcg acgtcaaagg cactaccgtt ggaggatgcc  11340
accatgtcac ctccagatac ctcccgcgct tccttcccaa ggaatcggtt gcggtagtcg  11400
gggtttcaag tcccggaaaa gccgcgaaag cattgtgcac actgacagat gtgtacctcc  11460
cagaccttga agcctatttc caccccggaga cccagtccaa gtgctggaga atgatgttgg  11520
acttcaagga agttcgacta atggtctgga aagacaaaac agcctatttc caacttgaag  11580
gtcgctattt cacctggtat cagcttgcta gctatgcctc gtacatccgt gttcctgtca  11640
actccacggt gtacttggac ccttgcatgg gccccgccct ttgcaacagg aaagtcgtcg  11700
ggtccactca ttggggagct gacctcgctg tcaccccta tgattacggc gctaaaatta  11760
tcctgtctag cgcgtaccat agtgaaatgc cccccggata caagattctg gcgtgcgcgg  11820
aattctcgtt ggatgaccca gtcaagtaca acatacctg gggggtttgaa tcggatacag  11880
cgtatctgta tgagttcacc ggaaacggtg aggactggga ggattacaat gatgcgtttc  11940
gtgcgcgcca ggaagggaaa atttataagg ctactgccac cagcatgaag tttatttttc  12000
ccccgggccc tgtcattgaa ccaactttag gcctgaattg aaatgaaatg gggtccatgc  12060
aaagcctttt tgacaaaatt ggccaacttt ttgtggatgc tttcacggag ttcttggtgt  12120
```

TABLE 3-continued

```
ccattgttga tatcattgta tttttggcca ttttgtttgg cttcaccatc gccggttggt    12180
tggtggtctt ttgcatcaga ttggtttgct ccgcgatact ccgtgcgcgc cctgccattc    12240
actctgagca attacagaag atcttatgaa gcctttcttt cccagtgcca agtggacatt    12300
cccacctggg gaactaaaca tcctttgggg atgttttggc accataaggt gtcaaccctg    12360
attgatgaga tggtgtcgcg tcgaatgtac cgcatcatgg aaaaagcagg acaggctgcc    12420
tggaaacagg tggtgagcga ggctacgctg tctcgcatta gtagtttgga tgtggtggct    12480
cattttcagc atcttgccgc cattgaagcc gagacctgta aatatttggc ctcccggctg    12540
cccatgctac acaacctgcg catgacaggg tcaaatgtaa ccatagtgta taatagtact    12600
ttgcatcagg tgtttgctat ttttccaacc cctggttccc ggccaaagct tcatgatttt    12660
cagcaatggt taatagctgt acattcctcc atattttcct ctgttgcagc ttcttgtact    12720
ctctttgttg tgctgtggtt gcgggttcca atactacgta ctgttttggg tttccgctgg    12780
ttaggggcaa ttttttcttt cgaactcacag tgaattacac ggtgtgtcca ccttgcctca    12840
cccggcaagc agccgcagag gcctacgaac ccggtaggtc tctttggtgc aggatagggt    12900
atgaccgatg tggggaggac gatcatgacg agctagggtt tatggtaccg tctggcctct    12960
ccagcgaagg ccacttgacc agtgtttacg cctggttggc gttcttgtcc ttcagctaca    13020
cggcccagtt ccatcccgag atattcggga tagggaatgt gagtcgagtt tatgttgaca    13080
tcgaacatca actcatctgc gccgaacatg acgggcagaa caccaccttg cctcgtcatg    13140
acaacatttc agccgtgttt cagacctatt accaacatca agtcgacggc ggcaattggt    13200
ttcacctaga atggctgcgt cccttctttt cctcatggtt ggttttaaat gtctcttggt    13260
ttctcaggcg ttcgcctgca aaccatgttt cagttcgagt cttgcagaca ttaagaccaa    13320
caccaccgca gcggcaagct ttgctgtcct ccaagacatc agttgcctta ggcatcgcaa    13380
ctcggcctct gaggcgattc gcaaaatccc tcagtgccgt acggcgatag ggacacccgt    13440
gtatattacc atcacagcca atgttacaga tgagaattat ttacattctt ctgatctcct    13500
catgctttct tcttgccttt tctatgcttc tgagatgagt gaaaagggat ttaaggtggt    13560
atttggcaat gtgtcaggca tcgtggctgt gtgtgtcaat tttaccagct acgtccaaca    13620
tgtcagggag tttacccaac gctccttgat ggtcgaccat gtgcggctgc tccatttcat    13680
gacacctgag accatgaggt gggcaactgt tttagcctgt cttttttgcca ttctgttggc    13740
aatttgaatg tttaagtatg ttggggaaat gcttgaccgc gggctgttgc tcgcgattgc    13800
tttctttgtg gtgtatcgtg ccgttctgtt ttgctgtgct cgtcaacgcc aacagcaaca    13860
gcagctctca tctacagttg atttacaact tgacgctatg tgagctgaat ggcacagatt    13920
ggctatctaa taaatttgat tgggcagtgg agagttttgt catctttccc gttttgactc    13980
acattgtctc ctatggtgcc ctcactacca gccatttcct tgacacagtc gctttagtca    14040
ctgtgtctac cgccgggttt gttcacgggc ggtatgtcct gagcagcatc tacgcggtct    14100
gtgccctggc tgcgttgact tgcttcgtca ttaggtttgc aaagaattgc atgtcctggc    14160
gctactcatg taccagatat actaactttc ttctggacac taagggcaga ctctatcgtt    14220
ggcggtcgcc tgtcatcata gagaaaaggg gcaaagttga ggtcgaaggt catctgatcg    14280
acctcaaaag agttgtgctt gatggttccg tggcaacccc tataaccaga gtttcagcgg    14340
aacaatgggg tcgtccttag atgacttttg ttatgatagc acggctccac aaaaggtgct    14400
tttggcgttt tctattacct acacgccagt gatgatatat gccctaaaag tgagtcgcgg    14460
ccgactgtta gggcttctgc acctttttgat cttcctgaac tgtgctttca ccttcgggta    14520
```

TABLE 3-continued

| | | | | | |
|---|---|---|---|---|---|
| catgacattc | gcgcactttc | agagtacaaa | taaggtcgcg | ctcactatgg | gagcagtagt | 14580 |
| tgcactcctt | tgggggtgt | attcagccat | agaaacctgg | aaattcatca | cctccagatg | 14640 |
| ccgtttgtgc | ttgctaggcc | gcaagtacat | tctggcccct | gcccaccacg | ttgagagtgc | 14700 |
| cgcaggcttt | catccgattg | cggcaaatga | taaccacgca | tttgtcgtcc | ggcgtcccgg | 14760 |
| ctccactacg | gtcaacggca | cattggtgcc | cgggttgaaa | ggcctcgtgt | tgggtggcag | 14820 |
| aaaagctgtt | aaacagggag | tggtaaacct | tgtcaaatat | gccaaataac | aacggcaagc | 14880 |
| agcagaagag | aaagaagggg | gatggccagc | cagtcaatca | gctgtgccag | atgctgggta | 14940 |
| agatcatcgc | ccagcaaaac | cagtccagag | gcaagggacc | gggaaagaaa | aataagaaga | 15000 |
| aaaacccgga | gaagccccat | tttcctctag | cgactgaaga | tgatgtcaga | catcacttta | 15060 |
| cccctagtga | gcggcaattg | tgtctgtcgt | caatccagac | tgcctttaat | caaggcgctg | 15120 |
| ggacttgcac | cctgtcagat | tcagggagga | taagttacac | tgtggagttt | agtttgccta | 15180 |
| cgcatcatac | tgtgcgcctg | atccgcgtca | cagcatcacc | ctcagcatga | tgggctggca | 15240 |
| ttcttgaggc | atctcagtgt | ttgaattgga | agaatgtgtg | gtgaatggca | ctgattgaca | 15300 |
| ttgtgcctct | aagtcaccta | ttcaattagg | gcgaccgtgt | gggggtaaga | tttaattggc | 15360 |
| gagaaccata | cggccgaaatt | | | | | 15381 |

TABLE 4

SEQ ID NO: 2
N (11766) . . . (11766) <223> A, G, T, or C

| | | | | | |
|---|---|---|---|---|---|
| catttgtgtt | gtcaggagct | gtgaccattg | gcacagccca | aaacttgctg | cacggaagcg | 60 |
| cccttctgtg | acagcctcct | tcaggggagc | ttggggtct | gtccctagca | ccttgcttcc | 120 |
| ggagttgcac | tgctttacgg | tctctccacc | cctttaacca | tgtctgggat | acttgatcgg | 180 |
| tgcacgtgta | cccccaatgc | cagggtgttt | atggcggagg | gccaagtcta | ctgcacacga | 240 |
| tgcctcagtg | cacggtctct | ccttcctctg | aatctccaag | tttctgaact | cggggtgcta | 300 |
| ggcctattct | acaggcccga | agagccactc | cggtggacgt | tgccacgtgc | attccccact | 360 |
| gttgagtgct | ccccgccgg | ggcctgctgg | ctttctgcaa | ttttttccaat | tgcacgaatg | 420 |
| accagtggaa | acctgaactt | ccaacaaaga | atggtacggg | tcgcagctga | actttacaga | 480 |
| gccggccagc | tcaccctac | agtcttaaag | actttacaag | tttatgaacg | gggttgccgc | 540 |
| tggtaccccca | tcgtaggacc | tgtcctggaa | gtggccgttt | tcgccaactc | cctacatgtg | 600 |
| agtgataaac | ctttcccggg | agcaactcac | gtgttaacca | acctgccgct | cccgcagaga | 660 |
| cccaagcctg | aagacttttg | cccctttgag | tgtgctatgg | ctaccgtcta | tgacattggt | 720 |
| catgacgccg | tcatgtatgt | ggccgaaggg | aaagtctcct | gggcccctcg | tggcggggat | 780 |
| gaagtgaaat | ttgaaactgt | ccccggggag | ttggagttga | ttgcgaatcg | actccgcacc | 840 |
| tccttcccgc | cccaccacac | agtggacatg | tctaagttcg | ccttcacagc | ccctgggcgt | 900 |
| ggtgtttcta | tgcgggtcga | acgccaacac | ggctgcctcc | ccgctgacac | tgtccctgaa | 960 |
| ggcaactgct | ggtggagctt | gtttaacttg | ctcccactgg | aagttcagaa | caaagaaatt | 1020 |
| cgccatgcta | accaatttgg | ctaccagacc | aagcatggtg | tctctggcaa | gtacctacgg | 1080 |
| cggaggctgc | aagttaatgg | tctccgagca | gtaactgacc | tgaatggacc | tatcgtcgta | 1140 |
| cagtacttct | ccgttaagga | gagttggatc | cgccacttga | aactggcgga | agaacccagc | 1200 |
| taccctgggt | ttgaggacct | cctcagaata | agggttgagc | ccaacacgtc | gccattggct | 1260 |
| gacaaggatg | aaaaaatttt | ccggtttggc | agtcacaagt | ggtacggcgc | tggaaagaga | 1320 |

TABLE 4-continued

```
gcaaggaaag cacgctctag tgcgactgct acagtcgctg ccgcgcttt gtccgttcgt    1280
gaaacccggc aggccaagga gcacgaggtt gccggcgcca acaaggctgg gcacctcaaa   1440
cattactccc cgcctgccga agggaattgt ggttggcact gcatttccgc catcgccaac   1500
cggatggtga attccaaatt tgaaaccacc cttcccgaaa gagtgagacc ttcagatgac   1560
tgggctactg acgaggatct tgtgaatgcc atccaaatcc tcaggctccc tgcggccttg   1620
aacaggaacg gcgcttgtgc tagcgccaag tacgtactta agctggaagg tgagcattgg   1680
actgtcactg tgacccctgg gatgtccccct tctttgctcc ctcttgaatg tgttcagggc  1740
tgttgtgagc ataagggcag tcttggttcc ccagatgcag tcgaggtttt cggatttgac   1800
cctgcctgcc ttgaccggct ggctgaggtg atgcacctgc ctagcagtgc tatcccagcc   1860
gctctggccg aaatgtccgg cgattccgat cgttcggctt ccccggtcac caccgtgtgg   1920
actgtttcgc agttctttgc ccgccacaat ggagggaatc accctgacca agtgcgctta   1980
gggaaaatta tcagcctttg tcaggtgatt gaggactgct gctgttccca gaacaaaacc   2040
aaccgggtca ccccggagga ggtcgcagca aagattgacc tgtaccttcg tggcgcaaca   2100
aatcttgaag aatgcttggc caggcttgag aaagcgcgcc cgccacgcgt aatggacacc   2160
tcctttgatt gggatgttgt gctccctggg gttgaggcgg caactcagac gaccgaactg   2220
ccccaggtca accagtgtcg cgctctggtc cctgttgtaa ctcaaaagtc cttgacaac    2280
aactcggtcc ccctgaccgc ctttttcactg gctaactact actaccgtgc gcaaggtgac  2340
gaagttcgtc accgtgaaag actaaccgcc gtgctctcca agttggaagg ggttgttcga   2400
gaagaatatg ggctcatgcc aaccgggcct ggtccacggc ccacactgcc acgcgggctc   2460
gacgaactca aagaccagat ggaggaggac ttgctgaaac tggctaacgc ccagacgact   2520
tcggacatga tggcctgggc agtcgagcag gttgacctaa aaacttgggt caagaactac   2580
ccgcggtgga caccaccacc ccctccgcca aaagttcagc ctcgaaaaac gaagcctgtc   2640
aagagcttgc cagagagaaa gcctgtcccc gccccgcgca ggaaggttgg gtccgattgt   2700
ggcagcccga tttcattggg cgacgatgtc cctaacagtt gggaagattt ggctgttggt   2760
agcccctttg atctctcgac cccacctgag ctggcaacac cttcaagtga gctggtgatt   2820
gtgtccgcac cgcaatgcat cttcaggccg gcgacaccct tgagtgagcc ggctccaatt   2880
cccgcacccc gcggggttgt gtctcgaccg gtgacaccct tgaatgagcc gatacctgtg   2940
cccgcaccgc ggcgtaagtt tcagcagatg agaagattga gttcggcggc ggtaatcccg   3000
ccgtaccagg acgagcccct agatttgtct gcttcctcac agactgaata tgaggcctct   3060
ccctagcac cgccgcagag cgagggtgtt ctgggagtag aggggcagga agctgaggaa    3120
gccctaagtg aaatctcgga catgtcgggt aacattaaac ctgcgtccgt atcatcaagc   3180
agctccttgt ccagcgtgag aatcactcgc ccaaaatact cagctcaagc catcatcgac   3240
tcgggcgggc cctgcagtgg gcatctccaa gaggtaaagg aaacatgcct cagtatcatg   3300
cgcgaggcat gtgatgcgac taagcttaag ttcctcccaa aaatgatact cgagacaccg   3360
ccgccctatc cgtgtgagtt tgtgatgatg cctcacacgc ctgcaccttc cgtaggtgcg   3420
gagagcgacc ttaccattgg ctcagtcgct actgaagatg ttccacgcat cctcgagaaa   3480
atagaaaatg tcgcgagat gaccaaccag ggacccttgg ccttctccga ggataaaccg    3540
gtagatgacc aacttgccaa agaccccccg atatcgtcgc agaggtctga cgagagcaca   3600
tcagctccgc ccgcaggcac aggtggcgcc ggctcattta ccgatttgcc gccttcggac   3660
ggcgtggatg cggacggagg ggggccgttt tggacggtaa aaagaaaagc tgaaaggctc   3720
```

TABLE 4-continued

```
tttgaccaac tgagccgtca ggttttttgac ctcgtctccc atctccctgt tttcttctca   3780
cgccttttca accctggcgg tggttattct ccgggtgatt ggggttttgc agcttttact    3840
ctattgtgcc tcttttatg ttacagttac ccagcctttg gtattgctcc cctcttgggt    3900
gtgttttctg ggtcttctcg gcgcgttcga atggggtttt ttggctgctg gttggctttt   3960
gctgttggtc tgttcaagtc tgtgtccgac ccagtcggcg ctgcttgtga gtttgactcg    4020
ccagagtgta gaaatatcct tcattctttt gagcttctca aaccttggga ccctgttcgc    4080
agccttgttg tgggccccgt cggtctcggt cttgccattc ttggcaggtt actgggcggg   4140
gcacgcagca tctggcactt tttgcttagg cttggcattg ttgcagactg tgtcttggct   4200
ggagcttatg tgctttctca aggtaggtgt aaaaagtgct ggggatcttg tataagaact   4260
gctcctaatg aggtcgcttt taacgtgttt cctttacac gtgcgaccag gtcgtcacta    4320
atcgacctgt gcgatcggtt ttgtgcgcca aaaggcatgg accccatttt tctcgccact   4380
gggtggcgcg ggtgctgggc cggccgaagc cccattgagc aaccctctga aaaacccatc   4440
gcgtttgccc agttggatga aaagaagatt acggctagga ctgtggtcgc ccagccttat   4500
gaccccaacc aagccgtaaa gtgcttgcgg gtattgcagg cgggtggggt gatggtggct   4560
aaggcagtcc caaaagtggt caaggttttcc gctgttccat tccgagcccc cttctttccc   4620
accggagtga aagttgaccc tgaatgcagg gtcgtggttg accccgacac tttcaccgca   4680
gctctccggt ctggctactc caccacaaac ctcgtcctcg gtgtagggga ttttgcccag    4740
ctgaatggat taaaaatcag gcaaatttcc aagccttcag gaggaggccc acacctcatg   4800
gctgccctgc atgttgcctg ctcgatggct ttgcacatgc ttgctgggat ttatgtgact   4860
gcggtgggtt cttgcggcac cggcaccaac gacccgtggt gcgctaaccc gtttgccgtc    4920
cctggctacg gacctggctc tctctgcacg tccagattgt gcatttccca acatggcctt   4980
accctgccct tgacagcact cgtggcggga ttccggtatc aagaaattgc cttggtcgtt   5040
ttgattttg tttccatcgg aggcatggct cacaggttga gttgtaaggc tgatatgctg   5100
tgtgttttgc ttgcaattgc cagctatgtt tgggtacctc ttacctggtt gctttgtgtg   5160
tttccttgct ggttgcgctg tttttctttg catcccctca ccatcctatg gttggtgttt   5220
ttcttgattt ctgtgaatat gccttcagga atcttggcca tggtgttgtt ggtttctctt   5280
tggcttcttg gtcgttatac taatgttgct ggtcttgtca cccctacga cattcatcat   5340
tacactagtg gccccgcgg tgttgccgcc ttggctaccg caccagatgg gacctacttg   5400
gccgctgtcc gccgcgctgc gttgactggc cgcaccatgc tgtttacccc gtcccagctt   5460
gggtctcttc ttgagggtgc tttcagaact cgaaaaccct cactgaacac cgtcaatgtg   5520
gtcgggtcct ccatgggctc tggcggggtg ttcaccatcg acggaaaaat taagtgcgta   5580
actgccgcac atgtccttac gggcaattca gctagggttt ccggggtcgg cttcaatcaa   5640
atgcttgact ttgacgtaaa gggagatttc gccatagctg attgcccgaa ttggcaaggg    5700
gctgccccca agacccaatt ctgcaaggat gggtggactg gccgtgccta ttggctaaca   5760
tcctctggcg tcgaacccgg cgtcattgga aaaggattcg ccttctgctt caccgcgtgc   5820
ggcgattccg ggtccccagt gatcaccgag gccggtgagc ttatcggcgt tcacacggga   5880
tcaaataaac aaggaggagg catcgttacg cgcccctcag gccagttttg taatgtggca   5940
cccatcaagc taagcgaatt aagtgaattc tttgctgggc ctaaggtccc gctcggtgat   6000
gtgaaggttg gcagccacat aattaaagac ataggcgagg tgccttcaga tcttttgtgcc   6060
ttgcttgctg ccaaacctga actggaagga ggcctctcca ccgtccaact tctttgtgtg   6120
```

TABLE 4-continued

```
tttttcctcc tgtggagaat gatgggacat gcctggacgc ccttggttgc tgtgggtttc    6180
tttatcttga atgaggttct cccagccgtc ctggtccgga gtgttttctc ctttggaatg    6240
tttgtgctat cctggctcac gccatggtct gcgcaagttc tgatgatcag gcttctaaca    6300 gcagcccttta acaggaacag atggtcactt gccttttttca gcctcggtgc agtgaccggt    6360
tttgtcgcag atcttgcggc tactcagggg catccgttgc aggcagttat gaatttgagc    6420
acctatgcat tcctgcctcg gatgatggtt gtgacctcac cagtcccagt gattgcgtgt    6480
ggtgttgtgc acctacttgc catcattttg tacttgttta agtaccgtgg cctgcaccaa    6540
atccttgttg gcgatggagt gttctctgcg gctttcttcc tgcgatactt tgccgaggga    6600
aagttgaggg aaggggtgtc gcaatcctgc ggaatgaatc atgagtctct gactggtgcc    6660
ctcgctatga gactcaatga cgaggacttg gatttcctta cgaaatggac tgattttaag    6720
tgctttgttt ctgcgtccaa catgaggaat gcagcgggtc aatttatcga ggctgcctat    6780
gctaaagcac ttagagtaga gcttgcccag ttggtgcagg ttgataaagt tcgaggaact    6840
ttggccaaac ttgaagcctt tgctgatacc gtggcacccc aactctcgcc cggtgacatt    6900
gttgtcgctc tcggccatac gcctgttggc agtatcttcg acctaaaggt tggtagcacc    6960
aagcataccc tccaagccat tgagaccaga gtccttgctg gtccaaaat gaccgtggcg    7020 cgcgtcgtcg acccgacccc cacgccccca cccgcacctg tgcccatccc cctcccaccg    7080
aaagttctgg agaatggccc caacgcttgg ggggatgagg accgtttgaa taagaagaag    7140
aggcgcagga tggaagccct cggcatctat gttatgggcg gaaaaagta ccagaaattt    7200 tgggataaga attccggtga tgtgttttat gaggaggtcc ataataacac agatgagtgg    7260
gagtgtctca gagttggcga ccctgccgac tttgaccctg agaagggaac tctgtgtgga    7320
catgtcacca ttgaagataa ggcttaccat gtttacacct caccatctgg taagaagttc    7380
ttggtccccg tcaatccaga gaatggaaga gtccaatggg aagctgcaaa gctttccgta    7440
gagcaggccc ttggtatgat gaacgtcgac ggcgaactga ctaccaaaga actggagaaa    7500
ctgaaaagaa taattgacaa actccagggc ctgactaagg agcagtgttt aaactgctag    7560
ccgccagcgg cttgacccgc tgtggtcgcg gcggcttggt tgttactgaa acagcggtaa    7620
aaatagtcaa atttcacaac cggaccttca ccctgggacc tgtgaattta aaagtggcca    7680
gtgaggttga gctaaaagac gcggttgagc acaaccaaca cccggttgcg agaccggtcg    7740
atggtggtgt tgtgctcctg cgttccgcgg ttccttcgct tatagacgtc ttgatctccg    7800
gtgctgatgc atctcccaag ttgcttgccc atcacgggcc gggaaacact gggatcgatg    7860
gcacgctctg ggattttgag tccgaagcca ctaaagagga agtcgcactt agtgcgcaaa    7920
taatacaggc ttgtgacatt aggcgcggcg acgctcctga aattggtctc ccttacaagc    7980
tgtaccctgt taggggtaac cctgagcggg taaaaggagt tctacagaat acaaggtttg    8040
gagacatacc ttacaaaacc cccagtgata ctggaaaccc agtgcacgcg gctgcctgcc    8100
ttacgcccaa cgccactccg gtgactgatg ggcgctccgt cttggccacg accatgccct    8160
ccgggtttga gttgtatgta ccaaccatac cagcgtctgt ccttgattac cttgattcta    8220
ggcctgactg ccctaaacag ttgacagagc acggctgtga agatgccgca ctgagagacc    8280
tctccaaata tgacttgtcc acccaaggct ttgttttacc tggagttttt cgccttgtac    8340
ggaaatacct gtttgcccat gtaggtaagt gcccacccgt tcatcggcct tctacttacc    8400
ctgctaagaa ttctatggct ggaataaatg gaataggtt cccaaccaag gatattcaga    8460
gcgtccctga aatcgacgtt ctgtgtgcac aggctgtgcg ggaaaactgg caaactgtta    8520
```

TABLE 4-continued

```
cccccttgtac tcttaagaaa cagtattgcg ggaagaagaa gactaggacc atactcggca   8580
ccaataattt tatcgcgcta gcccaccgag cagcgttgag tggtgtcacc cagggcttca   8640
tgaaaaaggc gtttaactcg cccatcgccc tcggaaaaaa caagtttaag gagctacaga   8700
ccccggtcct aggcaggtgc cttgaagctg atcttgcatc ctgcgaccga tccacacctg   8760
caattgtccg ctggtttgcc gccaacctcc tttatgaact tgcctgcgct gaagagcatt   8820
taccgtcgta cgtgctgaac tgctgccacg acttactggt cacgcagtcc ggcgcagtga   8880
ctaagagagg tggcctgtcg tctggcgacc cgatcacctc tgtgtctaac accatttaca   8940
gtttggtgat ctatgcacag catatggtgc tcagttactt caaaagtggt caccccccatg   9000
gcctcttgtt cttacaagac cagctaaagt ttgaggacat gctcaaggtt caaccccctga   9060
tcgtctattc ggacgacctc gtgctgtatg ccgagtctcc caccatgcca aactatcact   9120
ggtgggttga acacctgaat ttgatgctgg ggtttcagac ggatccaaaa aagacagcca   9180
taacagactc gccatcattt ctaggctgta gaataataaa tggacgccag ctagtcccca   9240
accgtgacag gattctcgcg gccctcgcct accacatgaa ggcgagtaat gtttctgaat   9300
actacgcctc agcggctgca atactcatgg acagctgtgc ttgtttggag tatgatcctg   9360
aatggtttga agaacttgta gttggaatag cgcaatgcgc ccgcaaggac ggttacagct   9420
ttcccggcac gccgttcttt atgtccatgt gggaaaaact caggtccaat tatgagggga   9480
agaagtcgag agtgtgcggg tactgcgggg ccccggccct gtacgctact gcctgtggcc   9540
tcgacgtctg catttaccac acccacttcc accagcattg tccagtcaca atctggtgtg   9600
gccatccagc gggttctggt tcttgtagtg agtgcaaatc ccctgtaggg aaaggcacaa   9660
gccctttaga cgaggtgctg gaacaagtcc cgtacaagcc cccacggacc gttatcatgc   9720
atgtggagca gggtctcacc cccctttgacc caggtagata ccagactcgc cgcggattag   9780
tctccgtcag gcgtggaatc aggggaaatg aggttgaact accagacggt gattatgcta   9840
gtaccgcctt gctccctacc tgtaaagaga tcaacatggt cgctgttgct tccaatgtat   9900
tgcgcagcag gttcatcatt ggtccacccg gtgctgggaa acatactggg ctccttcaac   9960
aggtccagga tggtgatgtt atttacacac caacccacca gaccatgctt gacatgatta  10020
gggctttggg gacgtgccgg ttcaacgtcc cggcaggcac aacgctgcaa ttccccgtcc  10080
cctcccgtac cggtccgtgg gttcgcatcc tggccggcgg ttggtgtcct ggcaagaatt  10140
ccttcctgga tgaagcagcg tattgcaatc accttgatgt cttgaggctt cttagcaaaa  10200
ctaccctcac ctgtctggga gacttcaaac aactccaccc agtgggtttt gattctcatt  10260
gctatgtttt taacatcatg cctcaaactc aactgaagac catctggagg tttggacaga  10320
atatctgtga tgccatccag ccagattaca gggacaaact catgtccatg gtcaacacaa  10380
cccgtgtgac ctacgtggaa aagcctgtca ggtatgggca agtcctcacc ccctaccaca  10440
gggaccgaga ggacgacgcc atcactattg actccagtca aggcgccaca ttcgatgtgg  10500
ttacactgca tttgcccaca aaagattcac tcaacaggca gagagccctt gttgctatca  10560
ccagggcaag acatgctatc tttgtgtatg acccacacag gcagctgcag agcctgtttg  10620
atcttcctgc aaaaggtaca cccgtcaacc ttgcagtgca ccgcgacggg cagctgatcg  10680
tgctagatag aaataacaaa gaatgcacgg ttgctcaggc tctaggtaac ggagataaat  10740
ttagggccac agacaaacgc gttgtagatt ctctccgcgc catttgtgct gatctagaag  10800
ggtcgagctc tccgctcccc aaggtcgcac acaacttggg attttatttc tcacctgatt  10860
taacacagtt tgctaaactc ccagcagaac ttgcacctca ctggccgtg gtgacaaccc  10920
```

TABLE 4-continued

```
agaacaatga aaagtggcca gatcggctgg ttaccagcct tcgccctatc cataaatata   10980
gccgcgcgtg catcggtgcc ggctatatgg tgggcccctc ggtgtttcta ggcactcctg   11040
gggtcgtgtc atactatctc acaaaatttg ttaagggcga ggctcaagtg cttccggaga   11100
cggttttcag caccggccga attgaggtag actgccggga atatcttgat gatcgggagc   11160
gagaggttgc tgcgtccctc ccacatgcct tcattggcga cgtcaaaggc actaccgttg   11220
gaggatgcca ccatgtcacc tccagatacc tcccgcgctt ccttcccaag gaatcggttg   11280
cggtagtcgg ggtttcaagt cccggaaaag ccgcgaaagc attgtgcaca ctgacagatg   11340
tgtacctccc agaccttgaa gcctatttcc acccggagac ccagtccaag tgctggagaa   11400
tgatgttgga cttcaaggaa gttcgactaa tggtctggaa agacaaaaca gcctatttcc   11460
aacttgaagg tcgctatttc acctggtatc agcttgctag ctatgcctcg tacatccgtg   11520
ttcctgtcaa ctccacggtg tacttggacc cctgcatggg cccgcccctt tgcaacagga   11580
aagtcgtcgg gtccactcat tggggagctg acctcgctgt caccccttat gattacggcg   11640
ctaaaattat cctgtctagc gcgtaccata gtgaaatgcc ccccggatac aagattctgg   11700
cgtgcgcgga attctcgttg gatgacccag tcaagtacaa acatacctgg gggtttgaat   11760
cggatncagc gtatctgtat gagttcaccg gaaacggtga ggactgggag gattacaatg   11820
atgcgtttcg tgcgcgccag gaagggaaaa tttataaggc tactgccacc agcatgaagt   11880
tttattttcc cccgggccct gtcattgaac caactttagg cctgaattga aatgaaatgg   11940
ggtccatgca aagcctttt gacaaaaattg gccaacttt tgtggatgct ttcacggagt   12000
tcttggtgtc cattgttgat atcattatat ttttggccat tttgtttggc ttcaccatcg   12060
ccggttggtt ggtggtcttt tgcatcagat tggtttgctc cgcgtactc cgtacgcgcc   12120
ctgccattca ctctgagcaa ttacagaaga tcttatgaag ccttctttc ccagtgccaa   12180
gtggacattc ccacctgggg aactaaacat cctttgggga tgttttggca ccataaggtg   12240
tcaaccctga ttgatgagat ggtgtcgcgt cgaatgtacc gcatcatgga aaaagcagga   12300
caggctgcct ggaaacaggt ggtgagcgag gctacgctgt ctcgcattag tagtttggat   12360
gtggtggctc attttcagca tcttgccgcc attgaagccg agacctgtaa atatttggcc   12420
tcccggctgc ccatgctaca caacctgcgc atgacagggt ctaatgtaac catagtgtat   12480
aatagtactt tgcatcaggt gttttgctatt tttccaaccc ctggttcccg gccaaagctt   12540
catgattttc agcaatggtt aatagctgta cattcctcca tattttcctc tgttgcagct   12600
tcttgtactc tctttgttgt gctgtggttg cgggttccaa tactacgtac tgttttggt   12660
ttccgctggt tagggcaat ttttctttcg aactcacagt gaattacacg gtgtgtccac   12720
cttgcctcac ccggcaagca gccgcagagg cctacgaacc cggtaggtct ctttggtgca   12780
ggatagggta tgaccgatgt ggggaggacg atcatgacga gctaggtttt atggtaccgt   12840
ctggcctctc cagcgaaggc cacttgacca gtgtttacgc ctggttggcg ttcttgtcct   12900
tcagctacac ggcccagttc catcccgaga tattcgggat agggaatgtg agtcgagttt   12960
atgttgacat cgaacatcaa ctcatctgcg ccgaacatga cgggcagaac accaccttgc   13020
ctcgtcatga caacatttca gccgtgtttc agacctatta ccaacatcaa gtcgacggcg   13080
gcaattggtt tcacctagaa tggctgcgtc ccttcttttc ctcatggttg gttttaaatg   13140
tctcttggtt tctcaggcgt tcgcctgcaa accatgtttc agttcgagtc ttgcagacat   13200
taagaccaac accaccgcag cggcaagctt tgctgtcctc caagcatca gttgcttag   13260
gcatcgcaac tcggcctctg aggcgattcg caaaatccct cagtgccgta cggcgatagg   13320
```

TABLE 4-continued

```
gacacccgtg tatattacca tcacagccaa tgtgacagat gagaattatt tacattcttc    13380
tgatctcctc atgctttctt cttgccttt  ctatgcttct gagatgagtg aaaagggatt    13440
taaggtggta tttggcaatg tgtcaggcat cgtggctgtg tgtgtcaatt ttaccagcta    13500
cgtccaacat gtcagggagt ttacccaacg ctccttgatg gtcgaccatg tgcggctgct    13560
ccatttcatg acacctgaga ccatgaggtg ggcaactgtt ttagcctgtc ttttgccat     13620 tctgttggca atttgaatgt ttaagtatgt tggggaaatg cttgaccgcg ggctgttgct    13680
cgcgattgct ttctttgtgg tgtatcgtgc cgttctgttt tgctgtgctc gtcaacgcca    13740
acagcaacag cagctctcat ctacagttga tttacaactt gacgctatgt gagctgaatg    13800
gcacggattg gctatctaat aaatttgatt gggcagtgga gagttttgtc atctttcccg    13860
ttttgactca cattgtctcc tatggtgccc tcactaccag ccatttcctt gacacagtcg    13920
ctttagtcac tgtgtctacc gccgggtttg ttcacgggcg tatgtcctg  agcagcatct    13980 acgcggtctg tgccctggct gcgttgactt gcttcgtcat caggtttgca aagaattgca    14040
tgtcctggcg ctactcatgt accagatata ctaactttct tctggacact aagggcagac    14100
tctatcgttg gcggtcgcct gtcatcatag agaaaagggg caaagttgag gtcgaaggtc    14160
atctgatcga cctcaaaaga gttgtgcttg atggttccgt ggcaaccct  ataaccagag    14220 tttcagcgga acaatgggt  cgtccttaga tgacttttgt tatgatagca cggctccaca    14280
aaaggtgctt ttggcgtttt ctattaccta cacgccagtg atgatatatg ccctaaaagt    14340
gagtcgcggc cgactgttag ggcttctgca cctttttgatc ttcctgaact gtgctttcac    14400
cttcgggtac atgacattcg cgcactttca gagtacaaat aaggtcgcgc tcactatggg    14460
agcagtagtt gcactccttt gggggtgta  ttcagccata gaaacctgga aattcatcac    14520
ctccagatgc cgtttgtgct tgctaggccg caagtacatt ctggcccctg cccaccacgt    14580
tgagagtgcc gcaggctttc atccgattgc ggcaaatgat aaccacgcat tgtcgtccg     14640 gcgtcccggc tccactacgg tcaacggcac attggtgccc gggttgaaag gcctcgtgtt    14700
gggtggcaga aaagctgtta acagggagt  ggtaaacctt gtcaaatatg ccaaataaca    14760
acggcaagca gcagaagaga aagaaggggg atggccagcc agtcaatcag ctgtgccaga    14820
tgctgggtaa gatcatcgcc cagcaaaacc agtccagagg caagggaccg ggaaagaaaa    14880
ataagaagaa aaacccggag aagccccatt ttcctctagc gactgaagat gatgtcagac    14940
atcactttac ccctagtgag cggcaattgt gtctgtcgtc aatccagact gcctttaatc    15000
aaggcgctgg gacttgcacc ctgtcagatt cagggaggat aagttacact gtggagttta    15060
gtttgcctac gcatcatact gtgcgcctga tccgcgtcac agcatcaccc tcagcatgat    15120
gggctggcat tcttgaggca tctcagtgtt tgaattggaa gaatgtgtgg tgaatggcac    15180
tgattgacat tgtgcctcta agtcacctat tcaattaggg cgaccgtgtg ggggtaagat    15240
ttaattggcg agaaccatac ggccgaaatt                                     15270
```

TABLE 5

```
SEQ ID NO: 3
catttgtgtt gtcaggagct gtgaccattg gcacagccca aaacttgctg cacggaagcg    60
cccttctgtg acagcctcct tcaggggagc ttgggggtct gtccctagca ccttgcttcc   120
ggagttgcac tgctttacgg tctctccacc cctttaacca tgtctgggat acttgatcgg   180
tgcacgtgta cccccaatgc cagggtgttt atggcggagg gccaagtcta ctgcacacga   240
```

TABLE 5-continued

```
tgcctcagtg cacggtctct ccttcctctg aatctccaag tttctgaact cggggtgcta    300
ggcctattct acaggcccga agagccactc cggtggacgt tgccacgtgc attccccact    360
gttgagtgct ccccgccgg ggcctgctgg ctttctgcaa tttttccaat tgcacgaatg     420
accagtggaa acctgaactt ccaacaaaga atggcacggg tcgcagctga actttacaga   480
gccggccagc tcaccctac agtcttaaag actttacaag tttatgaacg gggttgccgc    540
tggtacccca tcgtaggacc tgtccctgga gtggccgttt tcgccaactc cctacatgtg   600
agtgataaac ctttcccggg agcaactcac gtgttaacca acctgccgct cccgcagaga   660
cccaagcctg aagacttttg ccccttttgag tgtgctatgg ctaccgtcta tgacattggt   720
catgacgccg tcatgtatgt ggccgaaggg aaagtctcct gggcccctcg tggcggggat   780
gaagtgaaat ttgaaactgt ccccggggag ttggagttga ttgcgaatcg actccgcacc   840
tccttcccgc ccaccacac agtggacatg tctaagttcg ccttcacagc cctgggcgt     900
ggtgtttcta tgcgggtcga acgccaacac ggctgcctcc ccgctgacac tgtccctgaa   960
ggcaactgct ggtggagctt gtttaacttg ctcccactgg aagttcagaa caaagaaatt   1020
cgccatgcta accaatttgg ctaccagacc aagcatggtg tctctggcaa gtacctacag   1080
cggaggctgc aagttaatgg tctccgagca gtaactgacc tgaatggacc tatcgtcgta   1140
cagtacttct ccgttaagga gagttggatc cgccacttga aactggcgga agaacccagc   1200
taccctgggt ttgaggacct cctcagaata agggttgagc ccaacacgtc gccattggct   1260
gacaaggatg aaaaaattt ccggtttggc agtcacaagt ggtacggcgc tggaaagaga   1320
gcaaggaaag cacgctctag tgcgactgct acagtcgctg gccgcgcttt gtccgttcgt   1380
gaaacccggc aggccaagga gcacgaggtt gccggcgcca acaaggctgg gcacctcaaa   1440
cattactccc cgcctgccga agggaattgt ggttggcact gcatttccgc catcgccaac   1500
cggatggtga attccaaatt tgaaaccacc cttcccgaaa gagtgagacc ttcagatgac   1560
tgggctactg acgaggatct tgtgaatgcc atccaaatcc tcaggctccc tgcggccttg   1620
aacaggaacg gcgcttgtgc tagcgccaag tacgtactta agctggaagg tgagcattgg   1680
actgtcactg tgacccctgg gatgtcccct tctttgctcc ctcttgaatg tgttcagggc   1740
tgttgtgagc ataagggcag tcttggttcc ccagatgcag tcgaggtttt cggatttgac   1800
cctgcttgcc ttgaccggct ggctgaggtg atgcacctgc ctagcagtgc tatcccagcc   1860
gctctggccg aaatgtccgg cgattccgat cgttcggctt ccccggtcac caccgtgtgg   1920
actgtttcgc agctctttgc ccgccacaat ggagggaatc accctgacca agtgcgctta   1980
gggaaaatta tcagccttg tcaggtgatt gaggactgct gctgttccca gaacaaaacc   2040
aaccgggtca ccccggagga ggtcgcagca aagattgacc tgtaccttcg tggcgcaaca   2100
aatcttgaag aatgcttggc caggcttgag aaagcgcgcc cgccacgcgt aatgacacc    2160
tcctttgatt gggatgttgt gctccctggg gttgaggcgg caactcagac gaccgaactg   2220
ccccaggtca accagtgtcg cgctctggtc cctgttgtaa ctcaaaagtc cttggacaac   2280
aactcggtcc cctgaccgc cttttcactg gctaactacc actaccgtgc gcaaggtgac   2340
gaagttcgtc accgtgaaag actaaccgcc gtgctctcca gttggaagg ggttgttcga    2400
gaagaatatg ggctcatgcc aaccgggcct ggtccacggc ccacactgcc acgcgggctc   2460
gacgaactca agaccagat ggaggaggac ttgctgaaac tggctaacgc ccagacgact   2520
tcggacatga tggcctgggc agtcgagcag gttgacctaa aaacttgggt caagaactac   2580
ccgcggtgga caccaccacc ccctccgcca aaagttcagc ctcgaaaaac gaagcctgtc   2640
```

TABLE 5-continued

```
aagagcttgc cagagagaaa gcctgtcccc gccccgcgca ggaaggttgg gtccgattgt    2700
ggcagcccga tttcattggg cgacgatgtc cctaacagtt gggaagattt ggctgttggt    2760
agccccttcg atctctcgac cccacctgag ctggcaacac cttcaagtga gctggtgatt    2820
gtgtccgcac cgcaatgcat cttcaggccg gcgacaccct tgagtgagcc ggctccaatt    2880
cccgcacccc gcggggttgt gtctcgaccg gtgacaccct tgaatgagcc gatacctgtg    2940
cccgcaccgc ggcgtaagtt tcagcagatg agaagattga gttcggcggc ggtaatcccg    3000
ccgtaccagg acgagcccct agatttgtct gcttcctcac agactgaata tgaggcctct    3060
cccctagcac cgccgcagag cgaggtgtt ctggagtag aggggcagga agctgaggaa     3120
gccctaagtg aaatctcgga catgtcgggt aacattaaac ctgcgtccgt atcatcaagc    3180
agctccttgt ccagcgtgag aatcactcgc ccaaaatact cagctcaagc catcatcgac    3240
tcgggcgggc cctgcagtgg gcatctccaa gaggtaaagg aaacatgcct cagtatcatg    3300
cgcgaggcat gtgatgcgac taagcttgat gaccctgcta cgcaggagtg gctttctcgc    3360
atgtgggatc gggtggacat gctgacttgg cgcaacacgt ctgcttacca ggcgtttcgc    3420
accttagatg gcaggttaaa gttcctccca aaaatgatac tcgagacacc gccgccctat    3480
ccgtgtgagt ttgtgatgat gcctcacacg cctgcacctt ccgtaggtgc ggagagcgac    3540
cttaccattg gctcagtcgc tactgaagat gttccacgca tcctcgagaa aatagaaaat    3600
gtcggcgaga tgaccaacca gggacccttg gccttctccg aggataaacc ggtagatgac    3660
caacttgcca agaccccccg gatatcgtcg cagaggtctg acgagagcac atcagctccg    3720
cccgcaggca caggtggcgc cggctcattt accgatttgc cgccttcgga cggcgtggat    3780
gcggacggag gggggccgtt ttggacggta aaaagaaaag ctgaaaggct ctttgaccaa    3840
ctgagccgtc aggttttga cctcgtctcc catctccctg ttttcttctc acgccttttc     3900
aaccctggcg gtggttattc tccgggtgat tgggttttg cagctttac tctattgtgc      3960
ctctttttat gttacagtta cccagccttt ggtattgctc ccctcttggg tgtgttttct    4020
gggtcttctc ggcgcgttcg aatgggggtt tttggctgct ggttggcttt tgctgttggt    4080
ctgttcaagc ctgtgtccga cccagtcggc gctgcttgtg agtttgactc gccagagtgt    4140
agaaatatcc ttcattcttt tgagcttctc aaaccttggg accctgttcg cagccttgtt    4200
gtgggccccg tcggtctcgg tcttgccatt cttggcaggt tactgggcgg ggcacgcagc    4260
atctggcact ttttgcttag gcttggcatt gttgcagact gtgtcttggc tggagcttat    4320
gtgctttctc aaggtaggtg taaaaagtgc tgggatctt gtataagaac tgctcctaat     4380
gaggtcgctt ttaacgtgtt tccttttaca cgtgcgacca ggtcgtcact aatcgacctg    4440
tgcgatcggt tttgtgcgcc aaaaggcatg gaccccattt ttctcgccac tgggtggcgc    4500
gggtgctggg ccggccgaag ccccattgag caaccctctg aaaaacccat cgcgtttgcc    4560
cagttggatg aaaagaagat tacggctagg actgtggtcg cccagcctta tgaccccaac    4620
caagccgtaa agtgcttgcg ggtattgcag gcgggtgggg tgatggtggc taaggcagtc    4680
ccaaaagtgg tcaaggtttc cgctgttcca ttccgagccc ccttctttcc caccggagtg    4740
aaagttgacc ctgaatgcag ggtcgtggtt gaccccgaca cttttcaccgc agctctccgg   4800
tctggctact ccaccacaaa cctcgtcctc ggtgtagggg attttgccca gctgaatgga    4860
ttaaaaatca ggcaaatttc caagccttca ggaggaggcc cacacctcat ggctgccctg    4920
catgttgcct gctcgatggc tttgcacatg cttgctggga tttatgtgac tgcggtgggt    4980
tcttgcggca ccggcaccaa cgacccgtgg tgcgctaacc cgtttgccgt ccctggctac    5040
```

TABLE 5-continued

```
ggacctggct ctctctgcac gtccagattg tgcatttccc aacatggcct taccctgccc    5100
ttgacagcac tcgtggcggg attcggtatt caagaaattg ccttggtcgt tttgattttt    5160
gtttccatcg gaggcatggc tcacaggttg agttgtaagg ctgatatgct gtgtgttttg    5220
cttgcaattg ccagctatgt ttgggtacct cttacctggt tgctttgtgt gtttccttgc    5280
tggttgcgct gttttttctt tgcatcccctc accatcctat ggttggtgtt tttcttgatt    5340
tctgtgaata tgccttcagg aatcttggcc atggtgttgt tggtttctct ttggcttctt    5400
ggtcgttata ctaatgttgc tggtcttgtc accccctacg acattcatca ttacactagt    5460
ggcccccgcg gtgttgccgc cttggctacc gcaccagatg ggacctactt ggccgctgtc    5520
cgccgcgctg cgttgactgg ccgcaccatg ctgtttaccc cgtcccagct tgggtctctt    5580
cttgagggtg ctttcagaac tcgaaaaccc tcactgaaca ccgtcaatgt ggtcgggtcc    5640
tccatgggct ctggcggggt gttcaccatc gacggaaaaa ttaagtgcgt aactgccgca    5700
catgtcctta cgggcaattc agctagggtt tccggggtcg gcttcaatca aatgcttgac    5760
tttgacgtaa agggagattt cgccatagct gattgcccga attggcaagg ggctgccccc    5820
aagacccaat tctgcaagga tgggtggact ggccgtgcct attggctaac atcctctggc    5880
gtcgaacccg gcgtcattgg aaaaggattc gccttctgct tcaccgcgtg cggcgattcc    5940
gggtccccag tgatcaccga ggccggtgag cttatcggcg ttcacacggg atcaaataaa    6000
caaggaggag gcatcgttac gcgcccctca ggccagtttt gtaatgtggc acccatcaag    6060
ctaagcgaat taagtgaatt ctttgctggg cctaaggtcc cgctcggtga tgtgaaggtt    6120
ggcagccaca taattaaaga cataggcgag gtgccttcag atctttgtgc cttgcttgct    6180
gccaaacctg aactgaagg aggcctctcc accgtccaac ttctttgtgt gttttttcctc    6240 ctgtggagaa tgatgggaca tgcctggacg cccttggttg ctgtgggttt ctttatcttg    6300
aatgaggttc tcccagccgt cctggtccgg agtgttttct cctttggaat gtttgtgcta    6360
tcctggctca cgccatggtc tgcgcaagtt ctgatgatca ggcttctaac agcagccctt    6420
aacaggaaca gatggtcact tgcctttttc agcctcggtg cagtgaccgg ttttgtcgca    6480
gatcttgcgg ctactcaggg gcatccgttg caggcagtta tgaatttgag cacctatgca    6540
ttcctgcctc ggatgatggt tgtgacctca ccagtcccag tgattgcgtg tggtgttgtg    6600
cacctacttg ccatcatttt gtacttgttt aagtaccgtg gcctgcacca aatccttgtt    6660
ggcgatggag tgttctctgc ggcttttctt ctgcgatact ttgccgaggg aaagttgagg    6720
gaaggggtgt cgcaatcctg cggaatgaat catgagtctc tgactggtgc cctcgctatg    6780
agactcaatg acgaggactt ggatttcctt acgaaatgga ctgatttaa gtgctttgtt    6840 tctgcgtcca acatgaggaa tgcagcgggt caatttatcg aggctgccta tgctaaagca    6900
cttagagtag agcttgccca gttggtgcag gttgataaag ttcgaggaac tttggccaaa    6960
cttgaagcct ttgctgatac cgtggcaccc caactctcgc ccggtgacat tgttgtcgct    7020
ctcggccata cgcctgttgg cagtatcttc gacctaaagg ttggtagcac caagcataccc    7080 ctccaagcca ttgagaccag agtccttgct gggtccaaaa tgaccgtggc gcgcgtcgtc    7140
gacccgaccc ccacgccccc acccgcacct gtgcccatcc cctcccacc gaaagttctg    7200 gagaatggcc ccaacgcttg gggggatgag gaccgtttga taagaagaa gaggcgcagg    7260 atggaagccc tcgcatcta tgttatgggc gggaaaaagt accagaaatt tgggataag    7320 aattccggta atgtgttta tgaggaggtc cataataaca cagatgagtg ggagtgtctc    7380
agagttggcg accctgccga ctttgaccct gagaagggaa ctctgtgtgg acatgtcacc    7440
```

TABLE 5-continued

```
attgaagata aggcttacca tgtttacacc tcaccatctg gtaagaagtt cttggtcccc    7500
gtcaatccag agaatggaag agtccaatgg gaagctgcaa agctttccgt agagcaggcc    7560
cttggtatga tgaacgtcga cggcgaactg actaccaaag aactggagaa actgaaaaga    7620
ataattgaca aactccaggg cctgactaag gagcagtgtt taaactgcta gccgccagcg    7680
gcttgacccg ctgtggtcgc ggcggcttgg ttgttactga acagcggta aaaatagtca     7740 aatttcacaa ccggaccttc accctgggac ctgtgaattt aaaagtggcc agtgaggttg    7800
agctaaaaga cgcggttgag cacaaccaac acccggttgc gagaccggtc gatggtggtg    7860
ttgtgctcct gcgttccgcg gttccttcgc ttatagacgt cttgatctcc ggtgctgatg    7920
catctcccaa gttgcttgcc catcacgggc cgggaaacac tgggatcgat ggcacgctct    7980
gggattttga gtccgaagcc actaaagagg aagtcgcact tagtgcgcaa ataatacagg    8040
cttgtgacat taggcgcggc gacgctcctg aaattggtct cccttacaag ctgtaccctg    8100 ttagggggtaa ccctgagcgg gtaaaaggag ttctacagaa tacaaggttt ggagacatac   8160
cttacaaaac ccccagtgat actggaaacc cagtgcacgc ggctgcctgc cttacgccca    8220
acgccactcc ggtgactgat gggcgctccg tcttggccac gaccatgccc tccgggtttg    8280
agttgtatgt accaaccata ccagcgtctg tccttgatta ccttgattct aggcctgact    8340
gccctaaaca gttgacagag cacggctgtg aagatgccgc actgagagac ctctccaaat    8400
atgacttgtc cacccaaggc tttgttttac ctggagtttt tcgccttgta cggaaatacc    8460
tgtttgccca tgtaggtaag tgcccacccg ttcatcggcc ttctacttac cctgctaaga    8520
attctatggc tggaataaat gggaataggt tcccaaccaa ggatattcag agcgtccctg    8580
aaatcgacgt tctgtgtgca caggctgtgc gggaaaactg gcaaactgtt accccttgta    8640
ctcttaagaa acagtattgc gggaagaaga agactaggac catactcggc accaataatt    8700
ttatcgcgct agcccaccga gcagcgttga gtggtgtcac ccagggcttc atgaaaaagg    8760
cgtttaactc gcccatcgcc ctcggaaaaa acaagtttaa ggagctacag accccggtcc    8820
taggcaggtg ccttgaagct gatcttgcat cctgcgaccg atccacacct gcaattgtcc    8880
gctggtttgc cgccaacctc ctttatgaac ttgcctgcgc tgaagagcat ttaccgtcgt    8940
acgtgctgaa ctgctgccac gacttactgg tcacgcagtc cggcgcagtg actaagagag    9000
gtggcctgtc gtctggcgac ccgatcacct ctgtgtctaa caccatttac agtttggtga    9060
tctatgcaca gcatatggtg ctcagttact tcaaaagtgg tcaccccat ggcctcttgt     9120 tcttacaaga ccagctaaag tttgaggaca tgctcaaggt tcaacccctg atcgtctatt    9180
cggacgacct cgtgctgtat gccgagtctc ccaccatgcc aaaactatcac tggtgggttg   9240 aacacctgaa tttgatgctg gggtttcaga cggatccaaa aaagacagcc ataacagact    9300
cgccatcatt tctaggctgt agaataataa atggacgcca gctagtcccc aaccgtgaca    9360
ggattctcgc ggccctcgcc taccacatga aggcgagtaa tgtttctgaa tactacgcct    9420
cagcggctgc aatactcatg gacagctgtg cttgttttgga gtatgatcct gaatggtttg    9480
aagaacttgt agttggaata gcgcaatgcg cccgcaagga cggttacagc tttcccggca    9540
cgccgttctt tatgtccatg tgggaaaaac tcaggtccaa ttatgagggg aagaagtcga    9600
gagtgtgcgg gtactgcggg gccccggccc cgtacgctac tgcctgtggc ctcgacgtct    9660
gcatttacca cacccacttc caccagcatt gtccagtcac aatctggtgt ggccatccag    9720
cgggttctgt ttcttgtagt gagtgcaaat ccctgtagg gaaaggcaca agcccttag     9780 acgaggtgct ggaacaagtc ccgtacaagc ccccacggac cgttatcatg cgtgtggagc    9840
```

TABLE 5-continued

```
agggtcttac cccccttgac ccaggtagat accagactcg ccgcggatta gtctccgtca   9900
ggcgtggaat caggggaaat gaggttgaac taccagacgg tgattatgct agtaccgcct   9960
tgctccctac ctgtaaagag atcaacatgg tcgctgttgc ttccaatgta ttgcgcagca  10020
ggttcatcat tggtccaccc ggtgctggga aaacatactg gctccttcaa caggtccagg  10080
atggtgatgt tatttacaca ccaacccacc agaccatgct tgacatgatt agggctttgg  10140
ggacgtgccg gttcaacgtc ccggcaggca caacgctgca attccccgtc ccctcccgta  10200
ccggtccgtg ggttcgcatc ctggccgcg gttggtgtcc tggcaagaat tccttcctgg  10260
atgaagcagc gtattgcaat caccttgatg tcttgaggct tcttagcaaa actaccctca  10320
cctgtctggg agacttcaaa caactccacc cagtgggttt tgattctcat tgctatgttt  10380
ttaacatcat gcctcaaact caactgaaga ccatctggag gtttggacag aatatctgtg  10440
atgccatcca gccagattac agggacaaac tcatgtccat ggtcaacaca acccgtgtga  10500
cctacgtgga aaagcctgtc aggtatgggc aagtcctcac cccctaccac agggaccgag  10560
aggacgacgc catcactatt gactccagtc aaggcgccac attcgatgtg gttacactgc  10620
atttgcccac aaaagattca ctcaacaggc agagagccct tgttgctatc accagggcaa  10680
gacatgctat ctttgtgtat gacccacaca ggcagctgca gagcctgttt gatcttcctg  10740
caaaaggtac acccgtcaac cttgcagtgc accgcgacgg gcagctgatc gtgctagata  10800
gaaataacaa agaatgcacg gttgctcagg ctctaggtaa cggagataaa tttagggcca  10860
cagacaaacg cgttgtagat tctctccgcg ccatttgtgc tgatctagaa gggtcgagct  10920
ctccgctccc caaggtcgca cacaacttgg gattttattt ctcacctgat ttaacacagt  10980
ttgctaaact cccagcagaa cttgcacctc actggcccgt ggtgacaacc cagaacaatg  11040
aaaagtggcc agatcggctg gttaccagcc ttcgccctat ccataaatat agccgcgcgt  11100
gcatcggtgc cggctatatg gtgggcccct cggtgtttct aggcactcct ggggtcgtgt  11160
catactatct cacaaaattt gttaagggcg aggctcaagt gcttccggag acggttttca  11220
gcaccggccg aattgaggta gactgccggg aatatcttga tgatcgggag cgagaggttg  11280
ctgcgtccct cccacatgcc ttcattggcg acgtcaaagg cactaccgtt ggaggatgcc  11340
accatgtcac ctccagatac ctcccgcgct tccttcccaa ggaatcggtt gcggtagtcg  11400
gggtttcaag tcccggaaaa gccgcgaaag cattgtgcac actgacagat gtgtacctcc  11460
cagaccttga agcctatttc cacccggaga cccagtccaa gtgctggaga atgatgttgg  11520
acttcaagga agttcgacta atggtctgga agacaaaac agcctatttc caacttgaag  11580
gtcgctattt cacctggtat cagcttgcta gctatgcctc gtacatccgt gttcctgtca  11640
actccacggt gtacttggac ccctgcatgg gccccgccct ttgcaacagg aaagtcgtcg  11700
ggtccactca ttgggggagct gacctcgctg tcaccccta tgattacggc gctaaaatta  11760
tcctgtctag cgcgtaccat agtgaaatgc ccccggata caagattctg gcgtgcgcgg  11820
aattctcgtt ggatgaccca gtcaagtaca acatacctg ggggtttgaa tcggatacag  11880
cgtatctgta tgagttcacc ggaaacggtg aggactggga ggattacaat gatgcgtttc  11940
gtgcgcgcca ggaagggaaa atttataagg ctactgccac cagcatgaag ttttattttc  12000
cccccgggccc tgtcattgaa ccaactttag gcctgaattg aaatgaaatg gggtccatgc  12060
aaagcctttt tgacaaaatt ggccaacttt tgtggatgc tttcacggag ttcttggtgt  12120
ccattgttga tatcattata ttttttggcca ttttgtttgg cttcaccatc gccggttggt  12180
tggtggtctt ttgcatcaga ttggtttgct ccgcgatact ccgtacgcgc cctgccattc  12240
```

TABLE 5-continued

```
actctgagca attacagaag atcttatgaa gcctttcttt cccagtgcca agtggacatt   12300
cccacctggg gaactaaaca tcctttgggg atgttttggc accataaggt gtcaaccctg   12360
attgatgaga tggtgtcgcg tcgaatgtac cgcatcatgg aaaaagcagg acaggctgcc   12420
tggaaacagg tggtgagcga ggctacgctg tctcgcatta gtagtttgga tgtggtggct   12480
cattttcagc atcttgccgc cattgaagcc gagacctgta aatatttggc ctcccggctg   12540
cccatgctac acaacctgcg catgacaggg tcaaatgtaa ccatagtgta taatagtact   12600
ttgcatcagg tgtttgctat ttttccaacc cctggttccc ggccaaagct tcatgatttt   12660
cagcaatggt taatagctgt acattcctcc atattttcct ctgttgcagc ttcttgtact   12720
ctctttgttg tgctgtggtt gcgggttcca atactacgta ctgttttttgg tttccgctgg  12780
ttagggcaa ttttttctttc gaactcacag tgaattacac ggtgtgtcca ccttgcctca   12840
cccggcaagc agccgcagag gcctacgaac ccggtaggtc tctttggtgc aggatagggt   12900
atgaccgatg tggggaggac gatcatgacg agctagggtt tatggtaccg tctggcctct   12960
ccagcgaagg ccacttgacc agtgtttacg cctggttggc gttcttgtcc ttcagctaca   13020
cggcccagtt ccatcccgag atattcggga tagggaatgt gagtcgagtt tatgttgaca   13080
tcgaacatca actcatctgc gccgaacatg acgggcagaa caccaccttg cctcgtcatg   13140
acaacatttc agccgtgttt cagacctatt accaacatca agtcgacggc ggcaattggt   13200
ttcacctaga atggctgcgt cccttctttt cctcatggtt ggttttaaat gtctcttggt   13260
ttctcaggcg ttcgcctgca aaccatgttt cagttcgagt ctttcagaca ttaagaccaa   13320
caccaccgca gcggcaagct ttgctgtcct ccaagacatc agttgcctta ggcatcgcaa   13380
ctcggcctct gaggcgattc gcaaaatccc tcagtgccgt acggcgatag ggacacccgt   13440
gtatattacc atcacagcca atgtgacaga tgagaattat ttacattctt ctgatctcct   13500
catgcttttct tcttgccttt tctatgcttc tgagatgagt gaaaagggat ttaaggtggt   13560
atttggcaat gtgtcaggca tcgtggctgt gtgtgtcaat tttaccagct acgtccaaca   13620
tgtcagggag tttacccaac gctccttgat ggtcgaccat gtgcggctgc tccatttcat   13680
gacacctgag accatgaggt gggcaactgt tttagcctgt cttttttgcca ttctgttggc   13740
aatttgaatg tttaagtatg ttggggaaat gcttgaccgc gggctgttgc tcgcgattgc   13800
tttctttgtg gtgtatcgtg ccgttctgtt ttgctgtgct cgtcaacgcc aacagcaaca   13860
gcagctctca tctacagttg atttacaact tgacgctatg tgagctgaat ggcacagatt   13920
ggctatctaa taaatttgat tgggcagtgg agagttttgt catcttttccc gttttgactc   13980
acattgtctc ctatggtgcc ctcactacca gccatttcct tgacacagtc gctttagtca   14040
ctgtgtctac cgccgggttt gttcacgggc ggtatgtcct gagcagcatc tacgcggtct   14100
gtgccctggc tgcgttgact tgcttcgtca ttaggttttgc aaagaattgc atgtcctggc   14160
gctactcatg taccagatat actaactttc ttctggacac taagggcaga ctctatcgtt   14220
ggcggtcgcc tgtcatcata gagaaaaggg gcaaagttga ggtcgaaggt catctgatcg   14280
acctcaaaag agttgtgctt gatggttccg tggcaacccc tataaccaga gtttcagcgg   14340
aacaatgggg tcgtccttag atgactttttg ttatgatagc acggctccac aaaaggtgct   14400
tttggcgttt tctattacct acacgccagt gatgatatat gccctaaaag tgagtcgcgg   14460
ccgactgtta gggcttctgc accttttgat cttcctgaac tgtgctttca ccttcgggta   14520
catgacattc gcgcactttc agagtacaaa taaggtcgcg ctcactatgg gagcagtagt   14580
tgcactcctt tgggggggtgt attcagccat agaaacctgg aaattcatca cctccagatg   14640
```

TABLE 5-continued

```
ccgtttgtgc ttgctaggcc gcaagtacat tctggcccct gcccaccacg ttgagagtgc    14700
cgcaggcttt catccgattg cggcaaatga taaccacgca tttgtcgtcc ggcgtcccgg    14760
ctccactacg gtcaacggca cattggtgcc cgggttgaaa ggcctcgtgt tgggtggcag    14820
aaaagctgtt aaacagggag tggtaaacct tgtcaaatat gccaaataac aacggcaagc    14880
agcagaagag aaagaagggg gatggccagc cagtcaatca gctgtgccag atgctgggta    14940
agatcatcgc ccagcaaaac cagtccagag gcaagggacc gggaaagaaa aataagaaga    15000
aaaacccgga gaagccccat tttcctctag cgactgaaga tgatgtcaga catcacttta    15060
cccctagtga gcggcaattg tgtctgtcgt caatccagac tgcctttaat caaggcgctg    15120
ggacttgcac cctgtcagat tcagggagga taagttacac tgtggagttt agtttgccta    15180
cgcatcatac tgtgcgcctg atccgcgtca cagcatcacc ctcagcatga tgggctggca    15240
ttcttgaggc atctcagtgt ttgaattgga agaatgtgtg gtgaatggca ctgattgaca    15300
ttgtgcctct aagtcaccta ttcaattagg gcgaccgtgt gggggtaaga tttaattggc    15360
gagaaccata cggccgaaat t                                              15381
```

TABLE 6

Further SEQ ID NO: items and certain sequence listing information.

| Seq ID No: | Sequence |
|---|---|
| 4 | ANRMXNSKFE Xaa is Val or Met |
| 5 | ANRMVNSKFE |
| 6 | LANYYYRAQG |
| 7 | LANYHYRAQG |
| 8 | DLXTPPEPAT <223> Xaa is Pro or Ser |
| 9 | DLSTPPELAT |
| 10 | DLPTPPEPAT |
| 11 | VDIIIFLAIL |
| 12 | VDIIVFLAIL |
| 13 | AILRTRPAIH |
| 14 | AILRARPAIH |
| 15 | LGFMIPXGLS <223> Xaa is Pro or Ser |
| 16 | LGFMVPSGLS |
| 17 | SVRVLQTLRP |
| 18 | SVRVFQTLRP |
| 19 | SSSLADIKTN |
| 20 | SSSLSDIKTN |
| 21 | MVNSCTFLHI FLCCSFLYSL CCAVVAGSNT TYCFWFPLVR GNFSFELTVN YTVCPPCLIR 60<br>QAAAEAYEPG RSLWCRIGYD RCGEDDHDEL GFMIPXGLSS EGHLTSVYAW LAFLSFSYTA 120<br>QFHPEIFGIG NVSRVYVDIE HQLICAEHDG QNTTLPRHDN ISAVFQTYYQ HQVDGGNWFH 180<br>LEWLRPFFSS WLVLNVSWFL RRSPANHVSV RVLQTLRPTP PQRQALLSSK TSVALGIATR 240<br>PLRRFAKSLS AVRR 254<br><222> (96) . . . (96) <223> Xaa is Pro or Ser |

TABLE 6-continued

Further SEQ ID NO: items and certain sequence listing information.

| Seq ID No: | Sequence | |
|---|---|---|
| 22 | MVNSCTFLHI FLCCSFLYSL CCAVVAGSNT TYCFWFPLVR GNFSFELTVN YTVCPPCLIR | 60 |
| | QAAAEAYEPG RSLWCRIGYD RCGEDDHDEL GFMVPSGLSS EGHLTSVYAW LAFLSFSYTA | 120 |
| | QFHPEIFGIG NVSRVYVDIE HQLICAEHDG QNTTLPRHDN ISAVFQTYYQ HQVDGGNWFH | 180 |
| | LEWLRPPFSS WLVLNVSWFL RRSPANHVSV RVLQTLRPTP PQRQALLSSK TSVALGIATR | 240 |
| | PLRRFAKSLS AVRR | 254 |
| 23 | MAASLLFLMV GFKCLLVSQA FACKPCFSSS LADIKTNTTA AASFAVLQDI SCLRHRNSAS | 60 |
| | EAIRKIPQCR TAIGTPVYIT ITANVTDENY LHSSDLLMLS SCLFYASEMS EKGFKVVFGN | 120 |
| | VSGIVAVCVN FTSYVQHVRE FTQRSLMVDH VRLLHFMTPE TMRWATVLAC LFAILLAI | 178 |
| 24 | MAASLLFLMV GFKCLLVSQA FACKPCFSSS LSDIKTNTTA AASFAVLQDI SCLRHRNSAS | 60 |
| | EAIRKIPQCR TAIGTPVYIT ITANVTDENY LHSSDLLMLS SCLFYASEMS EKGFKVVFGN | 120 |
| | VSGIVAVCVN FTSYVQHVRE FTQRSLMVDH VRLLHFMTPE TMRWATVLAC LFAILLAI | 178 |
| 25 | MGSMQSLFDK IGQLFVDAFT EFLVSIVDII IFLAILFGFT IAGWLVVFCI RLVCSAILRT | 60 |
| | RPAIHSEQLQKIL | 73 |
| 26 | MGSMQSLFDK IGQLFVDAFT EFLVSIVDII VFLAILFGFT IAGWLVVFCI RLVCSAILRA | 60 |
| | RPAIHSEQLQ KIL | 73 |
| 27 | cacacggtcg ccctaattg | 19 |
| 28 | tggtgaatgg cactgattga c | 21 |
| 29 | tgtgcctcta agtcacc | 17 |
| 30 | caactgcaga gctcatatgc at | 22 |
| 31 | MKWGPCKAFL TKLANFLWML SRSSWCPLLI SLYFWPFCLA SPSPVGWWSF ASDWFAPRYS | 60 |
| | VRALPFTLSN YRRSYEAFLS QCQVDIPTWG TKHPLGMFWH HKVSTLIDEM VSRRMYRIME | 120 |
| | KAGQAAWKQV VSEATLSRIS SLDVVAHFQH LAAIEAETCK YLASRLPMLH NLRMIGSNVT | 180 |
| | IVYNSTLHQV FAIFPTPGSR PKLHDFQQWL IAVHSSIFSS VAASCTLFVV LWLRVPILRT | 240 |
| | VFGFRWLGAI FLSNSQ | 256 |
| 32 | MLGKCLTAGC CSRLLSLWCI VPFCFAVLVN ANSNSSSHLQ LIYNLTLCEL NGTDWLSNKF | 60 |
| | DWAVESFVIF PVLTHIVSYG ALTTSHFLDT VALVTVSTAG FVHGRYVLSS IYAVCALAAL | 120 |
| | TCFVIRFAKN CMSWRYSCTR YTNFLLDTKG RLYRWRSPVI IEKRGKVEVE GHLIDLKRVV | 180 |
| | LDGSVATPIT RVSAEQWGRP | 200 |
| 33 | MGSSLDDFCY DSTAPQKVLL AFSITYTPVM IYALKVSRGR LLGLLHLLIF LNCAFTFGYM | 60 |
| | TFAHFQSTNK VALTMGAVVA LLWGVYSAIE TWKFITSRCR LCLLGRKYIL APAHHVESAA | 120 |
| | GFHPIAANDN HAFVVRRPGS TTVNGTLVPG LKGLVLGGRK AVKQGVVNLV KYAK | 174 |
| 34 | MPNNNGKQQK RKKGDGQPVN QLCQMLGKII AQQNQSRGKG PGKKNKKKNP EKPHFPLATE | 60 |
| | DDVRHHFTPS ERQLCLSSIQ TAFNQGAGTC TLSDSGRISY TVEFSLPTHH TVRLIRVTAS | 120 |
| | PSA | 123 |
| 35 | MSGILDRCTC TPNARVFMAE GQVYCTRCLS ARSLLPLNLQ VSELGVLGLF YRPEEPLRWTI | 60 |
| | LPRAFPTVEC SPAGACWLSA IFPIARMISG NLNFQQRMVR VAAELYRAGQ LTPTVLKTLQ | 120 |
| | VYERGCRWYP IVGPVPGVAV FANSLHVSDK PFPGAIHVLT NLPLPQ | 166 |
| 36 | RPKPEDFCPF ECAMATVYDI GHDAVMYVAE GKVSWAPRGG DEVKFETVPG ELELIANRLR | 60 |
| | TSFPPHHTVD MSKFAPTAPG RGVSMRVERQ HGCLPADTVP EGNCWWSLFN LLPLEVQNKE | 120 |
| | IRHANQFGYQ TKHGVSGKYL QRRLQVNGLR AVTDLNGPIV VQYFSVKESW IRHLKLAEEP | 180 |
| | SYPGFEDLLR IRVEPNTSPL ADKDEKIFRF GSHKWY | 216 |
| 37 | AGKRARKARS SATATVAGRA LSVRETRQAK EHEVAGANKA GHLKHYSPPA EGNCGWHCIS | 60 |
| | AIANRMVNSK FETTLPERVR PSDDWATDED LVNAIQILRL PAALNRNGAC ASAKYVLKLE | 120 |
| | GEHWTVTVTP GMSPSLLPLE CVQGCCEHKG SLGSPDAVEV FGFDPACLDR LAEVMHLPSS | 180 |
| | AIPAALAEMS GDSDRSASPV TTVWTVSQFF ARHNGGNHPD QVRLGKIISL CQVIEDCCCS | 240 |
| | QNKTNRVTPE EVAAKIDLYL RGATNLEECL ARLEKARPPR VMDTSFDWDV VLPGVEAATQ | 300 |
| | TTELPQVNQC RALVPVVTQK SLDNNSVPLT AFSLANYYYR AQGDEVRHRE RLTAVLSKLE | 360 |
| | GVVREEYGLM PTGPGPRPTL PRGLDELKDG MEEDLLKLAN AQTTSDMMAW AVEQVDLKTW | 420 |
| | VKNYPRWTPP PPPPKVQPRK TKPVKSLPER KPVPAPRRKV GSDCGSPISL GDDVPNSWED | 480 |
| | LAVGSPFDLP TPPEPATPSS ELVIVSAPQC IFRPATPLSE PAPIPAPRGV VSRPVTPLNE | 540 |
| | PIPVPAPRRK FQQMRRLSSA AVIPPYQDEP LDLSASSQTE YEASPLAPPQ SEGVLGVEGQ | 600 |
| | EAEEALSEIS DMSGNIKPAS VSSSSSLSSV RITRPKYSAQ AIIDSGGPCS GHLQEVKETC | 660 |
| | LSIMREACDA TKLDDPATQE WLSRMWDRVD MLTWRNTSAY QAFRTLDGRL KFLPKMILET | 720 |
| | PPPYPCEFVM MPHTPAPSVG AESDLTIGSV ATEDVPRILE KIENVGEMTN QGPLAFSEDK | 780 |
| | PVDDQLAKDP RISSQRSDES TSAPPAGTGG AGSFTDLPPS DGVDADGGGP FWTVKRKAER | 840 |
| | LFDQLSRQVF DLVSHLPVFF SRLFNPGGGY SPGDWGFAAF TLLCLFLCYS YPAFGIAPLL | 900 |
| | GVFSGSSRRV RMGVFGCWLA FAVGLFKPVS DPVGAACEFD SPECRNILHS FELLKPWDPV | 960 |
| | RSLVVGPVGL GLAILGRLLG | 980 |

TABLE 6-continued

Further SEQ ID NO: items and certain sequence listing information.

| Seq ID No: | Sequence | |
|---|---|---|
| 38 | GARSIWHFLL RLGIVADCVL AGAYVLSQGR CKKCWGSCIR TAPNEVAFNV FPFTRATRSS | 60 |
| | LIDLCDRFCA PKGMDPIFLA TGWRGCWAGR SPIEQPSEKP IAFAQLDEKK ITARTVVAQP | 120 |
| | YDPNQAVKCL RVLQAGGVMV AKAVPKVVKV SAVPFRAPFF PTGVKVDPEC RVVVDPDTFT | 180 |
| | AALRSGYSTT NLVLGVGDFA QLNGLKIRQI SKPSGGGPHL MAALHVACSM ALHMLAGIYV | 240 |
| | TAVGSCGTGT NDPWCANPFA VPGYGPGSLC TSRLCISQHG LTLPLTALVA GFGIQEIALV | 300 |
| | VLIFVSIGGM AHRLSCKADM LCVLLAIASY VWVPLTWLLC VFPCWLRCFS LHPLTILWLV | 360 |
| | FFLISVNMPS GILAMVLLVS LWLLGRYTNV AGLVTPYDIH HYTSGPRGVA ALATAPDGTY | 420 |
| | LAAVRRAALT GRTMLFTPSQ LGSLLE | 446 |
| 39 | GAFRTRKPSL NTVNVVGSSM GSGGVFTIDG KIKCVTAAHV LTGNSARVSG VGFNQMLDFD | 60 |
| | VKGDFAIADC PNWQGAAPKT QFCKDGWTGR AYWLTSSGVE PGVIGKGFAF CFTACGDSGS | 120 |
| | PVITEAGELI GVHTGSNKQG GGIVTRPSGQ FCNVAPIKLS ELSEFFAGPK VPLGDVKVGS | 180 |
| | HIIKDIGEVP SDLCALLAAK PELE | 204 |
| 40 | GGLSTVQLLC VFFLLWRMMG HAWTPLVAVG FFILNEVLPA VLVRSVFSFG MFVLSWLTPW | 60 |
| | SAQVLMIRLL TAALNRNRWS LAFFSLGAVT GFVADLAATQ GHPLQAVMNL STYAFLPRMM | 120 |
| | VVTSPVPVIA CGVVHLLAII LYLFKYRGLH QILVGDGVFS AAFFLRYFAE | 170 |
| 41 | GKLREGVSQS CGMNHE | 16 |
| 42 | SLTGALAMRL NDEDLDFLTK WTDFKCFVSA SNMRNAAGQF IEAAYAKALR VELAQLVQVD | 60 |
| | KVRGTLAKLE AFADTVAPQL SPGDIVVALG HTPVGSIFDL KVGSTKHTLQ AIETRVLAGS | 120 |
| | KMTVARVVDP TPTPPPAPVP IPLPPKVLEN GPNAWGDEDR LNKKKRRRME ALGIYVMGGK | 180 |
| | KYQKFWDKNS GDVFYEEVHN NTDEWECLRV GDPADFDPEK GTLCGHVTIE DKAYHVYTSS | 240 |
| | SGKKFLVPVN PENGRVQWE | 259 |
| 43 | AAKLSVEQAL GMMNVDGELT TKELEKLKRI IDKLQGLTKE QCLNC | 45 |
| 44 | AAKLSVEQAL GMMNVDGELT TKELEKLKRI IDKLQGLTKE QCLNLLAASG LTRCGRGGLV | 60 |
| | VTETAVKIVK FHNRTFTLGP VNLKVASEVE LKDAVEHNQH PVARPVDGGV VLLRSAVPSL | 120 |
| | IDVLISGADA SPKLLAHHGP GNTGIDGTLW DFESEATKEE VALSAQIIQA CDIRRGDAPE | 180 |
| | IGLPYKLYPV RGNPERVKGV LQNTRFGDIP YKTPSDTGNP VHAAACLTPN ATPVTDGRSV | 240 |
| | LATTMPGSFE LYVPTIPASV LDYLDSRPDC PKQLTEHGCE DAALRDLSKY IDVLCAQAVR | 300 |
| | GVFRLVRKYL FAHVGKCPPV HRPSTYPAKN SMAGINGNRF PTKDIQSVPE IDVLCAQAVR | 360 |
| | ENWQTVTPCT LKKQYCGKKK TRTILGTNNF IALAHRAALS GVTQGFMKKA FNSPIALGKN | 420 |
| | KFKELQTPVL GRCLEADLAS CDRSTPAIVR WFAANLLYEL ACAEEHLPSY VLNCCHDLLV | 480 |
| | TQSGAVTKRG GLSSGDPITS VSNTIYSLVI YAQHMVLSYF KSGHPHGLLF LQDQLKFEDM | 540 |
| | LKVQPLIVYS DDLVLYAESP TMPNYHWWVE HLNSMLGFQT DPKKTAITDS PSFLGCRIIN | 600 |
| | GRQLVPNRDR ILAALAYHMK ASNVSEYYAS AAAILMDSCA CLEYDPEWFE ELVVGIAQCA | 660 |
| | RKDGYSFPGT PFFMSMWEKL RSNYE | 685 |
| 45 | GKKSRVCGYC GAPAPYATAC GLDVCIYHTH FHQHCPVTIW CGHPAGSGSC SECKSPVGKG | 60 |
| | TSPLDEVLEQ VPYKPPRTVI MRVEQGLTPL DPGRYQTRRG LVSVRRGIRG NEVELPDGGY | 120 |
| | ASTALLPTCK EINMVAVASN VLRSRFIIGP PGAGKTYWLL QQVQDGDVIY TPTHQTMLDM | 180 |
| | IRALGTCRFN VPAGTTLQFP VPSRTGPWVR ILAGGWCPGK NSFLDEAAYC NHLDVLRLLS | 240 |
| | KTTLTCLGDF KQLHPVGFDS HCYVFNIMPQ TQLKTIWRFG QNICDAIQPD YRDKLMSMVN | 300 |
| | TTRVTYVEKP VRYGQVLTPY HRDREDDAIT IDSSQGATFD VVTLHLPTKD SLNRQRALVA | 360 |
| | ITRARHAIFV YDPHRQLQSL FDLPAKGTPV NLAVHRDGQL IVLDRNNKEC TVAQALGNGD | 420 |
| | KFRATDKRVV DSLRAICADL E | 441 |
| 46 | GSSSPLPKVA HNLGFYFSPD LTQFAKLPAE LAPHWPVVTT QNNEKWPDRL VTSLRPIHKY | 60 |
| | SRACIGAGYM VGPSVFLGTP GVVSYYLTKF VKGEAQVLPE TVFSTGRIEV DCREYLDDRE | 120 |
| | REVAASLPHA FIGDVKGTTV GGCHHVTSRY LPRFLPKESV AVVGVSSPGK AAKALCTLTD | 180 |
| | VYLPDLEAYF HPETQSKCWR MMLDFKEVRL MVWKDKTAYF QLE | 223 |
| 47 | GRYFTWYQLA SYASYIRVPV NSTVYLDPCM GPALCNRKVV GSTHWGADLA VTPYDYGAKI | 60 |
| | ILSSAYHSEM PPGYKILACA EFSLDDPVKY KHTWGFESDT AYLYEFTGNG EDWEDYNDAF | 120 |
| | RARQEGKIYK ATATSMKFYF PPGPVIEPTL GLN | 153 |
| 48 | MVNSCTFLHI FLCCSFLYSL CCAVVAGSNT TYCFWFPLVR GNFSFELTVN YTVCPPCLTR | 60 |
| | QAAAEAYEPG RSLWCRIGYD RCGEDDHDEL GFMVPSGLSS EGHLTSVYAW LAFLSFSYTA | 120 |
| | QFHPEIFGIG NVSRVYVDIE HQLICAEHDG QNTTLPRHDN ISAVFQTYYQ HQVDGGNWFH | 180 |
| | LEWLRPFFSS WLVLNVSWFL RRSPANHVSV RVFQTLRPTP PQRQALLSSK TSVALGIATR | 240 |
| | PLRRFAKSLS AVRR | 254 |

SEQUENCE LISTING

<160> NUMBER OF SEQ ID NOS: 48

<210> SEQ ID NO 1
<211> LENGTH: 15381
<212> TYPE: DNA
<213> ORGANISM: PRRS Virus

<400> SEQUENCE: 1

| | | | | | |
|---|---|---|---|---|---|
| catttg

```
aatcttgaag aatgcttggc caggcttgag aaagcgcgcc cgccacgcgt aatggacacc   2160
tcctttgatt gggatgttgt gctccctggg gttgaggcgg caactcagac gaccgaactg   2220
ccccaggtca accagtgtcg cgctctggtc cctgttgtaa ctcaaaagtc cttggacaac   2280
aactcggtcc ccctgaccgc cttttcactg gctaactact actaccgtgc gcaaggtgac   2340
gaagttcgtc accgtgaaag actaaccgcc gtgctctcca agttggaagg ggttgttcga   2400
gaagaatatg ggctcatgcc aaccgggcct ggtccacggc ccacactgcc acgcgggctc   2460
gacgaactca agaccagatg gaggaggac ttgctgaaac tggctaacgc ccagacgact   2520
tcggacatga tggcctgggc agtcgagcag gttgacctaa aaacttgggt caagaactac   2580
ccgcggtgga caccaccacc ccctccgcca aaagttcagc ctcgaaaaac gaagcctgtc   2640
aagagcttgc cagagagaaa gcctgtcccc gccccgcgca ggaaggttgg gtccgattgt   2700
ggcagcccga tttcattggg cgacgatgtc cctaacagtt gggaagattt ggctgttggt   2760 agccccttttg atctcccgac cccacctgag ccggcaacac cttcaagtga gctggtgatt   2820
gtgtccgcac cgcaatgcat cttcaggccg gcgacaccct tgagtgagcc ggctccaatt   2880
cccgcacccc gcggggttgt gtctcgaccg gtgacaccct tgaatgagcc gatacctgtg   2940
cccgcaccgc ggcgtaagtt tcagcagatg agaagattga gttcggcggc ggtaatcccg   3000
ccgtaccagg acgagcccct agatttgtct gcttcctcac agactgaata tgaggcctct   3060
cccctagcac cgccgcagag cgagggtgtt ctgggagtag aggggcagga agctgaggaa   3120
gccctaagtg aaatctcgga catgtcgggt aacattaaac ctgcgtccgt atcatcaagc   3180
agctccttgt ccagcgtgag aatcactcgc ccaaaatact cagctcaagc catcatcgac   3240
tcgggcgggc cctgcagtgg gcatctccaa gaggtaaagg aaacatgcct cagtatcatg   3300
cgcgaggcat gtgatgcgac taagcttgat gaccctgcta cgcaggagtg gctttctcgc   3360
atgtgggatc gggtggacat gctgacttgg cgcaacacgt ctgcttacca ggcgtttcgc   3420
accttagatg gcaggttaaa gttcctccca aaaatgatac tcgagacacc gccgccctat   3480
ccgtgtgagt ttgtgatgat gcctcacacg cctgcacctt ccgtaggtgc ggagagcgac   3540
cttaccattg gctcagtcgc tactgaagat gttccacgca tcctcgagaa aatagaaaat   3600
gtcggcgaga tgaccaacca gggacccttg gccttctccg aggataaacc ggtagatgac   3660
caacttgcca aagaccccg gatatcgtcg cagaggtctg acgagagcac atcagctccg   3720
cccgcaggca caggtggcgc cggctcattt accgatttgc cgccttcgga cggcgtggat   3780
gcggacggag gggggccgtt ttggacggta aaaagaaaag ctgaaaggct ctttgaccaa   3840
ctgagccgtc aggttttga cctcgtctcc catctccctg ttttcttctc acgccttttc   3900
aaccctggcg gtggttattc tccgggtgat tggggttttg cagcttttac tctattgtgc   3960
ctctttttat gttacagtta cccagccttt ggtattgctc ccctcttggg tgtgttttct   4020
gggtcttctc ggcgcgttcg aatgggggtt tttggctgct ggttggcttt tgctgttggt   4080
ctgttcaagc ctgtgtccga cccagtcggc gctgcttgtg agtttgactc gccagagtgt   4140
agaaatatcc ttcattcttt tgagcttctc aaaccttggg accctgttcg cagccttgtt   4200
gtgggccccg tcggtctcgg tcttgccatt cttggcaggt tactgggcgg ggcacgcagc   4260
atctggcact ttttgcttag gcttggcatt gttgcagact gtgtcttggc tggagcttat   4320 gtgcttctc aaggtaggtg taaaaagtgc tggggatctt gtataagaac tgctcctaat   4380
gaggtcgctt ttaacgtgtt tccttttaca cgtgcgacca ggtcgtcact aatcgacctg   4440
```

```
tgcgatcggt tttgtgcgcc aaaaggcatg gacccatttt ttctcgccac tgggtggcgc    4500
gggtgctggg ccggccgaag ccccattgag caaccctctg aaaaacccat cgcgtttgcc    4560
cagttggatg aaaagaagat tacggctagg actgtggtcg cccagcctta tgaccccaac    4620
caagccgtaa agtgcttgcg ggtattgcag gcgggtgggg tgatggtggc taaggcagtc    4680
ccaaaagtgg tcaaggtttc cgctgttcca ttccgagccc ccttctttcc caccggagtg    4740
aaagttgacc ctgaatgcag ggtcgtggtt gaccccgaca cttttcaccg agctctccgg    4800
tctggctact ccaccacaaa cctcgtcctc ggtgtagggg attttgccca gctgaatgga    4860
ttaaaaatca ggcaaatttc caagccttca ggaggaggcc cacacctcat ggctgccctg    4920
catgttgcct gctcgatggc tttgcacatg cttgctggga tttatgtgac tgcggtgggt    4980
tcttgcggca ccggcaccaa cgacccgtgg tgcgctaacc cgtttgccgt ccctggctac    5040
ggacctggct ctctctgcac gtccagattg tgcatttccc aacatggcct taccctgccc    5100
ttgacagcac tcgtggcggg attcggtatt caagaaattg ccttggtcgt tttgattttt    5160
gtttccatcg gaggcatggc tcacaggttg agttgtaagg ctgatatgct gtgtgttttg    5220
cttgcaattg ccagctatgt ttgggtacct cttacctggt tgctttgtgt gtttccttgc    5280
tggttgcgct gtttttcttt gcatcccctc accatcctat ggttggtgtt tttcttgatt    5340
tctgtgaata tgccttcagg aatcttggcc atggtgttgt tggtttctct ttggcttctt    5400
ggtcgttata ctaatgttgc tggtcttgtc acccccacg acattcatca ttacactagt    5460
ggcccccgcg gtgttgccgc cttggctacc gcaccagatg ggacctactt ggccgctgtc    5520
cgccgcgctc cgttgactgg ccgcaccatg ctgtttaccc cgtcccagct tgggtctctt    5580
cttgagggtg ctttcagaac tcgaaaaccc tcactgaaca ccgtcaatgt ggtcgggtcc    5640
tccatgggct ctggcggggt gttcaccatc gacggaaaaa ttaagtgcgt aactgccgca    5700
catgtcctta cggcaattc agctagggtt ccggggtcg cttcaatca aatgcttgac    5760 tttgacgtaa agggagattt cgccatagct gattgcccga attggcaagg gctgccccc    5820 aagacccaat tctgcaagga tgggtggact ggccgtgcct attggctaac atcctctggc    5880
gtcgaacccg cgtcattgg aaaaggattc gccttctgct tcaccgcgtg cggcgattcc    5940
gggtccccag tgatcaccga ggccggtgag cttatcggcg ttcacacggg atcaaataaa    6000
caaggaggag gcatcgttac gcgcccctca ggccagtttt gtaatgtggc acccatcaag    6060
ctaagcgaat taagtgaatt cttttgctggg cctaaggtcc cgctcggtga tgtgaaggtt    6120
ggcagccaca taattaaaga cataggcgag gtgccttcag atctttgtgc cttgcttgct    6180
gccaaacctg aactggaagg aggcctctcc accgtccaac ttcttgtgt gtttttcctc    6240 ctgtggagaa tgatgggaca tgcctggacg cccttggttg ctgtgggttt ctttatcttg    6300
aatgaggttc tcccagccgt cctggtccgg agtgttttct cctttggaat gtttgtgcta    6360
tcctggctca cgccatggtc tgcgcaagtt ctgatgatca ggcttctaac agcagccctt    6420
aacaggaaca gatggtcact tgccttttc agcctcggtg cagtgaccgg ttttgtcgca    6480
gatcttgcgg ctactcaggg gcatccgttg caggcagtta tgaatttgag cacctatgca    6540
ttcctgcctc ggatgatggt tgtgacctca ccagtcccag tgattgcgtg tggtgttgtg    6600
cacctacttg ccatcatttt gtacttgttt aagtaccgtg gcctgcacca aatccttgtt    6660
ggtgatggag tgttctctgc ggctttcttc ctgcgatact tgccgagggg aaagttgagg    6720
gaaggggtgt cgcaatcctg cggaatgaat catgagtctc tgactggtgc cctcgctatg    6780
agactcaatg acgaggactt ggatttcctt acgaaatgga ctgattttaa gtgctttgtt    6840
```

```
tctgcgtcca acatgaggaa tgcagcgggt caatttatcg aggctgccta tgctaaagca   6900
cttagagtag agcttgccca gttggtgcag gttgataaag ttcgaggaac tttggccaaa   6960
cttgaagcct ttgctgatac cgtggcaccc caactctcgc ccggtgacat tgttgtcgct   7020
ctcggccata cgcctgttgg cagtatcttc gacctaaagg ttggtagcac caagcatacc   7080
ctccaagcca ttgagaccag agtccttgct gggtccaaaa tgaccgtggc gcgcgtcgtc   7140
gacccgaccc ccacgccccc acccgcacct gtgcccatcc ccctcccacc gaaagttctg   7200
gagaatggcc ccaacgcttg gggggatgag gaccgtttga ataagaagaa gaggcgcagg   7260
atggaagccc tcggcatcta tgttatgggc gggaaaaagt accagaaatt tgggataag    7320
aattccggtg atgtgtttta tgaggaggtc cataataaca cagatgagtg ggagtgtctc   7380
agagttggcg accctgccga ctttgaccct gagaagggaa ctctgtgtgg acatgtcacc   7440
attgaagata aggcttacca tgtttacacc tcatcatctg gtaagaagtt cttggtcccc   7500
gtcaatccag agaatggaag agtccaatgg gaagctgcaa agctttccgt agagcaggcc   7560
cttggtatga tgaacgtcga cggcgaactg actaccaaag aactggagaa actgaaaaga   7620
ataattgaca aactccaggg cctgactaag gagcagtgtt taaactgcta gccgccagcg   7680
gcttgacccg ctgtggtcgc ggcggcttgg ttgttactga acagcggta aaaatagtca    7740
aatttcacaa ccggaccttc accctgggac ctgtgaattt aaaagtggcc agtgaggttg   7800
agctaaaaga cgcggttgag cacaaccaac accggttgc gagaccggtc gatggtggtg    7860
ttgtgctcct gcgttccgcg gttccttcgc ttatagacgt cttgatctcc ggtgctgatg   7920
catctcccaa gttgcttgcc catcacgggc cgggaaacac tgggatcgat ggcacgctct   7980
gggattttga gtccgaagcc actaaagagg aagtcgcact tagtgcgcaa ataatacagg   8040
cttgtgacat taggcgcggc gacgctcctg aaattggtct cccttacaag ctgtaccctg   8100
ttaggggtaa ccctgagcgg gtaaaaggag ttctacagaa tacaaggttt ggagacatac   8160
cttacaaaac ccccagtgat actggaaacc cagtgcacgc ggctgcctgc cttacgccca   8220
acgccactcc ggtgactgat gggcgctccg tcttggccac gaccatgccc tccgggtttg   8280
agttgtatgt accaaccata ccagcgtctg tccttgatta ccttgattct aggcctgact   8340
gccctaaaca gttgacagag cacggctgtg aagatgccgc actgagagac ctctccaaat   8400
atgacttgtc cacccaaggc tttgttttac ctggagtttt tcgccttgta cggaaatacc   8460
tgttttgccca tgtaggtaag tgcccacccg ttcatcggcc ttctacttac cctgctaaga   8520
attctatggc tggaataaat gggaataggt cccaaccaa ggatattcag agcgtccctg    8580
aaatcgacgt tctgtgtgca caggctgtgc gggaaaactg gcaaactgtt acccccttgta  8640
ctcttaagaa acagtattgc gggaagaaga agactaggac catactcggc accaataatt   8700
ttatcgcgct agcccaccga gcagcgttga gtggtgtcac ccagggcttc atgaaaaagg   8760
cgtttaactc gcccatcgcc ctcggaaaaa acaagtttaa ggagctacag accccggtcc   8820
taggcaggtg ccttgaagct gatcttgcat cctgcgaccg atccacacct gcaattgtcc   8880
gctggtttgc cgccaacctc ctttatgaac ttgcctgcgc tgaagagcat ttaccgtcgt   8940
acgtgctgaa ctgctgccac gacttactgg tcacgcaatc cggcgcagtg actaagagag   9000
gtggcctgtc gtctggcgac ccgatcacct ctgtgtctaa caccatttac agtttggtga   9060
tctatgcaca gcatatggtg ctcagttact tcaaaagtgg tcaccccca  ggcctcttgt   9120
tcttacaaga ccagctaaag tttgaggaca tgctcaaggt tcaacccctg atcgtctatt   9180
```

-continued

```
cggacgacct cgtgctgtat gccgagtctc ccaccatgcc aaactatcac tggtgggttg   9240
aacacctgaa ttcgatgctg gggtttcaga cggatccaaa aaagacagcc ataacagact   9300
cgccatcatt tctaggctgt agaataataa atggacgcca gctagtcccc aaccgtgaca   9360
ggattctcgc ggccctcgcc taccacatga aggcgagtaa tgtttctgaa tactacgcct   9420
cagcggctgc aatactcatg gacagctgtg cttgtttgga gtatgatcct gaatggtttg   9480
aagaacttgt agttggaata gcgcaatgcg cccgcaagga cggttacagc tttcccggca   9540
cgccgttctt tatgtccatg tgggaaaaac tcaggtccaa ttatgagggg aagaagtcga   9600
gagtgtgcgg gtactgcggg gccccggccc cgtacgctac tgcctgtggc ctcgacgtct   9660
gcatttacca cacccacttc caccagcatt gtccagtcac aatctggtgt ggccatccag   9720
cgggttctgg ttcttgtagt gagtgcaaat ccctgtagg gaaaggcaca agcccttag    9780
acgaggtgct ggaacaagtc ccgtacaagc ccccacggac cgttatcatg cgtgtggagc   9840
agggtcttac cccccttgac ccaggtagat accagactcg ccgcggatta gtctccgtca   9900
ggcgtggaat caggggaaat gaggttgaac taccagacgg tgattatgct agtaccgcct   9960
tgctccctac ctgtaaagag atcaacatgg tcgctgttgc ttccaatgta ttgcgcagca  10020
ggttcatcat tggtccaccc ggtgctggga aaacatactg gctccttcaa caggtccagg  10080
atggtgatgt tatttacaca ccaacccacc agaccatgct tgacatgatt agggctttgg  10140
ggacgtgccg gttcaacgtc ccggcaggca caacgctgca attccccgtc ccctcccgta  10200
ccggtccgtg ggttcgcatc ctggccggcg gttggtgtcc tggcaagaat tccttcctgg  10260
atgaagcagc gtattgcaat caccttgatg tcttgaggct tcttagcaaa actaccctca  10320
cctgtctggg agacttcaaa caactccacc cagtgggttt tgattctcat tgctatgttt  10380
ttaacatcat gcctcaaact caactgaaga ccatctggag gtttggacag aatatctgtg  10440
atgccatcca gccagattac agggacaaac tcatgtccat ggtcaacaca acccgtgtga  10500
cctacgtgga aaagcctgtc aggtatgggc aagtcctcac cccctaccac agggaccgag  10560
aggacgacgc catcactatt gactccagtc aaggcgccac attcgatgtg gttacactgc  10620
atttgcccac aaaagattca ctcaacaggc agagagccct tgttgctatc accagggcaa  10680
gacatgctat ctttgtgtat gacccacaca ggcagctgca gagcctgttt gatcttcctg  10740
caaaaggtac acccgtcaac cttgcagtgc accgcgacgg gcagctgatc gtgctagata  10800
gaaataacaa agaatgcacg gttgctcagg ctctaggtaa cggagataaa tttagggcca  10860
cagacaaacg cgttgtagat tctctccgcg ccatttgtgc tgatctagaa gggtcgagct  10920
ctccgctccc caaggtcgca cacaacttgg gatttatttt ttcacctgat ttaacacagt  10980
ttgctaaact cccagcagaa cttgcacctc actggcctgt ggtgacaacc cagaacaatg  11040
aaaagtggcc agatcggctg gttaccagcc ttcgccctat ccataaatat agccgcgcgt  11100
gcatcggtgc cggctatatg gtgggcccct cggtgtttct aggcactcct ggggttgtgt  11160
catactatct cacaaaattt gttaagggcg aggctcaagt gcttccggag acggttttca  11220
gcaccggccg aattgaggta gactgccggg aatatcttga tgatcgggag cgagaggttg  11280
ctgcgtccct cccacatgcc ttcattggcg acgtcaaagg cactaccgtt ggaggatgcc  11340
accatgtcac ctccagatac ctcccgcgct tccttcccaa ggaatcggtt gcggtagtcg  11400
gggtttcaag tccggaaaa gccgcgaaag cattgtgcac actgacagat gtgtacctcc  11460
cagaccttga agcctatttc cacccggaga cccagtccaa gtgctggaga atgatgttgg  11520
acttcaagga agttcgacta atggtctgga agacaaaaac agcctatttc caacttgaag  11580
```

```
gtcgctattt cacctggtat cagcttgcta gctatgcctc gtacatccgt gttcctgtca   11640
actccacggt gtacttggac ccttgcatgg gccccgccct ttgcaacagg aaagtcgtcg   11700
ggtccactca ttggggagct gacctcgctg tcacccctta tgattacggc gctaaaatta   11760
tcctgtctag cgcgtaccat agtgaaatgc cccccggata caagattctg gcgtgcgcgg   11820
aattctcgtt ggatgaccca gtcaagtaca aacatacctg ggggtttgaa tcggatacag   11880
cgtatctgta tgagttcacc ggaaacggtg aggactggga ggattacaat gatgcgtttc   11940
gtgcgcgcca ggaagggaaa atttataagg ctactgccac cagcatgaag ttttattttc   12000
ccccgggccc tgtcattgaa ccaactttag gcctgaattg aaatgaaatg ggtccatgc    12060 aaagcctttt tgacaaaatt ggccaacttt ttgtggatgc tttcacggag ttcttggtgt   12120
ccattgttga tatcattgta tttttggcca ttttgtttgg cttcaccatc gccgttggt    12180 tggtggtctt ttgcatcaga ttggtttgct ccgcgatact ccgtgcgcgc cctgccattc   12240
actctgagca attacagaag atcttatgaa gcctttcttt cccagtgcca agtggacatt   12300
cccacctggg gaactaaaca tcctttgggg atgttttggc accataaggt gtcaaccctg   12360
attgatgaga tggtgtcgcg tcgaatgtac cgcatcatgg aaaaagcagg acaggctgcc   12420
tggaaacagg tggtgagcga ggctacgctg tctcgcatta gtagtttgga tgtggtggct   12480
cattttcagc atcttgccgc cattgaagcc gagacctgta atatttggc ctcccggctg    12540 cccatgctac acaacctgcg catgacaggg tcaaatgtaa ccatagtgta taatagtact   12600
ttgcatcagg tgtttgctat ttttccaacc cctggttccc ggccaaagct tcatgatttt   12660
cagcaatggt taatagctgt acattcctcc atatttcct ctgttgcagc ttcttgtact    12720
ctctttgttg tgctgtggtt gcgggttcca atactacgta ctgttttgg tttccgctgg    12780 ttaggggcaa ttttcttc gaactcacag tgaattacac ggtgtgtcca ccttgcctca    12840
cccggcaagc agccgcagag gcctacgaac ccggtaggtc tctttggtgc aggatagggt   12900
atgaccgatg tggggaggac gatcatgacg agctagggt tatggtaccg tctggcctct    12960
ccagcgaagg ccacttgacc agtgtttacg cctggttggc gttcttgtcc ttcagctaca   13020
cggcccagtt ccatcccgag atattcggga tagggaatgt gagtcgagtt tatgttgaca   13080
tcgaacatca actcatctgc gccgaacatg acgggcagaa caccaccttg cctcgtcatg   13140
acaacatttc agccgtgttt cagacctatt accaacatca agtcgacggc ggcaattggt   13200
ttcacctaga atggctgcgt cccttctttt cctcatggtt ggttttaaat gtctcttggt   13260
ttctcaggcg ttcgcctgca aaccatgttt cagttcgagt cttgcagaca ttaagaccaa   13320
caccaccgca gcggcaagct ttgctgtcct ccaagacatc agttgcctta ggcatcgcaa   13380
ctcggcctct gaggcgattc gcaaaatccc tcagtgccgt acggcgatag ggacaccgt    13440 gtatattacc atcacagcca atgttacaga tgagaattat ttacattctt ctgatctcct   13500
catgctttct tcttgccttt tctatgcttc tgagatgagt gaaaagggat ttaaggtggt   13560
atttggcaat gtgtcaggca tcgtggctgt gtgtgtcaat tttaccagct acgtccaaca   13620
tgtcagggag tttacccaac gctccttgat ggtcgaccat gtgcggctgc tccatttcat   13680
gacacctgag accatgaggt gggcaactgt tttagcctgt cttttttgcca ttctgttggc   13740 aatttgaatg tttaagtatg ttggggaaat gcttgaccgc gggctgttgc tcgcgattgc   13800
tttctttgtg gtgtatcgtg ccgttctgtt ttgctgtgct cgtcaacgcc aacagcaaca   13860
gcagctctca tctacagttg atttacaact tgacgctatg tgagctgaat ggcacagatt   13920
```

| | | | | |
|---|---|---|---|---|
|ggctatctaa|taaatttgat|tgggcagtgg|agagttttgt|catctttccc|gttttgactc|13980|
|acattgtctc|ctatggtgcc|ctcactacca|gccatttcct|tgacacagtc|gctttagtca|14040|
|ctgtgtctac|cgccgggttt|gttcacgggc|ggtatgtcct|gagcagcatc|tacgcggtct|14100|
|gtgccctggc|tgcgttgact|tgcttcgtca|ttaggtttgc|aaagaattgc|atgtcctggc|14160|
|gctactcatg|taccagatat|actaactttc|ttctggacac|taagggcaga|ctctatcgtt|14220|
|ggcggtcgcc|tgtcatcata|gagaaaaggg|gcaaagttga|ggtcgaaggt|catctgatcg|14280|
|acctcaaaag|agttgtgctt|gatggttccg|tggcaaccc|tataaccaga|gtttcagcgg|14340|
|aacaatgggg|tcgtccttag|atgacttttg|ttatgatagc|acggctccac|aaaaggtgct|14400|
|tttggcgttt|tctattacct|acacgccagt|gatgatatat|gccctaaaag|tgagtcgcgg|14460|
|ccgactgtta|gggcttctgc|accttttgat|cttcctgaac|tgtgctttca|ccttcgggta|14520|
|catgacattc|gcgcactttc|agagtacaaa|taaggtcgcg|ctcactatgg|gagcagtagt|14580|
|tgcactcctt|tgggggtgt|attcagccat|agaaacctgg|aaattcatca|cctccagatg|14640|
|ccgtttgtgc|ttgctaggcc|gcaagtacat|tctggcccct|gccaccacg|ttgagagtgc|14700|
|cgcaggcttt|catccgattg|cggcaaatga|taaccacgca|tttgtcgtcc|ggcgtcccgg|14760|
|ctccactacg|gtcaacggca|cattggtgcc|cgggttgaaa|ggcctcgtgt|tgggtggcag|14820|
|aaaagctgtt|aaacagggag|tggtaaacct|tgtcaaatat|gccaaataac|aacggcaagc|14880|
|agcagaagag|aaagaagggg|gatggccagc|cagtcaatca|gctgtgccag|atgctgggta|14940|
|agatcatcgc|ccagcaaaac|cagtccagag|gcaagggacc|gggaaagaaa|aataagaaga|15000|
|aaacccgga|gaagccccat|tttcctctag|cgactgaaga|tgatgtcaga|catcactta|15060|
|cccctagtga|gcggcaattg|tgtctgtcgt|caatccagac|tgcctttaat|caaggcgctg|15120|
|ggacttgcac|cctgtcagat|tcagggagga|taagttacac|tgtggagttt|agtttgccta|15180|
|cgcatcatac|tgtgcgcctg|atccgcgtca|cagcatcacc|ctcagcatga|tgggctggca|15240|
|ttcttgaggc|atctcagtgt|ttgaattgga|agaatgtgtg|gtgaatggca|ctgattgaca|15300|
|ttgtgcctct|aagtcaccta|ttcaattagg|gcgaccgtgt|ggggtaaga|tttaattggc|15360|
|gagaaccata|cggccgaaat|t| | |15381|

<210> SEQ ID NO 2
<211> LENGTH: 15270
<212> TYPE: DNA
<213> ORGANISM: PRRS Virus
<220> FEATURE:
<221> NAME/KEY: N
<222> LOCATION: (11766)..(11766)
<223> OTHER INFORMATION: A, G, T, or C
<220> FEATURE:
<221> NAME/KEY: misc_feature
<222> LOCATION: (11766)..(11766)
<223> OTHER INFORMATION: n is a, c, g, or t

<400> SEQUENCE: 2

| | | | | | |
|---|---|---|---|---|---|
|catttgtgtt|gtcaggagct|gtgaccattg|gcacagccca|aaacttgctg|cacggaagcg|60|
|cccttctgtg|acagcctcct|tcaggggagc|ttggggtct|gtccctagca|ccttgcttcc|120|
|ggagttgcac|tgctttacgg|tctctccacc|cctttaacca|tgtctgggat|acttgatcgg|180|
|tgcacgtgta|cccccaatgc|cagggtgttt|atggcggagg|ccaagtcta|ctgcacacga|240|
|tgcctcagtg|cacggtctct|ccttcctctg|aatctccaag|tttctgaact|cggggtgcta|300|
|ggcctattct|acaggcccga|agagccactc|cggtggacgt|tgccacgtgc|attccccact|360|
|gttgagtgct|ccccgccgg|ggcctgctgg|ctttctgcaa|tttttccaat|tgcacgaatg|420|

```
accagtggaa acctgaactt ccaacaaaga atggtacggg tcgcagctga actttacaga    480
gccggccagc tcacccctac agtcttaaag actttacaag tttatgaacg gggttgccgc    540
tggtacccca tcgtaggacc tgtccctgga gtggccgttt tcgccaactc cctacatgtg    600
agtgataaac ctttcccggg agcaactcac gtgttaacca acctgccgct cccgcagaga    660
cccaagcctg aagacttttg cccctttgag tgtgctatgg ctaccgtcta tgacattggt    720
catgacgccg tcatgtatgt ggccgaaggg aaagtctcct gggcccctcg tggcggggat    780
gaagtgaaat ttgaaactgt ccccggggag ttggagttga ttgcgaatcg actccgcacc    840
tccttcccgc cccaccacac agtggacatg tctaagttcg ccttcacagc ccctgggcgt    900
ggtgtttcta tgcgggtcga acgccaacac ggctgcctcc ccgctgacac tgtccctgaa    960
ggcaactgct ggtggagctt gtttaacttg ctcccactgg aagttcagaa caaagaaatt   1020
cgccatgcta accaatttgg ctaccagacc aagcatggtg tctctggcaa gtacctacgg   1080
cggaggctgc aagttaatgg tctccgagca gtaactgacc tgaatggacc tatcgtcgta   1140
cagtacttct ccgttaagga gagttggatc cgccacttga aactggcgga agaacccagc   1200
taccctgggt ttgaggacct cctcagaata agggttgagc ccaacacgtc gccattggct   1260
gacaaggatg aaaaaatttt ccggtttggc agtcacaagt ggtacggcgc tggaaagaga   1320
gcaaggaaag cacgctctag tgcgactgct acagtgctg gccgcgcttt gtccgttcgt    1380
gaaacccggc aggccaagga gcacgaggtt gccggcgcca acaaggctgg gcacctcaaa   1440
cattactccc cgcctgccga agggaattgt ggttggcact gcatttccgc catcgccaac   1500
cggatggtga attccaaatt tgaaaccacc cttcccgaaa gagtgagacc ttcagatgac   1560
tgggctactg acgaggatct tgtgaatgcc atccaaatcc tcaggctccc tgcggccttg   1620
aacaggaacg gcgcttgtgc tagcgccaag tacgtactta agctggaagg tgagcattgg   1680
actgtcactg tgaccctgg gatgtcccct tctttgctcc ctcttgaatg tgttcagggc   1740
tgttgtgagc ataagggcag tcttggttcc ccagatgcag tcgaggtttt cggatttgac   1800
cctgcctgcc ttgaccggct ggctgaggtg atgcacctgc ctagcagtgc tatcccagcc   1860
gctctggccg aaatgtccgg cgattccgat cgttcggctt ccccggtcac caccgtgtgg   1920
actgtttcgc agttctttgc ccgccacaat ggagggaatc accctgacca agtgcgctta   1980
gggaaaatta tcagcctttg tcaggtgatt gaggactgct gctgttccca gaacaaaacc   2040
aaccgggtca ccccggagga ggtcgcagca aagattgacc tgtaccttcg tggcgcaaca   2100
aatcttgaag aatgcttggc caggcttgag aaagcgcgcc cgccacgcgt aatggacacc   2160
tcctttgatt gggatgttgt gctccctggg gttgaggcgg caactcagac gaccgaactg   2220
ccccaggtca accagtgtcg cgctctggtc cctgttgtaa ctcaaaagtc cttggacaac   2280
aactcggtcc ccctgaccgc cttttcactg gctaactact actaccgtgc gcaaggtgac   2340
gaagttcgtc accgtgaaag actaaccgcc gtgctctcca gttggaaggg ggttgttcga   2400
gaagaatatg ggctcatgcc aaccgggcct ggtccacggc ccacactgcc acgcgggctc   2460
gacgaactca agaccagat ggaggaggac ttgctgaaac tggctaacgc ccagacgact   2520
tcggacatga tggcctgggc agtcgagcag gttgacctaa aaacttgggt caagaactac   2580
ccgcggtgga caccaccacc ccctccgcca aaagttcagc ctcgaaaaac gaagcctgtc   2640
aagagcttgc cagagagaaa gcctgtcccc gccccgcgca ggaaggttgg gtccgattgt   2700
ggcagcccga tttcattggg cgacgatgtc cctaacagtt gggaagattt ggctgttggt   2760
```

```
agccccttg  atctctcgac  cccacctgag  ctggcaacac  cttcaagtga  gctggtgatt   2820
gtgtccgcac  cgcaatgcat  cttcaggccg  gcgacaccct  tgagtgagcc  ggctccaatt   2880
cccgcacccc  gcggggttgt  gtctcgaccg  gtgacaccct  tgaatgagcc  gatacctgtg   2940
cccgcaccgc  ggcgtaagtt  tcagcagatg  agaagattga  gttcggcggc  ggtaatcccg   3000
ccgtaccagg  acgagcccct  agatttgtct  gcttcctcac  agactgaata  tgaggcctct   3060
cccctagcac  cgccgcagag  cgagggtgtt  ctgggagtag  aggggcagga  agctgaggaa   3120
gccctaagtg  aaatctcgga  catgtcgggt  aacattaaac  ctgcgtccgt  atcatcaagc   3180
agctccttgt  ccagcgtgag  aatcactcgc  ccaaaatact  cagctcaagc  catcatcgac   3240
tcgggcgggc  cctgcagtgg  gcatctccaa  gaggtaaagg  aaacatgcct  cagtatcatg   3300
cgcgaggcat  gtgatgcgac  taagcttaag  ttcctcccaa  aaatgatact  cgagacaccg   3360
ccgccctatc  cgtgtgagtt  tgtgatgatg  cctcacacgc  ctgcaccttc  cgtaggtgcg   3420
gagagcgacc  ttaccattgg  ctcagtcgct  actgaagatg  ttccacgcat  cctcgagaaa   3480
atagaaaatg  tcggcgagat  gaccaaccag  ggacccttgg  ccttctccga  ggataaaccg   3540
gtagatgacc  aacttgccaa  agaccccgg  atatcgtcgc  agaggtctga  cgagagcaca   3600
tcagctccgc  ccgcaggcac  aggtggcgcc  ggctcattta  ccgatttgcc  gccttcggac   3660
ggcgtggatg  cggacggagg  ggggccgttt  tggacggtaa  aaagaaaagc  tgaaaggctc   3720
tttgaccaac  tgagccgtca  ggttttgac  ctcgtctccc  atctccctgt  tttcttctca   3780
cgccttttca  accctggcgg  tggttattct  ccgggtgatt  ggggttttgc  agcttttact   3840
ctattgtgcc  tcttttatg  ttacagttac  ccagcctttg  gtattgctcc  cctcttgggt   3900
gtgttttctg  ggtcttctcg  gcgcgttcga  atggggggttt  ttggctgctg  gttggctttt   3960
gctgttggtc  tgttcaagtc  tgtgtccgac  ccagtcggcg  ctgcttgtga  gtttgactcg   4020
ccagagtgta  gaaatatcct  tcattctttt  gagcttctca  aaccttggga  ccctgttcgc   4080
agccttgttg  tgggccccgt  cggtctcggt  cttgccattc  ttggcaggtt  actgggcggg   4140
gcacgcagca  tctggcactt  tttgcttagg  cttggcattg  ttgcagactg  tgtcttggct   4200
ggagcttatg  tgctttctca  aggtaggtgt  aaaaagtgct  ggggatcttg  tataagaact   4260
gctcctaatg  aggtcgcttt  taacgtgttt  ccttttacac  gtgcgaccag  gtcgtcacta   4320
atcgacctgt  gcgatcggtt  ttgtgcgcca  aaaggcatgg  accccatttt  tctcgccact   4380
gggtggcgcg  ggtgctgggc  cggccgaagc  cccattgagc  aaccctctga  aaaacccatc   4440
gcgtttgccc  agttggatga  aaagaagatt  acggctagga  ctgtggtcgc  ccagccttat   4500
gaccccaacc  aagccgtaaa  gtgcttgcgg  gtattgcagg  cgggtggggt  gatggtggct   4560
aaggcagtcc  caaaagtggt  caaggtttcc  gctgttccat  tccgagcccc  cttctttccc   4620
accggagtga  agttgacccc  tgaatgcagg  gtcgtggttg  accccgacac  tttcaccgca   4680
gctctccggt  ctggctactc  caccacaaac  ctcgtcctcg  gtgtagggga  ttttgcccag   4740
ctgaatggat  taaaaatcag  gcaaatttcc  aagccttcag  gaggaggccc  acacctcatg   4800
gctgccctgc  atgttgcctg  ctcgatggct  ttgcacatgc  ttgctgggat  ttatgtgact   4860
gcggtgggtt  cttgcggcac  cggcaccaac  gacccgtggt  gcgctaaccc  gtttgccgtc   4920
cctggctacg  gacctggctc  tctctgcacg  tccagattgt  gcatttccca  acatggcctt   4980
accctgccct  tgacagcact  cgtggcggga  ttcggtattc  aagaaattgc  cttggtcgtt   5040 ttgattttg  tttccatcgg  aggcatggct  cacaggttga  gttgtaaggc  tgatatgctg   5100
tgtgttttgc  ttgcaattgc  cagctatgtt  tgggtacctc  ttacctggtt  gctttgtgtg   5160
```

```
tttccttgct ggttgcgctg tttttctttg catcccctca ccatcctatg gttggtgttt    5220
ttcttgattt ctgtgaatat gccttcagga atcttggcca tggtgttgtt ggtttctctt    5280
tggcttcttg gtcgttatac taatgttgct ggtcttgtca cccctacga cattcatcat    5340 tacactagtg gcccccgcgg tgttgccgcc ttggctaccg caccagatgg gacctacttg    5400
gccgctgtcc gccgcgctgc gttgactggc cgcaccatgc tgtttacccc gtcccagctt    5460
gggtctcttc ttgagggtgc tttcagaact cgaaaaccct cactgaacac cgtcaatgtg    5520
gtcgggtcct ccatgggctc tggcggggtg ttcaccatcg acggaaaaat taagtgcgta    5580
actgccgcac atgtccttac gggcaattca gctagggttt ccggggtcgg cttcaatcaa    5640
atgcttgact ttgacgtaaa gggagatttc gccatagctg attgcccgaa ttggcaaggg    5700
gctgccccca agacccaatt ctgcaaggat gggtggactg gccgtgccta ttggctaaca    5760
tcctctggcg tcgaacccgg cgtcattgga aaaggattcg ccttctgctt caccgcgtgc    5820
ggcgattccg ggtccccagt gatcaccgag gccggtgagc ttatcggcgt tcacacggga    5880
tcaaataaac aaggaggagg catcgttacg cgcccctcag gccagttttg taatgtggca    5940
cccatcaagc taagcgaatt aagtgaattc tttgctgggc ctaaggtccc gctcggtgat    6000
gtgaaggttg gcagccacat aattaaagac ataggcgagg tgccttcaga tctttgtgcc    6060
ttgcttgctg ccaaacctga actggaagga ggctctccca ccgtccaact tctttgtgtg    6120
tttttcctcc tgtggagaat gatgggacat gcctggacgc ccttggttgc tgtgggtttc    6180
tttatcttga atgaggttct cccagccgtc ctggtccgga gtgttttctc ctttggaatg    6240
tttgtgctat cctggctcac gccatggtct gcgcaagttc tgatgatcag gcttctaaca    6300 gcagcccttaa acaggaacag atggtcactt gccttttca gcctcggtgc agtgaccggt    6360
tttgtcgcag atcttgcggc tactcagggg catccgttgc aggcagttat gaatttgagc    6420
acctatgcat tcctgcctcg gatgatggtt gtgacctcac cagtcccagt gattgcgtgt    6480
ggtgttgtgc acctacttgc catcattttg tacttgttta agtaccgtgg cctgcaccaa    6540
atccttgttg gcgatggagt gttctctgcg gctttcttcc tgcgatactt tgccgaggga    6600
aagttgaggg aaggggtgtc gcaatcctgc ggaatgaatc atgagtctct gactggtgcc    6660
ctcgctatga gactcaatga cgaggacttg gatttcctta cgaaatggac tgattttaag    6720
tgctttgttt ctgcgtccaa catgaggaat gcagcgggtc aatttatcga ggctgcctat    6780
gctaaagcac ttagagtaga gcttgcccag ttggtgcagg ttgataaagt tcgaggaact    6840
ttggccaaac ttgaagcctt tgctgatacc gtggcacccc aactctcgcc cggtgacatt    6900
gttgtcgctc tcggccatac gcctgttggc agtatcttcg acctaaaggt tggtagcacc    6960
aagcataccc tccaagccat tgagaccaga gtccttgctg gtccaaaat gaccgtggcg    7020 cgcgtcgtcg acccgacccc cacgccccca cccgcacctg tgcccatccc cctcccaccg    7080
aaagttctgg agaatggccc caacgcttgg ggggatgagg accgtttgaa taagaagaag    7140
aggcgcagga tggaagccct cggcatctat gttatgggcg gaaaaagta ccagaaattt    7200 tgggataaga attccggtga tgtgttttat gaggaggtcc ataataacac agatgagtgg    7260
gagtgtctca gagttggcga ccctgccgac tttgacctg agaagggaac tctgtgtgga    7320
catgtcacca ttgaagataa ggcttaccat gtttacacct caccatctgg taagaagttc    7380
ttggtccccg tcaatccaga gaatggaaga gtccaatggg aagctgcaaa gctttccgta    7440
gagcaggccc ttggtatgat gaacgtcgac ggcgaactga ctaccaaaga actggagaaa    7500
```

```
ctgaaaagaa taattgacaa actccagggc ctgactaagg agcagtgttt aaactgctag    7560
ccgccagcgg cttgacccgc tgtggtcgcg gcggcttggt tgttactgaa acagcggtaa    7620
aaatagtcaa atttcacaac cggaccttca ccctgggacc tgtgaattta aaagtggcca    7680
gtgaggttga gctaaaagac gcggttgagc acaaccaaca cccggttgcg agaccggtcg    7740
atggtggtgt tgtgctcctg cgttccgcgg ttccttcgct tatagacgtc ttgatctccg    7800
gtgctgatgc atctcccaag ttgcttgccc atcacgggcc gggaaacact gggatcgatg    7860
gcacgctctg ggattttgag tccgaagcca ctaaagagga agtcgcactt agtgcgcaaa    7920
taatacaggc ttgtgacatt aggcgcgcg acgctcctga aattggtctc ccttacaagc     7980
tgtaccctgt taggggtaac cctgagcggg taaaaggagt tctacagaat acaaggtttg    8040
gagacatacc ttacaaaacc cccagtgata ctggaaaccc agtgcacgcg ctgcctgcc     8100
ttacgcccaa cgccactccg gtgactgatg ggcgctccgt cttggccacg accatgccct    8160
ccgggtttga gttgtatgta ccaaccatac cagcgtctgt ccttgattac cttgattcta    8220
ggcctgactg ccctaaacag ttgacagagc acggctgtga agatgccgca ctgagagacc    8280
tctccaaata tgacttgtcc acccaaggct ttgttttacc tggagttttt cgccttgtac    8340
ggaaatacct gtttgcccat gtaggtaagt gcccacccgt tcatcggcct tctacttacc    8400
ctgctaagaa ttctatggct ggaataaatg ggaataggtt cccaaccaag gatattcaga    8460
gcgtccctga aatcgacgtt ctgtgtgcac aggctgtgcg ggaaaactgg caaactgtta    8520
cccttgtac tcttaagaaa cagtattgcg ggaagaagaa gactaggacc atactcggca    8580
ccaataattt tatcgcgcta gcccaccgag cagcgttgag tggtgtcacc cagggcttca    8640
tgaaaaggc gtttaactcg cccatcgccc tcggaaaaaa caagtttaag gagctacaga    8700
ccccggtcct aggcaggtgc cttgaagctg atcttgcatc ctgcgaccga tccacacctg    8760
caattgtccg ctggtttgcc gccaacctcc tttatgaact tgcctgcgct gaagagcatt    8820
taccgtcgta cgtgctgaac tgctgccacg acttactggt cacgcagtcc ggcgcagtga    8880
ctaagagagg tggcctgtcg tctggcgacc cgatcacctc tgtgtctaac accatttaca    8940
gtttggtgat ctatgcacag catatggtgc tcagttactt caaaagtggt cacccccatg    9000
gcctcttgtt cttacaagac cagctaaagt ttgaggacat gctcaaggtt caacccctga    9060
tcgtctattc ggacgacctc gtgctgtatg ccgagtctcc caccatgcca aactatcact    9120
ggtgggttga acacctgaat ttgatgctgg ggtttcagac ggatccaaaa aagacagcca    9180
taacagactc gccatcattt ctaggctgta gaataataaa tggacgccag ctagtcccca    9240
accgtgacag gattctcgcg gccctcgcct accacatgaa ggcgagtaat gtttctgaat    9300
actacgcctc agcggctgca atactcatgg acagctgtgc ttgtttggag tatgatcctg    9360
aatggtttga agaacttgta gttggaatag cgcaatgcgc ccgcaaggac ggttacagct    9420
ttcccggcac gccgttcttt atgtccatgt gggaaaaact caggtccaat tatgagggga    9480
agaagtcgag agtgtgcggg tactgcgggg ccccggccct gtacgctact gcctgtggcc    9540
tcgacgtctg catttaccac acccacttcc accagcattg tccagtcaca atctggtgtg    9600
gccatccagc gggttctggt tcttgtagtg agtgcaaatc cctgtaggg aaaggcacaa     9660
gcccttttaga cgaggtgctg aacaagtcc cgtacaagcc cccacggacc gttatcatgc    9720
atgtggagca gggtctcacc cccccttgacc caggtagata ccagactcgc cgcggattag    9780
tctccgtcag gcgtggaatc aggggaaatg aggttgaact accagacggt gattatgcta    9840
gtaccgcctt gctccctacc tgtaaagaga tcaacatggt cgctgttgct tccaatgtat    9900
```

```
tgcgcagcag gttcatcatt ggtccacccg gtgctgggaa acatactggg ctccttcaac   9960
aggtccagga tggtgatgtt atttacacac caacccacca gaccatgctt gacatgatta  10020
gggctttggg gacgtgccgg ttcaacgtcc cggcaggcac aacgctgcaa ttccccgtcc  10080
cctcccgtac cggtccgtgg gttcgcatcc tggccggcgg ttggtgtcct ggcaagaatt  10140
ccttcctgga tgaagcagcg tattgcaatc accttgatgt cttgaggctt cttagcaaaa  10200
ctaccctcac ctgtctggga gacttcaaac aactccaccc agtgggtttt gattctcatt  10260
gctatgtttt taacatcatg cctcaaactc aactgaagac catctggagg tttggacaga  10320
atatctgtga tgccatccag ccagattaca gggacaaact catgtccatg gtcaacacaa  10380
cccgtgtgac ctacgtggaa aagcctgtca ggtatgggca agtcctcacc ccctaccaca  10440
gggaccgaga ggacgacgcc atcactattg actccagtca aggcgccaca ttcgatgtgg  10500
ttacactgca tttgcccaca aaagattcac tcaacaggca gagagcccdt gttgctatca  10560
ccagggcaag acatgctatc tttgtgtatg acccacacag gcagctgcag agcctgtttg  10620
atcttcctgc aaaaggtaca cccgtcaacc ttgcagtgca ccgcgacggg cagctgatcg  10680
tgctagatag aaataacaaa gaatgcacgg ttgctcaggc tctaggtaac ggagataaat  10740
ttagggccac agacaaacgc gttgtagatt ctctccgcgc catttgtgct gatctagaag  10800
ggtcgagctc tccgctcccc aaggtcgcac acaacttggg attttatttc tcacctgatt  10860
taacacagtt tgctaaactc ccagcagaac ttgcacctca ctggcccgtg gtgacaaccc  10920
agaacaatga aaagtggcca gatcggctgg ttaccagcct tcgccctatc cataaatata  10980
gccgcgcgtg catcggtgcc ggctatatgg tgggcccctc ggtgtttcta ggcactcctg  11040
gggtcgtgtc atactatctc acaaaatttg ttaagggcga ggctcaagtg cttccggaga  11100
cggttttcag caccggccga attgaggtag actgccggga atatcttgat gatcgggagc  11160
gagaggttgc tgcgtccctc ccacatgcct tcattggcga cgtcaaaggc actaccgttg  11220
gaggatgcca ccatgtcacc tccagatacc tcccgcgctt ccttcccaag gaatcggttg  11280
cggtagtcgg ggtttcaagt cccggaaaag ccgcgaaagc attgtgcaca ctgacagatg  11340
tgtacctccc agaccttgaa gcctatttcc acccggagac ccagtccaag tgctggagaa  11400
tgatgttgga cttcaaggaa gttcgactaa tggtctggaa agacaaaaca gcctatttcc  11460
aacttgaagg tcgctatttc acctggtatc agcttgctag ctatgcctcg tacatccgtg  11520
ttcctgtcaa ctccacggtg tacttggacc cctgcatggg ccccgcccdt tgcaacagga  11580
aagtcgtcgg gtccactcat tggggagctg acctcgctgt caccccttat gattacggcg  11640
ctaaaattat cctgtctagc gcgtaccata gtgaaatgcc ccccggatac aagattctgg  11700
cgtgcgcgga attctcgttg gatgacccag tcaagtacaa acataccdgg gggtttgaat  11760
cggatncagc gtatctgtat gagttcaccg gaaacggtga ggactgggag gattacaatg  11820
atgcgtttcg tgcgcgccag gaagggaaaa tttataaggc tactgccacc agcatgaagt  11880
tttattttcc cccgggccct gtcattgaac caactttagg cctgaattga aatgaaatgg  11940
ggtccatgca aagccttttt gacaaaattg gccaacttdt tgtggatgct ttcacggagt  12000
tcttggtgtc cattgttgat atcattatat ttttggccat tttgtttggc ttcaccatcg  12060
ccggttggtt ggtggtcttt tgcatcagat tggtttgctc cgcgatactc cgtacgcgcc  12120
ctgccattca ctctgagcaa ttacagaaga tcttatgaag cctttctttc ccagtgccaa  12180
gtggacattc ccacctgggg aactaaacat cctttgggga tgttttggca ccataaggtg  12240
```

```
tcaaccctga ttgatgagat ggtgtcgcgt cgaatgtacc gcatcatgga aaaagcagga    12300
caggctgcct ggaaacaggt ggtgagcgag gctacgctgt ctcgcattag tagtttggat    12360
gtggtggctc attttcagca tcttgccgcc attgaagccg agacctgtaa atatttggcc    12420
tcccggctgc ccatgctaca caacctgcgc atgacagggt ctaatgtaac catagtgtat    12480
aatagtactt tgcatcaggt gtttgctatt tttccaaccc ctggttcccg gccaaagctt    12540
catgattttc agcaatggtt aatagctgta cattcctcca tattttcctc tgttgcagct    12600
tcttgtactc tctttgttgt gctgtggttg cgggttccaa tactacgtac tgttttttggt    12660 ttccgctggt tagggggcaat ttttctttcg aactcacagt gaattacacg gtgtgtccac    12720
cttgcctcac ccggcaagca gccgcagagg cctacgaacc cggtaggtct ctttggtgca    12780
ggatagggta tgaccgatgt ggggaggacg atcatgacga gctagggttt atggtaccgt    12840
ctggcctctc cagcgaaggc cacttgacca gtgtttacgc ctggttggcg ttcttgtcct    12900
tcagctacac ggcccagttc catcccgaga tattcgggat agggaatgtg agtcgagttt    12960
atgttgacat cgaacatcaa ctcatctgcg ccgaacatga cgggcagaac accaccttgc    13020
ctcgtcatga caacatttca gccgtgtttc agacctatta ccaacatcaa gtcgacggcg    13080
gcaattggtt tcacctagaa tggctgcgtc ccttctttc ctcatggttg gtttaaatg    13140 tctcttggtt tctcaggcgt tcgcctgcaa accatgtttc agttcgagtc ttgcagacat    13200
taagaccaac accaccgcag cggcaagctt tgctgtcctc caagacatca gttgccttag    13260
gcatcgcaac tcggcctctg aggcgattcg caaaatccct cagtgccgta cggcgatagg    13320 gacaccgtg tatattacca tcacagccaa tgtgacagat gagaattatt acattcttc    13380 tgatctcctc atgctttctt cttgcctttt ctatgcttct gagatgagtg aaaagggatt    13440
taaggtggta tttggcaatg tgtcaggcat cgtggctgtg tgtgtcaatt ttaccagcta    13500
cgtccaacat gtcagggagt ttacccaacg ctccttgatg gtcgaccatg tgcggctgct    13560
ccatttcatg acacctgaga ccatgaggtg ggcaactgtt ttagcctgtc ttttgccat    13620 tctgttggca atttgaatgt ttaagtatgt tggggaaatg cttgaccgcg gctgttgct    13680 cgcgattgct ttcttgtgg tgtatcgtgc cgttctgttt tgctgtgctc gtcaacgcca    13740
acagcaacag cagctctcat ctacagttga tttacaactt gacgctatgt gagctgaatg    13800
gcacggattg gctatctaat aaatttgatt gggcagtgga gagttttgtc atctttcccg    13860
ttttgactca cattgtctcc tatggtgccc tcactaccag ccatttcctt gacacagtcg    13920
ctttagtcac tgtgtctacc gccgggtttg ttcacgggcg gtatgtcctg agcagcatct    13980
acgcggtctg tgccctggct gcgttgactt gcttcgtcat caggtttgca agaattgca    14040 tgtcctggcg ctactcatgt accagatata ctaactttct tctggacact aagggcagac    14100
tctatcgttg gcggtcgcct gtcatcatag agaaaagggg caaagttgag gtcgaaggtc    14160
atctgatcga cctcaaaaga gttgtgcttg atggttccgt ggcaaccct ataaccagag    14220 tttcagcgga acaatggggt cgtccttaga tgactttgt tatgatagca cggctccaca    14280
aaaggtgctt ttggcgtttt ctattaccta cacgccagtg atgatatatg ccctaaaagt    14340
gagtcgcggc cgactgttag ggcttctgca ccttttgatc ttcctgaact gtgctttcac    14400
cttcgggtac atgacattcg cgcactttca gagtacaaat aaggtcgcgc tcactatggg    14460
agcagtagtt gcactccttt gggggtgta ttcagccata gaaacctgga aattcatcac    14520
ctccagatgc cgtttgtgct tgctaggccg caagtacatt ctggcccctg cccaccacgt    14580
tgagagtgcc gcaggctttc atccgattgc ggcaaatgat aaccacgcat tgtcgtccg    14640
```

```
gcgtcccggc tccactacgg tcaacggcac attggtgccc gggttgaaag gcctcgtgtt    14700
gggtggcaga aaagctgtta acagggagt ggtaaacctt gtcaaatatg ccaaataaca    14760
acggcaagca gcagaagaga agaaggggg atggccagcc agtcaatcag ctgtgccaga    14820
tgctgggtaa gatcatcgcc cagcaaaacc agtccagagg caagggaccg ggaagaaaa    14880 ataagaagaa aaacccggag aagccccatt ttcctctagc gactgaagat gatgtcagac    14940
atcactttac ccctagtgag cggcaattgt gtctgtcgtc aatccagact gcctttaatc    15000
aaggcgctgg gacttgcacc ctgtcagatt cagggaggat aagttacact gtggagttta    15060
gtttgcctac gcatcatact gtgcgcctga tccgcgtcac agcatcaccc tcagcatgat    15120
gggctggcat tcttgaggca tctcagtgtt tgaattggaa gaatgtgtgg tgaatggcac    15180
tgattgacat tgtgcctcta agtcacctat tcaattaggg cgaccgtgtg ggggtaagat    15240
ttaattggcg agaaccatac ggccgaaatt                                    15270

<210> SEQ ID NO 3
<211> LENGTH: 15381
<212> TYPE: DNA
<213> ORGANISM: PRRS Virus

<400> SEQUENCE: 3
catttgtgtt gtcaggagct gtgaccattg gcacagccca aaacttgctg c

```
cattactccc cgcctgccga agggaattgt ggttggcact gcatttccgc catcgccaac    1500
cggatggtga attccaaatt tgaaaccacc cttcccgaaa gagtgagacc ttcagatgac    1560
tgggctactg acgaggatct tgtgaatgcc atccaaatcc tcaggctccc tgcggccttg    1620
aacaggaacg cgcttgtgc tagcgccaag tacgtactta agctggaagg tgagcattgg     1680
actgtcactg tgacccctgg gatgtcccct tctttgctcc ctcttgaatg tgttcagggc    1740
tgttgtgagc ataagggcag tcttggttcc ccagatgcag tcgaggtttt cggatttgac    1800
cctgcttgcc ttgaccggct ggctgaggtg atgcacctgc ctagcagtgc tatcccagcc    1860
gctctggccg aaatgtccgg cgattccgat cgttcggctt ccccggtcac caccgtgtgg    1920
actgtttcgc agttctttgc ccgccacaat ggagggaatc accctgacca agtgcgctta    1980
gggaaaatta tcagcctttg tcaggtgatt gaggactgct gctgttccca gaacaaaacc    2040
aaccgggtca ccccggagga ggtcgcagca aagattgacc tgtaccttcg tggcgcaaca    2100
aatcttgaag aatgcttggc caggcttgag aaagcgcgcc cgccacgcgt aatggacacc    2160
tcctttgatt gggatgttgt gctccctggg gttgaggcgg caactcagac gaccgaactg    2220
ccccaggtca accagtgtcg cgctctggtc cctgttgtaa ctcaaaagtc cttggacaac    2280
aactcggtcc ccctgaccgc cttttcactg gctaactacc actaccgtgc gcaaggtgac    2340
gaagttcgtc accgtgaaag actaaccgcc gtgctctcca gttggaaggg ggttgttcga    2400
gaagaatatg ggctcatgcc aaccgggcct ggtccacggc ccacactgcc acgcgggctc    2460
gacgaactca agaccagat ggaggaggac ttgctgaaac tggctaacgc ccagacgact    2520
tcggacatga tggcctgggc agtcgagcag gttgacctaa aaacttgggt caagaactac    2580
ccgcggtgga caccaccacc ccctccgcca aaagttcagc ctcgaaaaac gaagcctgtc    2640
aagagcttgc cagagagaaa gcctgtcccc gcccgcgca ggaaggttgg gtccgattgt     2700
ggcagcccga tttcattggg cgacgatgtc cctaacagtt gggaagattt ggctgttggt    2760 agccccttg atctctcgac cccacctgag ctggcaacac cttcaagtga gctggtgatt     2820
gtgtccgcac cgcaatgcat cttcaggccg gcgacaccct tgagtgagcc ggctccaatt    2880
cccgcacccc gcggggttgt gtctcgaccg gtgacacccct tgaatgagcc gatacctgtg    2940
cccgcaccgc ggcgtaagtt tcagcagatg agaagattga gttcggcggc ggtaatcccg    3000
ccgtaccagg acgagcccct agatttgtct gcttcctcac agactgaata tgaggcctct    3060
cccctagcac cgccgcagag cgagggtgtt ctgggagtag aggggcagga agctgaggaa    3120
gccctaagtg aaatctcgga catgtcgggt aacattaaac ctgcgtccgt atcatcaagc    3180
agctccttgt ccagcgtgag aatcactcgc ccaaaatact cagctcaagc catcatcgac    3240
tcgggcgggc cctgcagtgg gcatctccaa gaggtaaagg aaacatgcct cagtatcatg    3300
cgcgaggcat gtgatgcgac taagcttgat gaccctgcta cgcaggagtg gctttctcgc    3360
atgtgggatc gggtggacat gctgacttgg cgcaacacgt ctgcttacca ggcgtttcgc    3420
accttagatg gcaggttaaa gttcctccca aaaatgatac tcgagacacc gccgcctat    3480 ccgtgtgagt ttgtgatgat gcctcacacg cctgcacctt ccgtaggtgc ggagagcgac    3540
cttaccattg gctcagtcgc tactgaagat gttccacgca tcctcgagaa aatagaaaat    3600
gtcggcgaga tgaccaacca gggacccttg gccttctccg aggataaacc ggtagatgac    3660
caacttgcca agaccccccg gatatcgtcg cagaggtctg acgagagcac atcagctccg    3720
cccgcaggca caggtggcgc cggctcattt accgatttgc cgccttcgga cggcgtggat    3780
gcggacggag gggggccgtt ttggacggta aaaagaaaag ctgaaaggct ctttgaccaa    3840
```

```
ctgagccgtc aggttttttga cctcgtctcc catctccctg tttcttctc acgccttttc   3900
aaccctggcg gtggttattc tccgggtgat tggggttttg cagcttttac tctattgtgc   3960
ctctttttat gttacagtta cccagccttt ggtattgctc ccctcttggg tgtgttttct   4020
gggtcttctc ggcgcgttcg aatgggggtt tttggctgct ggttggcttt tgctgttggt   4080
ctgttcaagc ctgtgtccga cccagtcggc gctgcttgtg agtttgactc gccagagtgt   4140
agaaatatcc ttcattcttt tgagcttctc aaaccttggg accctgttcg cagccttgtt   4200
gtgggccccg tcggtctcgg tcttgccatt cttggcaggt tactgggcgg ggcacgcagc   4260
atctggcact ttttgcttag gcttggcatt gttgcagact gtgtcttggc tggagcttat   4320
gtgctttctc aaggtaggtg taaaaagtgc tggggatctt gtataagaac tgctcctaat   4380
gaggtcgctt ttaacgtgtt tccttttaca cgtgcgacca ggtcgtcact aatcgacctg   4440
tgcgatcggt tttgtgcgcc aaaaggcatg gaccccattt ttctcgccac tgggtggcgc   4500
gggtgctggg ccggccgaag ccccattgag caaccctctg aaaaacccat cgcgtttgcc   4560
cagttggatg aaaagaagat tacggctagg actgtggtcg cccagcctta tgaccccaac   4620
caagccgtaa agtgcttgcg ggtattgcag gcgggtgggg tgatggtggc taaggcagtc   4680
ccaaaagtgg tcaaggtttc cgctgttcca ttccgagccc ccttctttcc caccggagtg   4740
aaagttgacc ctgaatgcag ggtcgtggtt gaccccgaca ctttcaccgc agctctccgg   4800
tctggctact ccaccacaaa cctcgtcctc ggtgtagggg attttgccca gctgaatgga   4860
ttaaaaatca ggcaaatttc caagccttca ggaggaggcc cacacctcat ggctgccctg   4920
catgttgcct gctcgatggc tttgcacatg cttgctggga tttatgtgac tgcggtgggt   4980
tcttgcggca ccggcaccaa cgacccgtgg tgcgctaacc cgtttgccgt ccctggctac   5040
ggacctggct ctctctgcac gtccagattg tgcatttccc aacatggcct taccctgccc   5100
ttgacagcac tcgtggcggg attcggtatt caagaaattg ccttggtcgt tttgatttt   5160
gtttccatcg gaggcatggc tcacaggttg agttgtaagg ctgatatgct gtgtgttttg   5220
cttgcaattg ccagctatgt ttgggtacct cttacctggt tgctttgtgt gtttccttgc   5280
tggttgcgct gtttttcttt gcatcccctc accatcctat ggttggtgtt ttcttgatt   5340
tctgtgaata tgccttcagg aatcttggcc atggtgttgt tggtttctct ttggcttctt   5400
ggtcgttata ctaatgttgc tggtcttgtc accccctacg acattcatca ttacactagt   5460
ggcccccgcg tgttgccgc cttggctacc gcaccagatg ggacctactt ggccgctgtc   5520
cgccgcgctc cgttgactgg ccgcaccatg ctgtttaccc cgtcccagct ggggtctctt   5580
cttgagggtg ctttcagaac tcgaaaccc tcactgaaca ccgtcaatgt ggtcgggtcc   5640
tccatgggct ctggcgggt gttcaccatc gacggaaaaa ttaagtgcgt aactgccgca   5700
catgtcctta cggcaattc agctaggggtt tccggggtcg gcttcaatca aatgcttgac   5760
tttgacgtaa agggagattt cgccatagct gattgcccga attggcaagg gctgccccc   5820
aagacccaat tctgcaagga tgggtggact ggccgtgcct attggctaac atcctctggc   5880
gtcgaacccg cgtcattgg aaaaggattc gccttctgct tcaccgcgtg cggcgattcc   5940
gggtccccag tgatcaccga ggccggtgag cttatcggcg ttcacacggg atcaaataaa   6000
caaggaggag gcatcgttac gcgccctca ggccagtttt gtaatgtggc acccatcaag   6060
ctaagcgaat taagtgaatt ctttgctggg cctaaggtcc cgctcggtga tgtgaaggtt   6120
ggcagccaca taattaaaga cataggcgag gtgccttcag atcttttgtgc cttgcttgct   6180
```

```
gccaaacctg aactggaagg aggcctctcc accgtccaac ttctttgtgt gttttcctc    6240
ctgtggagaa tgatgggaca tgcctggacg cccttggttg ctgtgggttt ctttatcttg   6300
aatgaggttc tcccagccgt cctggtccgg agtgttttct cctttggaat gtttgtgcta   6360
tcctggctca cgccatggtc tgcgcaagtt ctgatgatca ggcttctaac agcagccctt   6420
aacaggaaca gatggtcact tgccttttc agcctcggtg cagtgaccgg ttttgtcgca    6480
gatcttgcgg ctactcaggg gcatccgttg caggcagtta tgaatttgag cacctatgca   6540
ttcctgcctc ggatgatggt tgtgacctca ccagtcccag tgattgcgtg tggtgttgtg   6600
cacctacttg ccatcatttt gtacttgttt aagtaccgtg gcctgcacca aatccttgtt   6660
ggcgatggag tgttctctgc ggcttttctt ctgcgatact ttgccgaggg aaagttgagg   6720
gaaggggtgt cgcaatcctg cggaatgaat catgagtctc tgactggtgc cctcgctatg   6780
agactcaatg acgaggactt ggatttcctt acgaaatgga ctgattttaa gtgctttgtt   6840
tctgcgtcca acatgaggaa tgcagcgggt caatttatcg aggctgccta tgctaaagca   6900
cttagagtag agcttgccca gttggtgcag gttgataaag ttcgaggaac tttggccaaa   6960
cttgaagcct ttgctgatac cgtggcaccc caactctcgc ccggtgacat tgttgtcgct   7020
ctcggccata cgcctgttgg cagtatcttc gacctaaagg ttggtagcac caagcatacc   7080
ctccaagcca ttgagaccag agtccttgct gggtccaaaa tgaccgtggc gcgcgtcgtc   7140
gacccgaccc ccacgccccc acccgcacct gtgcccatcc cctcccacc gaaagttctg    7200
gagaatggcc ccaacgcttg gggggatgag gaccgtttga ataagaagaa gaggcgcagg   7260
atggaagccc tcggcatcta tgttatgggc gggaaaaagt accagaaatt ttgggataag   7320
aattccggtg atgtgtttta tgaggaggtc cataataaca cagatgagtg ggagtgtctc   7380
agagttggcg accctgccga ctttgaccct gagaagggaa ctctgtgtgg acatgtcacc   7440
attgaagata aggcttacca tgtttacacc tcaccatctg gtaagaagtt cttggtcccc   7500
gtcaatccag agaatggaag agtccaatgg gaagctgcaa agctttccgt agagcaggcc   7560
cttggtatga tgaacgtcga cggcgaactg actaccaaag aactggagaa actgaaaaga   7620
ataattgaca aactccaggg cctgactaag gagcagtgtt taaactgcta gccgccagcg   7680
gcttgacccg ctgtggtcgc ggcggcttgg ttgttactga acagcggta aaaatagtca    7740
aatttcacaa ccggaccttc accctgggac ctgtgaattt aaaagtgcc agtgaggttg    7800
agctaaaaga cgcggttgag cacaaccaac accggttgc gagaccggtc gatggtggtg    7860
ttgtgctcct gcgttccgcg gttccttcgc ttatagacgt cttgatctcc ggtgctgatg   7920
catctcccaa gttgcttgcc catcacgggc cgggaaacac tgggatcgat ggcacgctct   7980
gggattttga gtccgaagcc actaaagagg aagtcgcact tagtgcgcaa ataatacagg   8040
cttgtgacat taggcgcggc gacgctcctg aaattggtct cccttacaag ctgtaccctg   8100
ttaggggtaa ccctgagcgg gtaaaaggag ttctacagaa tacaaggttt ggagacatac   8160
cttacaaaac ccccagtgat actggaaacc cagtgcacgc ggctgcctgc cttacgccca   8220
acgccactcc ggtgactgat gggcgctccg tcttggccac gaccatgccc tccgggtttg   8280
agttgtatgt accaaccata ccagcgtctg tccttgatta ccttgattct aggcctgact   8340
gccctaaaca gttgacagag cacggctgtg aagatgccgc actgagagac ctctccaaat   8400
atgacttgtc cacccaaggc tttgttttac ctggagtttt cgccttgta cggaaatacc    8460
tgtttgccca tgtaggtaag tgcccacccg ttcatcggcc ttctacttac cctgctaaga   8520
attctatggc tggaataaat gggaataggt tcccaaccaa ggatattcag agcgtccctg   8580
```

```
aaatcgacgt tctgtgtgca caggctgtgc gggaaaactg gcaaactgtt acccctttgta   8640
ctcttaagaa acagtattgc gggaagaaga agactaggac catactcggc accaataatt   8700
ttatcgcgct agcccaccga gcagcgttga gtggtgtcac ccagggcttc atgaaaaagg   8760
cgtttaactc gcccatcgcc ctcggaaaaa acaagtttaa ggagctacag accccggtcc   8820
taggcaggtg ccttgaagct gatcttgcat cctgcgaccg atccacacct gcaattgtcc   8880
gctggtttgc cgccaacctc ctttatgaac ttgcctgcgc tgaagagcat ttaccgtcgt   8940
acgtgctgaa ctgctgccac gacttactgg tcacgcagtc cggcgcagtg actaagagag   9000
gtggcctgtc gtctggcgac ccgatcacct ctgtgtctaa caccatttac agtttggtga   9060
tctatgcaca gcatatggtg ctcagttact tcaaaagtgg tcaccccat ggcctcttgt    9120
tcttacaaga ccagctaaag tttgaggaca tgctcaaggt tcaaccctg atcgtctatt     9180
cggacgacct cgtgctgtat gccgagtctc ccaccatgcc aaactatcac tggtgggttg   9240
aacacctgaa tttgatgctg gggtttcaga cggatccaaa aaagacagcc ataacagact   9300
cgccatcatt tctaggctgt agaataataa atggacgcca gctagtcccc aaccgtgaca   9360
ggattctcgc ggccctcgcc taccacatga aggcgagtaa tgtttctgaa tactacgcct   9420
cagcggctgc aatactcatg gacagctgtg cttgtttgga gtatgatcct gaatggtttg   9480
aagaacttgt agttggaata gcgcaatgcg cccgcaagga cggttacagc tttcccggca   9540
cgccgttctt tatgtccatg tgggaaaaac tcaggtccaa ttatgagggg aagaagtcga   9600
gagtgtgcgg gtactgcggg gccccggccc cgtacgctac tgcctgtggc ctcgacgtct   9660
gcatttacca cacccacttc caccagcatt gtccagtcac aatctggtgt ggccatccag   9720
cgggttctgg ttcttgtagt gagtgcaaat cccctgtagg gaaaggcaca agcccttag    9780
acgaggtgct ggaacaagtc ccgtacaagc ccccacggac cgttatcatg cgtgtggagc   9840
agggtcttac cccccttgac ccaggtagat accagactcg ccgcggatta gtctccgtca   9900
ggcgtggaat caggggaaat gaggttgaac taccagacgg tgattatgct agtaccgcct   9960
tgctccctac ctgtaaagag atcaacatgg tcgctgttgc ttccaatgta ttgcgcagca  10020
ggttcatcat tggtccaccc ggtgctggga aaacatactg gctccttcaa caggtccagg  10080
atggtgatgt tatttacaca ccaacccacc agaccatgct tgacatgatt agggctttgg  10140
ggacgtgccg gttcaacgtc ccggcaggca caacgctgca attccccgtc ccctcccgta  10200
ccggtccgtg ggttcgcatc ctggccggcg gttggtgtcc tggcaagaat tccttcctgg  10260
atgaagcagc gtattgcaat caccttgatg tcttgaggct tcttagcaaa actaccctca  10320
cctgtctggg agacttcaaa caactccacc cagtgggttt tgattctcat tgctatgttt  10380
ttaacatcat gcctcaaact caactgaaga ccatctggag gtttggacag aatatctgtg  10440
atgccatcca gccagattac agggacaaac tcatgtccat ggtcaacaca acccgtgtga  10500
cctacgtgga aaagcctgtc aggtatggc aagtcctcac cccctaccac agggaccgag   10560
aggacgacgc catcactatt gactccagtc aaggcgccac attcgatgtg ttacactgc    10620
atttgcccac aaaagattca ctcaacaggc agagagccct tgttgctatc accagggcaa  10680
gacatgctat ctttgtgtat gacccacaca ggcagctgca gagcctgttt gatcttcctg  10740
caaaaggtac acccgtcaac cttgcagtgc accgcgacgg gcagctgatc gtgctagata  10800
gaaataacaa agaatgcacg gttgctcagg ctctaggtaa cggagataaa tttagggcca  10860
cagacaaacg cgttgtagat tctctccgcg ccatttgtgc tgatctagaa gggtcgagct  10920
```

```
ctccgctccc caaggtcgca cacaacttgg gatttattt ctcacctgat ttaacacagt   10980
ttgctaaact cccagcagaa cttgcacctc actggcccgt ggtgacaacc cagaacaatg   11040
aaaagtggcc agatcggctg gttaccagcc ttcgccctat ccataaatat agccgcgcgt   11100
gcatcggtgc cggctatatg gtgggcccct cggtgtttct aggcactcct ggggtcgtgt   11160
catactatct cacaaaattt gttaagggcg aggctcaagt gcttccggag acggttttca   11220
gcaccggccg aattgaggta gactgccggg aatatcttga tgatcgggag cgagaggttg   11280
ctgcgtccct cccacatgcc ttcattggcg acgtcaaagg cactaccgtt ggaggatgcc   11340
accatgtcac ctccagatac ctcccgcgct tccttcccaa ggaatcggtt gcggtagtcg   11400
gggtttcaag tcccggaaaa gccgcgaaag cattgtgcac actgacagat gtgtacctcc   11460
cagaccttga agcctatttc cacccggaga cccagtccaa gtgctggaga atgatgttgg   11520
acttcaagga agttcgacta atggtctgga aagacaaaac agcctatttc caacttgaag   11580
gtcgctattt cacctggtat cagcttgcta gctatgcctc gtacatccgt gttcctgtca   11640
actccacggt gtacttggac ccctgcatgg gccccgccct ttgcaacagg aaagtcgtcg   11700
ggtccactca ttggggagct gacctcgctg tcaccccctta tgattacggc gctaaaatta   11760
tcctgtctag cgccgtaccat agtgaaatgc cccccgata caagattctg gcgtgcgcgg   11820
aattctcgtt ggatgaccca gtcaagtaca acatacctg ggggtttgaa tcggatacag   11880
cgtatctgta tgagttcacc ggaaacggtg aggactggga ggattacaat gatgcgtttc   11940
gtgcgcgcca ggaagggaaa atttataagg ctactgccac cagcatgaag ttttatttc   12000
cccgggcccc tgtcattgaa ccaactttag gcctgaattg aaatgaaatg gggtccatgc   12060
aaagccttt tgacaaaatt ggccaacttt ttgtggatgc tttcacggag ttcttggtgt   12120
ccattgttga tatcattata ttttggcca ttttgtttgg cttcaccatc gccggttggt   12180
tggtggtctt ttgcatcaga ttggtttgct ccgcgatact ccgtacgcgc cctgccattc   12240
actctgagca attacagaag atcttatgaa gcctttcttt cccagtgcca agtggacatt   12300
cccacctggg gaactaaaca tcctttgggg atgttttggc accataaggt gtcaaccctg   12360
attgatgaga tggtgtcgcg tcgaatgtac cgcatcatgg aaaaagcagg acaggctgcc   12420
tggaaacagg tggtgagcga ggctacgctg tctcgcatta gtagtttgga tgtggtggct   12480
cattttcagc atcttgccgc cattgaagcc gagacctgta aatatttggc ctcccggctg   12540
cccatgctac acaacctgcg catgacaggg tcaaatgtaa ccatagtgta taatagtact   12600
ttgcatcagg tgtttgctat ttttccaacc cctggttccc ggccaaagct tcatgatttt   12660
cagcaatggt taatagctgt acattcctcc atatttttcct ctgttgcagc ttcttgtact   12720
ctctttgttg tgctgtggtt gcgggttcca atactacgta ctgttttggg tttccgctgg   12780
ttagggcaa ttttctttc gaactcacag tgaattacac ggtgtgtcca ccttgcctca   12840
cccggcaagc agccgcagag gcctacgaac ccggtaggtc tctttggtgc aggatagggt   12900
atgaccgatg tggggaggac gatcatgacg agctagggtt tatggtaccg tctggcctct   12960
ccagcgaagg ccacttgacc agtgtttacg cctggttggc gttcttgtcc ttcagctaca   13020
cggcccagtt ccatcccgag atattcggga tagggaatgt gagtcgagtt tatgttgaca   13080
tcgaacatca actcatctgc gccgaacatg acgggcagaa caccaccttg cctcgtcatg   13140
acaacatttc agccgtgttt cagacctatt accaacatca agtcgacggc ggcaattggt   13200
ttcacctaga atggctgcgt cccttctttt cctcatggtt ggttttaaat gtctcttggt   13260
ttctcaggcg ttcgcctgca aaccatgttt cagttcgagt cttttcagaca ttaagaccaa   13320
```

```
caccaccgca gcggcaagct ttgctgtcct ccaagacatc agttgcctta ggcatcgcaa    13380
ctcggcctct gaggcgattc gcaaaatccc tcagtgccgt acggcgatag ggacacccgt    13440
gtatattacc atcacagcca atgtgacaga tgagaattat ttacattctt ctgatctcct    13500
catgcttct tcttgccttt tctatgcttc tgagatgagt gaaaagggat ttaaggtggt    13560
atttggcaat gtgtcaggca tcgtggctgt gtgtgtcaat tttaccagct acgtccaaca    13620
tgtcagggag tttacccaac gctccttgat ggtcgaccat gtgcggctgc tccatttcat    13680
gacacctgag accatgaggt gggcaactgt tttagcctgt cttttttgcca ttctgttggc    13740
aatttgaatg tttaagtatg ttggggaaat gcttgaccgc gggctgttgc tcgcgattgc    13800
tttctttgtg gtgtatcgtg ccgttctgtt ttgctgtgct cgtcaacgcc aacagcaaca    13860
gcagctctca tctacagttg atttacaact tgacgctatg tgagctgaat ggcacagatt    13920
ggctatctaa taaatttgat tgggcagtgg agagttttgt catctttccc gttttgactc    13980
acattgtctc ctatggtgcc ctcactacca gccatttcct tgacacagtc gctttagtca    14040
ctgtgtctac cgccgggttt gttcacgggc ggtatgtcct gagcagcatc tacgcggtct    14100
gtgccctggc tgcgttgact tgcttcgtca ttaggttgc aaagaattgc atgtcctggc    14160
gctactcatg taccagatat actaactttc ttctggacac aagggcaga ctctatcgtt    14220
ggcggtcgcc tgtcatcata gagaaaaggg gcaaagttga ggtcgaaggt catctgatcg    14280
acctcaaaag agttgtgctt gatggttccg tggcaacccc tataaccaga gtttcagcgg    14340
aacaatgggg tcgtccttag atgacttttg ttatgatagc acggctccac aaaaggtgct    14400
tttggcgttt tctattacct acacgccagt gatgatatat gccctaaaag tgagtcgcgg    14460
ccgactgtta gggcttctgc acctttgat cttcctgaac tgtgctttca ccttcgggta    14520
catgacattc gcgcactttc agagtacaaa taaggtcgcg ctcactatgg gagcagtagt    14580
tgcactcctt tgggggtgt attcagccat agaaacctgg aaattcatca cctccagatg    14640
ccgtttgtgc ttgctaggcc gcaagtacat tctggcccct gcccaccacg ttgagagtgc    14700
cgcaggcttt catccgattg cggcaaatga taaccacgca tttgtcgtcc ggcgtcccgg    14760
ctccactacg gtcaacggca cattggtgcc cggttgaaa ggcctcgtgt tgggtggcag    14820
aaaagctgtt aaacagggag tggtaaacct tgtcaaatat gccaaataac aacggcaagc    14880
agcagaagag aaagaagggg gatggccagc cagtcaatca gctgtgccag atgctgggta    14940
agatcatcgc ccagcaaaac cagtccagag gcaagggacc gggaaagaaa aataagaaga    15000
aaacccggga gaagccccat tttcctctag cgactgaaga tgatgtcaga catcactta    15060
ccctagtga gcggcaattg tgtctgtcgt caatccagac tgcctttaat caaggcgctg    15120
ggacttgcac cctgtcagat tcagggagga taagttacac tgtggagttt agtttgccta    15180
cgcatcatac tgtgcgcctg atccgcgtca cagcatcacc ctcagcatga tgggctggca    15240
ttcttgagcc atctcagtgt ttgaattgga agaatgtgtg gtgaatggca ctgattgaca    15300
ttgtgcctct aagtcaccta ttcaattagg gcgaccgtgt gggggtaaga tttaattggc    15360
gagaaccata cggccgaaat t                                              15381
```

<210> SEQ ID NO 4
<211> LENGTH: 10
<212> TYPE: PRT
<213> ORGANISM: PRRS Virus
<220> FEATURE:
<221> NAME/KEY: Xaa
<222> LOCATION: (5)..(5)

```
<223> OTHER INFORMATION: Xaa is Val or Met

<400> SEQUENCE: 4

Ala Asn Arg Met Xaa Asn Ser Lys Phe Glu
1               5                   10

<210> SEQ ID NO 5
<211> LENGTH: 10
<212> TYPE: PRT
<213> ORGANISM: PRRS Virus

<400> SEQUENCE: 5

Ala Asn Arg Met Val Asn Ser Lys Phe Glu
1               5                   10

<210> SEQ ID NO 6
<211> LENGTH: 10
<212> TYPE: PRT
<213> ORGANISM: PRRS Virus

<400> SEQUENCE: 6

Leu Ala Asn Tyr Tyr Tyr Arg Ala Gln Gly
1               5                   10

<210> SEQ ID NO 7
<211> LENGTH: 10
<212> TYPE: PRT
<213> ORGANISM: PRRS Virus

<400> SEQUENCE: 7

Leu Ala Asn Tyr His Tyr Arg Ala Gln Gly
1               5                   10

<210> SEQ ID NO 8
<211> LENGTH: 10
<212> TYPE: PRT
<213> ORGANISM: PRRS Virus
<220> FEATURE:
<221> NAME/KEY: Xaa
<222> LOCATION: (3)..(3)
<223> OTHER INFORMATION: Xaa is Pro or Ser

<400> SEQUENCE: 8

Asp Leu Xaa Thr Pro Pro Glu Pro Ala Thr
1               5                   10

<210> SEQ ID NO 9
<211> LENGTH: 10
<212> TYPE: PRT
<213> ORGANISM: PRRS Virus

<400> SEQUENCE: 9

Asp Leu Ser Thr Pro Pro Glu Leu Ala Thr
1               5                   10

<210> SEQ ID NO 10
<211> LENGTH: 10
<212> TYPE: PRT
<213> ORGANISM: PRRS Virus

<400> SEQUENCE: 10

Asp Leu Pro Thr Pro Pro Glu Pro Ala Thr
1               5                   10

<210> SEQ ID NO 11
```

```
<211> LENGTH: 10
<212> TYPE: PRT
<213> ORGANISM: PRRS Virus

<400> SEQUENCE: 11

Val Asp Ile Ile Ile Phe Leu Ala Ile Leu
1               5                   10

<210> SEQ ID NO 12
<211> LENGTH: 10
<212> TYPE: PRT
<213> ORGANISM: PRRS Virus

<400> SEQUENCE: 12

Val Asp Ile Ile Val Phe Leu Ala Ile Leu
1               5                   10

<210> SEQ ID NO 13
<211> LENGTH: 10
<212> TYPE: PRT
<213> ORGANISM: PRRS Virus

<400> SEQUENCE: 13

Ala Ile Leu Arg Thr Arg Pro Ala Ile His
1               5                   10

<210> SEQ ID NO 14
<211> LENGTH: 10
<212> TYPE: PRT
<213> ORGANISM: PRRS Virus

<400> SEQUENCE: 14

Ala Ile Leu Arg Ala Arg Pro Ala Ile His
1               5                   10

<210> SEQ ID NO 15
<211> LENGTH: 10
<212> TYPE: PRT
<213> ORGANISM: PRRS Virus
<220> FEATURE:
<221> NAME/KEY: Xaa
<222> LOCATION: (7)..(7)
<223> OTHER INFORMATION: Xaa is Pro or Ser

<400> SEQUENCE: 15

Leu Gly Phe Met Ile Pro Xaa Gly Leu Ser
1               5                   10

<210> SEQ ID NO 16
<211> LENGTH: 10
<212> TYPE: PRT
<213> ORGANISM: PRRS Virus

<400> SEQUENCE: 16

Leu Gly Phe Met Val Pro Ser Gly Leu Ser
1               5                   10

<210> SEQ ID NO 17
<211> LENGTH: 10
<212> TYPE: PRT
<213> ORGANISM: PRRS Virus

<400> SEQUENCE: 17

Ser Val Arg Val Leu Gln Thr Leu Arg Pro
1               5                   10
```

-continued

<210> SEQ ID NO 18
<211> LENGTH: 10
<212> TYPE: PRT
<213> ORGANISM: PRRS Virus

<400> SEQUENCE: 18

Ser Val Arg Val Phe Gln Thr Leu Arg Pro
1               5                   10

<210> SEQ ID NO 19
<211> LENGTH: 10
<212> TYPE: PRT
<213> ORGANISM: PRRS Virus

<400> SEQUENCE: 19

Ser Ser Ser Leu Ala Asp Ile Lys Thr Asn
1               5                   10

<210> SEQ ID NO 20
<211> LENGTH: 10
<212> TYPE: PRT
<213> ORGANISM: PRRS Virus

<400> SEQUENCE: 20

Ser Ser Ser Leu Ser Asp Ile Lys Thr Asn
1               5                   10

<210> SEQ ID NO 21
<211> LENGTH: 254
<212> TYPE: PRT
<213> ORGANISM: PRRS Virus
<220> FEATURE:
<221> NAME/KEY: Xaa
<222> LOCATION: (96)..(96)
<223> OTHER INFORMATION: Xaa is Pro or Ser

<400> SEQUENCE: 21

Met Val Asn Ser Cys Thr Phe Leu His Ile Phe Leu Cys Cys Ser Phe
1               5                   10                  15

Leu Tyr Ser Leu Cys Cys Ala Val Val Ala Gly Ser Asn Thr Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Ile Pro Xaa
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Glu His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu

```
                    180                 185                 190
Val Leu Asn Val Ser Trp Phe Leu Arg Arg Ser Pro Ala Asn His Val
            195                 200                 205

Ser Val Arg Val Leu Gln Thr Leu Arg Pro Thr Pro Gln Arg Gln
        210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 22
<211> LENGTH: 254
<212> TYPE: PRT
<213> ORGANISM: PRRS Virus

<400> SEQUENCE: 22

Met Val Asn Ser Cys Thr Phe Leu His Ile Phe Leu Cys Cys Ser Phe
1               5                   10                  15

Leu Tyr Ser Leu Cys Cys Ala Val Val Ala Gly Ser Asn Thr Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Val Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Glu His Gln Leu Ile
130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Thr Leu Arg Pro Thr Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 23
<211> LENGTH: 178
<212> TYPE: PRT
<213> ORGANISM: PRRS Virus

<400> SEQUENCE: 23

Met Ala Ala Ser Leu Leu Phe Leu Met Val Gly Phe Lys Cys Leu Leu
```

-continued

```
             1               5                  10                 15
Val Ser Gln Ala Phe Ala Cys Lys Pro Cys Phe Ser Ser Ser Leu Ala
                20                  25                 30

Asp Ile Lys Thr Asn Thr Thr Ala Ala Ser Phe Ala Val Leu Gln
        35                  40                  45

Asp Ile Ser Cys Leu Arg His Arg Asn Ser Ala Ser Glu Ala Ile Arg
        50                  55                  60

Lys Ile Pro Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Arg Glu Phe Thr Gln Arg
        130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

<210> SEQ ID NO 24
<211> LENGTH: 178
<212> TYPE: PRT
<213> ORGANISM: PRRS Virus

<400> SEQUENCE: 24

```
             1               5                  10                 15
Met Ala Ala Ser Leu Leu Phe Leu Met Val Gly Phe Lys Cys Leu Leu
1               5                   10                 15

Val Ser Gln Ala Phe Ala Cys Lys Pro Cys Phe Ser Ser Ser Leu Ser
                20                  25                 30

Asp Ile Lys Thr Asn Thr Thr Ala Ala Ser Phe Ala Val Leu Gln
        35                  40                  45

Asp Ile Ser Cys Leu Arg His Arg Asn Ser Ala Ser Glu Ala Ile Arg
        50                  55                  60

Lys Ile Pro Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Arg Glu Phe Thr Gln Arg
        130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

<210> SEQ ID NO 25

```
<211> LENGTH: 73
<212> TYPE: PRT
<213> ORGANISM: PRRS Virus

<400> SEQUENCE: 25

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
                20                  25                  30

Leu Ala Ile Leu Phe Gly Phe Thr Ile Ala Gly Trp Leu Val Val Phe
            35                  40                  45

Cys Ile Arg Leu Val Cys Ser Ala Ile Leu Arg Thr Arg Pro Ala Ile
    50                  55                  60

His Ser Glu Gln Leu Gln Lys Ile Leu
65                  70

<210> SEQ ID NO 26
<211> LENGTH: 73
<212> TYPE: PRT
<213> ORGANISM: PRRS Virus

<400> SEQUENCE: 26

Met Gly Ser Met Gln Ser Leu Phe Asp Lys Ile Gly Gln Leu Phe Val
1               5                   10                  15

Asp Ala

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
caactgcaga gctcatatgc at                                              22

<210> SEQ ID NO 31
<211> LENGTH: 256
<212> TYPE: PRT
<213> ORGANISM: PRRS virus

<400> SEQUENCE: 31

Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Leu
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu His Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser Gln
                245                 250                 255

<210> SEQ ID NO 32
<211> LENGTH: 200
<212> TYPE: PRT
<213> ORGANISM: PRRS virus

<400> SEQUENCE: 32

Met Leu Gly Lys Cys Leu Thr Ala Gly Cys Cys Ser Arg Leu Leu Ser
1               5                   10                  15

```
Leu Trp Cys Ile Val Pro Phe Cys Phe Ala Val Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Ser Asn Lys Phe Asp Trp Ala Val
 50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 33
<211> LENGTH: 174
<212> TYPE: PRT
<213> ORGANISM: PRRS virus

<400> SEQUENCE: 33

Met Gly Ser Ser Leu Asp Asp Phe Cys Tyr Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
 50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
130                 135                 140

Gly Thr Leu Val Pro Gly Leu Lys Gly Leu Val Leu Gly Gly Arg Lys
145                 150                 155                 160

Ala Val Lys Gln Gly Val Val Asn Leu Val Lys Tyr Ala Lys
                165                 170
```

```
<210> SEQ ID NO 34
<211> LENGTH: 123
<212> TYPE: PRT
<213> ORGANISM: PRRS virus

<400> SEQUENCE: 34

Met Pro Asn Asn Gly Lys Gln Gln Lys Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 35
<211> LENGTH: 166
<212> TYPE: PRT
<213> ORGANISM: PRRS virus

<400> SEQUENCE: 35

Met Ser Gly Ile Leu Asp Arg Cys Thr Cys Thr Pro Asn Ala Arg Val
1               5                   10                  15

Phe Met Ala Glu Gly Gln Val Tyr Cys Thr Arg Cys Leu Ser Ala Arg
            20                  25                  30

Ser Leu Leu Pro Leu Asn Leu Gln Val Ser Glu Leu Gly Val Leu Gly
        35                  40                  45

Leu Phe Tyr Arg Pro Glu Glu Pro Leu Arg Trp Thr Leu Pro Arg Ala
    50                  55                  60

Phe Pro Thr Val Glu Cys Ser Pro Ala Gly Ala Cys Trp Leu Ser Ala
65                  70                  75                  80

Ile Phe Pro Ile Ala Arg Met Thr Ser Gly Asn Leu Asn Phe Gln Gln
                85                  90                  95

Arg Met Val Arg Val Ala Ala Glu Leu Tyr Arg Ala Gly Gln Leu Thr
            100                 105                 110

Pro Thr Val Leu Lys Thr Leu Gln Val Tyr Glu Arg Gly Cys Arg Trp
        115                 120                 125

Tyr Pro Ile Val Gly Pro Val Pro Gly Val Ala Val Phe Ala Asn Ser
    130                 135                 140

Leu His Val Ser Asp Lys Pro Phe Pro Gly Ala Thr His Val Leu Thr
145                 150                 155                 160

Asn Leu Pro Leu Pro Gln
                165

<210> SEQ ID NO 36
<211> LENGTH: 216
<212> TYPE: PRT
<213> ORGANISM: PRRS virus

<400> SEQUENCE: 36
```

```
Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Gly Lys
            20                  25                  30

Val Ser Trp Ala Pro Arg Gly Gly Asp Glu Val Lys Phe Glu Thr Val
        35                  40                  45

Pro Gly Glu Leu Glu Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Arg Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asn Leu Leu
            100                 105                 110

Pro Leu Glu Val Gln Asn Lys Glu Ile Arg His Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Glu Glu Pro Ser Tyr Pro Gly Phe Glu Asp Leu Leu Arg Ile Arg
            180                 185                 190

Val Glu Pro Asn Thr Ser Pro Leu Ala Asp Lys Asp Glu Lys Ile Phe
        195                 200                 205

Arg Phe Gly Ser His Lys Trp Tyr
    210                 215

<210> SEQ ID NO 37
<211> LENGTH: 980
<212> TYPE: PRT
<213> ORGANISM: PRRS virus

<400> SEQUENCE: 37

Ala Gly Lys Arg Ala Arg Lys Ala Arg Ser Ser Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Gly His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Ser Asp Asp Trp Ala Thr Asp Glu Asp Leu Val Asn Ala Ile Gln
                85                  90                  95

Ile Leu Arg Leu Pro Ala Ala Leu Asn Arg Asn Gly Ala Cys Ala Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Ser Leu Gly Ser Pro Asp Ala Val Glu Val
```

```
            145                 150                 155                 160
        Phe Gly Phe Asp Pro Ala Cys Leu Asp Arg Leu Ala Glu Val Met His
                        165                 170                 175

Leu Pro Ser Ser Ala Ile Pro Ala Ala Leu Ala Glu Met Ser Gly Asp
                        180                 185                 190

Ser Asp Arg Ser Ala Ser Pro Val Thr Thr Val Trp Thr Val Ser Gln
                    195                 200                 205

Phe Phe Ala Arg His Asn Gly Asn His Pro Asp Gln Val Arg Leu
                210                 215                 220

Gly Lys Ile Ile Ser Leu Cys Gln Val Ile Glu Asp Cys Cys Cys Ser
        225                 230                 235                 240

Gln Asn Lys Thr Asn Arg Val Thr Pro Glu Glu Val Ala Ala Lys Ile
                        245                 250                 255

Asp Leu Tyr Leu Arg Gly Ala Thr Asn Leu Glu Cys Leu Ala Arg
                    260                 265                 270

Leu Glu Lys Ala Arg Pro Pro Arg Val Met Asp Thr Ser Phe Asp Trp
                275                 280                 285

Asp Val Val Leu Pro Gly Val Glu Ala Ala Thr Gln Thr Thr Glu Leu
        290                 295                 300

Pro Gln Val Asn Gln Cys Arg Ala Leu Val Pro Val Thr Gln Lys
        305                 310                 315                 320

Ser Leu Asp Asn Asn Ser Val Pro Leu Thr Ala Phe Ser Leu Ala Asn
                        325                 330                 335

Tyr Tyr Tyr Arg Ala Gln Gly Asp Glu Val Arg His Arg Glu Arg Leu
                    340                 345                 350

Thr Ala Val Leu Ser Lys Leu Glu Gly Val Val Arg Glu Glu Tyr Gly
                355                 360                 365

Leu Met Pro Thr Gly Pro Gly Pro Arg Pro Thr Leu Pro Arg Gly Leu
                370                 375                 380

Asp Glu Leu Lys Asp Gln Met Glu Glu Asp Leu Leu Lys Leu Ala Asn
        385                 390                 395                 400

Ala Gln Thr Thr Ser Asp Met Met Ala Trp Ala Val Glu Gln Val Asp
                        405                 410                 415

Leu Lys Thr Trp Val Lys Asn Tyr Pro Arg Trp Thr Pro Pro Pro
                    420                 425                 430

Pro Pro Lys Val Gln Pro Arg Lys Thr Lys Pro Val Lys Ser Leu Pro
                435                 440                 445

Glu Arg Lys Pro Val Pro Ala Pro Arg Arg Lys Val Gly Ser Asp Cys
                450                 455                 460

Gly Ser Pro Ile Ser Leu Gly Asp Asp Val Pro Asn Ser Trp Glu Asp
        465                 470                 475                 480

Leu Ala Val Gly Ser Pro Phe Asp Leu Pro Thr Pro Pro Glu Pro Ala
                        485                 490                 495

Thr Pro Ser Ser Glu Leu Val Ile Val Ser Ala Pro Gln Cys Ile Phe
                        500                 505                 510

Arg Pro Ala Thr Pro Leu Ser Glu Pro Ala Pro Ile Pro Ala Pro Arg
                    515                 520                 525

Gly Val Val Ser Arg Pro Val Thr Pro Leu Asn Glu Pro Ile Pro Val
                530                 535                 540

Pro Ala Pro Arg Arg Lys Phe Gln Gln Met Ala Arg Leu Ser Ser Ala
        545                 550                 555                 560

Ala Val Ile Pro Pro Tyr Gln Asp Glu Pro Leu Asp Leu Ser Ala Ser
                        565                 570                 575
```

```
Ser Gln Thr Glu Tyr Glu Ala Ser Pro Leu Ala Pro Pro Gln Ser Glu
            580                 585                 590

Gly Val Leu Gly Val Glu Gly Gln Glu Ala Glu Glu Ala Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Pro Cys Ser Gly His Leu Gln Glu Val
                645                 650                 655

Lys Glu Thr Cys Leu Ser Ile Met Arg Glu Ala Cys Asp Ala Thr Lys
                660                 665                 670

Leu Asp Asp Pro Ala Thr Gln Glu Trp Leu Ser Arg Met Trp Asp Arg
            675                 680                 685

Val Asp Met Leu Thr Trp Arg Asn Thr Ser Ala Tyr Gln Ala Phe Arg
        690                 695                 700

Thr Leu Asp Gly Arg Leu Lys Phe Leu Pro Lys Met Ile Leu Glu Thr
705                 710                 715                 720

Pro Pro Pro Tyr Pro Cys Glu Phe Val Met Met Pro His Thr Pro Ala
                725                 730                 735

Pro Ser Val Gly Ala Glu Ser Asp Leu Thr Ile Gly Ser Val Ala Thr
            740                 745                 750

Glu Asp Val Pro Arg Ile Leu Glu Lys Ile Glu Asn Val Gly Glu Met
        755                 760                 765

Thr Asn Gln Gly Pro Leu Ala Phe Ser Glu Asp Lys Pro Val Asp Asp
770                 775                 780

Gln Leu Ala Lys Asp Pro Arg Ile Ser Ser Gln Arg Ser Asp Glu Ser
785                 790                 795                 800

Thr Ser Ala Pro Pro Ala Gly Thr Gly Gly Ala Gly Ser Phe Thr Asp
                805                 810                 815

Leu Pro Pro Ser Asp Gly Val Asp Ala Asp Gly Gly Pro Phe Trp
            820                 825                 830

Thr Val Lys Arg Lys Ala Glu Arg Leu Phe Asp Gln Leu Ser Arg Gln
        835                 840                 845

Val Phe Asp Leu Val Ser His Leu Pro Val Phe Phe Ser Arg Leu Phe
850                 855                 860

Asn Pro Gly Gly Gly Tyr Ser Pro Gly Asp Trp Gly Phe Ala Ala Phe
865                 870                 875                 880

Thr Leu Leu Cys Leu Phe Leu Cys Tyr Ser Tyr Pro Ala Phe Gly Ile
                885                 890                 895

Ala Pro Leu Leu Gly Val Phe Ser Gly Ser Ser Arg Arg Val Arg Met
            900                 905                 910

Gly Val Phe Gly Cys Trp Leu Ala Phe Ala Val Gly Leu Phe Lys Pro
        915                 920                 925

Val Ser Asp Pro Val Gly Ala Ala Cys Glu Phe Asp Ser Pro Glu Cys
930                 935                 940

Arg Asn Ile Leu His Ser Phe Glu Leu Leu Lys Pro Trp Asp Pro Val
945                 950                 955                 960

Arg Ser Leu Val Val Gly Pro Val Gly Leu Gly Leu Ala Ile Leu Gly
                965                 970                 975

Arg Leu Leu Gly
            980
```

<210> SEQ ID NO 38
<211> LENGTH: 446
<212> TYPE: PRT
<213> ORGANISM: PRRS virus

<400> SEQUENCE: 38

```
Gly Ala Arg Ser Ile Trp His Phe Leu Leu Arg Leu Gly Ile Val Ala
1               5                   10                  15
Asp Cys Val Leu Ala Gly Ala Tyr Val Leu Ser Gln Gly Arg Cys Lys
            20                  25                  30
Lys Cys Trp Gly Ser Cys Ile Arg Thr Ala Pro Asn Glu Val Ala Phe
        35                  40                  45
Asn Val Phe Pro Phe Thr Arg Ala Thr Arg Ser Ser Leu Ile Asp Leu
    50                  55                  60
Cys Asp Arg Phe Cys Ala Pro Lys Gly Met Asp Pro Ile Phe Leu Ala
65                  70                  75                  80
Thr Gly Trp Arg Gly Cys Trp Ala Gly Arg Ser Pro Ile Glu Gln Pro
                85                  90                  95
Ser Glu Lys Pro Ile Ala Phe Ala Gln Leu Asp Glu Lys Lys Ile Thr
            100                 105                 110
Ala Arg Thr Val Val Ala Gln Pro Tyr Asp Pro Asn Gln Ala Val Lys
        115                 120                 125
Cys Leu Arg Val Leu Gln Ala Gly Gly Val Met Val Ala Lys Ala Val
    130                 135                 140
Pro Lys Val Val Lys Val Ser Ala Val Pro Phe Arg Ala Pro Phe Phe
145                 150                 155                 160
Pro Thr Gly Val Lys Val Asp Pro Glu Cys Arg Val Val Asp Pro
                165                 170                 175
Asp Thr Phe Thr Ala Ala Leu Arg Ser Gly Tyr Ser Thr Thr Asn Leu
            180                 185                 190
Val Leu Gly Val Gly Asp Phe Ala Gln Leu Asn Gly Leu Lys Ile Arg
        195                 200                 205
Gln Ile Ser Lys Pro Ser Gly Gly Pro His Leu Met Ala Ala Leu
    210                 215                 220
His Val Ala Cys Ser Met Ala Leu His Met Leu Ala Gly Ile Tyr Val
225                 230                 235                 240
Thr Ala Val Gly Ser Cys Gly Thr Gly Thr Asn Asp Pro Trp Cys Ala
                245                 250                 255
Asn Pro Phe Ala Val Pro Gly Tyr Gly Pro Gly Ser Leu Cys Thr Ser
            260                 265                 270
Arg Leu Cys Ile Ser Gln His Gly Leu Thr Leu Pro Leu Thr Ala Leu
        275                 280                 285
Val Ala Gly Phe Gly Ile Gln Glu Ile Ala Leu Val Val Leu Ile Phe
    290                 295                 300
Val Ser Ile Gly Gly Met Ala His Arg Leu Ser Cys Lys Ala Asp Met
305                 310                 315                 320
Leu Cys Val Leu Leu Ala Ile Ala Ser Tyr Val Trp Val Pro Leu Thr
                325                 330                 335
Trp Leu Leu Cys Val Phe Pro Cys Trp Leu Arg Cys Phe Ser Leu His
            340                 345                 350
Pro Leu Thr Ile Leu Trp Leu Val Phe Phe Leu Ile Ser Val Asn Met
        355                 360                 365
Pro Ser Gly Ile Leu Ala Met Val Leu Leu Val Ser Leu Trp Leu Leu
    370                 375                 380
```

```
Gly Arg Tyr Thr Asn Val Ala Gly Leu Val Thr Pro Tyr Asp Ile His
385                 390                 395                 400

His Tyr Thr Ser Gly Pro Arg Gly Val Ala Ala Leu Ala Thr Ala Pro
            405                 410                 415

Asp Gly Thr Tyr Leu Ala Ala Val Arg Arg Ala Ala Leu Thr Gly Arg
        420                 425                 430

Thr Met Leu Phe Thr Pro Ser Gln Leu Gly Ser Leu Leu Glu
        435                 440                 445

<210> SEQ ID NO 39
<211> LENGTH: 204
<212> TYPE: PRT
<213> ORGANISM: PRRS virus

<400> SEQUENCE: 39

Gly Ala Phe Arg Thr Arg Lys Pro Ser Leu Asn Thr Val Asn Val Val
1               5                   10                  15

Gly Ser Ser Met Gly Ser Gly Val Phe Thr Ile Asp Gly Lys Ile
            20                  25                  30

Lys Cys Val Thr Ala Ala His Val Leu Thr Gly Asn Ser Ala Arg Val
        35                  40                  45

Ser Gly Val Gly Phe Asn Gln Met Leu Asp Phe Asp Val Lys Gly Asp
    50                  55                  60

Phe Ala Ile Ala Asp Cys Pro Asn Trp Gln Gly Ala Ala Pro Lys Thr
65                  70                  75                  80

Gln Phe Cys Lys Asp Gly Trp Thr Gly Arg Ala Tyr Trp Leu Thr Ser
                85                  90                  95

Ser Gly Val Glu Pro Gly Val Ile Gly Lys Gly Phe Ala Phe Cys Phe
            100                 105                 110

Thr Ala Cys Gly Asp Ser Gly Ser Pro Val Ile Thr Glu Ala Gly Glu
        115                 120                 125

Leu Ile Gly Val His Thr Gly Ser Asn Lys Gln Gly Gly Gly Ile Val
    130                 135                 140

Thr Arg Pro Ser Gly Gln Phe Cys Asn Val Ala Pro Ile Lys Leu Ser
145                 150                 155                 160

Glu Leu Ser Glu Phe Phe Ala Gly Pro Lys Val Pro Leu Gly Asp Val
                165                 170                 175

Lys Val Gly Ser His Ile Ile Lys Asp Ile Gly Glu Val Pro Ser Asp
            180                 185                 190

Leu Cys Ala Leu Leu Ala Ala Lys Pro Glu Leu Glu
        195                 200

<210> SEQ ID NO 40
<211> LENGTH: 170
<212> TYPE: PRT
<213> ORGANISM: PRRS virus

<400> SEQUENCE: 40

Gly Gly Leu Ser Thr Val Gln Leu Leu Cys Val Phe Phe Leu Leu Trp
1               5                   10                  15

Arg Met Met Gly His Ala Trp Thr Pro Leu Val Ala Val Gly Phe Phe
            20                  25                  30

Ile Leu Asn Glu Val Leu Pro Ala Val Leu Val Arg Ser Val Phe Ser
        35                  40                  45

Phe Gly Met Phe Val Leu Ser Trp Leu Thr Pro Trp Ser Ala Gln Val
    50                  55                  60
```

```
Leu Met Ile Arg Leu Leu Thr Ala Ala Leu Asn Arg Asn Arg Trp Ser
 65                  70                  75                  80

Leu Ala Phe Phe Ser Leu Gly Ala Val Thr Gly Phe Val Ala Asp Leu
                 85                  90                  95

Ala Ala Thr Gln Gly His Pro Leu Gln Ala Val Met Asn Leu Ser Thr
            100                 105                 110

Tyr Ala Phe Leu Pro Arg Met Met Val Thr Ser Pro Val Pro Val
        115                 120                 125

Ile Ala Cys Gly Val Val His Leu Leu Ala Ile Ile Leu Tyr Leu Phe
130                 135                 140

Lys Tyr Arg Gly Leu His Gln Ile Leu Val Gly Asp Gly Val Phe Ser
145                 150                 155                 160

Ala Ala Phe Phe Leu Arg Tyr Phe Ala Glu
                165                 170

<210> SEQ ID NO 41
<211> LENGTH: 16
<212> TYPE: PRT
<213> ORGANISM: PRRS virus

<400> SEQUENCE: 41

Gly Lys Leu Arg Glu Gly Val Ser Gln Ser Cys Gly Met Asn His Glu
1               5                   10                  15

<210> SEQ ID NO 42
<211> LENGTH: 259
<212> TYPE: PRT
<213> ORGANISM: PRRS virus

<400> SEQUENCE: 42

Ser Leu Thr Gly Ala Leu Ala Met Arg Leu Asn Asp Glu Asp Leu Asp
1               5                   10                  15

Phe Leu Thr Lys Trp Thr Asp Phe Lys Cys Phe Val Ser Ala Ser Asn
                 20                  25                  30

Met Arg Asn Ala Ala Gly Gln Phe Ile Glu Ala Ala Tyr Ala Lys Ala
             35                  40                  45

Leu Arg Val Glu Leu Ala Gln Leu Val Gln Val Asp Lys Val Arg Gly
 50                  55                  60

Thr Leu Ala Lys Leu Glu Ala Phe Ala Asp Thr Val Ala Pro Gln Leu
 65                  70                  75                  80

Ser Pro Gly Asp Ile Val Val Ala Leu Gly His Thr Pro Val Gly Ser
                 85                  90                  95

Ile Phe Asp Leu Lys Val Gly Ser Thr Lys His Thr Leu Gln Ala Ile
            100                 105                 110

Glu Thr Arg Val Leu Ala Gly Ser Lys Met Thr Val Ala Arg Val Val
        115                 120                 125

Asp Pro Thr Pro Thr Pro Pro Ala Pro Val Pro Ile Pro Leu Pro
130                 135                 140

Pro Lys Val Leu Glu Asn Gly Pro Asn Ala Trp Gly Asp Glu Asp Arg
145                 150                 155                 160

Leu Asn Lys Lys Lys Arg Arg Arg Met Glu Ala Leu Gly Ile Tyr Val
                165                 170                 175

Met Gly Gly Lys Lys Tyr Gln Lys Phe Trp Asp Lys Asn Ser Gly Asp
            180                 185                 190

Val Phe Tyr Glu Glu Val His Asn Asn Thr Asp Glu Trp Glu Cys Leu
        195                 200                 205
```

Arg Val Gly Asp Pro Ala Asp Phe Asp Pro Glu Lys Gly Thr Leu Cys
            210                 215                 220

Gly His Val Thr Ile Glu Asp Lys Ala Tyr His Val Tyr Thr Ser Ser
225                 230                 235                 240

Ser Gly Lys Lys Phe Leu Val Pro Val Asn Pro Glu Asn Gly Arg Val
                245                 250                 255

Gln Trp Glu

<210> SEQ ID NO 43
<211> LENGTH: 45
<212> TYPE: PRT
<213> ORGANISM: PRRS virus

<400> SEQUENCE: 43

Ala Ala Lys Leu Ser Val Glu Gln Ala Leu Gly Met Met Asn Val Asp
1               5                   10                  15

Gly Glu Leu Thr Thr Lys Glu Leu Glu Lys Leu Lys Arg Ile Ile Asp
                20                  25                  30

Lys Leu Gln Gly Leu Thr Lys Glu Gln Cys Leu Asn Cys
            35                  40                  45

<210> SEQ ID NO 44
<211> LENGTH: 685
<212> TYPE: PRT
<213> ORGANISM: PRRS virus

<400> SEQUENCE: 44

Ala Ala Lys Leu Ser Val Glu Gln Ala Leu Gly Met Met Asn Val Asp
1               5                   10                  15

Gly Glu Leu Thr Thr Lys Glu Leu Glu Lys Leu Lys Arg Ile Ile Asp
                20                  25                  30

Lys Leu Gln Gly Leu Thr Lys Glu Gln Cys Leu Asn Leu Leu Ala Ala
            35                  40                  45

Ser Gly Leu Thr Arg Cys Gly Arg Gly Gly Leu Val Val Thr Glu Thr
50                  55                  60

Ala Val Lys Ile Val Lys Phe His Asn Arg Thr Phe Thr Leu Gly Pro
65                  70                  75                  80

Val Asn Leu Lys Val Ala Ser Glu Val Glu Leu Lys Asp Ala Val Glu
                85                  90                  95

His Asn Gln His Pro Val Ala Arg Pro Val Asp Gly Gly Val Val Leu
            100                 105                 110

Leu Arg Ser Ala Val Pro Ser Leu Ile Asp Val Leu Ile Ser Gly Ala
            115                 120                 125

Asp Ala Ser Pro Lys Leu Leu Ala His His Gly Pro Gly Asn Thr Gly
130                 135                 140

Ile Asp Gly Thr Leu Trp Asp Phe Glu Ser Glu Ala Thr Lys Glu Glu
145                 150                 155                 160

Val Ala Leu Ser Ala Gln Ile Ile Gln Ala Cys Asp Ile Arg Arg Gly
                165                 170                 175

Asp Ala Pro Glu Ile Gly Leu Pro Tyr Lys Leu Tyr Pro Val Arg Gly
            180                 185                 190

Asn Pro Glu Arg Val Lys Gly Val Leu Gln Asn Thr Arg Phe Gly Asp
            195                 200                 205

Ile Pro Tyr Lys Thr Pro Ser Asp Thr Gly Asn Pro Val His Ala Ala
            210                 215                 220

```
Ala Cys Leu Thr Pro Asn Ala Thr Pro Val Thr Asp Gly Arg Ser Val
225                 230                 235                 240

Leu Ala Thr Thr Met Pro Ser Gly Phe Glu Leu Tyr Val Pro Thr Ile
            245                 250                 255

Pro Ala Ser Val Leu Asp Tyr Leu Asp Ser Arg Pro Asp Cys Pro Lys
        260                 265                 270

Gln Leu Thr Glu His Gly Cys Glu Asp Ala Ala Leu Arg Asp Leu Ser
        275                 280                 285

Lys Tyr Asp Leu Ser Thr Gln Gly Phe Val Leu Pro Gly Val Phe Arg
    290                 295                 300

Leu Val Arg Lys Tyr Leu Phe Ala His Val Gly Lys Cys Pro Pro Val
305                 310                 315                 320

His Arg Pro Ser Thr Tyr Pro Ala Lys Asn Ser Met Ala Gly Ile Asn
                325                 330                 335

Gly Asn Arg Phe Pro Thr Lys Asp Ile Gln Ser Val Pro Glu Ile Asp
            340                 345                 350

Val Leu Cys Ala Gln Ala Val Arg Glu Asn Trp Gln Thr Val Thr Pro
        355                 360                 365

Cys Thr Leu Lys Lys Gln Tyr Cys Gly Lys Lys Thr Arg Thr Ile
    370                 375                 380

Leu Gly Thr Asn Asn Phe Ile Ala Leu Ala His Arg Ala Ala Leu Ser
385                 390                 395                 400

Gly Val Thr Gln Gly Phe Met Lys Lys Ala Phe Asn Ser Pro Ile Ala
                405                 410                 415

Leu Gly Lys Asn Lys Phe Lys Glu Leu Gln Thr Pro Val Leu Gly Arg
            420                 425                 430

Cys Leu Glu Ala Asp Leu Ala Ser Cys Asp Arg Ser Thr Pro Ala Ile
        435                 440                 445

Val Arg Trp Phe Ala Ala Asn Leu Leu Tyr Glu Leu Ala Cys Ala Glu
    450                 455                 460

Glu His Leu Pro Ser Tyr Val Leu Asn Cys Cys His Asp Leu Leu Val
465                 470                 475                 480

Thr Gln Ser Gly Ala Val Thr Lys Arg Gly Gly Leu Ser Ser Gly Asp
                485                 490                 495

Pro Ile Thr Ser Val Ser Asn Thr Ile Tyr Ser Leu Val Ile Tyr Ala
            500                 505                 510

Gln His Met Val Leu Ser Tyr Phe Lys Ser Gly His Pro His Gly Leu
        515                 520                 525

Leu Phe Leu Gln Asp Gln Leu Lys Phe Glu Asp Met Leu Lys Val Gln
    530                 535                 540

Pro Leu Ile Val Tyr Ser Asp Asp Leu Val Leu Tyr Ala Glu Ser Pro
545                 550                 555                 560

Thr Met Pro Asn Tyr His Trp Trp Val Glu His Leu Asn Ser Met Leu
                565                 570                 575

Gly Phe Gln Thr Asp Pro Lys Lys Thr Ala Ile Thr Asp Ser Pro Ser
            580                 585                 590

Phe Leu Gly Cys Arg Ile Ile Asn Gly Arg Gln Leu Val Pro Asn Arg
        595                 600                 605

Asp Arg Ile Leu Ala Ala Leu Ala Tyr His Met Lys Ala Ser Asn Val
    610                 615                 620

Ser Glu Tyr Tyr Ala Ser Ala Ala Ile Leu Met Asp Ser Cys Ala
625                 630                 635                 640

Cys Leu Glu Tyr Asp Pro Glu Trp Phe Glu Glu Leu Val Val Gly Ile
```

Ala Gln Cys Ala Arg Lys Asp Gly Tyr Ser Phe Pro Gly Thr Pro Phe
            645                 650                 655
                660                 665                 670

Phe Met Ser Met Trp Glu Lys Leu Arg Ser Asn Tyr Glu
                675                 680                 685

<210> SEQ ID NO 45
<211> LENGTH: 441
<212> TYPE: PRT
<213> ORGANISM: PRRS virus

<400> SEQUENCE: 45

Gly Lys Lys Ser Arg Val Cys Gly Tyr Cys Gly Ala Pro Ala Pro Tyr
1               5                   10                  15

Ala Thr Ala Cys Gly Leu Asp Val Cys Ile Tyr His Thr His Phe His
            20                  25                  30

Gln His Cys Pro Val Thr Ile Trp Cys Gly His Pro Ala Gly Ser Gly
        35                  40                  45

Ser Cys Ser Glu Cys Lys Ser Pro Val Gly Lys Gly Thr Ser Pro Leu
    50                  55                  60

Asp Glu Val Leu Glu Gln Val Pro Tyr Lys Pro Pro Arg Thr Val Ile
65                  70                  75                  80

Met Arg Val Glu Gln Gly Leu Thr Pro Leu Asp Pro Gly Arg Tyr Gln
                85                  90                  95

Thr Arg Arg Gly Leu Val Ser Val Arg Arg Gly Ile Arg Gly Asn Glu
            100                 105                 110

Val Glu Leu Pro Asp Gly Asp Tyr Ala Ser Thr Ala Leu Leu Pro Thr
        115                 120                 125

Cys Lys Glu Ile Asn Met Val Ala Val Ala Ser Asn Val Leu Arg Ser
    130                 135                 140

Arg Phe Ile Ile Gly Pro Pro Gly Ala Gly Lys Thr Tyr Trp Leu Leu
145                 150                 155                 160

Gln Gln Val Gln Asp Gly Asp Val Ile Tyr Thr Pro Thr His Gln Thr
                165                 170                 175

Met Leu Asp Met Ile Arg Ala Leu Gly Thr Cys Arg Phe Asn Val Pro
            180                 185                 190

Ala Gly Thr Thr Leu Gln Phe Pro Val Pro Ser Arg Thr Gly Pro Trp
        195                 200                 205

Val Arg Ile Leu Ala Gly Gly Trp Cys Pro Gly Lys Asn Ser Phe Leu
    210                 215                 220

Asp Glu Ala Ala Tyr Cys Asn His Leu Asp Val Leu Arg Leu Leu Ser
225                 230                 235                 240

Lys Thr Thr Leu Thr Cys Leu Gly Asp Phe Lys Gln Leu His Pro Val
                245                 250                 255

Gly Phe Asp Ser His Cys Tyr Val Phe Asn Ile Met Pro Gln Thr Gln
            260                 265                 270

Leu Lys Thr Ile Trp Arg Phe Gly Gln Asn Ile Cys Asp Ala Ile Gln
        275                 280                 285

Pro Asp Tyr Arg Asp Lys Leu Met Ser Met Val Asn Thr Thr Arg Val
    290                 295                 300

Thr Tyr Val Glu Lys Pro Val Arg Tyr Gly Gln Val Leu Thr Pro Tyr
305                 310                 315                 320

His Arg Asp Arg Glu Asp Asp Ala Ile Thr Ile Asp Ser Ser Gln Gly
                325                 330                 335

```
Ala Thr Phe Asp Val Val Thr Leu His Leu Pro Thr Lys Asp Ser Leu
            340                 345                 350

Asn Arg Gln Arg Ala Leu Val Ala Ile Thr Arg Ala Arg His Ala Ile
        355                 360                 365

Phe Val Tyr Asp Pro His Arg Gln Leu Gln Ser Leu Phe Asp Leu Pro
    370                 375                 380

Ala Lys Gly Thr Pro Val Asn Leu Ala Val His Arg Asp Gly Gln Leu
385                 390                 395                 400

Ile Val Leu Asp Arg Asn Asn Lys Glu Cys Thr Val Ala Gln Ala Leu
                405                 410                 415

Gly Asn Gly Asp Lys Phe Arg Ala Thr Asp Lys Arg Val Val Asp Ser
            420                 425                 430

Leu Arg Ala Ile Cys Ala Asp Leu Glu
        435                 440

<210> SEQ ID NO 46
<211> LENGTH: 223
<212> TYPE: PRT
<213> ORGANISM: PRRS virus

<400> SEQUENCE: 46

Gly Ser Ser Ser Pro Leu Pro Lys Val Ala His Asn Leu Gly Phe Tyr
1               5                   10                  15

Phe Ser Pro Asp Leu Thr Gln Phe Ala Lys Leu Pro Ala Glu Leu Ala
            20                  25                  30

Pro His Trp Pro Val Val Thr Thr Gln Asn Asn Glu Lys Trp Pro Asp
        35                  40                  45

Arg Leu Val Thr Ser Leu Arg Pro Ile His Lys Tyr Ser Arg Ala Cys
    50                  55                  60

Ile Gly Ala Gly Tyr Met Val Gly Pro Ser Val Phe Leu Gly Thr Pro
65                  70                  75                  80

Gly Val Val Ser Tyr Tyr Leu Thr Lys Phe Val Lys Gly Glu Ala Gln
                85                  90                  95

Val Leu Pro Glu Thr Val Phe Ser Thr Gly Arg Ile Glu Val Asp Cys
            100                 105                 110

Arg Glu Tyr Leu Asp Asp Arg Glu Arg Glu Val Ala Ala Ser Leu Pro
        115                 120                 125

His Ala Phe Ile Gly Asp Val Lys Gly Thr Thr Val Gly Gly Cys His
    130                 135                 140

His Val Thr Ser Arg Tyr Leu Pro Arg Phe Leu Pro Lys Glu Ser Val
145                 150                 155                 160

Ala Val Val Gly Val Ser Ser Pro Gly Lys Ala Ala Lys Ala Leu Cys
                165                 170                 175

Thr Leu Thr Asp Val Tyr Leu Pro Asp Leu Glu Ala Tyr Phe His Pro
            180                 185                 190

Glu Thr Gln Ser Lys Cys Trp Arg Met Met Leu Asp Phe Lys Glu Val
        195                 200                 205

Arg Leu Met Val Trp Lys Asp Lys Thr Ala Tyr Phe Gln Leu Glu
    210                 215                 220

<210> SEQ ID NO 47
<211> LENGTH: 153
<212> TYPE: PRT
<213> ORGANISM: PRRS virus

<400> SEQUENCE: 47
```

```
Gly Arg Tyr Phe Thr Trp Tyr Gln Leu Ala Ser Tyr Ala Ser Tyr Ile
1               5                   10                  15

Arg Val Pro Val Asn Ser Thr Val Tyr Leu Asp Pro Cys Met Gly Pro
            20                  25                  30

Ala Leu Cys Asn Arg Lys Val Val Gly Ser Thr His Trp Gly Ala Asp
        35                  40                  45

Leu Ala Val Thr Pro Tyr Asp Tyr Gly Ala Lys Ile Ile Leu Ser Ser
    50                  55                  60

Ala Tyr His Ser Glu Met Pro Pro Gly Tyr Lys Ile Leu Ala Cys Ala
65                  70                  75                  80

Glu Phe Ser Leu Asp Asp Pro Val Lys Tyr Lys His Thr Trp Gly Phe
                85                  90                  95

Glu Ser Asp Thr Ala Tyr Leu Tyr Glu Phe Thr Gly Asn Gly Glu Asp
            100                 105                 110

Trp Glu Asp Tyr Asn Asp Ala Phe Arg Ala Arg Gln Glu Gly Lys Ile
        115                 120                 125

Tyr Lys Ala Thr Ala Thr Ser Met Lys Phe Tyr Phe Pro Pro Gly Pro
    130                 135                 140

Val Ile Glu Pro Thr Leu Gly Leu Asn
145                 150
```

<210> SEQ ID NO 48
<211> LENGTH: 254
<212> TYPE: PRT
<213> ORGANISM: PRRS virus

<400> SEQUENCE: 48

```
Met Val Asn Ser Cys Thr Phe Leu His Ile Phe Leu Cys Cys Ser Phe
1               5                   10                  15

Leu Tyr Ser Leu Cys Cys Ala Val Val Ala Gly Ser Asn Thr Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Val Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Glu His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

-continued

```
Val Leu Asn Val Ser Trp Phe Leu Arg Arg Ser Pro Ala Asn His Val
        195                 200             205

Ser Val Arg Val Phe Gln Thr Leu Arg Pro Thr Pro Pro Gln Arg Gln
    210             215             220

Ala Leu Leu Ser Ser Lys Thr Ser Val Ala Leu Gly Ile Ala Thr Arg
225             230             235                     240

Pro Leu Arg Arg Phe Ala Lys Ser Leu Ser Ala Val Arg Arg
                245             250
```

We claim:

1. An isolated Porcine Reproductive and Respiratory Syndrome (PRRS) virus, wherein the virus comprises a nucleic acid sequence of at least 95% identity to SEQ ID NO:1, wherein the nucleic acid sequence encodes a Protein E amino acid sequence comprising SEQ ID NO:12 and a GP3 amino acid sequence comprising SEQ ID NO:16.

2. The isolated PRRS virus of claim 1, wherein the virus comprises the nucleic acid sequence of SEQ ID NO:1.

3. An immunogenic composition comprising the virus of claim 1 and a pharmaceutical carrier.

4. The immunogenic composition of claim 3 further comprising an immunological adjuvant.

5. The immunogenic composition of claim 4, wherein the immunological adjuvant comprises at least one of interferon α, interferon β, interleukin-12, interleukin-15, interleukin-18, a nucleic acid encoding interferon α which is expressed in a pig cell, a nucleic acid encoding interleukin-12 which is expressed in a pig cell, a nucleic acid encoding interleukin-15 which is expressed in a pig cell, a nucleic acid encoding interleukin-18 which is expressed in a pig cell, a nucleic acid encoding interferon β which is expressed in a pig cell, or poly IC.

6. A method of inducing an immune response specific for Porcine Reproductive and Respiratory Syndrome virus in a swine, said method comprising the step of administering the immunogenic composition of claim 3 to the swine.

7. The method of claim 6, wherein the immunogenic composition further comprises an immunological adjuvant.

8. The method of claim 7, wherein the immunological adjuvant comprises interferon α, interferon β, a nucleic acid encoding interferon α expressible in a pig cell, a nucleic acid encoding interferon β which is expressed in a pig cell, interleukin-12, interleukin-15, interleukin-18, a nucleic acid encoding interferon α which is expressed in a pig cell, a nucleic acid encoding interleukin-12 which is expressed in a pig cell, a nucleic acid encoding interleukin-15 which is expressed in a pig cell, a nucleic acid encoding interleukin-18 which is expressed in a pig cell, or poly IC.

9. The method of claim 6, wherein an immunological adjuvant is administered simultaneously with the immunogenic composition, within 24 hours after the immunogenic composition, or within 24 hours before the immunogenic composition.

10. The method of claim 6, wherein the administering of the immunogenic composition is intramuscular, intradermal, mucosal, oral, sublingual, intraocular, intranasal, intravenous, intraperitoneal, topical, or transdermal.

11. The method of claim 10, wherein the administering is intramuscular.

12. An isolated PRRS virus having a Protein E sequence characterized by SEQ ID NO:12, a Nsp2 sequence characterized by SEQ ID NO:7, or both a Protein E sequence characterized by SEQ ID NO:12 and a Nsp2 sequence characterized by SEQ ID NO:7.

13. An isolated PRRS virus represented by a deposit with the American Type Culture Collection designated as ATCC Patent Deposit No. PTA-120658.

\* \* \* \* \*